US009605101B2

(12) United States Patent
Kaneko et al.

(10) Patent No.: US 9,605,101 B2
(45) Date of Patent: *Mar. 28, 2017

(54) PIGMENT MULTIMER, COLORING COMPOSITION, CURED FILM, COLOR FILTER, METHOD FOR MANUFACTURING COLOR FILTER, SOLID-STATE IMAGING ELEMENT, AND IMAGE DISPLAY DEVICE

(71) Applicant: FUJIFILM Corporation, Tokyo (JP)

(72) Inventors: Yuushi Kaneko, Shizuoka (JP); Tetsuya Watanabe, Shizuoka (JP); Suguru Samejima, Shizuoka (JP); Junichi Ito, Shizuoka (JP); Naotsugu Muro, Shizuoka (JP); Yoshinori Taguchi, Shizuoka (JP); Kazuya Oota, Shizuoka (JP)

(73) Assignee: FUJIFILM Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/978,898

(22) Filed: Dec. 22, 2015

(65) Prior Publication Data

US 2016/0108161 A1 Apr. 21, 2016

Related U.S. Application Data

(63) Continuation of application No. PCT/JP2014/067615, filed on Jul. 2, 2014.

(30) Foreign Application Priority Data

Jul. 5, 2013 (JP) .................................. 2013-141996
Jun. 4, 2014 (JP) .................................. 2014-115703

(51) Int. Cl.

| | | |
|---|---|---|
| G02B 5/23 | (2006.01) |
| G03F 7/00 | (2006.01) |
| C08F 224/00 | (2006.01) |
| C08F 12/22 | (2006.01) |
| C08F 12/26 | (2006.01) |
| C08F 20/36 | (2006.01) |
| G02B 5/20 | (2006.01) |
| G03F 7/031 | (2006.01) |
| C09B 11/12 | (2006.01) |
| C09B 11/24 | (2006.01) |
| C09B 23/04 | (2006.01) |
| C09B 23/06 | (2006.01) |
| C09B 23/08 | (2006.01) |
| C09B 47/00 | (2006.01) |
| C09B 69/10 | (2006.01) |
| C08F 12/32 | (2006.01) |
| C07D 311/88 | (2006.01) |
| C08G 18/38 | (2006.01) |
| G02B 5/22 | (2006.01) |
| G03F 7/105 | (2006.01) |
| G03F 7/029 | (2006.01) |
| G03F 7/033 | (2006.01) |
| G03F 7/038 | (2006.01) |

(Continued)

(52) U.S. Cl.

CPC .......... *C08F 224/00* (2013.01); *C07D 311/88* (2013.01); *C08F 12/22* (2013.01); *C08F 12/26* (2013.01); *C08F 12/32* (2013.01); *C08F 20/36* (2013.01); *C08G 18/3819* (2013.01); *C09B 11/12* (2013.01); *C09B 11/24* (2013.01); *C09B 23/04* (2013.01); *C09B 23/06* (2013.01); *C09B 23/08* (2013.01); *C09B 47/00* (2013.01); *C09B 69/103* (2013.01); *C09B 69/105* (2013.01); *C09B 69/108* (2013.01); *G02B 5/20* (2013.01); *G02B 5/223* (2013.01); *G03F 7/0007* (2013.01); *G03F 7/029* (2013.01); *G03F 7/031* (2013.01); *G03F 7/033* (2013.01); *G03F 7/0388* (2013.01); *G03F 7/105* (2013.01); *C08F 8/00* (2013.01); *C08F 290/12* (2013.01); *C08G 18/32* (2013.01)

(58) Field of Classification Search

USPC ............ 252/79.1, 586; 349/106; 428/7, 220, 428/281.1; 216/41, 83, 93, 12, 24; 430/7, 430/270.1, 281.1; 526/243; 528/70; 549/227

See application file for complete search history.

(56) References Cited

U.S. PATENT DOCUMENTS

| 4,397,651 A | 8/1983 | Degen et al. |
| 5,541,235 A * | 7/1996 | Busman .................... C08F 2/46 522/25 |

(Continued)

FOREIGN PATENT DOCUMENTS

| CN | 101010290 A | 8/2007 |
| CN | 102575113 A | 7/2012 |

(Continued)

OTHER PUBLICATIONS

International Search Report for PCT/JP2014/067615 dated Sep. 22, 2014 [PCT/ISA/210].
Written Opinion for PCT/JP2014/067615 dated Sep. 22, 2014 [PCT/ISA/210].
International Preliminary Report on Patentability issued from the international Bureau in counterpart application No. PCT/JP2014/067615, mailed on Jan. 14, 2016.

(Continued)

*Primary Examiner* — Bijan Ahvazi
(74) *Attorney, Agent, or Firm* — Sughrue Mion, PLLC

(57) ABSTRACT

Provided is a pigment multimer whereby a pattern can be appropriately formed during formation of a pattern. Further, provided are a coloring composition using the pigment multimer; and a cured film, a color filter, a method for manufacturing a color filter, a solid-state imaging element, and an image display device, each of which uses the coloring composition. The pigment multimer (A) has a non-nucleophilic counter anion.

18 Claims, No Drawings

(51) Int. Cl.
  *G03F 1/00* (2012.01)
  *G03C 1/00* (2006.01)
  *C08F 8/00* (2006.01)
  *C08F 290/12* (2006.01)
  *C08G 18/32* (2006.01)

(56) References Cited

U.S. PATENT DOCUMENTS

| | | | | |
|---|---|---|---|---|
| 6,509,125 | B1* | 1/2003 | Ito | G02B 5/201 |
| | | | | 349/106 |
| 7,901,851 | B2 | 3/2011 | Mizukawa et al. | |
| 8,778,235 | B2 | 7/2014 | Ito et al. | |
| 9,081,273 | B2 | 7/2015 | Nagata et al. | |
| 9,116,426 | B2 | 8/2015 | Arayama et al. | |
| 2006/0163208 | A1* | 7/2006 | Park | G03F 7/422 |
| | | | | 216/93 |
| 2007/0117031 | A1 | 5/2007 | Mizukawa et al. | |
| 2008/0067478 | A1* | 3/2008 | Ikeda | B32B 17/10761 |
| | | | | 252/587 |
| 2011/0294049 | A1* | 12/2011 | Makino | C08F 2/50 |
| | | | | 430/7 |
| 2012/0187351 | A1 | 7/2012 | Ito et al. | |
| 2012/0235099 | A1* | 9/2012 | Ushijima | G02B 5/201 |
| | | | | 252/586 |
| 2012/0242940 | A1 | 9/2012 | Nagata et al. | |
| 2013/0137018 | A1 | 5/2013 | Arayama et al. | |
| 2015/0316687 | A1* | 11/2015 | Park | G03F 7/04 |
| | | | | 252/586 |

FOREIGN PATENT DOCUMENTS

| | | | |
|---|---|---|---|
| JP | 55-120661 | A | 9/1980 |
| JP | 2000-95960 | A | 4/2000 |
| JP | 2000-162429 | A | 6/2000 |
| JP | 2003-246935 | A | 9/2003 |
| JP | 2007-138051 | A | 6/2007 |
| JP | 2009-541555 | A | 11/2009 |
| JP | 2012-32754 | A | 2/2012 |
| JP | 2012032754 | * | 2/2012 |
| JP | 2012-46708 | A | 3/2012 |
| JP | 2012-46712 | A | 3/2012 |
| JP | 2012-158740 | A | 8/2012 |
| JP | 2012-162677 | A | 8/2012 |
| JP | 2012-215806 | A | 11/2012 |
| JP | 2013-010814 | A | 1/2013 |
| JP | 2013-67776 | A | 4/2013 |
| JP | 2013-107954 | A | 6/2013 |
| WO | 2008/003604 | A2 | 1/2008 |
| WO | 2014/126167 | A1 | 8/2014 |

OTHER PUBLICATIONS

Office Action dated May 17, 2016 from the State Intellectual Property Office of the P.R.C. in counterpart Chinese Application No. 201480036159.7.

Office Action dated Oct. 25, 2016, issued by the Japanese Patent Office in corresponding Japanese Application No. 2014-115703.

Office Action dated Dec. 8, 2016, from the State Intellectual Property Office of the P.R.C., in counterpart Chinese Application No. 201480036159.7.

Office Action dated Jan. 17, 2017, from the Japanese Patent Office in counterpart Japanese Application No. 2014-115703.

* cited by examiner

PIGMENT MULTIMER, COLORING COMPOSITION, CURED FILM, COLOR FILTER, METHOD FOR MANUFACTURING COLOR FILTER, SOLID-STATE IMAGING ELEMENT, AND IMAGE DISPLAY DEVICE

CROSS-REFERENCE TO RELATED APPLICATIONS

This application is a Continuation of PCT International Application No. PCT/JP2014/067615 filed on Jul. 2, 2014, which claims priority under 35 U.S.C §119(a) to Japanese Patent Application No. 2013-441996 filed on Jul. 5, 2013 and Japanese Patent Application No. 2014-115703 filed on Jun. 4, 2014. Each of the above application(s) is hereby expressly incorporated by reference, in its entirety, into the present application.

BACKGROUND OF THE INVENTION

1. Field of the Invention

The present invention relates to a pigment multimer, a coloring composition, and a cured film using the same. The present invention further relates to a color filter having a cured film, a method for manufacturing a color filter, a solid-state imaging element having a color filter, and an image display device.

2. Description of the Related Art

As one of the methods for manufacturing a color filter which is used for a liquid crystal display device, a solid-state imaging element, or the like, there is a pigment dispersion method. As the pigment dispersion method, there is a method for manufacturing a color filter by a photolithography method by using a coloring photosensitive composition which is obtained by dispersing pigments in various photosensitive compositions. That is, a curable composition is applied onto a substrate by using a spin coater, a roll coater, or the like, the substrate is dried to form a coating film, and the coating film is developed by pattern exposure, thereby obtaining colored pixels. This operation is repeated for the number of the desired hues to manufacture a color filter.

The method is stable with respect to light or heat due to a use of pigments, and positional accuracy is sufficiently secured since patterning is performed by a photolithography method. Accordingly, the method has been widely used as a method suitable for manufacturing a color filter for color display, or the like.

Meanwhile, in recent years, there has been a demand for a color filter for a solid-state imaging element such as a CCD to have high definition. As the definition of the color filter is heightened, the pattern size tends to be decreased, but it is considered that the pigment dispersion method which has been widely used in the related art has difficulty in further improving resolution while also decreasing the pattern size. One of the reasons therefor is that coarse particles generated due to the aggregation of pigment particles cause color unevenness in a fine pattern. Accordingly, the pigment dispersion method which has been widely used so far has been in a recent situation where it has not necessarily been used for purposes requiring a fine pattern, such as in a solid-state imaging element.

In the related art, a color filter has been manufactured using a pigment as a coloring agent, but use of a dye instead of a pigment is under examination. In the case of using the dye, the points shown below particularly become problems.

(1) A dye is generally inferior to a pigment in terms of light fastness and heat resistance. In particular, there is a problem in that optical characteristics are changed due to a high-temperature process performed at the time when a film is formed of indium tin oxide (ITO) which is widely used as an electrode of a liquid crystal display or the like.

(2) Since a dye tends to inhibit a radical polymerization reaction, there is difficulty in designing a coloring photosensitive composition in a system using radical polymerization as curing means.

Particularly, in the case where a photolithography method is used for the manufacture of a color filter, the following points become problems.

(3) Since an ordinary dye exhibits low solubility in an aqueous alkaline solution or an organic solvent (hereinafter simply referred to as a solvent), it is difficult to obtain a coloring photosensitive composition having a desired spectrum.

(4) A dye interacts with other components in a coloring photosensitive composition in many cases, and thus, it is difficult to regulate the solubility (developability) of exposed and unexposed areas.

(5) In the case where the molar absorption coefficient (s) of a dye is low, it is necessary to add the dye in a large amount. As a result, amounts of other components in a coloring photosensitive composition, such as a polymerizable compound (monomer), a binder, and a photopolymerization initiator, have to be relatively reduced, and curability of the composition as well as heat resistance, developability, and the like of the cured composition deteriorate.

Due to these problems, it has been difficult so far to form a colored pattern which is constituted with a fine and thin film for a high-definition color filter and has excellent fastness by using a dye. Further, in the case of a color filter for a solid-state imaging element, a colored layer is required to be formed of a thin film of 1 μm or less. Accordingly, in order to obtain desired absorption, a large amount of a pigment needs to be added to a curable composition, and as a result, the aforementioned problems arise.

Furthermore, for a coloring photosensitive composition including a dye, it is pointed out that in the case where a heating treatment is carried out after forming a film, a phenomenon of color migration easily occurs between different hues of colored patterns adjacent to each other or between layers disposed and stacked on each other, in addition to color migration, there are also problems in that a pattern is easily peeled off in an area with a low exposure dose due to decrease in sensitivity; since the amount of photosensitive components contributing to photolithographic properties is relatively reduced, an intended shape or color density cannot be obtained due to heat sagging or elution caused at the time of development; and the like.

As methods for solving such problems, methods for resolving the problems by polymerizing a pigment have been suggested (see, for example, JP2012-32754A, JP2007-138051A, JP2000-162429A, and JP2003-246935A).

SUMMARY OF THE INVENTION

However, it could be seen that in some cases where when a pigment is polymerized, the pigment is decomposed in an excessive heating process and further, color migration to other patterns occurs. Further, it could be seen that in some cases, there is a problem in pattern formability in the case of forming a pattern. The present invention has been made to solve these problems, and has an object to provide a pigment multimer which can appropriately form a pattern when forming a pattern. The present invention further relates to a coloring composition using such a pigment multimer, a cured film, and a color filter, each of which uses the coloring composition, a method for manufacturing a color filter, a solid-state imaging element, and an image display device.

The present inventors have conducted extensive studies, and as a result, they have found that it is possible to solve the problems by using a pigment multimer having a non-nucleophilic counter anion.

Specifically, the problems were solved by the following means <1>, and preferably <2> to <17>.

<1> A pigment multimer (A) having a non-nucleophilic counter anion.

<2> The pigment multimer as described in <1>, in which the pigment multimer (A) having a non-nucleophilic counter anion has a partial structure derived from a pigment selected from a dipyrromethene pigment, a triarylmethane pigment, a xanthene pigment, and a cyanine pigment.

<3> The pigment multimer as described in <1> or <2>, in which the pigment multimer having a non-nucleophilic counter anion has a partial structure derived from a xanthene pigment.

<4> The pigment multimer as described in any one of <1> to <3>, in which the non-nucleophilic counter anion is selected from an imide anion, a tris(sulfonyl)methide anion, a tetraarylborate anion, $B^-(CN)_{n1}(OR^a)_{4-n1}$, $PF_{n2}R^P_{(6-n2)}{}^-$, and $BF_{n3}R^P_{(4-n3)}{}^-$; in $B^-(CN)_{n1}(OR^a)_{4-n}$, $R^a$ represents an alkyl group having 1 to 10 carbon atoms or an aryl group having 6 to 10 carbon atoms, and n1 represents an integer of 1 to 4; in $PF_{n2}R^P_{(6-n2)}{}^-$, $R^P$ represents a fluorinated alkyl group having 1 to 10 carbon atoms, and n2 represents an integer of 1 to 6; and in $BF_{n3}R^P_{(4-n3)}{}^-$, $R^P$ represents a fluorinated alkyl group having 1 to 10 carbon atoms, and n3 represents an integer of 1 to 4.

<5> The pigment multimer as described in any one of <1> to <4>, in which the pigment multimer has the following repeating unit.

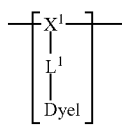

General Formula (A)

(In General Formula (A), $X^1$ represents a group capable of forming a main chain and $L^1$ represents a single bond or a divalent linking group. DyeI represents a pigment structure having a cationic moiety.)

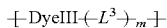

General Formula (C)

(In General Formula (C), $L^3$ represents a single bond or a divalent linking group. DyeIII represents a pigment structure having a cationic moiety. m represents 0 or 1.)

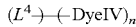

General Formula (D)

(In General Formula (D), $L^4$ represents an n-valent linking group. n represents an integer of 2 to 20. DyeIV represents a pigment structure having a cationic moiety.)

<6> The pigment multimer as described in any one of <1> to <5>, in which the pigment multimer has a polymerizable group.

<7> The pigment multimer as described in any one of <1> to <6>, in which the pigment multimer has a group containing an ethylenically unsaturated bond.

<8> The pigment multimer as described in any one of <1> to <7>, in which the pigment multimer has a repeating unit having an acid group.

<9> A coloring composition including the pigment multimer (A) as described in any one of <1> to <8>, a curable compound (B), and a pigment (C).

<10> The coloring composition as described in <9>, further including a photopolymerization initiator (D).

<11> The coloring composition as described<10>, in which the photopolymerization initiator (D) is an oxime compound.

<12> The coloring composition as described in any one of <9> to <11>, which is used for forming a colored layer of a color filter.

<13> A cured film formed by curing the coloring composition as described in any one of <9> to <12>.

<14> A method for manufacturing a color filter, including a step of applying the coloring composition as described in any one of <9> to <12> onto a support to form a coloring composition layer, a step of patternwise exposing the coloring composition layer, and a step of removing an unexposed area by development to form a colored pattern.

<15> A method for manufacturing a color filter, including:

a step of applying the coloring composition as described in any one of <9> to <12> onto a support to form a coloring composition layer, and curing the coloring composition layer to form a colored layer;

a step of forming a photoresist layer on the colored layer;

a step of patterning the photoresist layer by exposure and development to obtain a resist pattern; and a step of dry-etching the colored layer using a resist pattern as an etching mask.

<16> A color filter having the cured film as described in <13> or a color filter manufactured by the method for manufacturing a color filter as described in <14> or <15>.

<17> A solid-state imaging element or an image display device including the color filter as described in <16>.

According to the present invention, it became possible to provide a pigment multimer capable of appropriately forming a pattern when forming the pattern. It also became to provide a coloring composition using the pigment multimer; and a cured film, a color filter, a method for manufacturing a color filter, a solid-state imaging element, and an image display device, each of which uses the coloring composition.

DESCRIPTION OF THE PREFERRED EMBODIMENTS

Hereinafter, the pigment multimer, the coloring composition, the cured film, the color filter, the pattern forming method, the method for manufacturing a color filter, the solid-state imaging element, and the image display device of the present invention will be described in detail.

The explanation of constituents in the present invention as described below will be based on typical embodiments of the present invention, but the present invention is not limited to such embodiments.

In citations for a group (atomic group) in the present specification, when the group is denoted without specifying whether it is substituted or unsubstituted, the group includes both a group having no substituent and a group having a substituent. For example, an "alkyl group" includes not only an alkyl group having no substituent (unsubstituted alkyl group), but also an alkyl group having a substituent (substituted alkyl group).

Furthermore, "radiation" in the present specification means, for example, a bright line spectrum of a mercury lamp, far ultraviolet rays represented by an excimer laser, extreme ultraviolet rays (EUV rays), X-rays, electron beams, or the like. In addition, in the present invention, light means actinic rays or radiation. "Exposure" in the present specification includes, unless otherwise specified, not only exposure by a mercury lamp, far ultraviolet rays represented by an excimer laser, X-rays, EUV rays, or the like, but also writing by particle rays such as electron beams and ion beams.

In the present specification, a numeral value range represented by "(a value) to (a value)" means a range including the numeral values represented before and after "(a value) to (a value)" as a lower limit value and an upper limit value, respectively.

In the present specification, the total solid content refers to a total mass of the components remaining when a solvent is excluded from the entire composition of a coloring composition.

Furthermore, in the present specification, "(meth)acrylate" represents either or both of an acrylate and a methacrylate, "(meth)acryl" represents either or both of an acryl and a methacryl, and "(meth)acryloyl" represents either or both of an acryloyl and a methacryloyl.

In addition, in the present specification, a "monomer material" and a "monomer" have the same definition. The monomer in the present specification refers to a compound which is distinguished from an oligomer or a polymer and has a weight-average molecular weight of 2,000 or less. In the present specification, a polymerizable compound refers to a compound having a polymerizable functional group, and may be a monomer or a polymer. The polymerizable functional group refers to a group involved in a polymerization reaction.

In the present specification, in formulae, Me represents a methyl group, Et represents an ethyl group, Pr represents a propyl group, Bu represents a butyl group, and Ph represents a phenyl group.

In the present specification, a term "step" includes not only an independent step, but also steps which are not clearly distinguished from other steps if an intended action of the steps is obtained.

The present invention has been made in consideration of the above circumstances, and has an object to provide a coloring composition having excellent color characteristics.

The pigment multimer (A) of the present invention may have a non-nucleophilic counter anion. By adopting such a configuration, it is possible to effectively prevent the pigment from being decomposed even in an excessive heating process. This problem easily occurs with a dye, but also in the case of using a pigment, in particular, in the case of using a pigment having performance similar to a dye, the present invention is preferably adopted.

Moreover, the coloring composition of the present invention (hereinafter simply referred to as "the composition of the present invention" in some cases) may include a pigment multimer (A) having a non-nucleophilic counter anion and a polymerizable compound (B). The coloring composition of the present invention preferably further includes a pigment (C) (provided that a case where it corresponds to a pigment multimer (A) having a non-nucleophilic counter anion is excluded) and/or a photopolymerization initiator (D), and may include other components such as a crosslinking agent, if desired.

By adopting such a configuration, it becomes possible to form a pattern having inhibited color migration into other patterns and excellent pattern formability.

Furthermore, for a coloring composition produced by blending pigment multimers in the related art, there have been some cases where pattern deficit occurs or pattern linearity deteriorates when a fine pattern is formed by a photolithography method. In contrast, in the present invention, it becomes possible to inhibit pattern deficit or to inhibit deterioration of pattern linearity.

In addition, for a coloring composition produced by blending a pigment multimer, there have been some cases where the resistance to a developing liquid or the resistance to a peeling solution of a photoresist is poor when a pattern is formed by a dry etching method. In contrast, in the present invention, it becomes possible to improve the resistance to a developing liquid or the resistance to a peeling solution of a photoresist.

Therefore, it is possible to provide a cured film having excellent color characteristics and a color filter having the cured film according to the present invention. Further, it is possible to provide a pattern forming method which is capable of forming a colored pattern having excellent color characteristics and a method for manufacturing a color filter according to the present invention. In addition, it is possible to provide a solid-state imaging element and an image display device (a liquid crystal display device, an organic EL display device, and the like), including a color filter having excellent color characteristics, according to the present invention.

The mechanism of action has not been clarified, but one of the reasons is presumed to be that heat resistance is improved by inhibiting the attacking by counter anions during heating, and further, curing and invasion of a developing liquid become uniform by inhibiting a pigment multimer from being aggregated by incorporating a specific counter anion structure into the pigment multimer.

Details of the present invention will be described below.

<Pigment Multimer (A) Having Non-Nucleophilic Counter Anion>

The coloring composition of the present invention contains at least one kind of pigment multimer having a non-nucleophilic counter anion (hereinafter simply referred to as a "pigment multimer (A)" in some cases).

Herein, the non-nucleophilicity means a property of not attacking a pigment nucleophilically by heating.

The pigment multimer (A) is typically a multimer having a partial structure derived from a pigment whose maximum absorption wavelength is present in a range of 400 nm to 780 nm, in a molecular structure thereof, and includes the structure of a dimer, a trimer, a polymer, or the like. The pigment multimer of the present invention more preferably includes a repeating unit containing a pigment monomer; more preferably includes a repeating unit containing a pigment monomer and a repeating unit containing a polymerizable group; and still more preferably includes a repeating unit containing a pigment monomer, a repeating unit containing a polymerizable group, and a repeating unit having an acid group. In addition, in the present invention, the pigment structure preferably has a cationic moiety.

The pigment multimer (A) functions as, for example, a coloring agent in the coloring composition of the present invention.

Furthermore, the maximum absorption wavelength of the pigment multimer (A) of the present invention is preferably 420 nm to 700 nm, and more preferably 450 nm to 650 nm.

Furthermore, the acid value of the pigment multimer (A) of the present invention is preferably 5 mgKOH/g to 100 mgKOH/g, and more preferably 15 mgKOH/g to 60 mgKOH/g.

In the present invention, the content of the repeating units containing a structure derived from a pigment is preferably 10% by mole to 100% by mole, more preferably 50% by mole to 100% by mole, and particularly preferably 60% by mole to 100% by mole in the pigment multimer (A) of the present invention, when the total content of the repeating units is 100% by mole.

Hereinafter, the non-nucleophilic counter anion and the partial structure derived from a pigment in the pigment multimer (A) will be described.

<<Non-Nucleophilic Counter Anion>>

The non-nucleophilic counter anion which the pigment multimer (A) has may be an organic anion or an inorganic anion, and preferably an organic anion. Examples of the counter anion used in the present invention include the known non-nucleophilic anions described in paragraph No. "0075" of JP2007-310315A, the contents of which are incorporated herein.

Preferred examples of the non-nucleophilic counter anion include an imide anion (for example, a bis(sulfonyl)imide anion), a tris(sulfonyl)methide anion, a tetraarylborate anion, $B^-(CN)_{n1}(OR^a)_{4-n1}$ (in which $R^a$ represents an alkyl group having 1 to 10 carbon atoms or an aryl group having 6 to 10 carbon atoms, and n1 represents 1 to 4), $PF_{n2}R^P_{(6-n2)}{}^-$ (in which $R^P$ represents a fluorinated alkyl group having 1 to 10 carbon atoms, and n2 represents an integer of 1 to 6), and $BF_{n3}R^P_{(4-n3)}{}^-$ (in which $R^P$ represents a fluorinated alkyl group having 1 to 10 carbon atoms, and n3 represents an integer of 1 to 4), and the non-nucleophilic counter anion is more preferably one selected from a bis(sulfonyl)imide anion, a tris(sulfonyl)methide anion, and a tetraarylborate anion, and still more preferably a bis(sulfonyl)imide anion. The effects of the present invention tend to be more effectively exerted by using such a non-nucleophilic counter anion.

As the imide anion which is an non-nucleophilic counter anion, a structure represented by the following General Formula (AN-1) is preferable.

$$X^1—Y^1—\overset{-}{N}—Y^2—X^2 \quad (AN-1)$$

(In Formula (AN-1), $X^1$ and $X^2$ each independently represent a halogen atom, an alkyl group, or an aryl group. $X^1$ and $X^2$ may be bonded to each other to form a ring. $Y^1$ and $Y^2$ each independently represent $—SO_2—$ or $—CO—$.)

$X^1$ and $X^2$ are each independently preferably a fluorine atom, a fluorine atom-containing alkyl group having 1 to 10 carbon atoms, or an aryl group having 6 to 10 carbon atoms, more preferably a perfluoroalkyl group having 1 to 10 carbon atoms, still more preferably a perfluoroalkyl group having 1 to 4 carbon atoms, and particularly preferably a trifluoromethyl group.

It is preferable that at least one of $Y^1$ and $Y^2$ represents $—SO_2—$, and it is more preferable that both of $Y^1$ and $Y^2$ represent $—SO_2—$.

As the tris(sulfonyl)methide anion which is a non-nucleophilic counter anion, a structure of the following General Formula (AN-2) is preferable.

(AN-2)

(In Formula (AN-2), $X^3$, $X^4$, and $X^5$ each independently represent a fluorine atom, or a fluorine atom-containing alkyl group having 1 to 10 carbon atoms.)

$X^3$, $X^4$, and $X^5$ each independently have the same definitions as $X^1$, and the preferred ranges thereof are also the same.

As the tetraarylborate anion which is a non-nucleophilic counter anion, a compound represented by the following General Formula (AN-5) is preferable.

$$\begin{array}{c} Ar^1 \\ | \\ Ar^2—B—Ar^4 \\ | \\ Ar^3 \end{array} \quad (AN-5)$$

(In Formula (AN-5), $Ar^1$, $Ar^2$, $Ar^3$, and $Ar^4$ each independently represent an aryl group.)

$Ar^1$, $Ar^2$, $Ar^3$ and $Ar^4$ are each independently preferably an aryl group having 6 to 20 carbon atoms, more preferably an aryl group having 6 to 14 carbon atoms, and still more preferably an aryl group having 6 to 10 carbon atoms.

The aryl group represented by $Ar^1$, $Ar^2$, $Ar^3$, and $Ar^4$ may have a substituent. In the case where the aryl group has a substituent, examples of the substituent include a halogen atom, an alkyl group, an aryl group, an alkoxy group, a carbonyl group, a carbonyloxy group, a carbamoyl group, a sulfo group, a sulfonamide group, and a nitro group, among which a halogen atom and an alkyl group are preferable, a fluorine atom and an alkyl group are more preferable, and a fluorine atom and a perfluoroalkyl group having 1 to 4 carbon atoms are still more preferable.

$Ar^1$, $Ar^2$, $Ar^3$, and $Ar^4$ are each independently more preferably a phenyl group having a halogen atom and/or a halogen atom-containing alkyl group, and still more preferably a phenyl group having a fluorine atom and/or a fluorine-containing alkyl group.

The non-nucleophilic counter anion is preferably $—B(CN)_{n1}(OR^a)_{4-n1}$ (in which $R^a$ represents an alkyl group having 1 to 10 carbon atoms or an aryl group having 6 to 10 carbon atoms, and n1 represents an integer of 1 to 4). $R^a$ as alkyl group having 1 to 10 carbon atoms is preferably an alkyl group having 1 to 6 carbon atoms, and more preferably an alkyl group having 1 to 4 carbon atoms. $R^a$ as aryl group having 6 to 10 carbon atoms is preferably a phenyl group and a naphthyl group.

n1 is preferably 1 to 3, and more preferably 1 to 2.

Furthermore, the non-nucleophilic counter anion is preferably $—PF_6R^P_{(6-n2)}{}^-$ (in which $R^P$ represents a fluorinated alkyl group having 1 to 10 carbon atoms, and n2 represents an integer of 1 to 6). $R^P$ is preferably a fluorine atom-containing alkyl group having 1 to 6 carbon atoms, more preferably a fluorine-containing alkyl group having 1 to 4 carbon atoms, and still more preferably a perfluoroalkyl group having 1 to 3 carbon atoms. n2 is preferably an integer of 1 to 4, and more preferably 1 or 2.

Moreover, the non-nucleophilic counter anion is preferably $—BF_{n3}R^P_{(4-n3)}{}^-$ (in which $R^P$ represents a fluorinated alkyl group having 1 to 10 carbon atoms, and n3 represents an integer of 1 to 4). R is preferably a fluorine atom-containing alkyl group having 1 to 6 carbon atoms, more preferably a fluorine-containing alkyl group having 1 to 4 carbon atoms, and still more preferably a perfluoroalkyl group having 1 to 3 carbon atoms.

The mass per molecule of the non-nucleophilic counter anion used in the present invention is preferably 100 to 1,000, and more preferably 200 to 500.

The pigment multimer of the present invention may include one kind or two or more kinds of non-nucleophilic counter anion.

Specific examples of the non-nucleophilic counter anion used in the present invention are shown below, but the present invention is not limited thereto.

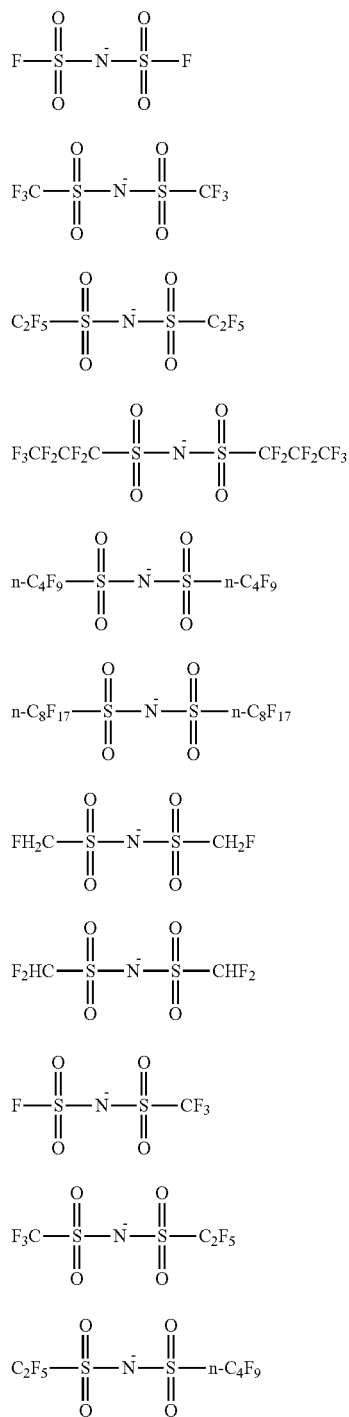
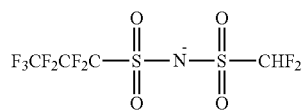
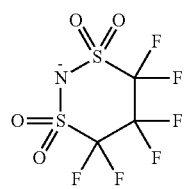
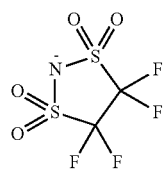
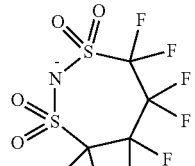
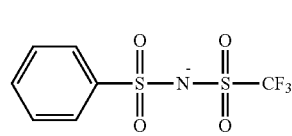
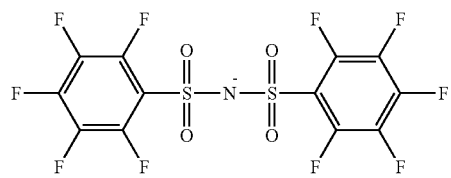
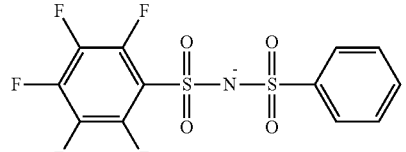
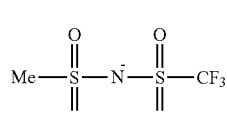
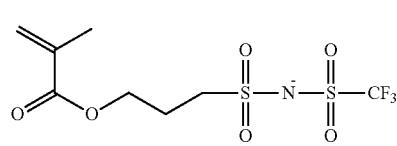
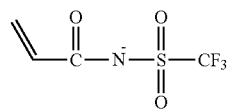

(IM-22) 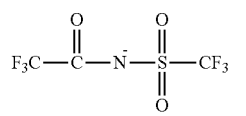
(IM-23) 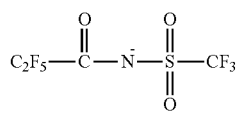
(IM-24) 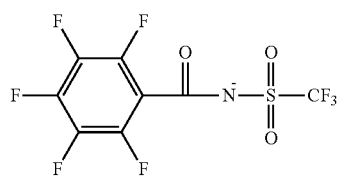
(MD-1) 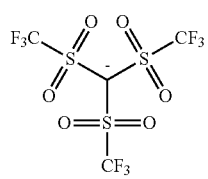
(MD-2) 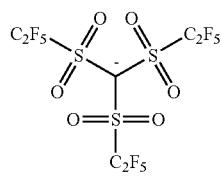
(MD-3) 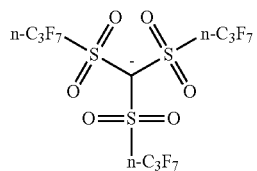
(MD-4) 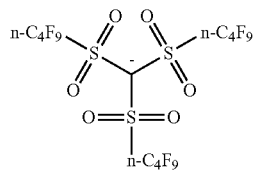
(MD-5) 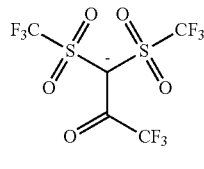
(MD-6) 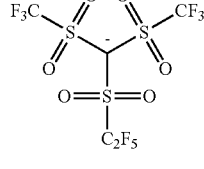
(MD-7) 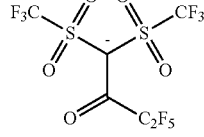
(MD-8) 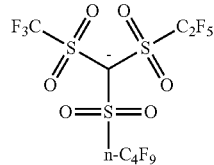
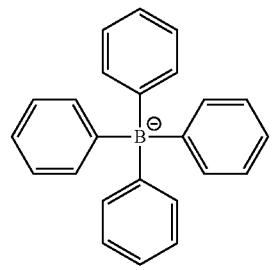
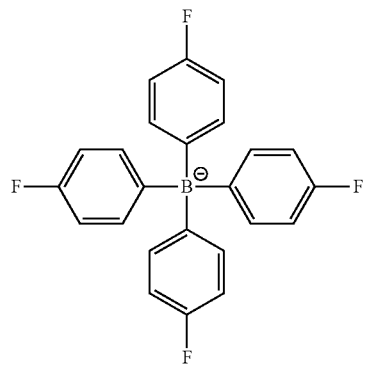
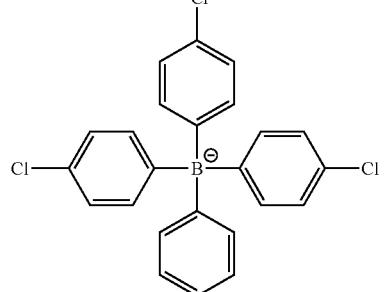
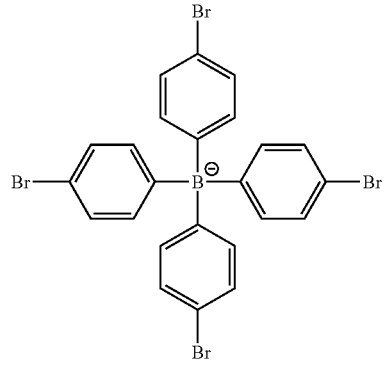

- CF₃SO₃⁻ (a-1)
- C₄F₁₈SO₃⁻ (a-2)
- C₈F₁₇SO₃⁻ (a-3)

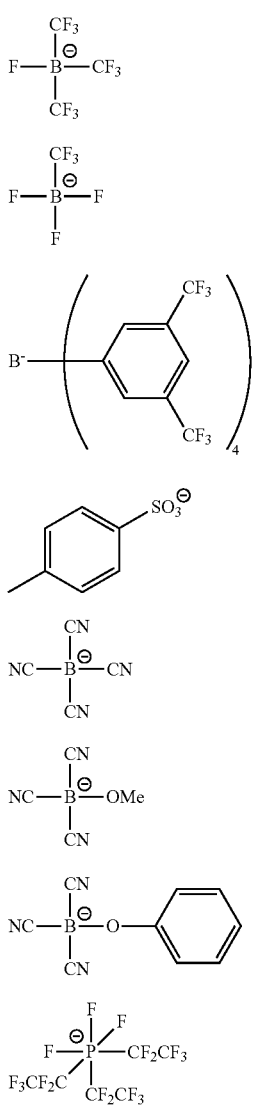

(a-20)
(a-21)
(a-22)
(a-23)
(a-24)
(a-25)
(a-27)
(a-28)

<<Pigment Structure>>

The pigment structure in the present invention is a part derived from the pigment in the pigment multimer (A), and refers to a structure which is formed when hydrogen atoms are removed from a specific pigment (hereinafter also referred to as a "pigment compound") which can form a pigment structure, and can be linked to a pigment multimer linking portion (a polymer chain, a core of dendrimer, and the like). Details thereof will be described below.

The pigment structure in the pigment multimer (A) is not particularly limited as long as it is a structure including a cationic moiety in the molecule thereof, and various structures including known pigment structures can be applied as the structure.

Specific examples thereof include pigment structures derived from a pigment selected from a dipyrromethene pigment, a carbonium pigment (a diphenylmethane pigment, a triarylmethane pigment, a xanthene pigment, an acridine pigment, and the like), a polymethine pigment (an oxonol pigment, a merocyanine pigment, an arylidene pigment, a styryl pigment, a cyanine pigment, a croconium pigment, and the like), a subphthalocyanine pigment, and metal complex pigments thereof.

Among these pigment structures, from the viewpoint of color characteristics, pigment structures derived from a pigment selected from a dipyrromethene pigment, a carbonium pigment, and a polymethine pigment are preferable; pigment structures derived from a pigment selected from a triarylmethane pigment, a xanthene pigment, a cyanine pigment, a quinophthalone pigment, a phthalocyanine pigment, and a subphthalocyanine pigment are more preferable; pigment structures derived from a pigment selected from a dipyrromethene pigment, a triarylmethane pigment, a xanthene pigment, and a cyanine pigment are still more preferable; and pigment structures derived from a pigment selected from xanthene pigments are particularly preferable. When such a pigment is used, heat resistance and light fastness tend to be more improved.

Specific pigment compounds which can form a pigment structure are described in "New Edition of Dye Handbook" (edited by The Society of Synthetic Organic Chemistry, Japan; Maruzen Co., Ltd., 1970), "Color index" (edited by The Society of Dyers and colourists), "Dye Handbook" (Ogawara, et al.; Kodansha, Ltd., 1986), and the like.

In the pigment multimer (A), a particularly preferred pigment (pigment compound) which can form a pigment structure will be described in detail.

<<<Dipyrromethene Pigment>>>

One of the embodiments of the pigment multimer (A) according to the present invention is a pigment multimer having a partial structure derived from the dipyrromethene pigment shown below as a partial structure of the pigment moiety.

As the dipyrromethene pigment in the present invention, a dipyrromethene compound, and a dipyrromethene metal complex compound obtained from a dipyrromethene compound with a metal or a metal compound are preferable.

Incidentally, in the present invention, a compound including a dipyrromethene structure is referred to as a dipyrromethene compound, and a complex in which a metal or a metal compound is coordinated to the compound having a dipyrromethene structure is referred to as a dipyrromethene metal complex compound.

As the dipyrromethene metal complex compound, a dipyrromethene metal complex compound obtained from a dipyrromethene compound represented by the following General Formula (M) with a metal or a metal compound and a tautomer thereof are preferable. Among these, a dipyrromethene metal complex compound represented by the following General Formula (7) and a dipyrromethene metal complex compound represented by the following General Formula (8) are exemplified as preferred embodiments, and the dipyrromethene metal complex compound represented by the following General Formula (8) is more preferable.

(Dipyrromethene Metal Complex Compound Obtained from Dipyrromethene Compound Represented by General Formula (M) with Metal or a Metal Compound, and Tautomer Thereof)

One of the preferred embodiments of the pigment structure in the pigment multimer (A) is a pigment structure which includes, as a pigment moiety, a complex (hereinafter appropriately referred to as a "specific complex") in which a compound (dipyrromethene compound) represented by the following General Formula (M) or a tautomer thereof is coordinated to a metal or a metal compound. In the present invention, the following compound forms a cationic structure and for example, a metal atom to which General Formula (M) is coordinated can form a cationic structure.

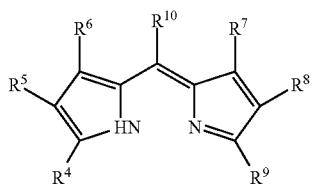

(M)

(In General Formula (M), $R^4$ to $R^{10}$ each independently represent a hydrogen atom or a monovalent substituent, provided that there is no case where $R^4$ and $R^9$ are bonded to each other to form a ring.)

When the compound represented by General Formula (M) is introduced into structural units represented by General Formula (A) to General Formula (C), or a multimer represented by General Formula (D), each of which will be described later, the introduction site is not particularly limited. However, in view of synthesis suitability, the compound is preferably introduced at any one site of $R^4$ to $R^9$, more preferably introduced at any one site of $R^4$, $R^6$, $R^7$, and $R^9$, and still more preferably introduced at any one site of $R^4$ and $R^9$.

In the case where $R^4$ to $R^9$ in General Formula (M) represent a monovalent substituent, examples of the monovalent substituent include the substituents exemplified in the section of the substituent group A which will be described later.

In the case where the monovalent substituents represented by $R^4$ to $R^9$ in General Formula (M) are each a group which can be further substituted, the group may further have the substituent(s) described for $R^4$ to $R^9$, and in the case where the group has two or more substituents, these substituents may be the same as or different from each other.

In General Formula (M), $R^4$ and $R^5$, $R^5$ and $R^6$, $R^7$ and $R^8$, and $R^8$ and $R^9$ may be each independently bonded to each other to form a 5-, 6-, or 7-membered saturated or unsaturated ring, provided that there is no case where $R^4$ and $R^9$ are bonded to each other to form a ring. In the case where the formed 5-, 6-, or 7-membered ring is a group which can be further substituted, the ring may be substituted with the substituents described for $R^4$ to $R^9$, and in the case where the ring is substituted with two or more substituents, these substituents may be the same as or different from each other.

In General Formula (M), in the case where $R^4$ and $R^5$, $R^5$ and $R^6$, $R^7$ and $R^8$, and $R^8$ and $R^9$ are each independently bonded to each other to form a 5-, 6-, or 7-membered saturated or unsaturated ring not having a substituent, examples of the 5-, 6-, or 7-membered saturated or unsaturated ring not having a substituent include a pyrrole ring, a furan ring, a thiophene ring, a pyrazole ring, an imidazole ring, a triazole ring, an oxazole ring, a thiazole ring, a pyrrolidine ring, a piperidine ring, a cyclopentene ring, a cyclohexene ring, a benzene ring, a pyridine ring, a pyrazine ring, and a pyridazine ring, and preferably a benzene ring and a pyridine ring.

$R^{10}$ in General Formula (M) preferably represents a hydrogen atom, a halogen atom, an alkyl group, an aryl group, or a heterocyclic group. The halogen atom, the alkyl group, the aryl group, and the heterocyclic group have the same definitions as those of the halogen atom, the alkyl group, the aryl group, and the heterocyclic group, respectively, described in the section of the substituent group A which will be described later, and a preferred range thereof is also the same.

In the case where $R^{10}$ represents an alkyl group, an aryl group, or a heterocyclic group, if the alkyl group, the aryl group, and the heterocyclic group are groups which can be further substituted, they may be substituted with the substituents described in the section of the substituent group A which will be described later. In the case where the groups are substituted with two or more substituents, the substituents may be the same as or different from each other.

~Metal or Metal Compound~

The specific complex in the present invention is a complex in which the dipyrromethene compound represented by General Formula (M) or a tautomer thereof is coordinated to a metal or a metal compound.

Herein, the metal or metal compound may be any types of metal or metal compound as long as they can form a complex, and examples thereof include a divalent metal atom, a divalent metal oxide, a divalent metal hydroxide, and a divalent metal chloride. Examples of the metal or metal compound include metals such as Zn, Mg, Si, Sn, Rh, Pt, Pd, Mo, Mn, Pb, Cu, Ni, Co, and Fe, metal chlorides such as AlCl, InCl, FeCl, $TiCl_2$, $SnCl_2$, $SiCl_2$, and $GeGl_2$, metal oxides such as TiO and VO, and metal hydroxides such as $Si(OH)_2$.

Among these, in view of the stability, spectral characteristics, heat resistance, light fastness, and production suitability of the complex, Fe, Zn, Mg, Si, Pt, Pd, Mo, Mn, Cu, Ni, Co, TiO, or VO is preferable, Zn, Mg, Si, Pt, Pd, Cu, Ni, Co, or VO is more preferable, and Zn is particularly preferable.

Next, a more preferred range of the specific complex of the compound represented by General Formula (M) in the present invention will be described.

A preferred range of the specific complex in the present invention is a range in which in General Formula (M), $R^4$ and $R^9$ are each independently a hydrogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an amino group, an anilino group, a heterocyclic amino group, a carbonamide group, a ureido group, an imide group, an alkoxycarbonylamino group, an aryloxycarbonylamino group, a sulfonamide group, an azo group, an alkyl thin group, an arylthio group, a heterocyclic thio group, an alkylsulfonyl group, an arylsulfonyl group, or a phosphinoylamino group; $R^5$ and $R^8$ are each independently a hydrogen atom, a halogen atom, an alkyl group, an alkenyl group, an aryl group, a heterocyclic group, a hydroxyl group, a cyano group, a nitro group, an alkoxy group, an aryloxy group, a heterocyclic oxy group, an acyl group, an alkoxycarbonyl group, an aryloxycarbonyl group, a carbamoyl group, an imide group, an alkoxycarbonylamino group, a sulfonamide group, an azo group, an alkylthio group, an arylthio group, a heterocyclic thio group, an alkylsulfonyl group, an arylsulfonyl group, or a sulfamoyl group; $R^6$ and $R^7$ are each independently a hydrogen atom, a halogen atom, an alkyl group, an alkenyl group, an aryl group, a heterocyclic group, a silyl group, a hydroxyl group, a cyano group, an alkoxy group, an aryloxy group, a heterocyclic oxy group, an acyl group, an alkoxycarbonyl group, a carbamoyl group, an anilino group, a carbonamide group, a ureido group, an imide group, an alkoxycarbonylamino group, a sulfonamide group, an azo group, an alkylthio group, an arylthio group, a heterocyclic thio group, an alkylsulfonyl group, an arylsulfonyl group, a sulfamoyl group, or a phosphinoylamino group; $R^{10}$ is a hydrogen atom, a halogen atom, an alkyl group, an aryl group, or a heterocyclic group; and the metal or metal compound is Zn, Mg, Si, Pt, Pd, Mo, Mn, Cu, Ni, Co, TiO, or V=O.

A more preferred range of the specific complex in the present invention is a range in which in General Formula (M), $R^4$ and $R^9$ are each independently a hydrogen atom, an alkyl group, an alkenyl group, an aryl group, a heterocyclic group, a cyano group, an acyl group, an alkoxycarbonyl group, a carbamoyl group, an amino group, a heterocyclic amino group, a carbonamide group, a ureido group, an imide group, an alkoxycarbonylamino group, an aryloxycarbonylamino group, a sulfonamide group, an azo group, an alkylsulfonyl group, an arylsulfonyl group, or a phosphinoylamino group; $R^5$ and $R^8$ are each independently an alkyl group, an alkenyl group, an aryl group, a heterocyclic group, a cyano group, a nitro group, an acyl group, an alkoxycarbonyl group, an aryloxycarbonyl group, a carbamoyl group, an imide group, an alkylsulfonyl group, an arylsulfonyl group, or a sulfamoyl group; $R^6$ and $R^7$ are each independently a hydrogen atom, an alkyl group, an alkenyl group, an aryl group, a heterocyclic group, a cyano group, an acyl group, an alkoxycarbonyl group, a carbamoyl group, a carbonamide group, a ureido group, an imide group, an alkoxycarbonylamino group, a sulfonamide group, an alkylthio group, an arylthio group, a heterocyclic thio group, an alkylsulfonyl group, an arylsulfonyl group, or a sulfamoyl group; $R^{10}$ is a hydrogen atom, a halogen atom, an alkyl group, an aryl group, or a heterocyclic group; and the metal or metal compound is Zn, Mg, Si, Pt, Pd, Cu, Ni, Co, or V=O.

A particularly preferred range of the specific complex in the present invention is a range in which in General Formula (M), $R^4$ and $R^9$ are each independently a hydrogen atom, an alkyl group, an aryl group, a heterocyclic group, an amino group, a heterocyclic amino group, a carbonamide group, a ureido group, an imide group, an alkoxycarbonylamino group, a sulfonamide group, an azo group, an alkylsulfonyl group, an arylsulfonyl group, or a phosphinoylamino group; $R^5$ and $R^8$ are each independently an alkyl group, an aryl group, a heterocyclic group, a cyano group, an acyl group, an alkoxycarbonyl group, a carbamoyl group, an alkylsulfonyl group, or an arylsulfonyl group; $R^6$ and $R^7$ are each independently a hydrogen atom, an alkyl group, an aryl group, or a heterocyclic group; $R^{10}$ is a hydrogen atom, an alkyl group, an aryl group, or a heterocyclic group; and the metal or metal compound is Zn, Cu, Co, or V=O.

Moreover, a dipyrromethene metal complex compound represented by General Formula (7) or General Formula (8), which will be described in detail below, is also a particularly preferred embodiment of the dipyrromethene pigment.

Dipyrromethene Metal Complex Compound Represented by General Formula (7)

One of the suitable embodiments of the pigment structure in the pigment multimer (A) is a pigment structure derived from a dipyrromethene metal complex compound represented by the following General Formula (7). In the present invention, the following compound forms a cationic structure, and for example, Ma in General Formula (7) can form a cationic structure.

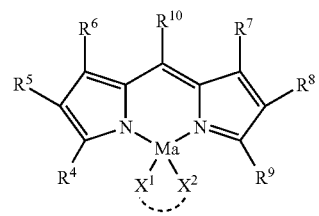

(7)

(In General Formula (7), $R^4$ to $R^9$ each independently represent a hydrogen atom or a monovalent substituent, and $R^{10}$ represents a hydrogen atom, a halogen atom, an alkyl group, an aryl group, or a heterocyclic group. Ma represents a metal atom or a metal compound. $X^1$ represents a group which can be bonded to Ma, $X^2$ represents a group which neutralizes the charge of Ma, and $X^1$ and $X^2$ may be bonded to each other to form a 5-, 6-, or 7-membered ring together with Ma, provided that there is no case where $R^4$ and $R^9$ are bonded to each other to form a ring.)

Incidentally, the dipyrromethene metal complex compound represented by General Formula (7) includes a tautomer.

In the case where the dipyrromethene metal complex compound represented by General Formula (7) is introduced into structural units represented by General Formula (A) to General Formula (C), or a multimer represented by General Formula (D), each of which will be described later, the introduction site is not particularly limited. However, in view of synthesis suitability, the compound is preferably introduced at any one site of $R^4$ to $R^9$, more preferably introduced at any one site of $R^4$, $R^6$, $R^7$, and $R^9$, and still more preferably introduced at any one site of $R^4$ and $R^9$.

In the case where the pigment multimer (A) has an alkali-soluble group, as a method of introducing the alkali-soluble group, a method of bonding the alkali-soluble group to one, two, or more substituents out of $R^4$ to $R^{10}$, $X^1$ and $X^2$ in General Formula (7) can be used. Among these substituents, any one of $R^4$ to $R^9$ and $X^1$ is preferable, any one of $R^4$, $R^6$, $R^7$, and $R^9$ is more preferable, and any one of $R^4$ and $R^9$ is still more preferable.

The dipyrromethene metal complex compound represented by General Formula (7) may have a functional group other than the alkali-soluble group as long as the effects of the present invention are not diminished.

$R^4$ to $R^9$ in General Formula (7) have the same definitions as $R^4$ to $R^9$ in General Formula (M), and preferred embodiments thereof are also the same.

In General Formula (7), Ma represents a metal atom or a metal compound. The metal atom or metal compound may be any type as long as it is a metal atom or a metal compound which can form a complex, and examples thereof include a divalent metal atom, a divalent metal oxide, a divalent metal hydroxide, or a divalent metal chloride.

Examples of the metal atom or metal compound include Zn, Mg, Si, Sn, Rh, Pt, Pd, Mo, Mn, Pb, Cu, Ni, Co, and Fe; metal chlorides such as AlCl, InCl, FeCl, $TiCl_2$, $SnCl_2$, and $GeCl_2$; metal oxides such as TiO and V=O; and metal hydroxides such as $Si(OH)_2$.

Among these, in view of stability, spectral characteristics, heat resistance, light fastness, and production suitability of the complex, as the metal atom or metal compound, Fe, Zn, Mg, Si, Pt, Pd, Mo, Mn, Cu, Ni, Co, TiO, and V=O are preferable, Zn, Mg, Si, Pt, Pd, Cu, Ni, Co, and V=O are more preferable, Zn, Co, V=O, and Cu are still more preferable, and Zn is particularly preferable.

In General Formula (7), $R^{10}$ represents a hydrogen atom, a halogen atom, an alkyl group, an aryl group, or a heterocyclic group, and is preferably a hydrogen atom.

In General Formula (7), $X^1$ may be any group as long as the group can be bonded to Ma, and specific examples thereof include water, alcohols (for example, methanol, ethanol, and propanol), and compounds disclosed in "Metal Chelates" ([1] Takeichi Sakaguchi and Kagehira Ueno (1995, Nankodo Co., Ltd.), [2] (1996), [3] (1997), and the like). Among these, in view of production thereof, water, a carboxylic acid compound, and alcohols are preferable, and water and a carboxylic acid compound are more preferable.

In General Formula (7), examples of the "group which neutralizes the charge of Ma" represented by $X^2$ include a halogen atom, a hydroxyl group, a carboxylic acid group, a phosphoric acid group, a sulfonic acid group, and the like. Among these, in view of production thereof, a halogen atom, a hydroxyl group, a carboxylic acid group, and a sulfonic acid group are preferable, and a hydroxyl group and a carboxylic acid group are more preferable.

In General Formula (7), $X^1$ and $X^2$ may be bonded to each other to form a 5-, 6-, or 7-membered ring together with Ma. The formed 5-, 6-, or 7-membered ring may be a saturated or unsaturated ring. In addition, the 5-, 6-, or 7-membered ring may be constituted only with carbon atoms or may form a heterocycle having at least one atom selected from a nitrogen atom, an oxygen atom, or/and a sulfur atom.

In a preferred embodiment of the compound represented by General Formula (7), $R^4$ to $R^9$ each independently represent the group described as the preferred embodiment of $R^4$ to $R^9$; $R^{10}$ represents the group described as the preferred embodiment of $R^{10}$; Ma is Zn, Cu, Co, or V=O; $X^1$ is water or a carboxylic acid compound; $X^2$ is a hydroxyl group or a carboxylic acid group; and $X^1$ and $X^2$ may be bonded to each other to form a 5- or 6-membered ring.

Dipyrromethene Metal Complex Compound Represented by General Formula (8)

One of suitable embodiments of the pigment structure in the pigment multimer (A) is a pigment structure derived from a dipyrromethene metal complex compound represented by the following General Formula (8). In the present invention, the following compound forms a cationic structure, and for example, Ma in General Formula (8) can form a cationic structure.

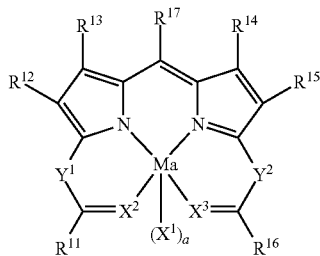

(8)

(In General Formula (8), $R^{11}$ and $R^{16}$ each independently represent an alkyl group, an alkenyl group, an aryl group, a heterocyclic group, an alkoxy group, an aryloxy group, an alkylamino group, an arylamino group, or a heterocyclic amino group. $R^{12}$ to $R^{15}$ each independently represent a hydrogen atom or a substituent. $R^{17}$ represents a hydrogen atom, a halogen atom, an alkyl group, an aryl group, or a heterocyclic group. Ma represents a metal atom or a metal compound. $X^2$ and $X^3$ each independently represent NR (in which R represents a hydrogen atom, an alkyl group, an alkenyl group, an aryl group, a heterocyclic group, an acyl group, an alkylsulfonyl group, or an arylsulfenyl group), a nitrogen atom, an oxygen atom, or a sulfur atom. $Y^1$ and $Y^2$ each independently represent $NR^c$ (in which $R^c$ represents a hydrogen atom, an alkyl group, an alkenyl group, an aryl group, a heterocyclic group, an acyl group, an alkylsulfonyl group, or an arylsulfonyl group), a nitrogen atom, or a carbon atom. $R^{11}$ and $Y^1$ may be bonded to each other to form a 5-, 6-, or 7-membered ring, and $R^{16}$ and $Y^2$ may be bonded to each other to term a 5-, 6-, or 7-membered ring. $X^1$ represents a group which can be bonded to Ma, and a represents 0, 1, or 2.)

Incidentally, the dipyrromethene metal complex compound represented by General Formula (8) includes a tautomer.

The site at which the dipyrromethene metal complex compound represented by General Formula (8) is introduced into structural units represented by General Formula (A) to General Formula (C), or a multimer represented by General Formula (D), each of which will be described later, is not particularly limited as long as the effects of the present invention are not diminished. However, the site is preferably at least one of $R^{11}$ to $R^{17}$, $X^1$, $Y^1$ to $Y^2$. Among these, in view of synthesis suitability, it is preferable that the compound is introduced at one of $R^{11}$ to $R^{16}$ and $X^1$. In a more preferred embodiment, the compound is inserted at one of $R^{11}$, $R^{13}$, $R^{14}$, and $R^{16}$. In a still more preferred embodiment, the compound is inserted at one of $R^{11}$ and $R^{16}$.

In the case where the pigment multimer (A) has an alkali-soluble group, if a pigment monomer or a structural unit having the alkali-soluble group is used, as a method for introducing the alkali-soluble group, it is possible to use a method for introducing the alkali-soluble group into one, two, or more substituents out of $R^{11}$ to $R^{17}$, $X^1$, $Y^1$ to $Y^2$ in General Formula (8). Among these substituents, one of $R^{11}$ to $R^{16}$ and $X^1$ is preferable, one of $R^{11}$, $R^{13}$, $R^{14}$, and $R^{16}$ is more preferable, and one of $R^{11}$ and $R^{16}$ is still more preferable.

The dipyrromethene metal complex compound represented by General Formula (8) may have a functional group other than the alkali-soluble group as long as the effects of the present invention are not diminished.

In General Formula (8), $R^{12}$ to $R^{15}$ have the same definitions as $R^5$ to $R^8$ in General Formula (M), and preferred embodiments thereof are also the same. $R^{17}$ has the same definition as $R^{10}$ in General Formula (M), and preferred embodiments thereof are also the same. Ma has the same definition as Ma in General Formula (7), and preferred ranges thereof are also the same.

More specifically, among $R^{12}$ to $R^{15}$ in General Formula (8), as $R^{12}$ and $R^{15}$, an alkoxycarbonyl group, an aryloxycarbonyl group, a carbamoyl group, an alkylsulfonyl group, an arylsulfonyl group, a nitrile group, an imide group, and a carbamoylsulfonyl group are preferable, an alkoxycarbonyl group, an aryloxycarbonyl group, a carbamoyl group, an alkylsulfonyl group, a nitrile group, an imide group, and a carbamoylsulfonyl group are more preferable, an alkoxycarbonyl group, an aryloxycarbonyl group, a carbamoyl group, a nitrile group, an imide group, and a carbamoylsulfonyl group are still more preferable, and an alkoxycarbonyl group, an aryloxycarbonyl group, and a carbamoyl group are particularly preferable.

As $R^{13}$ and $R^{14}$, a substituted or unsubstituted alkyl group, a substituted or unsubstituted aryl group, and a substituted or unsubstituted heterocyclic group are preferable, and a substituted or unsubstituted alkyl group and a substituted or unsubstituted aryl group are more preferable. Specific examples of the more preferable alkyl group, aryl group, and heterocyclic group include the same specific examples as listed for $R^6$ and $R^7$ of General Formula (M).

In General Formula (8), $R^{11}$ and $R^{16}$ each represent an alkyl group (a linear, branched, or cyclic alkyl group preferably having 1 to 36 carbon atoms, and more preferably having 1 to 12 carbon atoms, for example, a methyl group, an ethyl group, a propyl group, an isopropyl group, a butyl group, an isobutyl group, a tert-butyl group, a hexyl group, a 2-ethylhexyl group, a dodecyl group, a cyclopropyl group, a cyclopentyl group, a cyclohexyl group, and a 1-adamantyl group), an alkenyl group (an alkenyl group preferably having 2 to 24 carbon atoms, and more preferably having 2 to 12 carbon atoms, for example, a vinyl group, an allyl group, and a 3-buten-1-yl group), an aryl group (an aryl group preferably having 6 to 36 carbon atoms, and more preferably having 6 to 18 carbon atoms, for example, a phenyl group and a naphthyl group), a heterocyclic group (a heterocyclic group preferably having 1 to 24 carbon atoms, and more preferably having 1 to 12 carbon atoms, for example, a 2-thienyl group, a 4-pyridyl group, a 2-furyl group, a 2-pyrimidinyl group, a 2-pyridyl group, a 2-benzothiazolyl group, a 1-imidazolyl group, a 1-pyrazolyl group, and a benzotriazol-1-yl group), an alkoxy group (an alkoxy group preferably having 1 to 36 carbon atoms, and more preferably having 1 to 18 carbon atoms, for example, a methoxy group, an ethoxy group, a propyloxy group, a butoxy group, a hexyloxy group, a 2-ethylhexyloxy group, a dodecyloxy group, and a cyclohexyloxy group), an aryloxy group (an aryloxy group preferably having 6 to 24 carbon atoms, and more preferably having 1 to 18 carbon atoms, for example, a phenoxy group and a naplathyloxy group), an alkylamino group (an alkylamino group preferably having 1 to 36 carbon atoms, and more preferably having 1 to 18 carbon atoms, for example, a methylamino group, an ethylamino group, a propylamino group, a butylamino group, a hexylamino group, a 2-ethylhexylamino group, an isopropylamino group, a tert-butylamino group, a tert-octylamino group, a cyclohexylamino group, an N,N-diethylamino group, an N,N-dipropylamino group, an N,N-dibutylamino group, and an N-methyl-N-ethylamino group), an arylamino group (an arylamino group preferably having 6 to 36 carbon atoms, and more preferably having 6 to 18 carbon atoms, for example, a phenylamino group, a naphthylamino group, an N,N-diphenylamino group, and an N-ethyl-N-phenylamino group), and a heterocyclic amino group (a heterocyclic amino group preferably having 1 to 24 carbon atoms, and more preferably having 1 to 12 carbon atoms, for example, a 2-aminopyrrole group, 3-aminopyrazole, a 2-aminopyridine group, and a 3-aminopyridine group).

Among the above groups, as $R^{11}$ and $R^{16}$, an alkyl group, an alkenyl group, an aryl group, a heterocyclic group, an alkylamino group, an arylamino group, and a heterocyclic amino group are preferable, an alkyl group, an alkenyl group, an aryl group, and a heterocyclic group are more preferable, an alkyl group, an alkenyl group, and an aryl group are still more preferable, and an alkyl group is particularly preferable.

In General Formula (8), in the case where the alkyl group, the alkenyl group, the aryl group, the heterocyclic group, the alkoxy group, the aryloxy group, the alkylamino group, the arylamino group, or the heterocyclic amino group represented by $R^{11}$ and $R^{16}$ is a group which can be further substituted, the group may be substituted with the substituents described in the section of the substituent group A which will be described later. In the case where the group is substituted with two or more substituents, these substituents may be the same as or different from each other.

In General Formula (8), $X^2$ and $X^3$ each independently represent NR, a nitrogen atom, an oxygen atom, or a sulfur atom. Herein, R represents a hydrogen atom, an alkyl group (a linear, branched, or cyclic alkyl group preferably having 1 to 36 carbon atoms, and more preferably having 1 to 12 carbon atoms, for example, a methyl group, an ethyl group, a propyl group, an isopropyl group, a butyl group, an isobutyl group, a tert-butyl group, a hexyl group, a 2-ethylhexyl group, a dodecyl group, a cyclopropyl group, a cyclopentyl group, a cyclohexyl group, and a 1-adamantyl group), an alkenyl group (an alkenyl group preferably having 2 to 24 carbon atoms, and more preferably having 2 to 12 carbon atoms, for example, a vinyl group, an allyl group, and a 3-buten-1-yl group), an aryl group (an aryl group preferably having 6 to 36 carbon atoms, and more preferably having 6 to 18 carbon atoms, for example, a phenyl group and a naphthyl group), a heterocyclic group (a heterocyclic group preferably having 1 to 24 carbon atoms, and more preferably having 1 to 12 carbon atoms, for example, a 2-thienyl group, a 4-pyridyl group, a 2-furyl group, a 2-pyrimidinyl group, a 1-pyridyl group, a 2-benzothiazolyl group, a 1-imidazolyl group, a 1-pyrazolyl group, and a benzotriazol-1-yl group), an acyl group (an acyl group preferably having 1 to 24 carbon atoms, and more preferably having 2 to 18 carbon atoms, for example, an acetyl group, a pivaloyl group, a 2-ethylhexyl group, a benzoyl group, and a cyclohexanoyl group), an alkylsulfonyl group (an alkylsulfonyl group preferably having 1 to 24 carbon atoms, and more preferably having 1 to 18 carbon atoms, for example, a methylsulfonyl group, an ethylsulfonyl group, an isopropylsulfonyl group, and a cyclohexylsulfonyl group), and an arylsulfonyl group (an arylsulfonyl group preferably having 6 to 24 carbon atoms, and more preferably having 6 to 18 carbon atoms, for example, a phenylsulfonyl group and a naphthylsulfonyl group).

In General Formula (8), $Y^1$ and $Y^2$ each independently represent $NR^c$, a nitrogen atom, or a carbon atom. $R^c$ has the same definition as R of $X^2$ and $X^3$, and the preferred embodiments thereof are also the same.

In General Formula (8), $R^{11}$ and $Y^1$ may be bonded to each other to form a 5-membered ring (for example, a cyclopentane ring, a pyrrolidine ring, a tetrahydrofuran ring, a dioxolane ring, a tetrahydrothiophene ring, a pyrrole ring, a furan ring, a thiophene ring, an indole ring, a benzofuran ring, and a benzothiophene ring), a 6-membered ring (for example, a cyclohexane ring, a piperidine ring, a piperazine ring, a morpholine ring, a tetrahydropyran ring, a dioxane ring, a pentamethylene sulfide ring, a dithiane ring, a benzene ring, a piperidine ring, a piperazine ring, a pyridazine ring, a quinoline ring, and a quinazoline ring), or a 7-membered ring (for example, a cycloheptane ring and a hexamethyleneimine ring) together with a carbon atom.

In General Formula (8), $R^{16}$ and $Y^2$ may be bonded to each other to form a 5-membered ring (for example, a cyclopentane ring, a pyrrolidine ring, a tetrahydrofuran ring, a dioxolane ring, a tetrahydrothiophene ring, a pyrrole ring, a furan ring, a thiophene ring, an indole ring, a benzofuran ring, and a benzothiophene ring), a 6-membered ring (for example, a cyclohexane ring, a piperidine ring, a piperazine ring, a morpholine ring, a tetrahydropyran ring, a dioxane ring, a pentamethylene sulfide ring, a dithiane ring, a benzene ring, a piperidine ring, a piperazine ring, a pyridazine ring, a quinoline ring, and a quinazoline ring), or a 7-membered ring (for example, a cycloheptane ring and a hexamethyleneimine ring) together with a carbon atom.

In General Formula (8), in the case where the 5-, and 7-membered rings formed by mutual bonding of $R^{11}$ and $Y^1$ as well as $R^{16}$ and $Y^2$ are substitutable rings, the rings may be substituted with the substituents described in the section of the substituent group A which will be described later. In the case where the rings are substituted with two or more substituents, these substituents may be the same as or different from each other.

In General Formula (8), $R^{11}$ and $R^{16}$ are each independently a monovalent substituent having an -Es' value, which is a steric parameter, is preferably 1.5 or more, more preferably 2.0 or more, still more preferably 3.5 or more, and particularly preferably 5.0 or more.

Herein, the -Es' value as a steric parameter is a parameter which represents steric bulkiness of a substituent. As the value, the -Es' value disclosed in the document (J. A. Macphee, et al, Tetrahedron, Vol. 34, pp 3553-3562, and Chemistry Special Edition 107, Structure-activity Correlation and Drug Design, edited by Toshio Fujita, published on Feb. 20, 1986 (Kagaku-Doujin Publishing Company, Inc.)) is used.

In General Formula (8), $X^1$ represents a group which can be bonded to Ma. Specific examples thereof include the same group as represented by $X^1$ in General Formula (7), and the preferred embodiments are also the same.

a represents 0, 1, or 2.

With respect to a preferred embodiment of the compound represented by General Formula (8), $R^{12}$ to $R^{15}$ are each independently one in the preferred embodiment cited in the description of $R^5$ to $R^8$ in General Formula (M), $R^{17}$ is one in the preferred embodiment cited in the description of $R^{10}$ in General Formula (M), Ma is Zn, Cu, Co, or V=O, $X^2$ is NR (in which R represents a hydrogen atom or an alkyl group), a nitrogen atom, or an oxygen atom, $X^3$ is NR (in which R represents a hydrogen atom or an alkyl group) or an oxygen atom, $Y^1$ is $NR^c$ (in which $R^c$ represents a hydrogen atom or an alkyl group), a nitrogen atom, or a carbon atom, $Y^2$ is a nitrogen atom or a carbon atom, $R^{11}$ and $R^{16}$ are each independently an alkyl group, an aryl group, a heterocyclic group, an alkoxy group, or an alkylamino group, $X^1$ is a group bonded via an oxygen atom, and a is 0 or 1. $R^{11}$ and $Y^1$ may be bonded to each other to form a 5- or 6-membered ring, or $R^{16}$ and $Y^2$ may be bonded to each other to form a 5- or 6-membered ring.

With respect to a more preferred embodiment of the compound represented by General Formula (8), $R^{12}$ to $R^{15}$ are each independently one in the preferred embodiment cited in the description of $R^5$ to $R^8$ in the compound represented by General Formula (M), $R^{17}$ is one in the preferred embodiment cited in the description of $R^{10}$ in General Formula (M), Ma is Zn, $X^2$ and $X^3$ are each an oxygen atom, $Y^1$ is NH, $Y^2$ is a nitrogen atom, $R^{11}$ and $R^{16}$ are each independently an alkyl group, an aryl group, a heterocyclic group, an alkoxy group, or an alkylamino group, $X^1$ is a group bonded via an oxygen atom, and a is 0 or 1. $R^{11}$ and $Y^1$ may be bonded to each other to form a 5- or 6-membered ring, or $R^{16}$ and $Y^2$ may be bonded to each other to form a 5- or 6-membered ring.

From the viewpoint of coloring ability, the molar absorption coefficient of the dipyrromethene metal complex compound represented by General Formula (7) and General Formula (8) is preferably as high as possible. Farther, from the viewpoint of improving color purity, the maximum absorption wavelength λmax is preferably 520 nm to 580 nm, and more preferably 530 nm to 570 nm. If the value is within this range, it is possible to manufacture a color filter having excellent color reproducibility by using the coloring composition of the present invention.

Furthermore, an absorbance at the maximum absorption wavelength (λmax) of the pigment multimer (A) having a pigment structure derived from a dipyrromethene pigment is preferably 1,000 times or more, more preferably 10,000 times or more, and still more preferably 100,000 times or more the absorbance at 450 nm. If the ratio is within this range, particularly in the case where a blue color filter is manufactured using the coloring composition of the present invention, a color filter having a higher transmittance can be formed. Incidentally, the maximum absorption wavelength and the molar absorption coefficient are measured by a spectrophotometer Cary 5 (manufactured by Varian Medical Systems, Inc.).

From the viewpoint of solubility, it is preferable that the melting points of the dipyrromethene metal complex compounds represented by General Formula (7) and General Formula (8) are not too high.

The dipyrromethene metal complex compounds represented by General Formula (7) and General Formula (8) can be synthesized by the method described in U.S. Pat. No. 4,774,339A, U.S. Pat. No. 5,433,896A, JP2001-240761A, JP2002-155052A, JP3614586B, Aust. J. Chem., 1965, 11, 1835-1845, J. H. Boger, et al., Heteroatom Chemistry, Vol. 1, No. 5,389 (1990), and the like. Specifically, the method described in paragraphs "0131" to "0157" of JP2008-292970A can be applied.

Specific examples of the dipyrromethene pigment are shown below, but the present invention is not limited thereto.

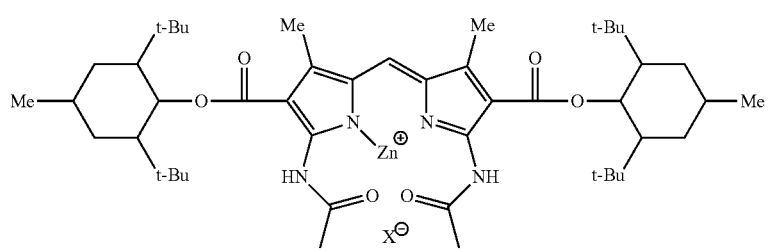

(PM-1)

(PM-2)
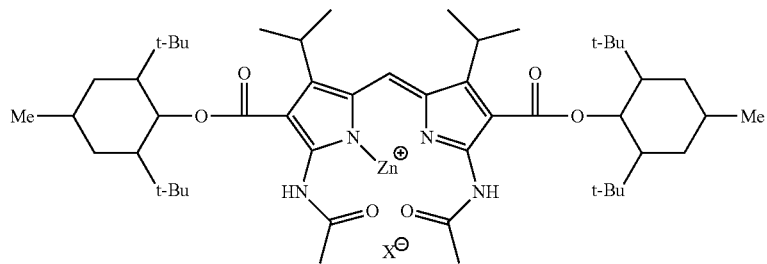
(PM-3)
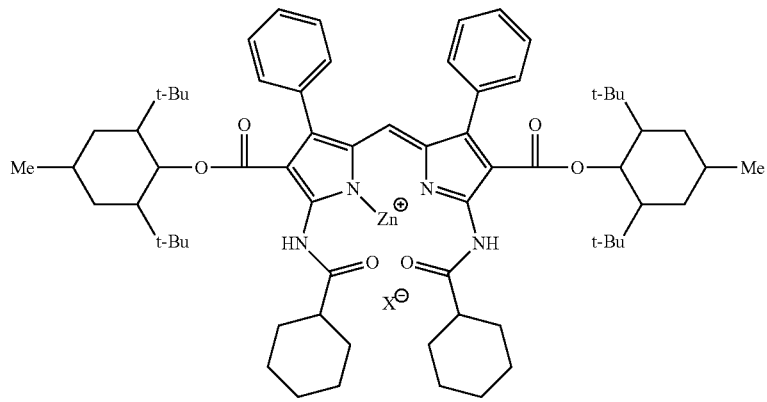
(PM-4)
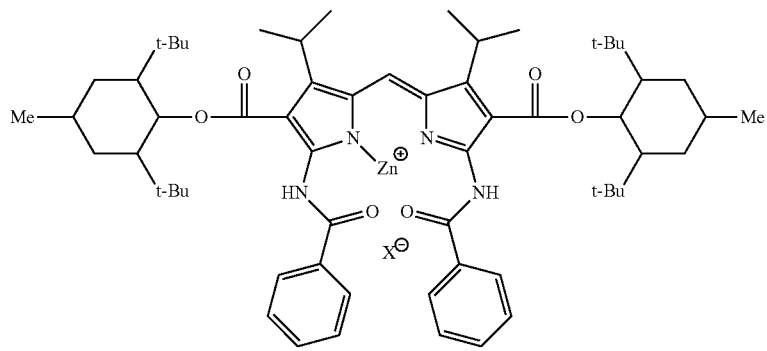
(PM-5)
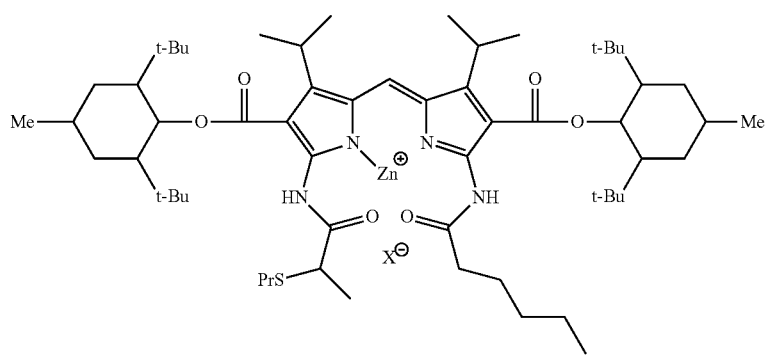

-continued

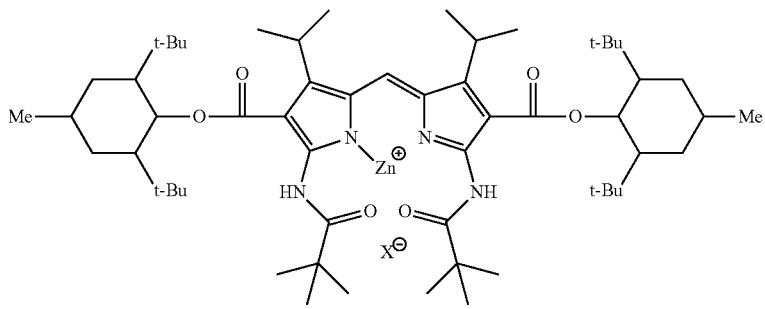
(PM-6)

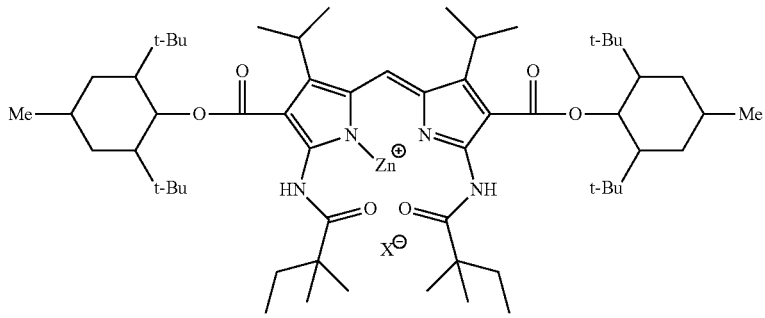
(PM-7)

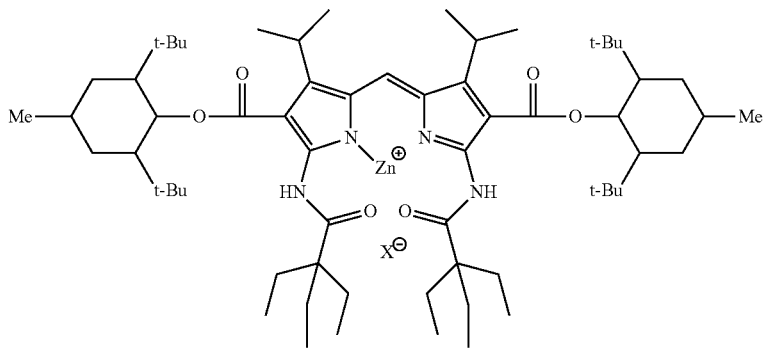
(PM-8)

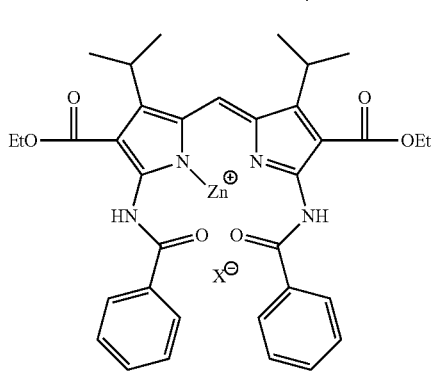
(PM-9)

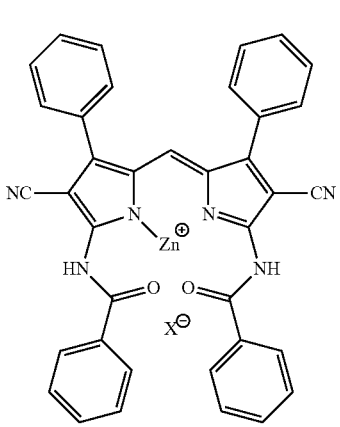
(PM-10)

Among the specific examples, (PM-8) and (PM-10) are particularly preferable from the viewpoints of color characteristics and heat resistance.

<<<Carbonium Pigment>>>

Among the carbonium pigments, a triarylmethane pigment and a xanthene pigment are preferable.

Triarylmethane Pigment

One of the embodiments of the pigment multimer according to the present invention is one having a partial structure derived from a triarylmethane pigment (triarylmethane compound). Examples of the pigment multimer (A) include a pigment multimer which has a partial structure derived from a compound (triarylmethane compound) represented by the following General Formula (TP) as a partial structure of a pigment moiety. The triarylmethane compounds in the present invention collectively refer to compounds having a pigment moiety containing a triarylmethane skeleton in a molecule thereof.

Genreal Formula (TP)

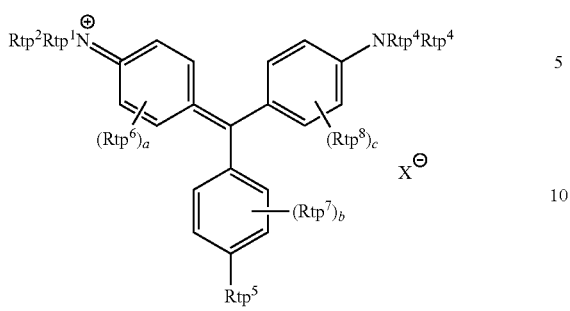

(In General Formula (TP), $Rtp^1$ to $Rtp^4$ each independently represent a hydrogen atom, an alkyl group, or an aryl group. $Rtp^5$ represents a hydrogen atom, an alkyl group, an aryl group, or $NRtp^9Rtp^{10}$ (in which $Rtp^9$ and $Rtp^{10}$ represent a hydrogen atom, an alkyl group, or an aryl group). $Rtp^6$, $Rtp^7$, and $Rtp^8$ represent substituents a, b, and c represent an integer of 0 to 4. In the case where a, b, and c are 2 or more, $Rtp^6$, $Rtp^7$, and $Rtp^8$ may be linked to each other to form a ring. $X^-$ represents a non-nucleophilic counter anion.)

$Rtp^1$ to $Rtp^6$ are preferably a hydrogen atom, a linear or branched alkyl group having 1 to 5 carbon atoms, or a phenyl group. $Rtp^5$ is preferably a hydrogen atom or $NRtp^9Rtp^{10}$, and particularly preferably $NRtp^9Rtp^{10}$. $Rtp^9$ and $Rtp^{10}$ are preferably a hydrogen atom, a linear or branched alkyl group having 1 to 5 carbon atoms, or a phenyl group. As the substituents represented by $Rtp^6$, $Rtp^7$, and $Rtp^8$, the substituents exemplified in the section of the substituent group A which will be described later can be used. In particular, a linear or branched alkyl group having 1 to 5 carbon atoms, an alkenyl group having 1 to 5 carbon atoms, an aryl group having 6 to 15 carbon atoms, a carboxyl group, or a sulfo group is preferable, and a linear or branched alkyl group having 1 to 5 carbon atoms, an alkenyl group having 1 to 5 carbon atoms, a phenyl group, or a carboxyl group is more preferable. $Rtp^6$ and $Rtp^8$ are particularly preferably an alkyl group having 1 to 5 carbon atoms, and $Rtp^7$ is preferably an alkenyl group (particularly preferably a phenyl group formed by linking two adjacent alkenyl groups to each other), a phenyl group, or a carboxyl group.

a, b, or c each independently represents an integer of 0 to 4. In particular, a and b are each preferably 0 or 1, and c is preferably an integer of 0 to 2.

Specific examples of the compounds represented by General Formula (TP) are shown below, but the present invention is not limited thereto. $X^-$ represents a non-nucleophilic counter anion (which applies to the description below unless otherwise specified).

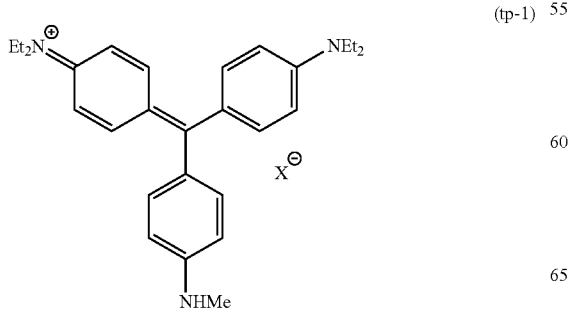
(tp-1)

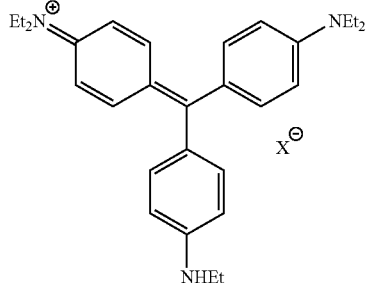
(tp-2)

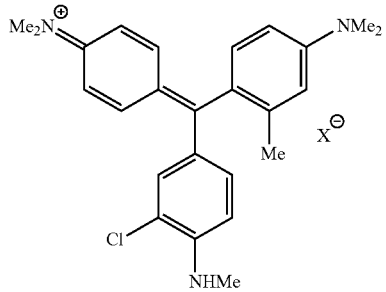
(tp-3)

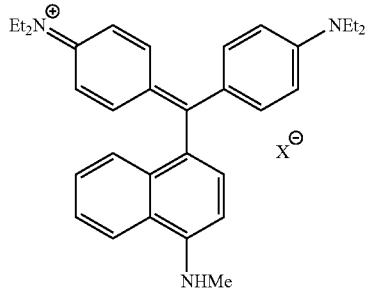
(tp-4)

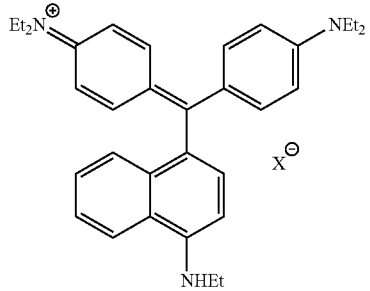
(tp-5)

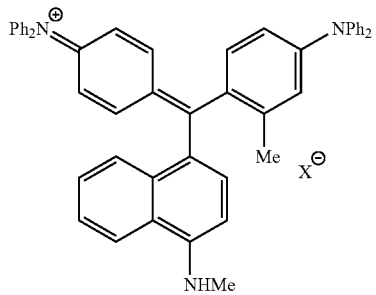
(tp-6)

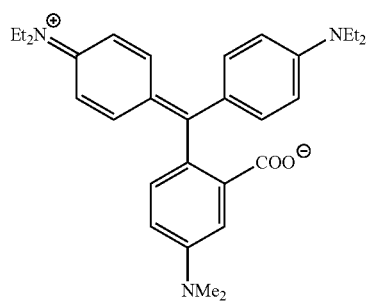
(tp-7)
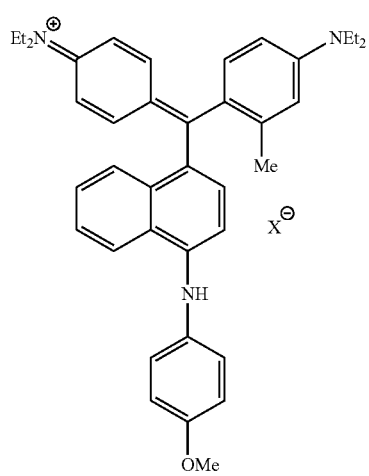
(tp-8)
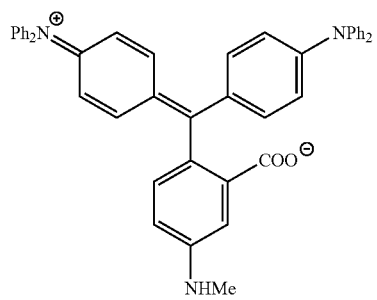
(tp-9)
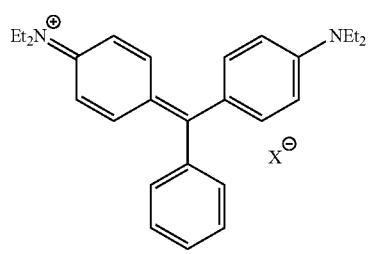
(tp-10)
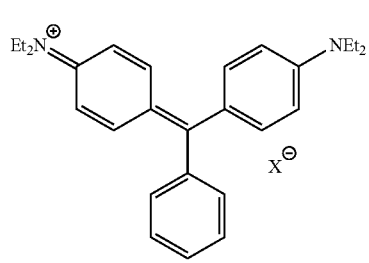
(tp-11)
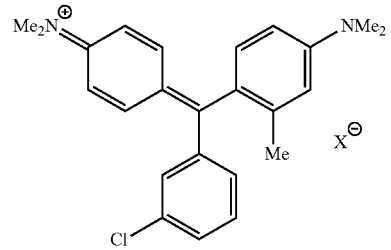
(tp-12)
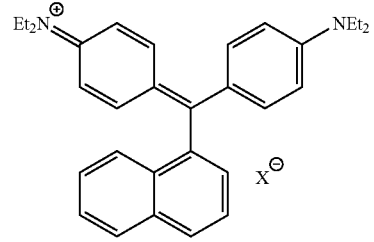
(tp-13)
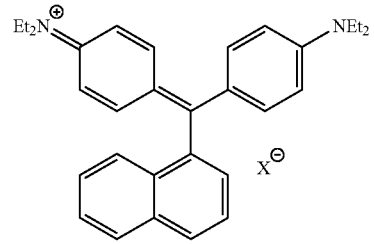
(tp-14)
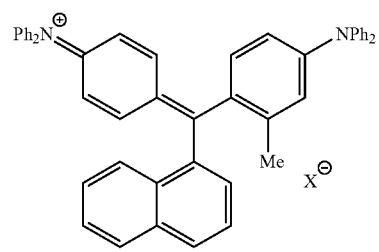
(tp-15)
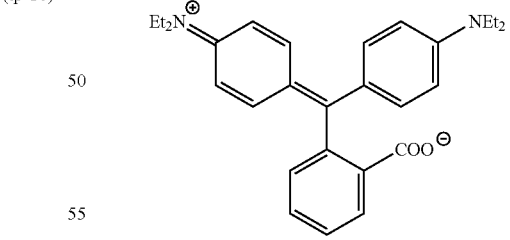
(tp-16)
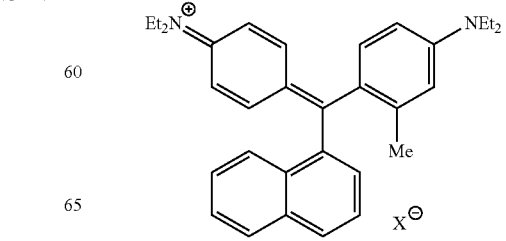
(tp-17)

-continued

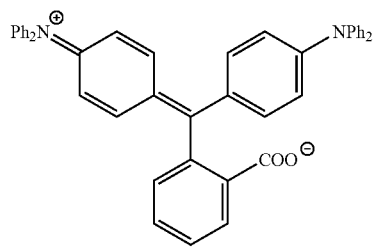

(tp-18)

Among the specific examples, (tp-4), (tp-5), (tp-6), and (tp-8) are particularly preferable from the viewpoints of color characteristics and heat resistance.

Xanthene Pigment

A preferred embodiment of the pigment multimer in the present invention is one having a partial structure derived from a xanthene pigment (xanthene compound). Examples of the pigment multimer (A) include a pigment multimer which has a partial structure derived from a xanthene compound represented by the following General Formula (J) as a partial structure of a pigment moiety.

General Formula (J)

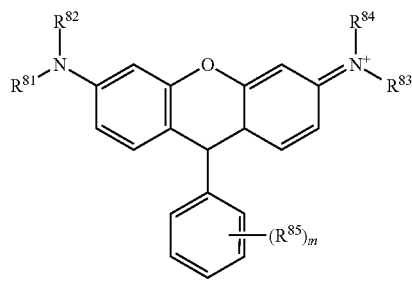

(In General Formula (J), $R^{81}$, $R^{82}$, $R^{83}$, and $R^{84}$ each independently represent a hydrogen atom, or a monovalent substituent. $R^{85}$'s each independently represent a monovalent substituent, and m represents an integer of 0 to 5. $X^-$ represents a non-nucleophilic counter anion.)

The substituents which $R^{81}$ to $R^{84}$ and $R^{85}$ in General Formula (J) may contain have the same definitions as the substituents exemplified in the section of the substituent group A which will be described later.

In General Formula (J), $R^{81}$ and $R^{82}$, $R^{83}$ and $R^{84}$, and $R^{85}$'s in a case where m is 2 or more may be each independently bonded to each other to form a 5-, 6-, or 7-membered saturated ring or a 5-, 6-, or 7-membered unsaturated ring. In the case where the formed 5-, 6-, or 7-membered ring is a group which can be further substituted, the ring may be substituted with the substituents described for $R^{81}$ to $R^{85}$. In the case where the ring is substituted with two or more substituents, these substituents may be the same as or different from each other.

In General Formula (J), in the case where $R^{81}$ and $R^{82}$, $R^{83}$ and $R^{84}$, and $R^{85}$'s in a case where m is 2 or more are each independently bonded to each other to form 5-, 6-, and 7-membered saturated rings not having a substituent or form 5-, 6-, and 7-membered unsaturated rings, examples of the 5-, 6-, and 7-membered saturated rings not having a substituent or the 5-, 6-, and 7-membered unsaturated rings include a pyrrole ring, a furan ring, a thiophene ring, a pyrazole ring, an imidazole ring, a triazole ring, an oxazole ring, a thiazole ring, a pyrrolidine ring, a piperidine ring, a cyclopentene ring, a cyclohexene ring, a benzene ring, a pyridine ring, a pyrazine ring, and a pyridazine ring, and preferably a benzene ring and a pyridine ring.

$R^{82}$ and $R^{83}$ are particularly preferably a hydrogen atom or a substituted or unsubstituted alkyl group, and $R^{81}$ and $R^{84}$ are particularly preferably a substituted or unsubstituted alkyl group or phenyl group. Further, $R^{85}$ is preferably a halogen atom, a linear or branched alkyl group having 1 to 5 carbon atoms, a sulfo group, a sulfonamide group, a carboxyl group, or an amide group, and more preferably a sulfo group, a sulfonamide group, a carboxyl group, or an amide group. $R^{85}$ is preferably bonded to an adjacent portion of carbon linked to a xanthene ring. The substituent which the phenyl group represented by $R^{81}$ and $R^{84}$ has is particularly preferably a hydrogen atom, a halogen atom, a linear or branched alkyl group having 1 to 5 carbon atoms, a sulfo group, a sulfonamide group, or a carboxyl group.

The compounds having xanthene skeletons represented by General Formula (J) may be synthesized using methods disclosed in the literature. Specifically, the methods disclosed in Tetrahedron Letters, 2003, vol. 44, No. 23, pp. 4355 to 4360; Tetrahedron Letters, 2005, vol. 61, No. 12, pp. 3097 to 3106; and the like can be applied.

Specific examples of the xanthene compounds are shown below, but the present invention is not limited thereto.

TABLE 1

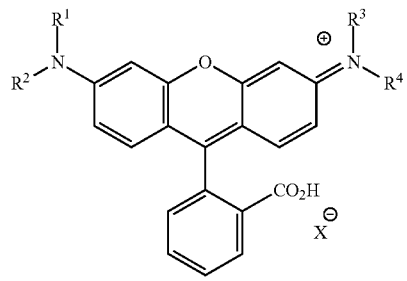

| No. | $R^1$ | $R^2$ | $R^3$ | $R^4$ |
|---|---|---|---|---|
| (XT-1) | Me | Me | Me | Me |
| (XT-2) | Et | Et | Et | Et |
| (XT-3) | n-Pr | n-Pr | n-Pr | n-Pr |
| (XT-4) | i-Pr | i-Pr | i-Pr | i-Pr |
| (XT-5) | n-Bu | n-Bu | n-Bu | n-Bu |
| (XT-6) | sec-Bu | sec-Bu | sec-Bu | sec-Bu |
| (XT-7) | i-Bu | i-Bu | i-Bu | i-Bu |
| (XT-8) | tert-Bu | tert-Bu | tert-Bu | tert-Bu |
| (XT-9) | n-$C_6H_{13}$ | n-$C_6H_{13}$ | n-$C_6H_{13}$ | n-$C_6H_{13}$ |
| (XT-10) | n-$C_{18}H_{37}$ | n-$C_{18}H_{37}$ | n-$C_{18}H_{37}$ | n-$C_{18}H_{37}$ |
| (XT-11) | Me | Et | Me | Et |
| (XT-12) | —$CH_2CH_2OCH_2CH_2$— | | —$CH_2CH_2OCH_2CH_2$— | |
| (XT-13) | —$(CH_2)_5$— | | —$(CH_2)_5$— | |
| (XT-14) | —$(CH_2)_4$— | | —$(CH_2)_4$— | |
| (XT-15) | —$(CH_2)_5$— | | —$(CH_2)_4$— | |
| (XT-16) | $CH_2Ph$ | $CH_2Ph$ | $CH_2Ph$ | $CH_2Ph$ |
| (XT-17) | Et | $CH_2CH_2OMe$ | Et | $CH_2CH_2OMe$ |
| (XT-18) | Me | cyclo-$C_8H_{11}$ | Me | cyclo-$C_8H_{11}$ |
| (XT-19) | $CH_2C{\equiv}CH$ | $CH_2C{\equiv}CH$ | $CH_2C{\equiv}CH$ | $CH_2C{\equiv}CH$ |
| (XT-20) | $CH_2CH{=}CH_2$ | $CH_2CH{=}CH_2$ | $CH_2CH{=}CH_2$ | $CH_2CH{=}CH_2$ |
| (XT-21) | Me | H | Me | H |
| (XT-22) | Et | H | Et | H |
| (XT-23) | n-Pr | H | n-Pr | H |
| (XT-24) | i-Pr | H | i-Pr | H |
| (XT-25) | n-Bu | H | n-Bu | H |
| (XT-26) | H | H | H | H |
| (XT-27) | i-Bu | H | i-Bu | H |
| (XT-28) | tert-Bu | H | tert-Bu | H |
| (XT-29) | n-$C_6H_{13}$ | H | n-$C_6H_{13}$ | H |
| (XT-30) | n-$C_{18}H_{37}$ | H | n-$C_{18}H_{37}$ | H |

TABLE 1-continued

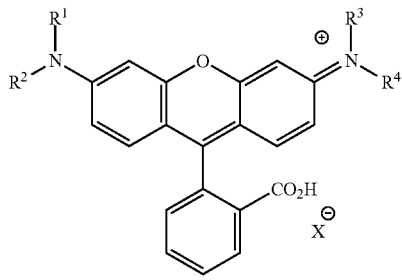

| No. | R¹ | R² | R³ | R⁴ |
|---|---|---|---|---|
| (XT-31) | Ph | H | Ph | H |
| (XT-32) | CH₂Ph | H | CH₂Ph | H |
| (XT-33) | cyclo-C₈H₁₁ | H | cyclo-C₈H₁₁ | H |
| (XT-34) | cyclo-C₅H₉ | H | cyclo-C₅H₉ | H |
| (XT-35) | CH₂C≡CH | H | CH₂C≡CH | H |
| (XT-36) | CH₂CH=CH₂ | H | CH₂CH=CH₂ | H |
| (XT-37) | 2,6-dimethylphenyl | H | 2,6-dimethylphenyl | H |
| (XT-38) | 4-Cl-C₆H₄ | H | 4-Cl-C₆H₄ | H |

TABLE 2

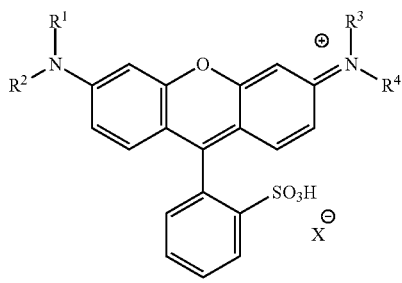

| No. | R¹ | R² | R³ | R⁴ |
|---|---|---|---|---|
| (XT-39) | Me | Me | Me | Me |
| (XT-40) | Et | Et | Et | Et |
| (XT-41) | n-Pr | n-Pr | n-Pr | n-Pr |
| (XT-42) | i-Pr | i-Pr | i-Pr | i-Pr |
| (XT-43) | n-Bu | n-Bu | n-Bu | n-Bu |
| (XT-44) | sec-Bu | sec-Bu | sec-Bu | sec-Bu |
| (XT-45) | i-Bu | i-Bu | i-Bu | i-Bu |
| (XT-46) | tert-Bu | tert-Bu | tert-Bu | tert-Bu |
| (XT-47) | n-C₆H₁₃ | n-C₆H₁₃ | n-C₆H₁₃ | n-C₆H₁₃ |
| (XT-48) | n-C₁₈H₃₇ | n-C₁₈H₃₇ | n-C₁₈H₃₇ | n-C₁₈H₃₇ |
| (XT-49) | Me | Et | Me | Et |
| (XT-50) | —CH₂CH₂OCH₂CH₂— | | —CH₂CH₂OCH₂CH₂— | |
| (XT-51) | —(CH₂)₅— | | —(CH₂)₅— | |
| (XT-52) | —(CH₂)₄— | | —(CH₂)₄— | |
| (XT-53) | —(CH₂)₅— | | —(CH₂)₄— | |
| (XT-54) | CH₂Ph | CH₂Ph | CH₂Ph | CH₂Ph |
| (XT-55) | Et | CH₂CH₂OMe | Et | CH₂CH₂OMe |
| (XT-56) | Me | cyclo-C₈H₁₁ | Me | cyclo-C₈H₁₁ |
| (XT-57) | CH₂C≡CH | CH₂C≡CH | CH₂C≡CH | CH₂C≡CH |
| (XT-58) | CH₂CH=CH₂ | CH₂CH=CH₂ | CH₂CH=CH₂ | CH₂CH=CH₂ |
| (XT-59) | Me | H | Me | H |
| (XT-60) | Et | H | Et | H |
| (XT-61) | n-Pr | H | n-Pr | H |
| (XT-62) | i-Pr | H | i-Pr | H |
| (XT-63) | H | H | H | H |
| (XT-64) | sec-Bu | H | sec-Bu | H |

TABLE 2-continued

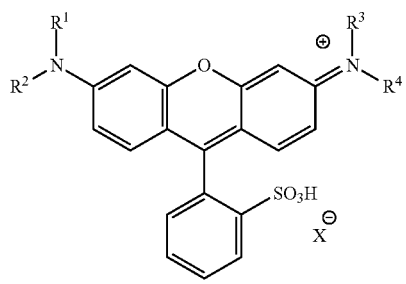

| No. | R¹ | R² | R³ | R⁴ |
|---|---|---|---|---|
| (XT-65) | i-Bu | H | i-Bu | H |
| (XT-66) | tert-Bu | H | tert-Bu | H |
| (XT-67) | n-C₆H₁₃ | H | n-C₆H₁₃ | H |
| (XT-68) | n-C₁₈H₃₇ | H | n-C₁₈H₃₇ | H |
| (XT-69) | Ph | H | Ph | H |
| (XT-70) | CH₂Ph | H | CH₂Ph | H |
| (XT-71) | cyclo-C₈H₁₁ | H | cyclo-C₈H₁₁ | H |
| (XT-72) | cyclo-C₅H₉ | H | cyclo-C₅H₉ | H |
| (XT-73) | CH₂C≡CH | H | CH₂C≡CH | H |
| (XT-74) | CH₂CH=CH₂ | H | CH₂CH=CH₂ | H |
| (XT-75) | 2,6-dimethylphenyl | H | 2,6-dimethylphenyl | H |
| (XT-76) | 4-Cl-C₆H₄ | H | 4-Cl-C₆H₄ | H |

(XT-77)

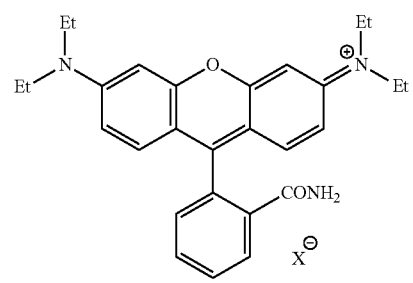

(XT-78)

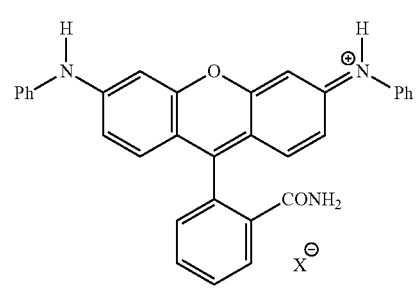

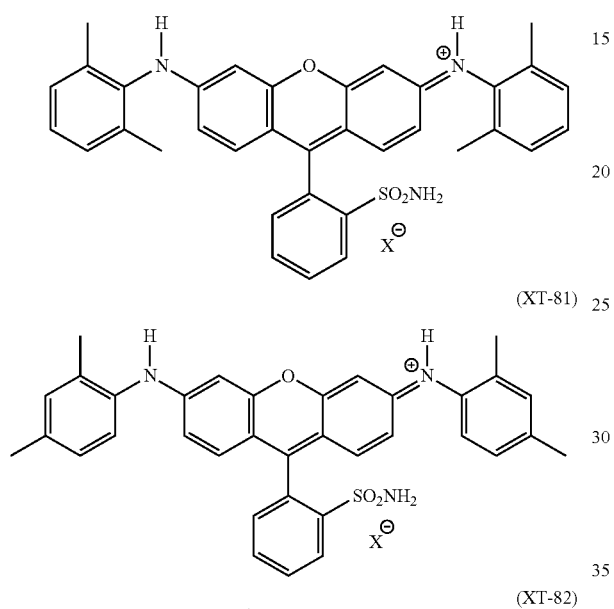

(XT-79)

(XT-80)

(XT-81)

(XT-82)

Cyanine Pigment

One of the embodiments of the pigment multimer according to the present invention is one having a partial structure derived from a cyanine pigment (cyanine compound). Examples of the pigment multimer (A) include a pigment multimer which has a partial structure derived from a compound (cyanine compound) represented by the following General Formula (PM) as a partial structure of a pigment moiety. The cyanine compounds in the present invention collectively refer to compounds having a pigment moiety containing a cyanine skeleton in a molecule thereof.

General Formula (PM)

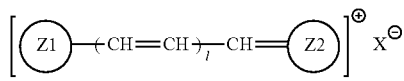

(In General Formula (PM), a ring Z1 and a ring Z2 each independently represent a heterocycle which may have a substituent. 1 represents an integer of 0 to 3, and $X^-$ represents a non-nucleophilic counter anion.)

Examples of the ring Z1 and the ring Z2 each independently include oxazole, benzoxazole, oxazoline, thiazole, thiazoline, benzothiazole, indolenine, benzoindolenine, and 1,3-thiadiazine.

The substituents which the ring Z1 and the ring Z2 may have are the same substituents exemplified in the section of the substituent group A which will be described later. $X^-$ represents a non-nucleophilic counter anion.

The compound represented by General Formula (PM) is preferably a compound represented by the following General Formula (PM-2).

General Formula (PM-2)

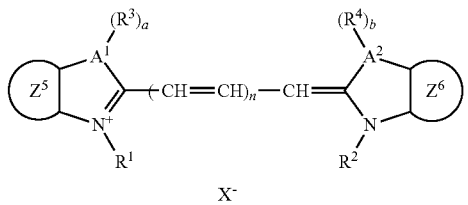

(In General Formula (PM-2), the ring $Z^5$ and the ring $Z^6$ each independently represent a benzene ring which may have a substituent or a naphthalene ring which may have a substituent. $X^-$ represents a non-nucleophilic counter anion.)

n represents an integer of 0 to 3.

$A^1$ and $A^2$ each independently represent an oxygen atom, a sulfur atom, a selenium atom, a carbon atom, or a nitrogen atom.

$R^1$ and $R^2$ each independently represent a monovalent aliphatic hydrocarbon group having 1 to 20 carbon atoms which may have a substituent.

$R^3$ and $R^4$ each independently represent a hydrogen atom, a monovalent aliphatic hydrocarbon group having 1 to 6 carbon atoms, or a divalent aliphatic hydrocarbon group having 2 to 6 carbon atoms, which is formed when one $R^3$ and one $R^4$ are combined with each other.

a and b each independently represent an integer of 0 to 2.

Specific examples of the cyanine compound are shown below, but the present invention is not limited thereto.

(pm-1)

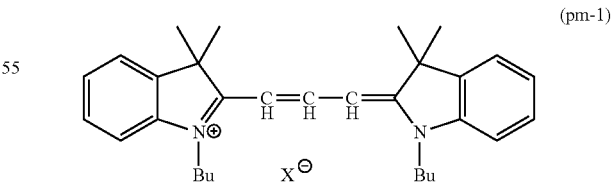

(pm-2)

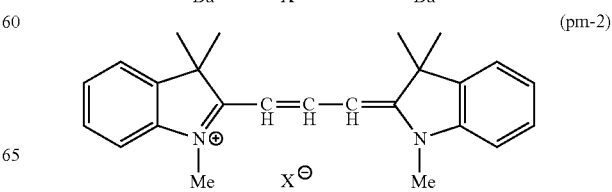

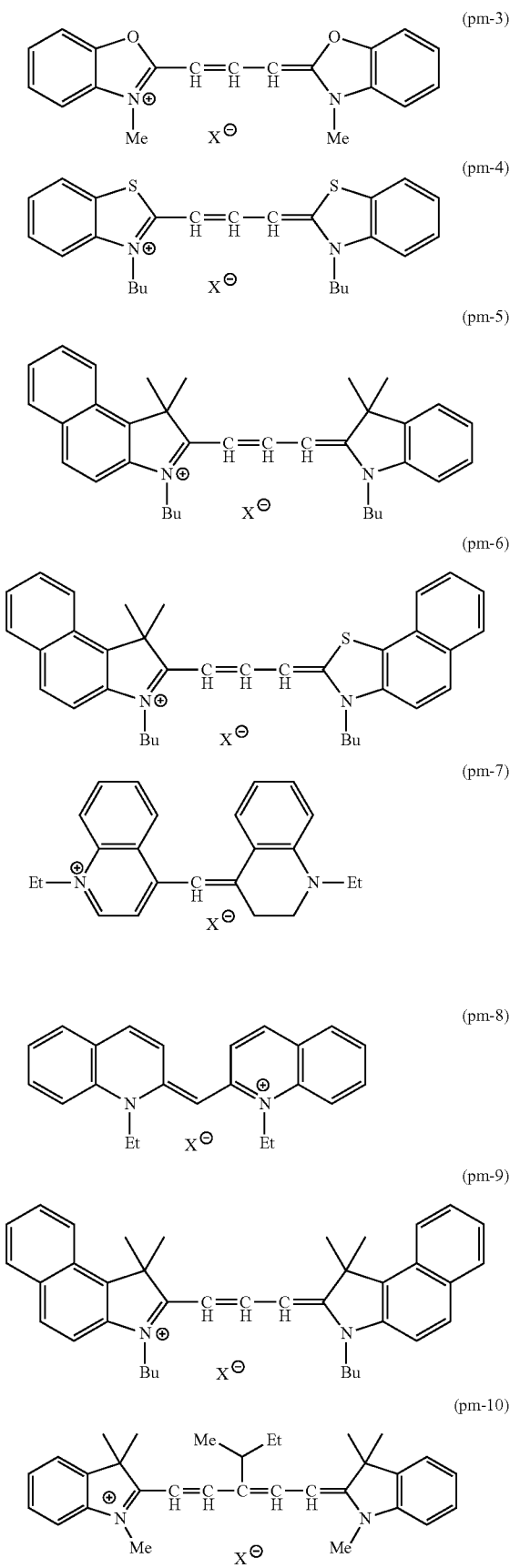
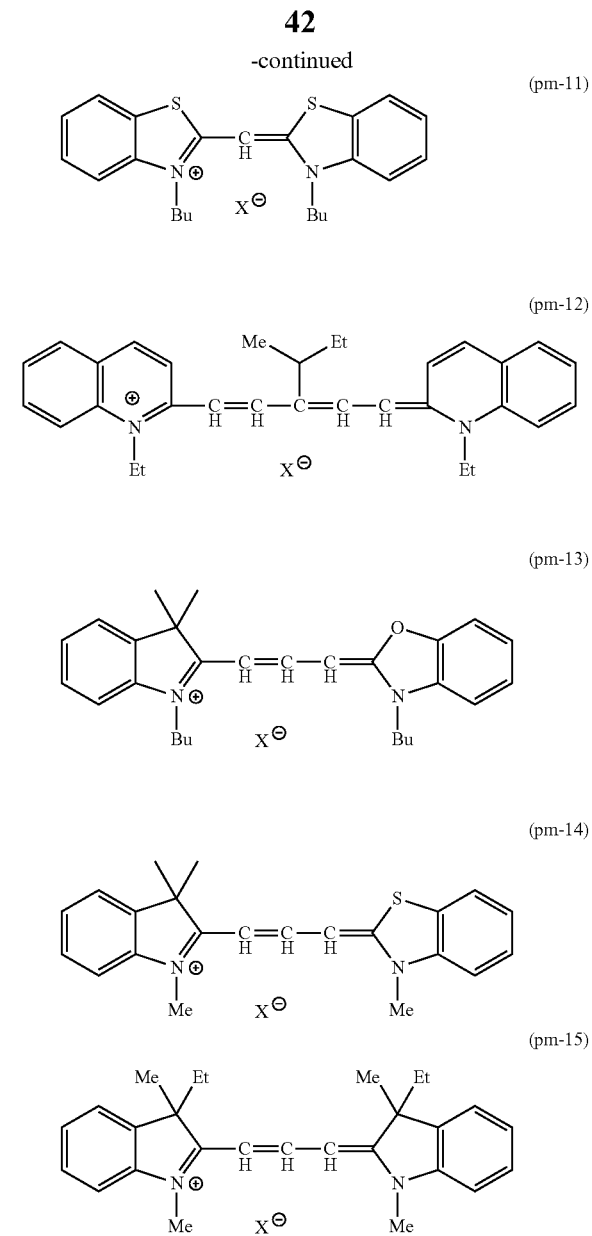

Among the specific examples, the structures represented by (pm-1) to (pm-6) and (pm-9) are preferable, and among these, the pigment structures represented by (pm-1) and (pm-2) are particularly preferable, from the viewpoint of color characteristics and heat resistance.

Subphthalocyanine Pigment

One of the embodiments of the pigment multimer according to the present invention is one having a partial structure derived from a subphthalocyanine pigment. Examples of the pigment multimer (A) include a pigment multimer which has a partial structure derived from a subphthalocyanine pigment represented by the following General Formula (SP) as a partial structure of a pigment moiety. The subphthalocyanine pigments in the present invention collectively refer to compounds having a pigment moiety including a subphthalocyanine skeleton in a molecule thereof. In the present invention, the following compound forms a cationic structure, but, for example, a boron atom in General Formula (SP) can form a cationic structure.

General Formula (SP)

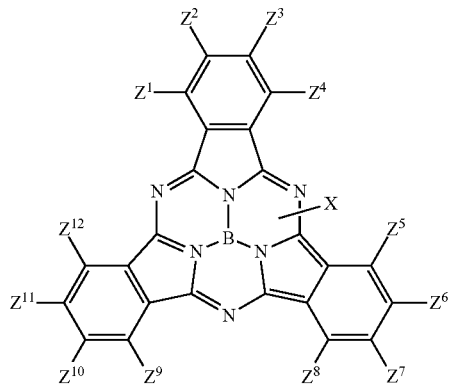

(In General Formula (SP), $Z^1$ to $Z^{12}$ each independently represent a hydrogen atom, an alkyl group, an aryl group, a hydroxyl group, a mercapto group, an amino group, an alkoxy group, an aryloxy group, or a thioether group. X represents a non-nucleophilic counter anion.)

General Formula (SP) will be described in detail.

The alkyl group which $Z^1$ to $Z^{12}$ in General Formula (SP) may have represents a linear or branched substituted or unsubstituted alkyl group. In particular, $Z^1$ to $Z^{12}$ preferably have 1 to 20 carbon atoms, and more preferably have 1 to 10 carbon atoms. Examples of the substituents which $Z^1$ to $Z^{12}$ have include the substituents exemplified in the section of the substituent group A which will be described later, and among those, a fluorine atom, a hydroxyl group, and a mercapto group are particularly preferable.

Specific examples of the subphthalocyanine pigment are shown below, but the present invention is not limited thereto.

(SP-1)

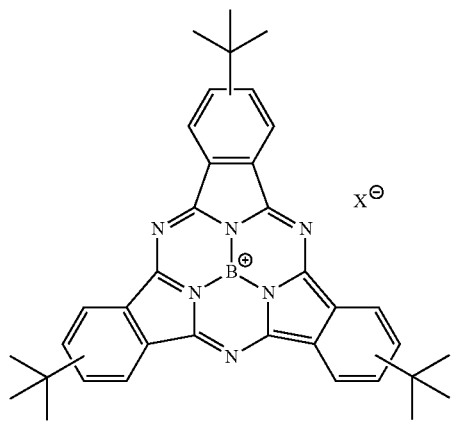

(SP-2)

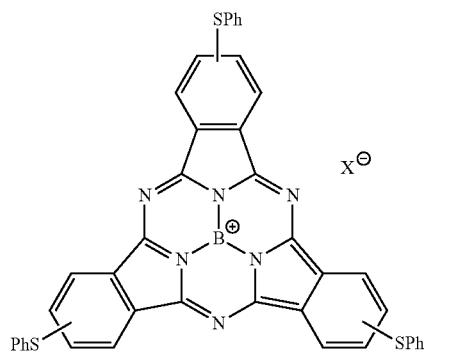

(SP-3)

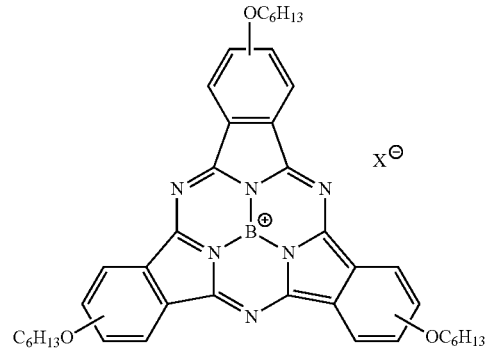

(SP-4)

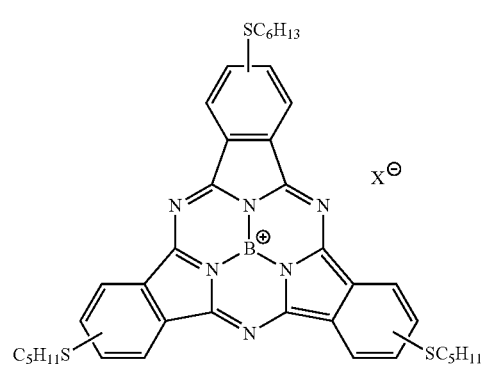

(SP-5)

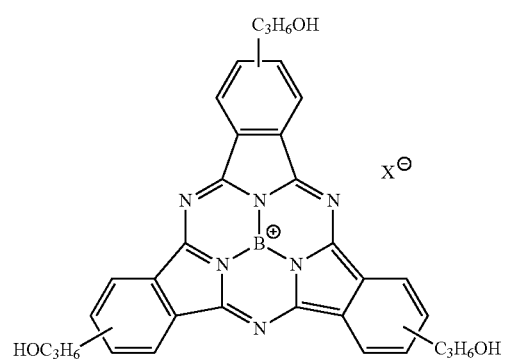

(SP-6)

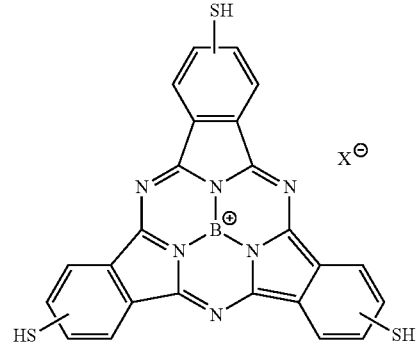

-continued

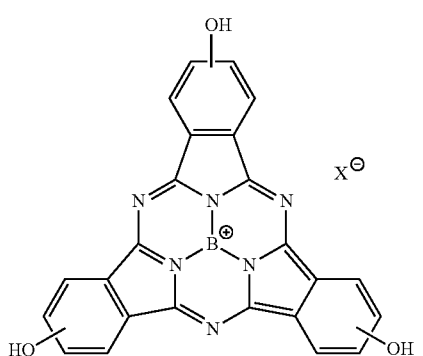
(SP-7)

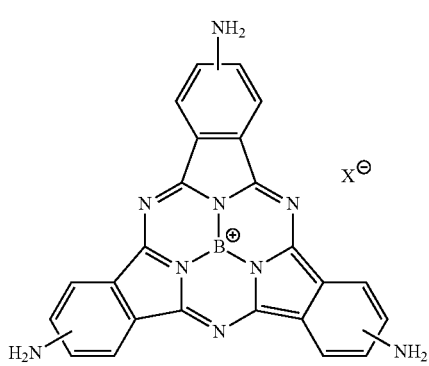
(SP-8)

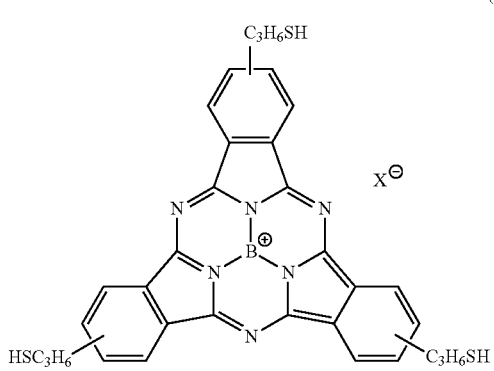
(SP-9)

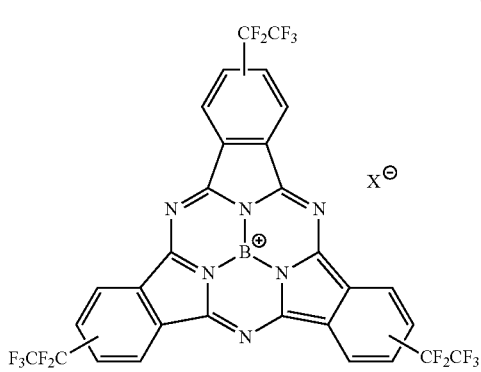
(SO-10)

Among the specific examples, (SP-2), (SP-3), (SP-4), (SP-5), (SP-6), and (SP-7) are particularly preferable from the viewpoint of color characteristics and heat resistance.

For the pigment multimer (A) according to the present invention, a hydrogen atom in the pigment structure may be substituted with a substituent selected from the following substituent group A as long as the gist of the present invention is not impaired.

Substituent Group A:

Examples of the substituent which the pigment multimer may contain include a halogen atom, an alkyl group, a cycloalkyl group, an alkenyl group, a cycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an amino group (including an alkylamino group and an anilino group), an acylamino group, an aminocarbonylamino group, an alkoxycarbonylamino group, an aryloxycarbonylamino group, a sulfamoylamino group, an alkylsulfonylamino or arylsulfonylamino group, a mercapto group, an alkylthio group, an arylthio group, a heterocyclic thio group, a sulfonyl group, a sulfo group, an alkylsulfinyl or arylsulfinyl group, an alkylsulfonyl or arylsulfonyl group, an acyl group, an aryloxycarbonyl group, an alkoxycarbonyl group, a carbamoyl group, an arylazo or heterocyclic azo group, an imide group, a phosphino group, a phosphinyl group, a phosphinyloxy group, a phosphinylamino group, and a silyl group. These will be described in detail below.

Examples of the substituent include a halogen atom (for example, a fluorine atom, a chlorine atom, a bromine atom, and an iodine atom), a linear or branched alkyl group (a linear or branched substituted or unsubstituted alkyl group, and preferably an alkyl group having 1 to 30 carbon atoms, for example, methyl, ethyl, n-propyl, isopropyl, tert-butyl, n-octyl, 2-chloroethyl, 2-cyanoethyl, and 2-ethylhexyl), a cycloalkyl group (preferably a substituted or unsubstituted cycloalkyl group having 3 to 30 carbon atoms, for example, cyclohexyl and cyclopentyl, or a polycycloalkyl group, for example, a group having a polycyclic structure such as a bicycloalkyl group (preferably a substituted or unsubstituted bicycloalkyl group having 5 to 30 carbon atoms, for example, bicyclo[1,2,2]heptan-2-yl and bicyclo[2,2,2]octan-3-yl), and a tricycloalkyl group. Among these, a monocyclic cycloalkyl group and a bicycloalkyl group are preferable, and a monocyclic cycloalkyl group is particularly preferable), a linear or branched alkenyl group (a linear or branched substituted or unsubstituted alkenyl group, which is preferably an alkenyl group having 2 to 30 carbon atoms, for example, vinyl, allyl, prenyl, geranyl, and oleyl), a cycloalkenyl group (preferably a substituted or unsubstituted cycloalkenyl group having 3 to 30 carbon atoms, for example, 2-cyclopenten-1-yl and 2-cyclohexen-1-yl, a polycyclic alkenyl group, for example, a bicycloalkenyl group (which is preferably a substituted or unsubstituted bicycloalkenyl group having 5 to 30 carbon atoms, for example, bicyclo[2,2,1]hepto-2-en-1-yl and bicyclo[2,2,2]octo-2-en-4-yl), or a tricycloalkenyl group. Among these, a monocyclic cycloalkenyl group is particularly preferable), an alkynyl group (preferably a substituted or unsubstituted alkynyl group having 2 to 30 carbon atoms, for example, an ethynyl group, a propargyl group, and a trimethylsilylethynyl group), an aryl group (preferably a substituted or unsubstituted aryl group having 6 to 30 carbon atoms, for example, phenyl, p-tolyl, naphthyl, m-chlorophenyl, and o-hexadecanoylaminophenyl), a heterocyclic group (preferably a substituted or unsubstituted, saturated or unsaturated, aromatic or non-aromatic, and monocyclic or ring-fused 5- to 7-membered heterocyclic group, more preferably a heterocyclic group of which ring-constituting atoms are selected from a carbon atom, a nitrogen atom, and a sulfur atom, and which has at least any one of hetero atoms including a nitrogen atom, an oxygen atom, and a sulfur atom, and still more preferably a 5- or 6-membered aromatic heterocyclic group having 3 to 30 carbon atoms, for example, 2-furyl, 2-thienyl, 2-pyridyl, 4-pyridyl, 2-pyrimidinyl, and 2-benzothiazolyl), a cyano group, a hydroxyl group, a nitro group, a carboxyl group, an alkoxy group (preferably a substituted or unsubstituted alkoxy group having 1 to 30 carbon atoms, for example, methoxy, ethoxy, isopropoxy, tert-butoxy, n-octyloxy, and 2-methoxyethoxy), an aryloxy group (preferably a substituted or unsubstituted aryloxy group having 6 to 30 carbon atoms, for example, phenoxy, 2-methylphenoxy, 2,4-di-tert-amylphenoxy; 4-tert-butylphenoxy, 3-nitrophenoxy, and 2-tetradecanoylaminophenoxy), a silyloxy group (preferably a silyloxy group having 3 to 20 carbon atoms, for example, trimethylsilyloxy and tert-butyldimethylsilyloxy), a heterocyclic oxy group (preferably a substituted or unsubstituted heterocyclic oxy group having 2 to 30 carbon atoms, in which a heterocyclic moiety is preferably the heterocyclic moiety explained for the aforementioned heterocyclic group, the heterocyclic oxy group is, for example, 1-phenyltetrazol-5-oxy or 2-tetrahydropyranyloxy), an acyloxy group (preferably a formyloxy group, a substituted or unsubstituted alkylcarbonyloxy group having 2 to 30 carbon atoms, and a substituted or unsubstituted arylcarbonyloxy group having 6 to 30 carbon atoms, for example, formyloxy, acetyloxy, pivaloyloxy, stearoyloxy, benzoyloxy, and p-methoxyphenylcarbonyloxy), a carbamoyloxy group (preferably a substituted or unsubstituted carbamoyloxy group having 1 to 30 carbon atoms, for example, N,N-dimethylcarbamoyloxy, N,N-diethylcarbamoyloxy, morpholinocarbonyloxy, N,N-di-n-octylaminocarbonyloxy, and N-n-octylcarbamoyloxy), an alkoxycarbonyloxy group (preferably a substituted or unsubstituted alkoxycarbonyloxy group having 2 to 30 carbon atoms, for example, methoxycarbonyloxy ethoxycarbonyloxy, tert-butoxycarbonyloxy, and n-octylcarbonyloxy), an aryloxycarbonyloxy group (preferably a substituted or unsubstituted aryloxycarbonyloxy group having 7 to 30 carbon atoms, for example, phenoxycarbonyloxy, p-methoxyphenoxycarbonyloxy, and p-n-hexadecyloxyphenoxycarbonyloxy), an amino group (preferably an amino group, a substituted or unsubstituted alkylamino group having 1 to 30 carbon atoms, a substituted or unsubstituted arylamino group having 6 to 30 carbon atoms, and a heterocyclic amino group having 0 to 30 carbon atoms, for example, amino, methylamino, dimethylmino, anilino, N-methyl-anilino, diphenylamino, and N-1,3,5-triazin-2-ylamino), an acylamino group (preferably a formylamino group, a substituted or unsubstituted alkylcarbonylamino group having 1 to 30 carbon atoms, and a substituted or unsubstituted arylcarbonylamino group having 6 to 30 carbon atoms, for example, formylamino, acetylamino, pivaloylamino, lauroylamino, benzoylamino, and 3,4,5-tri-n-octyloxyphenyl carbonylamino), an aminocarbonylamino group (preferably a substituted or unsubstituted aminocarbonylamino group having 1 to 30 carbon atoms, for example, carbamoylamino, N,N-dimethylaminocarbonylamino, N,N-diethylaminocarbonylamino, and morpholinocarbonylamino), an alkoxycarbonylamino group (preferably a substituted or unsubstituted alkoxycarbonylamino group having 2 to 30 carbon atoms, for example, methoxycarbonylamino, ethoxycarbonylamino, tert-butoxycarbonylamino, n-octadecyloxycarbonylamino, and N-methyl-methoxycarbonylamino), an aryloxycarbonylamino group (preferably a substituted or unsubstituted aryloxycarbonylamino group having 7 to 30 carbon atoms, for example, phenoxycarbonylamino, p-chlorophenoxycarbonylamino, and m-n-octyloxyphenoxycarbonylamino), a sulfamoylamino group (preferably a substituted or unsubstituted sulfamoylamino group having 0 to 30 carbon atoms, for example, sulfamoylamino, N,N-dimethylaminosulfonylamino, and N-n-octylaminosulfonylamino), an alkylsulfonylamino or arylsulfonylamino group (preferably a substituted or unsubstituted alkylsulfonylamino group having 1 to 30 carbon atoms, or a substituted or unsubstituted arylsulfonylamino group having 6 to 30 carbon atoms, for example, methylsulfonylamino, butylsulfonylamino, phenylsulfonylamino, 2,3,5-trichlorophenylsulfonylamino, and p-methylphenyisulfonylamino), a mercapto group, an alkylthio group (preferably a substituted or unsubstituted alkylthio group having 1 to 30 carbon atoms, for example, methylthio, ethylthio, and n-hexadecylthio), an arylthio group (preferably a substituted or unsubstituted arylthio group having 6 to 30 carbon atoms, for example, phenylthio, p-chlorophenylthio, and m-methoxyphenylthio), a heterocyclic thio group (preferably a substituted or unsubstituted heterocyclic thio group having 2 to 30 carbon atoms, in which a heterocyclic moiety is preferably the heterocyclic moiety explained for the aforementioned heterocyclic group, for example, 2-benzothiazolylthio and 1-phenyltetrazol-5-ylthio), a sulfamoyl group (preferably a substituted or unsubstituted sulfamoyl group having 0 to 30 carbon atoms, for example, N-ethylsulfamoyl, N-(3-dodecyloxypropyl) sulfamoyl, N,N-dimethylsulfamoyl, N-acetylsulfamoyl, N-benzoylsulfamoyl, and N—(N'-phenylcarbamoyl)sulfamoyl), a sulfo group, an alkylsulfinyl or arylsulfinyl group (preferably a substituted or unsubstituted alkylsulfinyl group having 1 to 30 carbon atoms or a substituted or unsubstituted arylsulfinyl group having 6 to 30 carbon atoms, for example, methylsulfinyl, ethylsulfinyl, phenylsulfinyl, and p-methylphertylsulfinyl), an alkylsulfonyl or arylsulfonyl group (preferably a substituted or unsubstituted alkylsulfonyl group having 1 to 30 carbon atoms or a substituted or unsubstituted arylsulfonyl group having 6 to 30 carbon atoms, for example, methylsulfonyl, ethylsulfonyl, phenylsulfonyl, and p-methylphenylsulfonyl), an acyl group (preferably a formyl group, a substituted or unsubstituted alkyl carbonyl group having 2 to 30 carbon atoms, or a substituted or unsubstituted arylcarbonyl group having 7 to 30 carbon atoms, for example, acetyl, pivaloyl, 2-chloroacetyl, stearoyl, benzoyl, and p-n-octyloxyphenylcarbonyl), an aryloxycarbonyl group (preferably a substituted or unsubstituted aryloxycarbonyl group having 7 to 30 carbon atoms, for example, phenoxycarbonyl, o-chlorophenoxycarbonyl, m-nitrophenoxycarboryl, and p-tert-butylphenoxycarbonyl), an alkoxycarbonyl group (preferably a substituted or unsubstituted alkoxycarbonyl group having 2 to 30 carbon atoms, for example, methoxycarbonyl, ethoxycarbonyl, tert-butoxycarbonyl, and n-octadecyloxycarbonyl), a carbamoyl group (preferably substituted or unsubstituted carbamoyl having 1 to 30 carbon atoms, for example, carbamoyl, N-methylcarbamoyl, N,N-dimethylcarbamoyl, N,N-di-n-octylcarbamoyl, and N-(methylsulfonyl)carbamoyl), an arylazo or heterocyclic azo group (preferably a substituted or unsubstituted arylazo group having 6 to 30 carbon atoms, or a substituted or unsubstituted heterocyclic azo group having 3 to 30 carbon atoms (in which a heterocyclic moiety is preferably the heterocyclic moiety explained for the aforementioned heterocyclic group), for example, phenylazo, p-chlorophenylazo, and 5-ethylthio-1,3,4-thiadiazol-2- ylazo), an imide group (preferably a substituted or unsubstituted imide group having 2 to 30 carbon atoms, for example, N-succinimide and N-phthalimide), a phosphino group (preferably a substituted or unsubstituted phosphino group having 2 to 30 carbon atoms, for example, dimethylphosphino, diphenylphosphino, and methylphenoxyphosphino), a phosphinyl group (preferably a substituted or unsubstituted phosphinyl group having 2 to 30 carbon atoms, for example, phosphinyl, dioctyloxyphosphinyl, and diethoxyphosphinyl), a phosphinyloxy group (preferably a substituted or unsubstituted phosphinyloxy group having 2 to 30 carbon atoms, for example, diphenoxyphosphinyloxy and dioctyloxyphosphinyloxy), a phosphinylamino group (preferably a substituted or unsubstituted phosphinylamino group having 2 to 30 carbon atoms, for example, dimethoxyphosphinylamino and dimethylaminophosphinylamino), and a silyl group (preferably a substituted or unsubstituted silyl group having 3 to 30 carbon atoms, for example, trimethylsilyl, tert-butyldimethylsilyl, and phenyldimethylsilyl).

Among the above functional groups, in the functional groups having hydrogen atoms, the portion of hydrogen atoms in the functional groups may be substituted with any one of the above groups. Examples of the functional groups which can be introduced as substituents include an alkylcarbonylaminosulfonyl group, an arylcarbonylaminosulfonyl group, an alkylsulfonylaminocarbonyl group, and an arylsulfonylaminocarbonyl group, and specific examples thereof include methylsulfonylaminocarbonyl, p-methylphenylsulthnylaminocarbonyl, acetylaminosulfonyl, and benzoylaminosulfonyl.

<Structure of Pigment Multimer Used in Coloring Composition of the Invention>

The pigment multimer (A) used in the coloring composition of the present invention is not particularly defined, but it is preferably a pigment multimer which contains at least one of the repeating units represented by the following General Formulae (A) and (C), or a pigment multimer represented by General Formula (D). One kind of the pigment multimer may include one kind or two or more kinds of the repeating unit represented by General Formula (A), which are also applied to General Formulae (C) to (D). Further, the pigment multimer may include other repeating units as described later.

In the present invention, it is preferable that the pigment multimer represented by General Formula (A) is included. These will be described in order.

<<Repeating Unit Represented by General Formula (A)>>

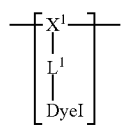

General Formula (A)

(In General Formula (A), $X^1$ represents a group capable of forming a main chain and $L^1$ represents a single bond or a divalent linking group. DyeI represents a pigment structure having a cationic moiety.)

General Formula (A) will be described in detail below.

In General Formula (A), $X^1$ represents a group capable of forming a main chain. That is, $X^1$ refers to a portion that forms a repeating unit corresponding to a main chain formed by a polymerization reaction. $X^1$ is not particularly limited as long as it is a linking group formed of a known polymerizable monomer. Particularly, $X^1$ is preferably linking chains represented by the following (XX-1) to (XX-24), and more preferably selected from (meth)acrylic linking groups represented by (XX-1) and (XX-2), styrene-based linking chains represented by (XX-10) to (XX-17), and a vinyl-based linking chain represented by (XX-24). The (meth)acrylic linking chains represented by (XX-1) and (XX-2), and the styrene-based linking chain represented by (XX-11) are more preferable.

In (XX-1) to (X-24), * represents a site for linking to $L^1$.

Me represents a methyl group. Further, R in (XX-18) and (XX-19) represents a hydrogen atom, an alkyl group having 1 to 5 carbon atoms, or a phenyl group.

(XX-1)

(XX-2)

(XX-3)

(XX-4)

(XX-5)

(XX-6)

(XX-7)

-continued
(XX-8)
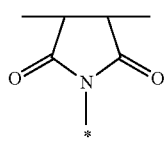
(XX-9)
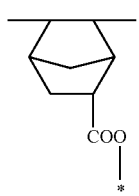
(XX-10)
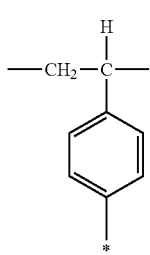
(XX-11)
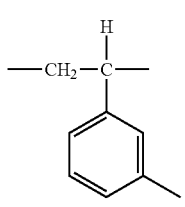
(XX-12)
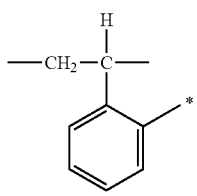
(XX-13)
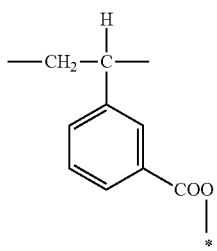
(XX-14)
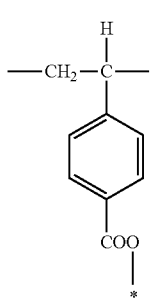
(XX-15)
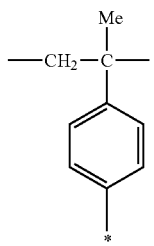
(XX-16)
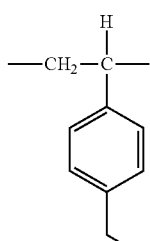
(XX-17)
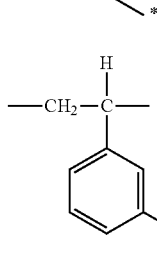
(XX-18)
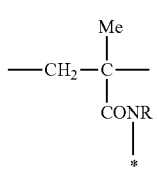
(XX-19)
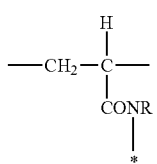
(XX-20)
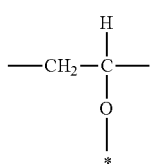
(XX-21)
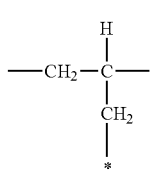

(XX-22)

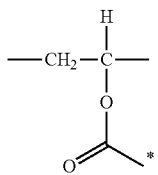

(XX-23)

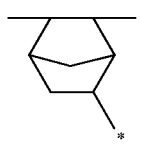

(XX-24)

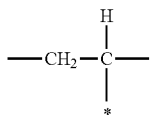

In General Formula (A), $L^1$ represents a single bond or a divalent linking group. In the case where $L^1$ represents a divalent linking group, the divalent linking group represents a substituted or unsubstituted alkylene group having 1 to 30 carbon atoms (for example, a methylene group, an ethylene group, a trimethylene group, a propylene group, and a butylene group), a substituted or unsubstituted arylene group having 6 to 30 carbon atoms (for example, a phenylene group and a naphthalene group), a substituted or unsubstituted heterocyclic linking group, —CH=CH—, —O—, —S—, —C(=O)—, —CO$_2$—, —NR—, —CONR—, —O$_2$C—, —SO—, —SO$_2$—, and a linking group formed of two or more of these linked to each other. $L^1$ is more preferably a single bond or an alkylene group, and still more preferably a single bond or —(CH$_2$)n- (in which n is an integer of 1 to 5). Herein, R's each independently represent a hydrogen atom, an alkyl group, an aryl group, or a heterocyclic group.

The divalent linking group represented by $L^1$ may be a group which can form an ionic bond or a coordinate bond with DyeI, and in this case, it may be either an anionic group or a cationic bond.

Examples of the anionic group include —COO$^-$, —PO$_3$H$^-$, —SO$_3^-$, —SO$_3$NH$^-$, and —SO$_3$NC$^-$CO—, and among these, —COO$^-$, —PO$_3$H$^-$, and —SO$_3^-$ are preferable.

Examples of the cationic group include substituted or unsubstituted onium cations (for example, ammonium, pyridinium, imidazolium, and phosphonium), among which an ammonium cation is particularly preferable.

In the case where $L^1$ has a group which can form an ionic bond or a coordinate bond with DyeI, $L^1$ can be bonded to an anion portion (—COO$^-$, —SO$_3^-$, —O$^-$, or the like) or a cation portion (the onium cation described above, a metal cation, or the like) which DyeI has.

In General Formula (A), DyeI represents a pigment structure derived from the aforementioned pigment compound.

The pigment multimer having the repeating unit represented by General Formula (A) can be synthesized by (1) a method for synthesizing the multimer by means of addition polymerization using monomers having a pigment residue, or (2) a method for synthesizing the multimer by causing a reaction between a polymer having a highly reactive functional group such as an isocyanate group, an acid anhydride group, and an epoxy group, and a pigment having a functional group (a hydroxyl group, a primary or secondary amino group, a carboxyl group, or the like) which can react with the highly reactive group.

For the addition polymerization, known addition polymerization (radical polymerization, anionic polymerization, or cationic polymerization) can be applied. Among these, it is particularly preferable that the pigment multimer is synthesized by radical polymerization, since the reaction condition can be set to be mild conditions, and the pigment structure is not degraded. For the radical polymerization, known reaction conditions can be applied.

Among these, from the viewpoint of heat resistance, the pigment multimer having the repeating unit represented by General Formula (A) in the present invention is preferably a radical polymer which is obtained by radical polymerization using a pigment monomer having an ethylenically unsaturated bond.

Specific examples of the repeating unit represented by General Formula (A) are shown below, but the present invention is not limited thereto.

(A-pm-1)

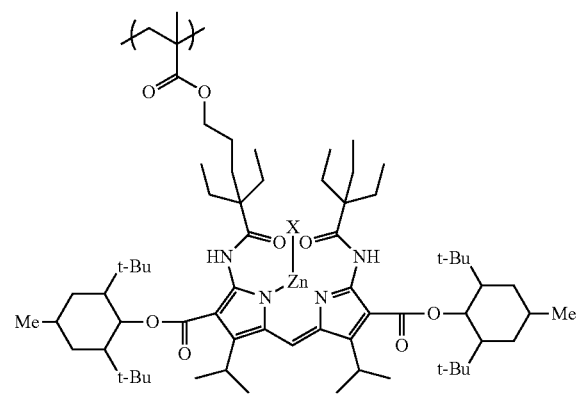

(A-pm-2)

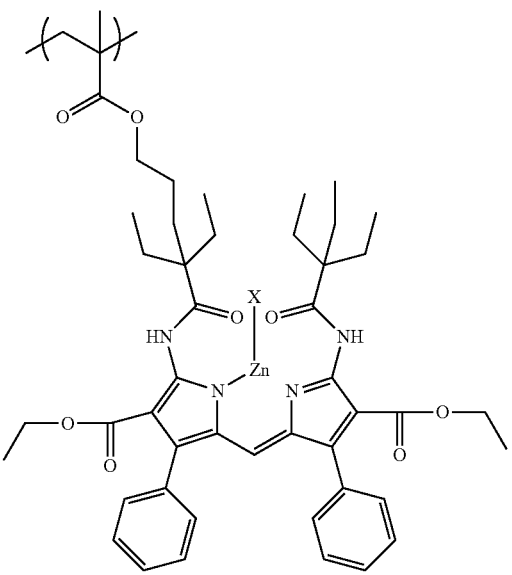

(A-pm-3)
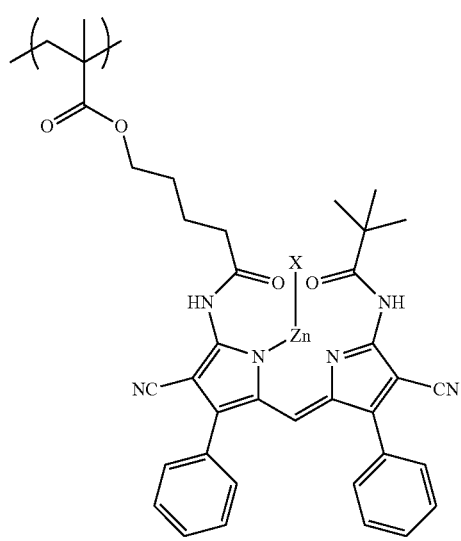
(A-pm-4)
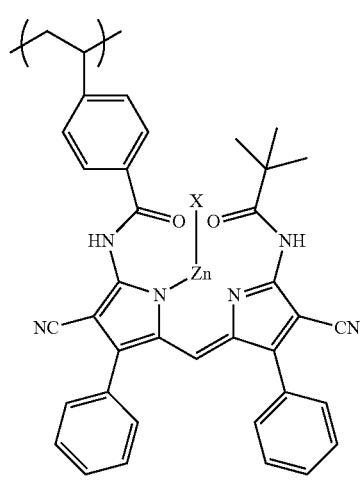
(A-tp-1)
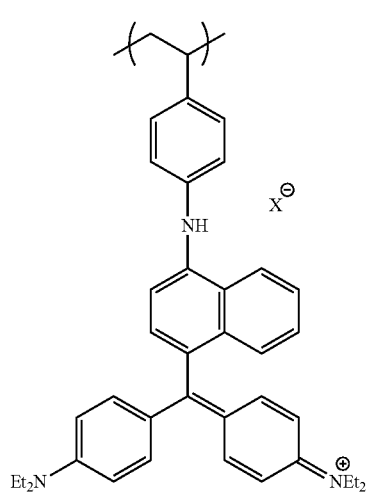
(A-tp-2)
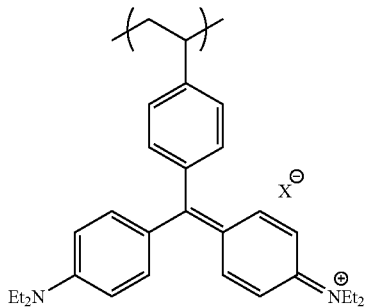
(A-tp-3)
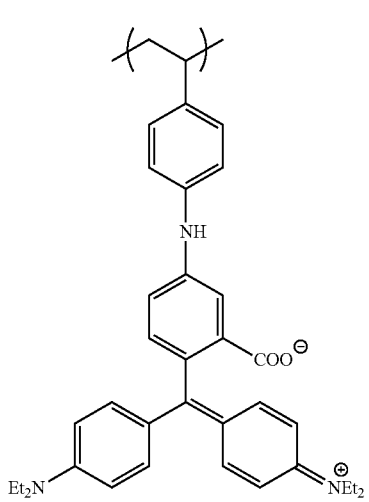
(a-xt-1)
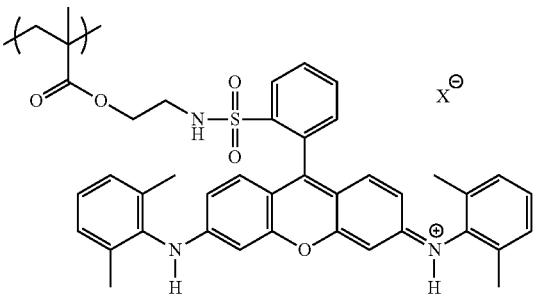
(a-xt-2)
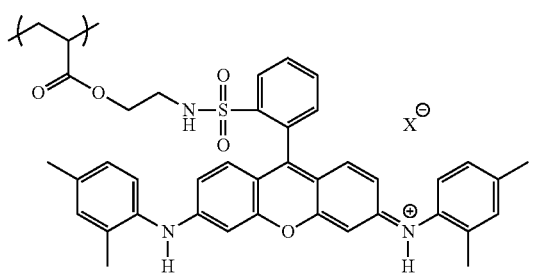

-continued
(a-xt-3)
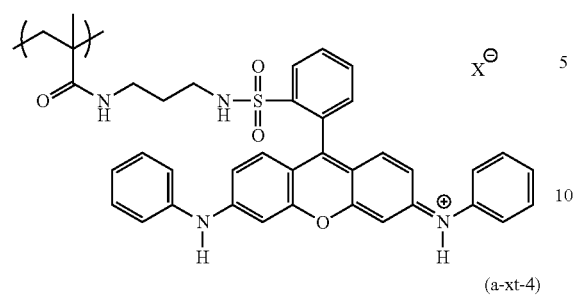
(a-xt-4)
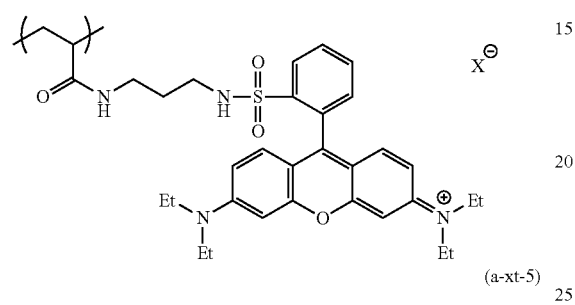
(a-xt-5)
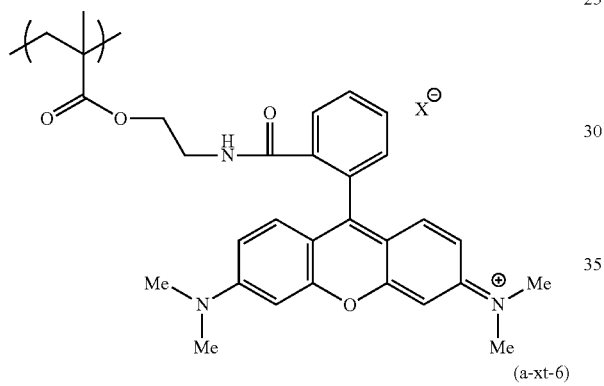
(a-xt-6)
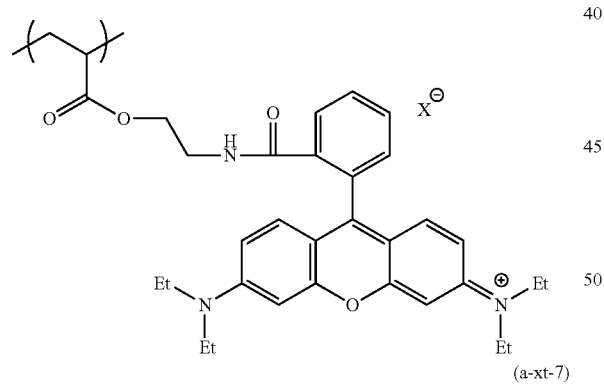
(a-xt-7)
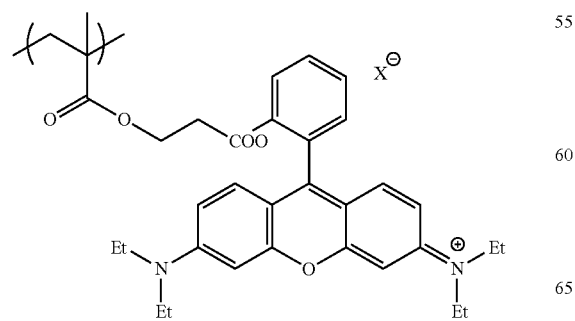
-continued
(a-xt-8)
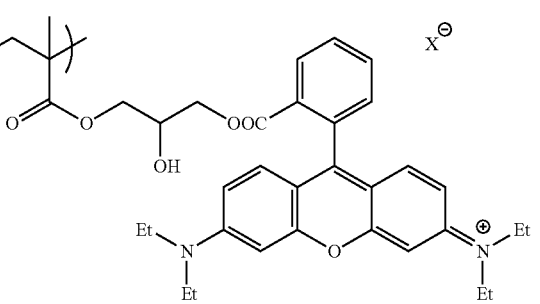
(a-xt-9)
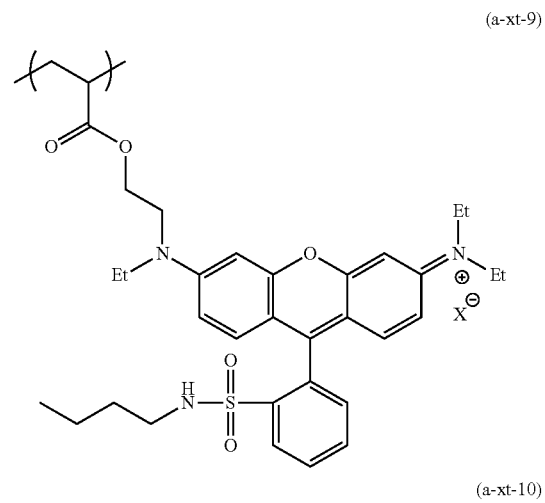
(a-xt-10)
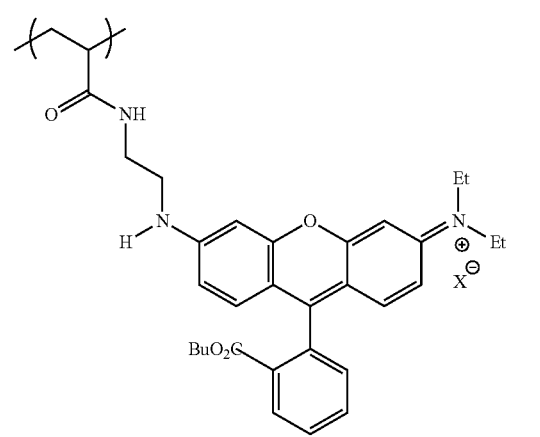
(a-xt-11)
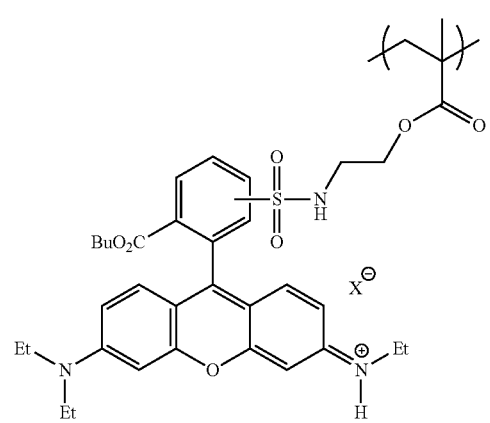

59
-continued
(a-xt-12)
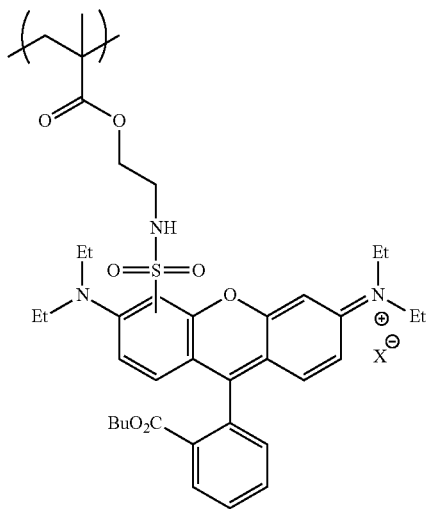
(A-pm-1)
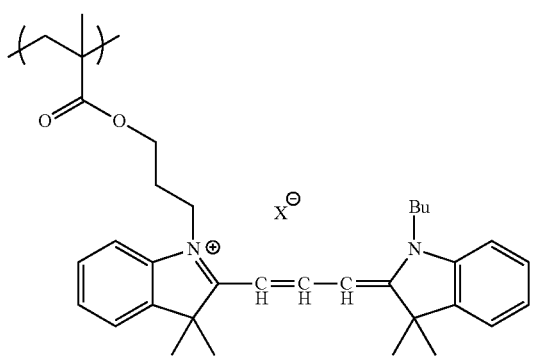
(A-pm-2)
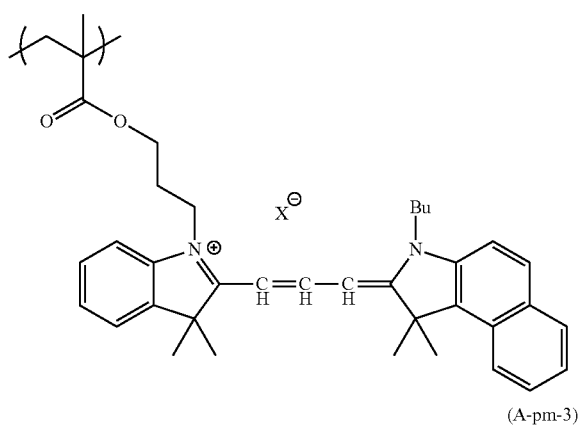
(A-pm-3)
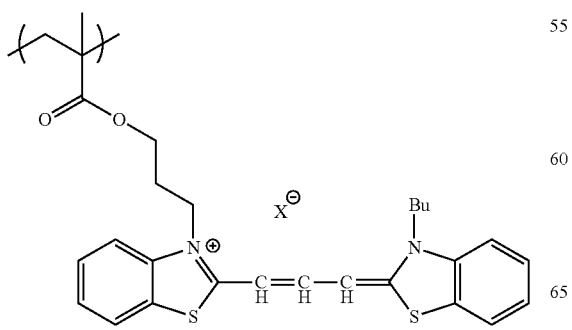
60
-continued
(A-pm-4)
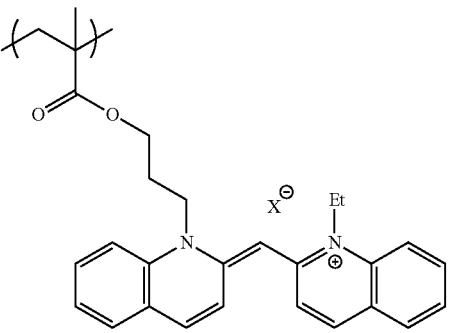
(A-SP-1)
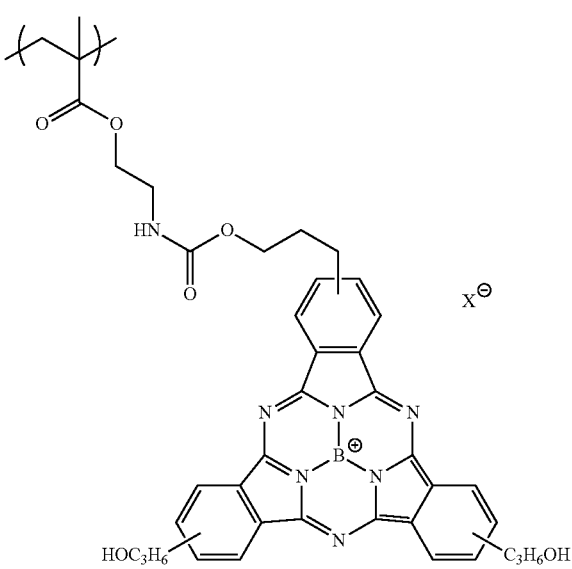
(A-SP-2)
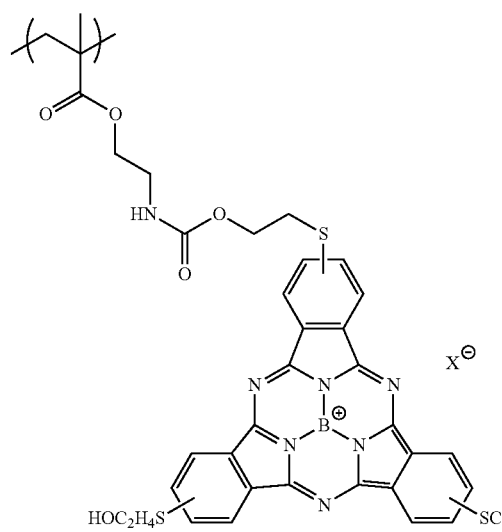

-continued (A-SP-3)

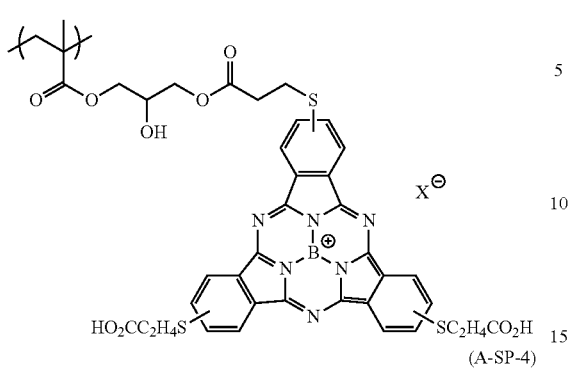

(A-SP-4)

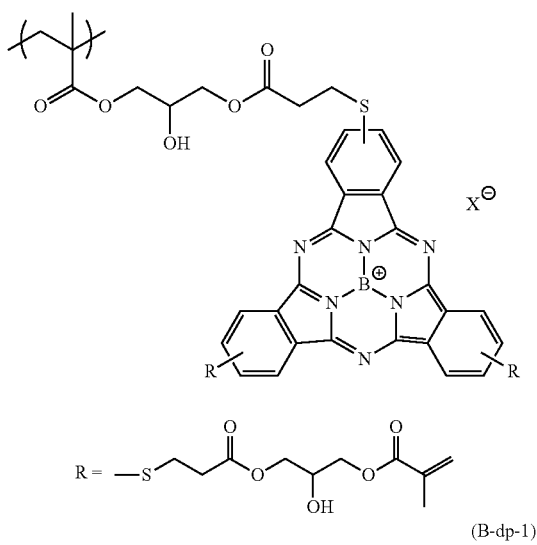

(B-dp-1)

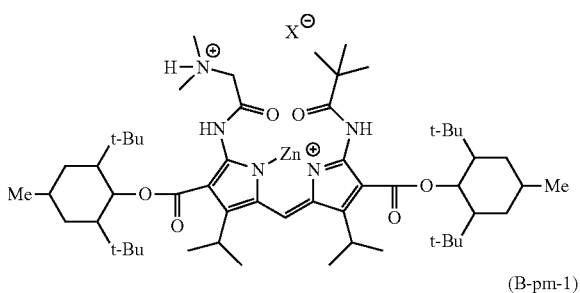

(B-pm-1)

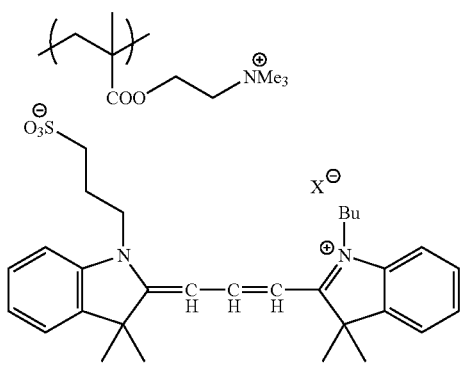

-continued (B-xt-1)

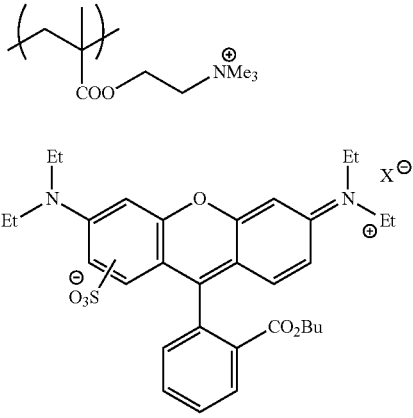

(B-xt-2)

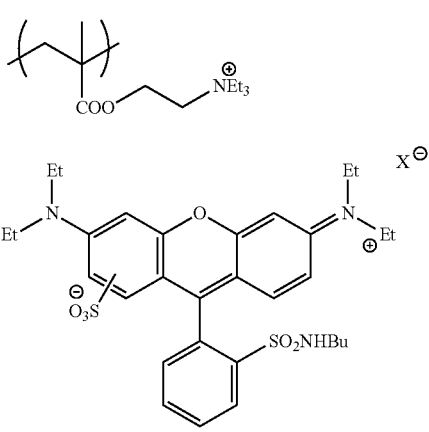

<<Repeating Unit Represented by General Formula (C)>>

Next, details of a pigment multimer represented by General Formula (C) will be described.

$$\{DyeIII\text{-}(L^3)_m\}$$  General Formula (C)

(In General Formula (C), $L^3$ represents a single bond or a divalent linking group. DyeIII represents a pigment structure having a cationic moiety. m represents 0 or 1.)

In General Formula (C), $L^3$ represents a single bond or a divalent linking group. Suitable examples of the divalent linking group represented by $L^3$ include a substituted or unsubstituted linear, branched, or cyclic alkylene group having 1 to 30 carbon atoms (for example, a methylene group, an ethylene group, a trimethylene group, a propylene group, and a butylene group), a substituted or unsubstituted arylene group having 6 to 30 carbon atoms (for example, a phenylene group and a naphthalene group), a substituted or unsubstituted heterocyclic linking group, —CH=CH—, —O—, —S—, —NR— (in which R's each independently represent a hydrogen atom, an alkyl group, an aryl group, or a heterocyclic group), —C(=O)—, —SO—, —SO$_2$—, and a linking group that is formed of two or more of these groups linked to each other.

m represents 0 or 1, and is preferably 1.

Specific examples which are suitably used as the divalent linking group represented by $L^3$ in General Formula (C) are shown below, but $L^3$ of the present invention is not limited thereto. * represents a linking moiety to DyeIII or the like.

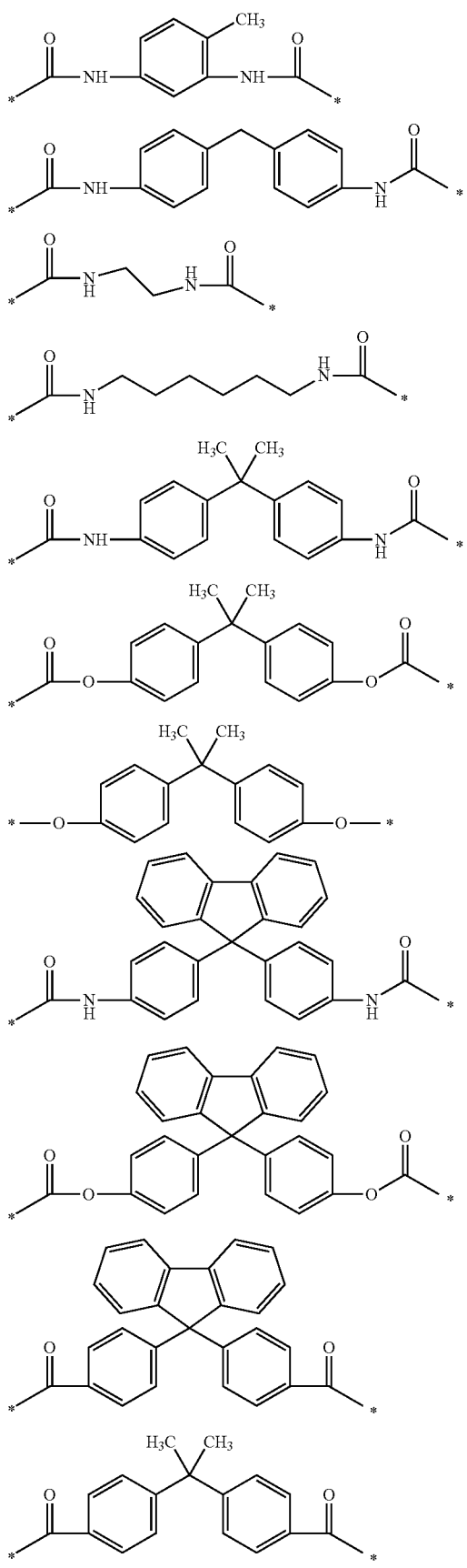
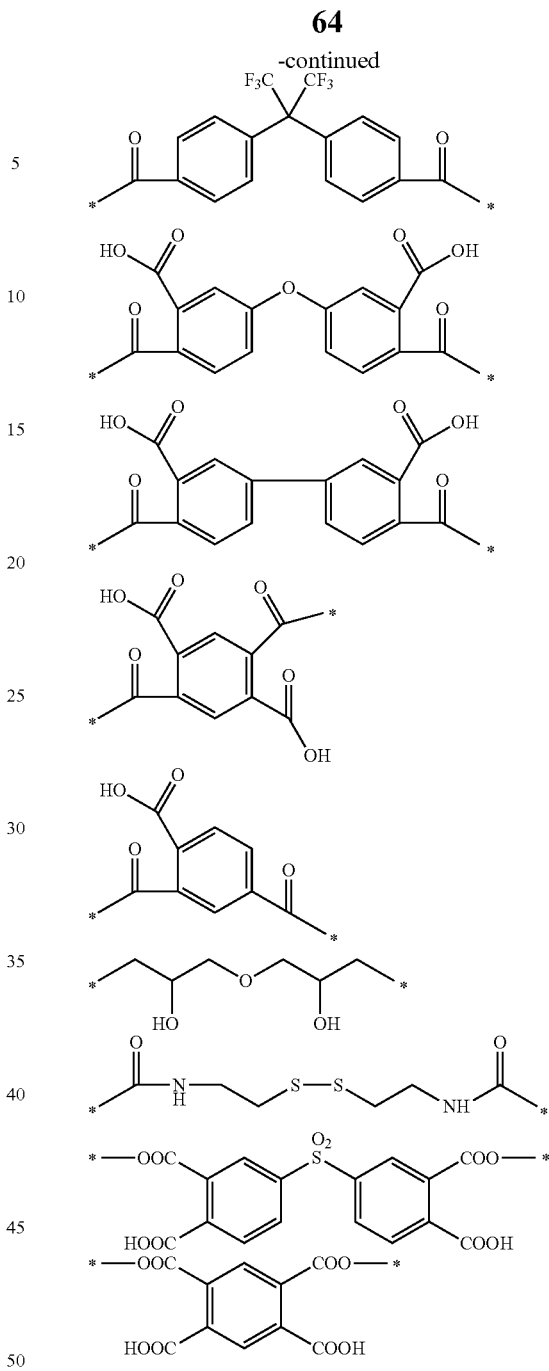

The pigment multimer having the repeating unit represented by General Formula (C) is synthesized by sequential polymerization. Examples of the sequential polymerization include polyaddition (for example, a reaction between an diisocyanate compound and diol, a reaction between a diepoxy compound and a dicarboxylic acid, a reaction between a tetracarboxylic dianhydride and diol, or the like) and polycondensation (for example, a reaction between a dicarboxylic acid and diol, a reaction between a dicarboxylic acid, and diamine, or the like). Among these, it is particularly preferable to use the polyaddition reaction to synthesize the pigment multimer, since the reaction conditions can be set to be mild, and a pigment structure is not degraded by the reaction. For the sequential polymerization, known reaction conditions can be applied.

Specific examples of the repeating unit represented by General Formula (C) will be shown below, but the present invention is not limited thereto.

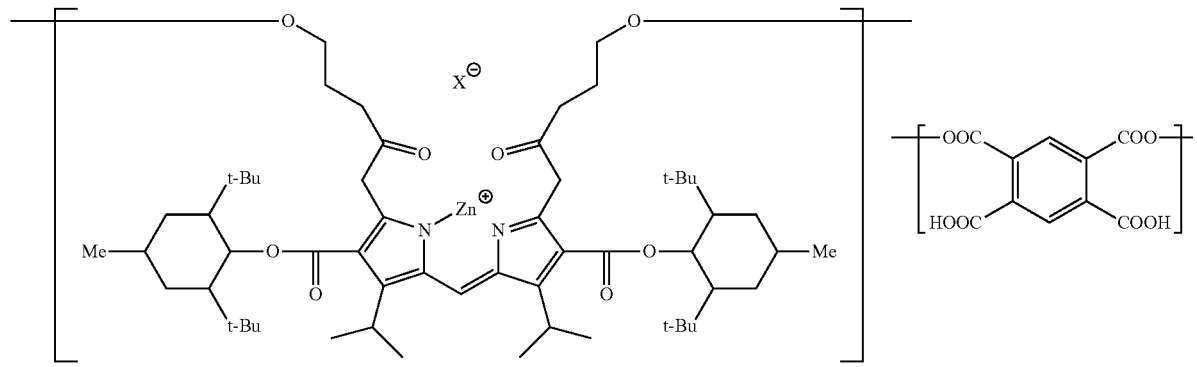

(C-dp-1)

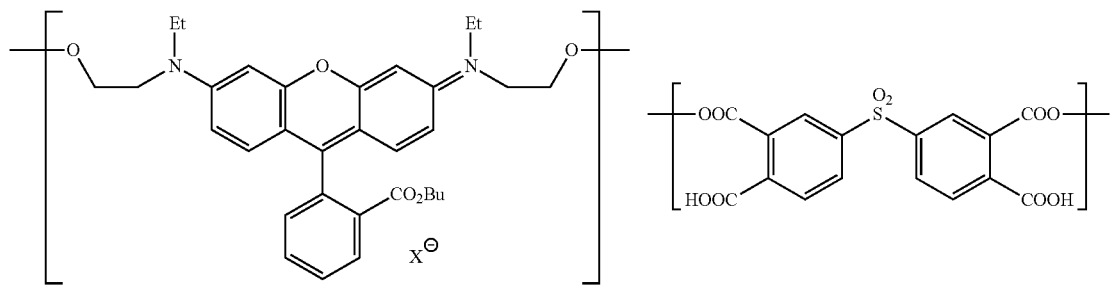

(C-xt-1)

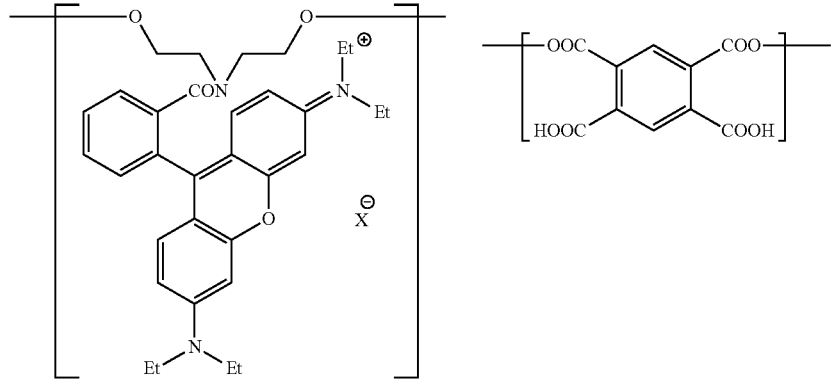

(C-xt-2)

phenylene group and a naphthalene group), a substituted or unsubstituted heterocyclic linking group, —CH═CH—, —O—, —S—, —NR— (in which R's each independently represent a hydrogen atom, an alkyl group, an aryl group, or a heterocyclic group), —C(═O)—, —SO—, —SO$_2$—, and a linking group that is formed of two or more of these groups linked to each other.

In the case where n is 3 or more, examples of the linking group having a valency of n include linking groups which have, as a central core, a substituted or unsubstituted arylene group (a 1,3,5-phenylene group, a 1,2,4-phenylene group, a 1,4,5,8-naphthalene group, or the like), a heterocyclic linking group (for example, a 1,3,5-triazine group), an alkylene linking group, or the like, and are formed when the divalent linking group is substituted.

Specific examples of $L^4$ in General Formula (D) are shown below, but the present invention is not limited thereto. Further, the site represented by * represents a linking moiety to DyeIV.

<<Pigment Multimer Represented by General Formula (D)>>

Next, details of the pigment multimer represented by General Formula (D) will be described.

$(L^4)$—$(DyeIV)_n$  General Formula (D)

(In General Formula (D), $L^4$ represents an n-valent linking group. n represents an integer of 2 to 20. DyeIV represents a pigment structure having a cationic moiety.)

In General Formula (D), n is preferably 3 to 15, and particularly preferably 3 to 6.

In General Formula (D), in the case where n is 2, suitable examples of divalent linking groups represented by $L^4$ include a substituted or unsubstituted alkylene group having 1 to 30 carbon atoms (for example, a methylene group, an ethylene group, a trimethylene group, a propylene group, and a butylenes group), a substituted or unsubstituted arylene group having 6 to 30 carbon atoms (for example, a

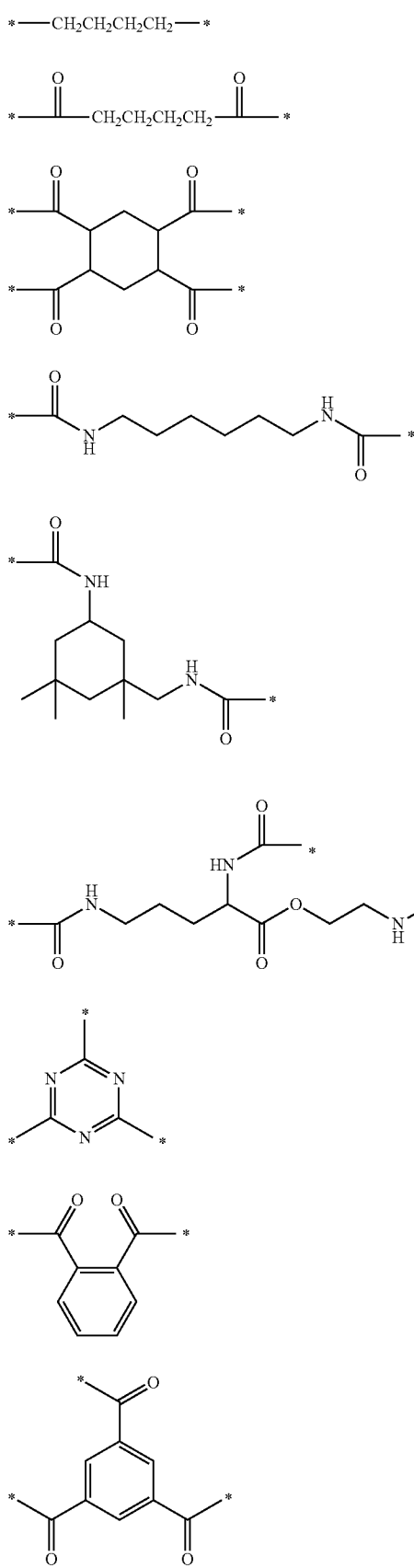
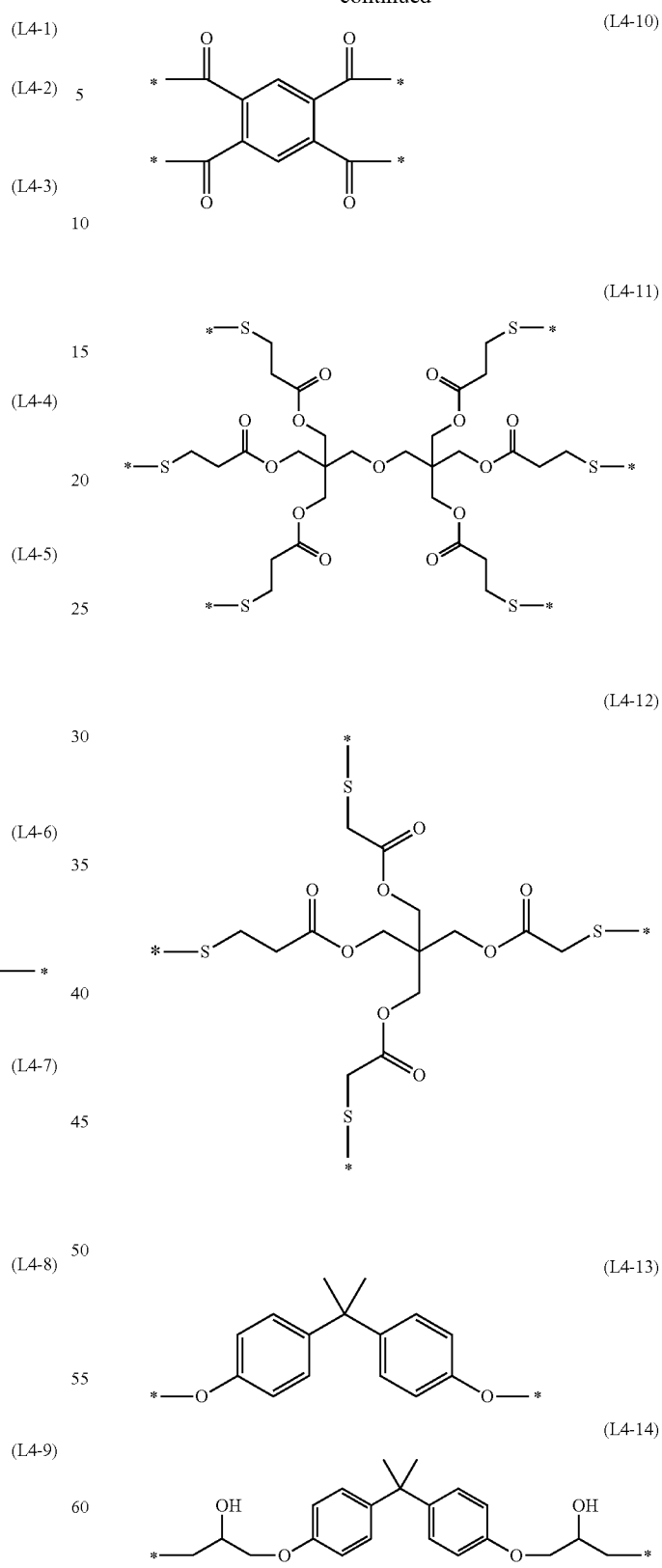
Specific examples of DyeIV in General Formula (D) are shown below, but the present invention is not limited thereto.

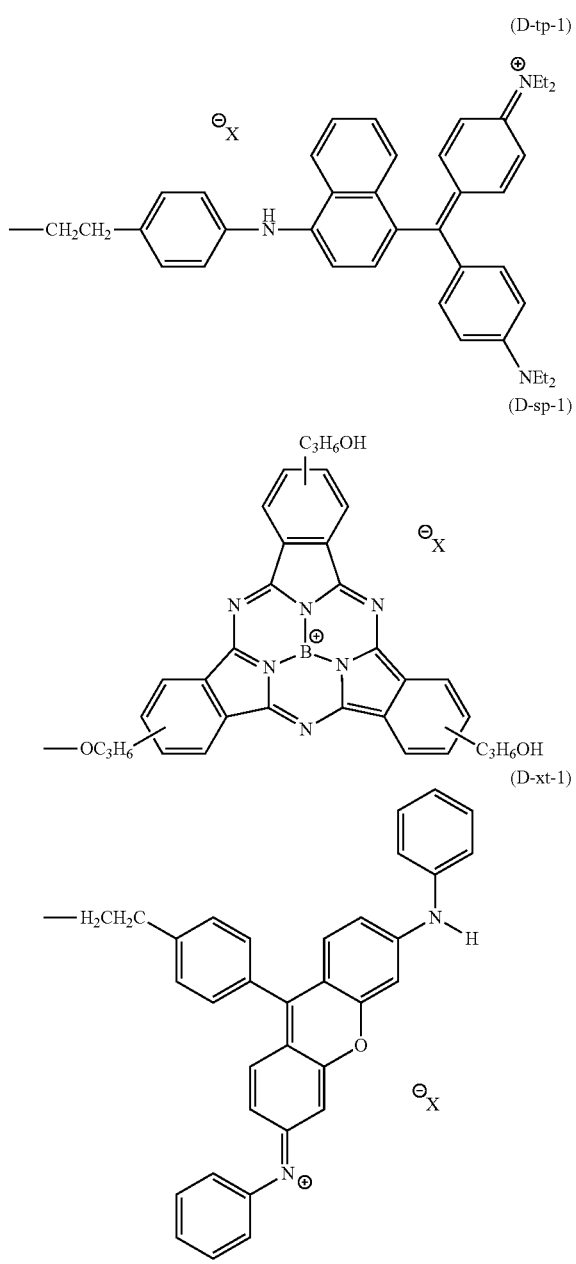

(D-tp-1)
(D-sp-1)
(D-xt-1)

Among the pigment multimer having at least one of the repeating units represented by General Formula (A) and General Formula (C), and the pigment multimer represented by General Formula (D), in the pigment multimer having the repeating unit represented by General Formula (A), the pigment multimer having the repeating unit represented by General Formula (C), and the pigment multimer represented by General Formula (D), the partial structures derived from a pigment are linked to each other through a covalent bond in the molecular structure. Accordingly, the coloring composition containing such a pigment multimer has excellent heat resistance. Therefore, in the case where the coloring composition is used for a pattern forming process including a high-temperature process, the coloring composition is preferable since an effect of inhibiting color migration to another colored pattern adjacent thereto is obtained. Further, in particular, the compound represented by General Formula (A) is preferable since the compound makes it easy to control the molecular weight of the pigment multimer.

<<Other Functional Groups and Repeating Units>>

In the pigment multimer (A) of the present invention, the pigment multimer may have other functional groups in the pigment structure moiety of the aforementioned pigment multimer. Examples of such other functional groups include a polymerizable group, an acid group, and an alkali-soluble group.

Furthermore, the pigment multimer (A) of the present invention may include other repeating units in addition to the repeating unit including the aforementioned pigment structure. Such other repeating unit may have a functional group.

Moreover, examples of such other repeating units include repeating units including at least one of a polymerizable group, an acid group, and an alkali-soluble group.

That is, the pigment multimer (A) of the present invention may have other repeating units, in addition to the repeating units represented by General Formulae (A) to (C). One kind or two or more kinds of other repeating unit may be included in one pigment multimer.

Furthermore, the pigment multimer (A) of the present invention may have other functional groups in the pigment multimers represented by General Formulae (A) to (D). Details thereof will be described below.

<<<Polymerizable Group Which Pigment Multimer (A) Has>>>

The pigment multimer (A) of the present invention preferably includes a polymerizable group. One kind or two or more kinds of the polymerizable group may be included.

For the polymerizable group, the pigment structure may contain a polymerizable group, or include other moieties. In the present invention, it is preferable that the pigment structure contains a polymerizable group. By using this configuration, heat resistance tends to be improved.

Furthermore, in the present invention, an embodiment in which other moiety other than the pigment structure contains a polymerizable group is also preferable.

As the polymerizable group, known polymerizable groups which can be crosslinked by a radical, an acid, or heat can be used, and examples thereof include a group having an ethylenically unsaturated bond, a cyclic ether group (an epoxy group and an oxetane group), and a methylol group. Particularly, a group having an ethylenically unsaturated bond is preferable, a (meth)acryloyl group is more preferable, and (meth)acryloyl groups derived from glycidyl (meth)acrylate and 3,4-epoxycyclohexyl methyl(meth)acrylate are still more preferable.

The polymerizable group is preferably contained as a repeating unit having a polymerizable group in the pigment multimer, and is more preferably contained as a repeating unit having an ethylenically unsaturated bond. That is, one examples of preferred embodiments of the pigment multimer (A) of the present invention is an embodiment in which the pigment multimer (A) includes a repeating unit containing a pigment monomer and a repeating unit having a polymerizable group, and more preferably an embodiment in which the pigment multimer (A) includes a repeating unit containing a pigment monomer and a repeating unit having an ethylenically unsaturated bond.

As the method for introducing the polymerizable group, there are (1) a method for introducing the polymerizable group by modifying the pigment multimer with a polymerizable group-containing compound, (2) a method for introducing the polymerizable group by copolymerizing the pigment multimer with a polymerizable group-containing compound, and the like. Hereinafter, the methods will be described in detail.

(1) Method for Introducing Polymerizable Group by Modifying Pigment Multimer with Polymerizable Group-Containing Compound:

As the method for introducing the polymerizable group by modifying the pigment multimer with a polymerizable group-containing compound, known methods can be used without particular limitation. For example, from the viewpoint of production, (a) a method of reacting a carboxylic acid which the pigment multimer has with an unsaturated bond-containing epoxy compound, (b) a method of reacting a hydroxyl group or an amino group which the pigment multimer has with an unsaturated bond-containing isocyanate compound, and (c) a method of reacting an epoxy compound which the pigment multimer has with an unsaturated bond-containing carboxylic acid compound are preferable from the viewpoint of production.

Examples of the unsaturated bond-containing epoxy compound include (a) the method of reacting a carboxylic acid which the pigment multimer has with an unsaturated bond-containing epoxy compound include glycidyl methacrylate, glycidyl acrylate, allylglycidyl ether, 3,4-epoxycyclohexylmethyl acrylate, and 3,4-epoxycyclohexylmethyl methacrylate, and the like. Glycidyl methacrylate and 3,4-epoxycyclohexylmethyl methacrylate are particularly preferable since these compounds have excellent crosslinking properties and storage stability. Known conditions can be used as the reaction conditions.

Examples of the unsaturated bond-containing isocyanate compound in (b) the method of reacting a hydroxyl group or an amino group which the pigment multimer has with an unsaturated bond-containing isocyanate compound include 2-isocyanatoethyl methacrylate, 2-isocyanatoethyl acrylate, and 1,1-bis(acryloyloxymethyl)ethyl isocyanate. Among these, 2-isocyanatoethyl methacrylate is preferable since it has excellent crosslinking properties and storage stability. Known conditions can be used as the reaction conditions.

As the unsaturated bond-containing carboxylic acid compound in (e) the method of reacting an epoxy compound which the pigment multimer has with an unsaturated bond-containing carboxylic acid compound, any carboxylic acid compounds can be used without particular limitation as long as the compound has a known (meth)acryloyloxy group. Among these, methacrylic acid and acrylic acid are preferable, and methacrylic acid is particularly preferable since this acid has excellent crosslinking properties and storage stability. Known conditions can be used as the reaction conditions.

(2) Method for Introducing Polymerizable Group by Copolymerizing Pigment Monomer and Polymerizable Group-Containing Compound:

As (2) the method for introducing a polymerizable group by copolymerizing a pigment monomer and a polymerizable group-containing compound, any known methods can be used without particular limitation. Among these, (d) a method of copolymerizing a radically polymerizable pigment monomer with a polymerizable group-containing compound which can be radically polymerized, and (e) a method of copolymerizing a pigment monomer which can be subjected to polyaddition with a polymerizable group-containing compound which can be subjected to polyaddition are preferable.

Examples of the polymerizable group-containing compound which can be radically polymerized in (d) a method of copolymerizing a radically polymerizable pigment monomer with a polymerizable group-containing compound which can be radically polymerized particularly include an allyl group-containing compound (for example, allyl(meth)acrylate or the like), an epoxy group-containing compound (for example, glycidyl(meth)acrylate, 3,4-epoxycyclohexyl methyl(meth)acrylate), an oxetane group-containing compound (for example, 3-methyl-3-oxetanyl methyl(meth)acrylate or the like), and a methylol group-containing compound (for example, N-(hydroxymethyl)acrylamide or the like). Among these, an epoxy group-containing compound and an oxetane group-containing compound are particularly preferable. Known conditions can be used as the reaction conditions.

Examples of the polymerizable group-containing compound which can be subjected to polyaddition in (e) a method of copolymerizing a pigment monomer which can be subjected to polyaddition with a polymerizable group-containing compound which can be subjected to polyaddition include an unsaturated bond-containing diol compound (for example, 2,3-dihydroxypropyl(meth)acrylate), and the like. Known conditions can be used as the reaction conditions.

As the method for introducing a polymerizable group, a method of reacting a carboxylic acid which the pigment multimer has with an unsaturated bond-containing epoxy compound which the pigment multimer has is particularly preferable.)

The amount of the polymerizable group which the pigment multimer (A) has is preferably 0.1 mmol to 2.0 mmol, more preferably 0.2 mmol to 1.5 mmol, and particularly preferably 0.3 mmol to 1.0 mmol, with respect to 1 g of the pigment multimer (A).

Furthermore, the proportion of the repeating units containing the repeating unit in which the pigment multimer (A) contains a polymerizable group is preferably, for example, from 5 moles to 50 moles, and more preferably 10 moles to 20 moles, with respect to 100 moles of the total repeating units.

As the method for introducing a polymerizable group, a method in which a carboxylic acid which the pigment multimer has is reacted with an unsaturated bond-containing epoxy compound is particularly preferable.

Specific examples of repeating units having the polymerizable group will be shown below, but the present invention is not limited thereto.

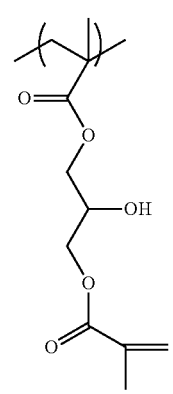

(G-1)

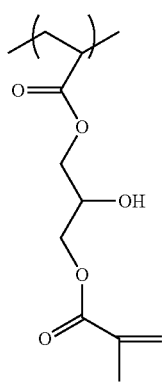
(G-2)
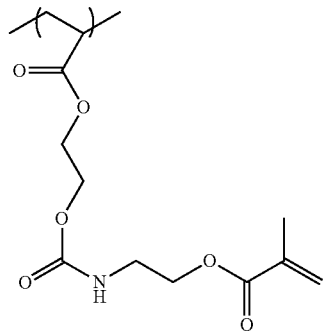
(G-6)
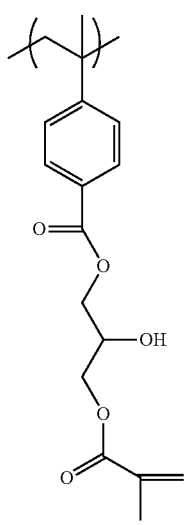
(G-3)
(G-7)
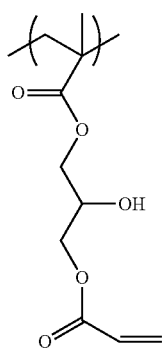
(G-4)
(G-8)
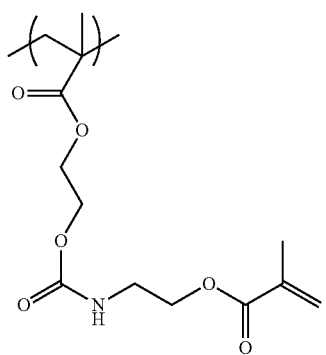
(G-5)
(G-9)
(G-10)

(G-11)

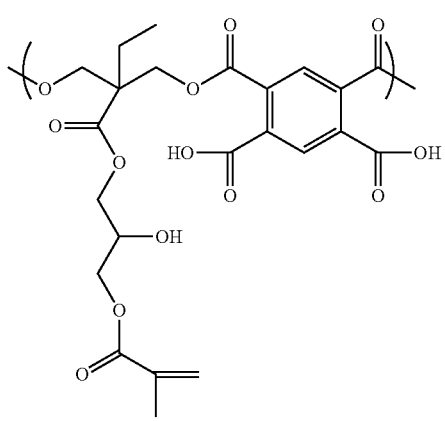

(G-12)

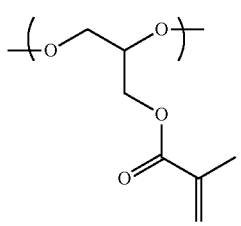

(G-13)

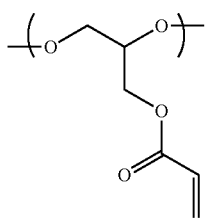

(G-14)

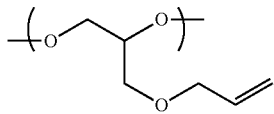

(G-15)

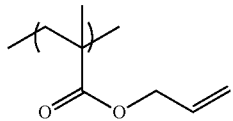

(G-16)

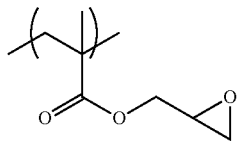

(G-17)

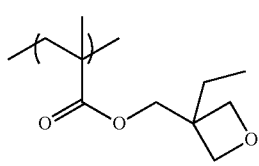

Among the above specific examples, from the viewpoint of substrate adhesiveness and surface roughness, pigment monomers having an ethylenically unsaturated bond are preferable. Among these, a methacryloyl group, an acryloyl group, a styryl group, or a vinyloxy group is preferable, a methacryloyl group, acryloyl group are more preferable, and a methacryloyl group is still more preferable.

<<<Acid Group and Alkali-Soluble Group Which Pigment Multimer (A) Has>>>

Examples of the acid group which the pigment multimer (A) in the present invention may have include a carboxylic acid group, a sulfonic acid group, and a phosphoric acid group. Further, examples of the alkali-soluble group include a phenolic hydroxyl group and a carboxylic acid.

In the present invention, it is preferable that an acid group and/or an alkali-soluble group is/are contained in the multimer (A) as a repeating unit having an acid group and/or an alkali-soluble group.

In the present invention, the acid value of the repeating unit having an acid group is preferably 15 mgKOH/g to 110 mgKOH/g, more preferably 20 mgKOH/g to 90 mgKOH/g, and still more preferably 30 mgKOH/g to 60 mgKOH/g.

In the present invention, the acid value of the pigment multimer can be calculated from, for example, an average content of acid groups in the pigment multimer. Further, it is possible to obtain a resin having a desired acid value by changing the content of monomer units containing an acid group constituting the pigment multimer.

Examples of the method for introducing the alkali-soluble group into the pigment multimer include a method in which an alkali-soluble group is introduced into a pigment monomer in advance and a method of copolymerizing monomers (a caprolactone-modified derivative of (meth)acrylic acids and acrylic acids, a succinic anhydride-modified derivative of 2-hydroxyethyl(meth)acrylate, a phthalic anhydride-modified derivative of 2-hydroxyethyl(meth)acrylate, a 1,2-cyclohexane dicarboxylic acid anhydride-modified derivative of 2-hydroxyethyl(meth)acrylate, carboxylic acid-containing monomers such as styrenecarboxylic acid, itaconic acid, maleic acid, and norbornene carboxylic acid, phosphoric acid-containing monomers such as acid phosphoxyethyl methacrylate, and vinyl phosphonic acid, and sulfonic acid-containing monomers such as vinyl sulfonic acid and 2-acrylamide-2-methylsulfonic acid) other than a pigment monomer having an alkali-soluble group. It is preferable to use both of the methods.

The amount of the alkali-soluble groups which the pigment multimer (A) has is preferably 0.3 mmol to 2.0 mmol, more preferably 0.4 mmol to 1.5 mmol, and particularly preferably 0.5 mmol to 1.0 mmol, with respect to 1 g of the pigment multimer (A).

Furthermore, in the case where the pigment multimer (A) includes a repeating unit having pigment monomer and a repeating unit having an acid group, the proportion of the repeating units containing a repeating unit having an acid group is, for example, preferably 5 mole to 70 moles, and more preferably 10 moles to 50 moles, with respect to 100 moles of the repeating unit containing the pigment monomer.

Examples of other functional groups which the pigment multimer (A) has include a development accelerator such as lactone, acid anhydride, amide, —COCH$_2$CO—, and a cyano group, or a hydrophobicity- or hydrophilicity-regulating group such as a long chain-alkyl group, a cyclic alkyl group, an aralkyl group, an aryl group, a polyalkylene oxide group, a hydroxyl group, a maleimide group, and an amino group, and the like. These can be appropriately introduced.

Examples of the method for introducing the functional group include a method for introducing the functional group in advance to the pigment monomer and a method of copolymerizing a monomer having the functional group.

Specific examples of repeating units having other functional groups which the pigment multimer (A) has are shown below, but the present invention is not limited thereto.

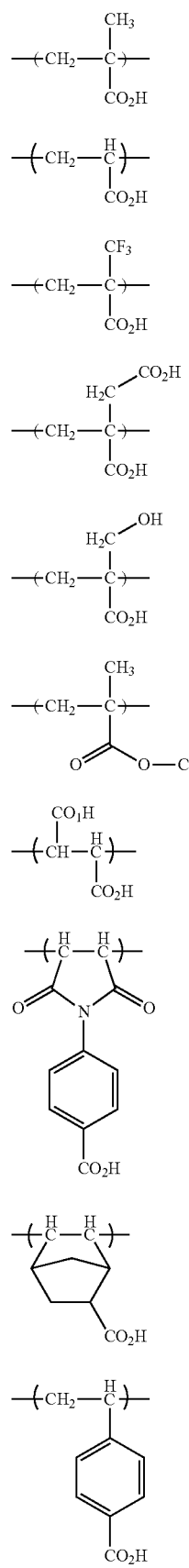
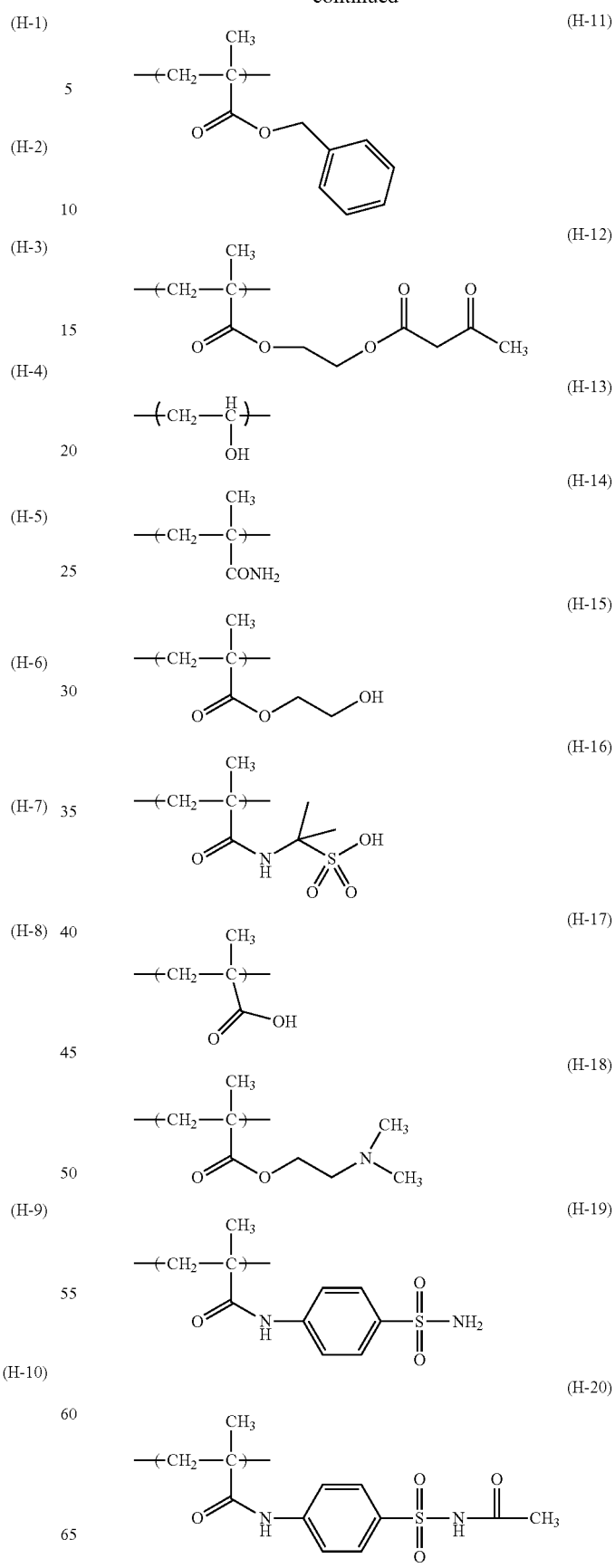

(H-21) 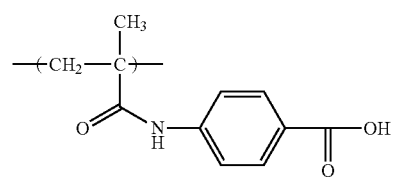
(H-22) 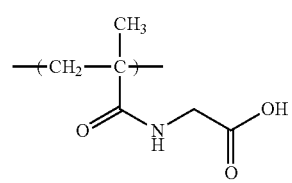
(H-23) 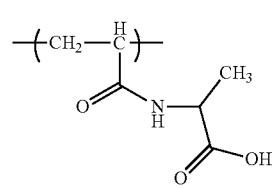
(H-24) 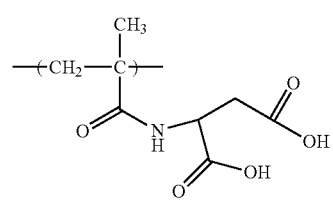
(H-25) 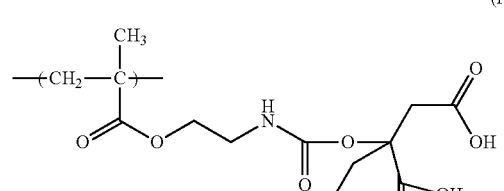
(H-26) 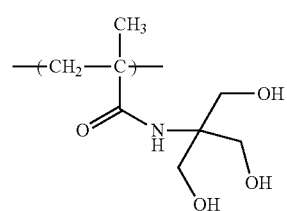
(H-27) 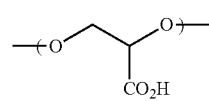
(H-28) 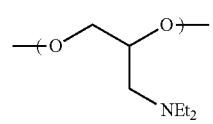
(H-29) 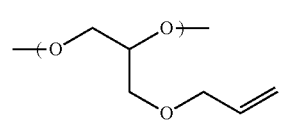
(H-30) 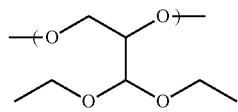
(H-31) 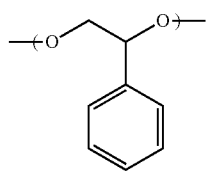
(H-32) 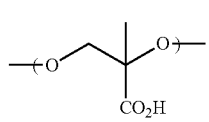
(H-33) 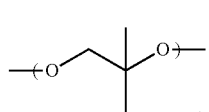
(H-34) 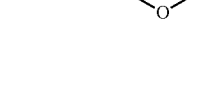
(H-35) 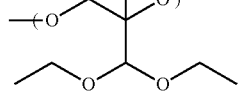
(H-36) 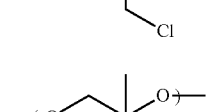
(H-37) 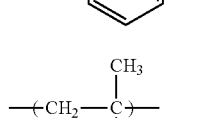
(H-38) 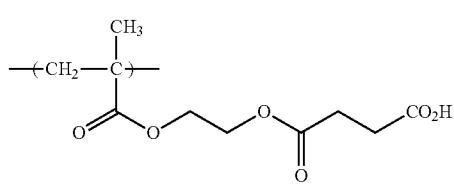
(H-39) 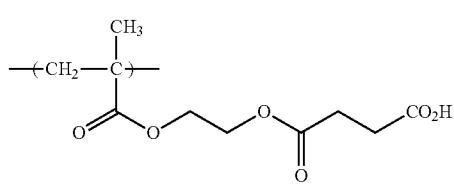

-continued

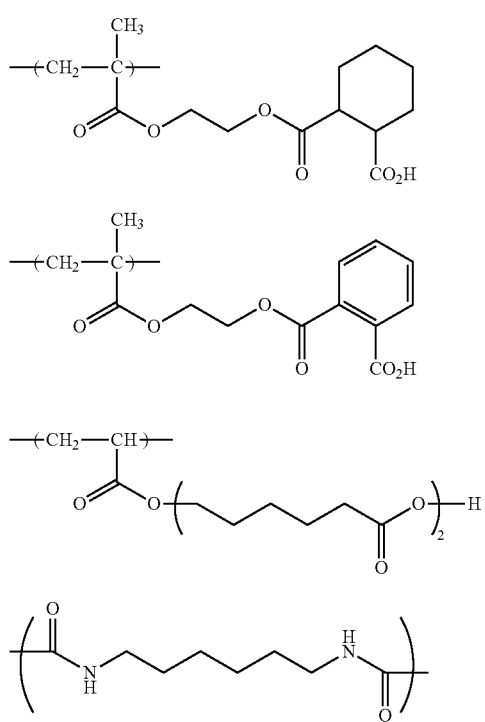

(H-40)
(H-41)
(H-42)
(H-43)

The weight-average molecular weight of the pigment multimer (A) is preferably 2,000 to 20,000, more preferably 3,000 to 15,000, and particularly preferably 4,000 to 10,000.

The weight-average molecular weight and the number-average molecular weight can be determined by gel permeation chromatography (GPC).

Moreover, a ratio [(Mw)/(Mn)] between the weight-average molecular weight (Mw) and the number average molecular weight (Mn) of the pigment multimer (A) is preferably 1.0 to 3.0, more preferably 1.6 to 2.5, and particularly preferably 1.6 to 2.0.

The glass transition temperature (Tg) of the pigment multimer (A) according to the present invention is preferably 50° C. or higher, and more preferably 100° C. or higher. Further, a 5% weight reduction temperature measured by a thermogravimetric analysis (TGA measurement) is preferably 120° C. or higher, more preferably 150° C. or higher, and still more preferably 200° C. or higher. Within this region, when the coloring composition of the present invention is applied to preparation of a color filter and the like, the change in concentration due to a heating process can be decreased.

In addition, the absorption coefficient (hereinafter described as $\in'$. $\in'=\in$/average molecular weight, unit: L/g·cm) per unit weight of the pigment multimer according to the present invention is preferably 30 or more, more preferably 60 or more, and still more preferably 100 or more. If the absorption coefficient is within this range, in the case where a color filter is manufactured using the coloring composition of the present invention, a color filter having excellent color reproducibility can be manufactured.

The molar absorption coefficient of the pigment multimer (A) used in the coloring composition of the present invention is preferably as high as possible from the viewpoint of coloring ability.

The reduced viscosity of the pigment multimer (A) used in the coloring composition of the present invention is preferably 4.0 to 10.0, more preferably 5.0 to 9.0, and still more preferably 6.0 to 7.0, from the viewpoint of color migration. The reduced viscosity can be measured by using, for example, an Ubbelohde type viscometer.

The pigment multimer (A) according to the present invention is preferably a compound which is dissolved in the following organic solvent.

Examples of the organic solvent include esters (for example, methyl 3-ethoxypropionate, ethyl 3-ethoxypropionate, ethyl lactate, butyl acetate, and methyl 3-methoxypropionate), ethers (for example, methyl cellosolve acetate, ethyl cellosolve acetate, propylene glycol monomethyl ether, and propylene glycol monomethyl ether acetate), ketones (methyl ethyl ketone, cyclohexanone, 2-heptanone, and 3-heptanone), and aromatic hydrocarbons (for example, toluene and xylene). The pigment multimer (A) dissolves in the amount of preferably 1% by mass to 50% by mass, more preferably 5% by mass to 40% by mass, and still more preferably 10% by mass to 30% by mass, with respect to these solvents. If the solubility is within this range, when the coloring composition of the present invention is applied to the manufacture of a color filter or the like, suitable coating surface properties can be obtained or reduction in concentration caused by elution after coating of other colors can be decreased.

In the coloring composition of the present invention, the pigment multimer (A) may be used alone or in combination of two or more kinds thereof. In the case of using two or more kinds, the total amount thereof preferably corresponds to the content which will be described later.

The content of the pigment multimer (A) in the coloring composition of the present invention is determined after consideration of its content ratio to a pigment (B) which will be described later.

The mass ratio of the pigment multimer to the pigment (pigment multimer (A)/pigment) is preferably 0.1 to 5, more preferably 0.2 to 2, and still more preferably 0.3 to 1.

<Coloring Composition>

Next, the coloring composition of the present invention will be described. The coloring composition of the present invention is used for formation of a colored layer of the color filter. The coloring composition used in the present invention preferably includes a curable compound (B) and a pigment (C). Examples of the curable compound (B) include a polymerizable compound and an alkali-soluble resin (including an alkali-soluble resin containing a polymerizable group), and the curable compound (B) is suitably selected according to the purpose or production method therefor. Further, the coloring composition of the present invention preferably includes a photopolymerization initiator (D).

For example, in the case of forming a colored layer by a photoresist, the coloring composition of the present invention is preferably a composition including the pigment multimer (A) of the present invention, the alkali-soluble resin as a curable compound, the pigment (C), and the photopolymerization initiator (D). Further, the coloring composition may include components such as a surfactant and a solvent.

In addition, in the case of forming a colored layer by dry etching, the coloring composition is preferably a composition including the pigment multimer (A) of the present invention, the polymerizable compound as a curable compound, the pigment (C), and the photopolymerization initiator (D). Further, the coloring composition may include components such as a surfactant and a solvent.

Details thereof will be described below.

<Polymerizable Compound (B)>

The coloring composition of the present invention contains a polymerizable compound.

Known polymerizable compounds which can be cross-linked by a radical, an acid, or heat can be used. Examples thereof include polymerizable compounds having an ethylenically unsaturated bond, a cyclic ether (epoxy or oxetane), methylol, or the like. From the viewpoint of sensitivity, the polymerizable compound is suitably selected from compounds having at least one and preferably two or more terminal ethylenically unsaturated bonds. Among these, polyfunctional polymerizable compounds having 4 or more functional groups are preferable, and polyfunctional polymerizable compounds having 5 or more functional groups are more preferable.

Such compound groups are widely known in the industrial field of the relevant art and can be used in the present invention without particular limitation. These may be in any type of chemical forms such as a monomer, a prepolymer, that is, a dimer, a trimer, an oligomer, mixture thereof, and a multimer thereof. The polymerizable compound in the present invention may be used alone or in combination of two or more kinds thereof.

More specifically, examples of the monomer and prepolymer include unsaturated carboxylic acids (for example, acrylic acid, methacrylic acid, itaconic acid, crotonic acid, isocrotonic acid, maleic acid, and the like) or esters thereof, amides, and multimers of these, and among these, an ester of unsaturated carboxylic acid and an aliphatic polyol compound, amides of unsaturated carboxylic acid and an aliphatic polyamine compound, and multimers of these are preferable. Moreover, products of an addition reaction between unsaturated carboxylic esters or amides having nucleophilic substituent such as a hydroxyl group, an amino group, or a mercapto group and monofunctional or polyfunctional isocyanates or epoxies, products of a dehydration condensation reaction between the unsaturated carboxylic esters or amides and a monofunctional or polyfunctional carboxylic acid, and the like are also suitably used. In addition, products of an addition reaction between unsaturated carboxylic esters or amides having an electrophilic substituent such as an isocyanate group or an epoxy group and monofunctional or polyfunctional alcohols, amines, or thiols, and products of a substitution reaction between unsaturated carboxylic esters or amides having an eliminatable substituent such as a halogen group or tosyloxy group and monofunctional or polyfunctional alcohols, amines, or thiols are also suitable. As other examples, instead of the above unsaturated carboxylic acid, vinyl benzene derivatives of unsaturated phosphonic acid, styrene, and the like and compound groups substituted with vinyl ether, allyl ether, or the like can also be used.

As these specific compounds, the compounds described in paragraph Nos. "0095" to "0108" of JP2009-288705A can also be suitably used in the present invention.

Moreover, as the polymerizable compound, a compound which has at least one addition-polymerizable ethylene group and has an ethylenically unsaturated group having a boiling point of 100° C. or higher under normal pressure is also preferable. Examples of the compound include a monofunctional acrylate or methacrylate such as polyethylene glycol mono(meth)acrylate, polypropylene glycol mono(meth)acrylate, and phenoxyethyl(meth)acrylate; a compound which is obtained by adding ethylene oxide or propylene oxide to a polyfunctional alcohol, and then (meth)acrylating the resultant, such as polyethylene glycol di(meth)acrylate, trimethylolethane tri(meth)acrylate, neopentyl glycol di(meth)acrylate, pentaerythritol tri(meth)acrylate, pentaerythritol tetra(meth)acrylate, dipentaerythritol penta(meth)acrylate, dipentaerythritol hexa(meth)acrylate, hexanediol(meth)acrylate, trimethylolpropane tri(acryloyloxypropyether, tri(acryloyloxyethyl)isocyanurate, glycerin, and trimethylolethane; the urethane(meth)acrylates described in JP1973-41708B (JP-S48-41708B), JP1975-6034B (JP-S50-6034B), and JP1976-37193A (JP-S51-37193A); the polyester acrylates described in JP1973-64183A (JP-S48-64183A), JP1974-43191B (JP-S49-43191B), and JP1977-30490B (JP-S52-30490B); a polyfunctional acrylate or methacrylate such as epoxy acrylate as a product of a reaction between an epoxy resin and a (meth)acrylic acid; and a mixture thereof.

Other examples thereof include a polyfunctional (meth)acrylate which is obtained by reacting a polyfunctional carboxylic acid with a compound having a cyclic ether group such as glycidyl(meth)acrylate, and an ethylenically unsaturated group.

Furthermore, as other preferred polymerizable compounds, the compounds having a fluorene ring and an ethylenically unsaturated group having 2 or more functional groups described in JP2010-160418A, JP2010-129825A, and JP4364216B, and a cardo resin can also be used.

Moreover, as the compound which has a boiling point of 100° C. or nigher under normal pressure and has at least one addition-polymerizable ethylenically unsaturated group, compounds described in paragraph Nos. "0254" to "0257" of JP2008-292970A are also suitable.

In addition to those above, radically polymerizable monomers represented by the following General Formulae (MO-1) to (MO-5) can also be used. Incidentally, in the formulae, in the case where T is an oxyalkylene group, the terminal at a carbon atom side binds to R.

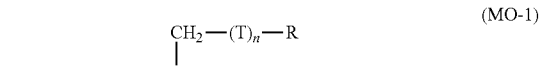

(MO-1)

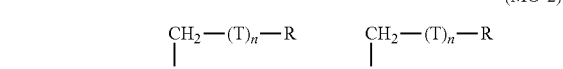

(MO-2)

(MO-3)

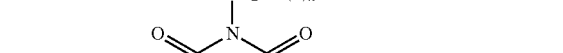

(MO-4)

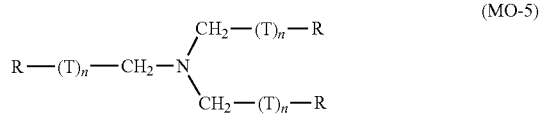

(MO-5)

-continued

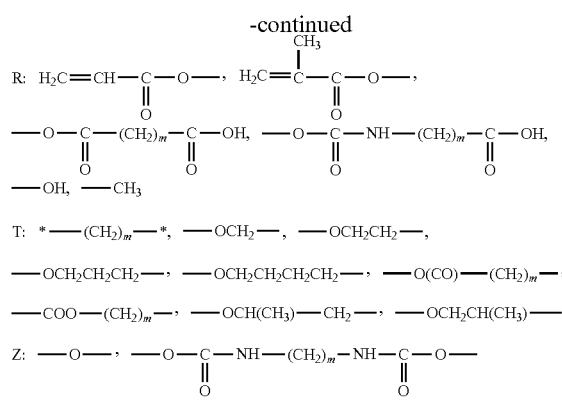

In General Formulae, n is 0 to 14, and m is 1 to 8. A plurality of R's and T's which are present in the same molecule may be the same as or different from each other.

In each of the polymerizable compounds represented by General Formulae (MO-1) to (MO-5), at least one of the plurality of R's represents a group represented by —OC(=O)CH=CH$_2$ or —OC(=O)C(CH$_3$)=CH$_2$.

As specific examples of the polymerizable compounds represented by General Formulae (MO-1) to (MO-5), the compounds described in paragraph Nos. "0248" to "0251" of JP2007-269779A can also be suitably used in the present invention.

In addition, a compound which is obtained by adding ethylene oxide or propylene oxide to the polyfunctional alcohol, which is described as General Formulae (1) and (2) in JP1998-62986A (JP-1110-62986A) together with the specific examples thereof, and then (meth)acrylated can also be used as the polymerizable compound.

Among these, as the polymerizable compound, dipentaerythritol triacrylate (KAYARAD D-330 as a commercially available product; manufactured by Nippon Kayaku Co., Ltd.), dipentaerythritol tetraacrylate (KAYARAD D-320 as a commercially available product; manufactured by Nippon Kayaku Co., Ltd.), dipentaerythritol penta(meth)acrylate (KAYARAD D-310 as a commercially available product; manufactured by Nippon Kayaku Co., Ltd.), dipentaerythritol hexa(meth)acrylate (KAYARAD DPHA as a commercially available product; manufactured by Nippon Kayaku. Co., Ltd.), and a structure in which ethylene glycol or a propylene glycol residue is interposed between these (meth)acryloyl groups are preferable. Oligomer types of these can also be used.

The polymerizable compound is a polyfunctional monomer and may have an acid group such as a carboxyl group, a sulfonic acid group, and a phosphoric acid group. If an ethylenic compound has an unreacted carboxyl group as in a case where the ethylene compound is a mixture described above, this compound can be used as is, but if desired, a hydroxyl group of the above ethylenic compound may be reacted with a non-aromatic carboxylic anhydride so as to introduce an acid group. In this case, specific examples of the non-aromatic carboxylic anhydride used include tetrahydrophthalic anhydride, alkylated tetrahydrophthalic anhydride, hexahydrophthalic anhydride, alkylated hexahydrophthalic anhydride, succinic anhydride, and maleic anhydride.

In the present invention, as a monomer having an acid group, preferable is a polyfunctional monomer which is an ester obtained between an aliphatic polyhydroxy compound and an unsaturated carboxylic acid and provides an acid group by reacting an unreacted hydroxyl group of the aliphatic polyhydroxy compound with a non-aromatic carboxylic anhydride. A monomer in which the aliphatic polyhydroxy compound in the ester is pentaerythritol and/or dipentaerythritol is particularly preferable. Examples of commercially available products thereof include M-510 and M-520, which are polybasic modified acryl oligomers manufactured by TOAGOSEI, CO., LTD.

These monomers may be used alone, but since it is difficult to use a single compound in production; two or more kinds thereof may be used as a mixture. Moreover, if desired, a polyfunctional monomer not having an acid group and a polyfunctional monomer having an acid group may be used in combination therewith as the monomer.

The acid value of the polyfunctional monomer having an acid group is preferably 0.1 mg KOH/g to 40 mg KOH/g, and particularly preferably 5 mg KOH/g to 30 mg KOH/g. If the acid value of the polyfunctional monomer is too low, the development solubility characteristics deteriorates. If the acid value is too high, difficulty is caused in the production and handleability, hence a photopolymerization performance deteriorates, which leads to deterioration of curability such as surface smoothness of pixels. Therefore, in the case where a combination of two or more kinds of polyfunctional monomers having different acid groups is used, or when a combination of polyfunctional monomers not having an acid group is used, it is preferable to adjust the acid value such that the acid groups as all the polyfunctional monomers fall within the above range.

Moreover, it is also a preferred embodiment that a polyfunctional monomer having a caprolactone structure is contained as a polymerizable monomer.

The polyfunctional monomer having a caprolactone structure is not particularly limited as long as it has a caprolactone structure in a molecule thereof, and examples thereof include ε-caprolactone-modified polyfunctional (meth)acrylates which are obtained by esterifying polyols such as trimethylolethane, ditrimethylolethane, trimethylolpropane, ditrimethylolpropane, pentaerythritol, dipentaerythritol, tripentaerythritol, glycerin, diglycerol, and trimethylolmelamine with (meth)acrylic acid and ε-caprolactone. Among these, a polyfunctional monomer having a caprolactone structure represented by the following General Formula (Z-1) is preferable.

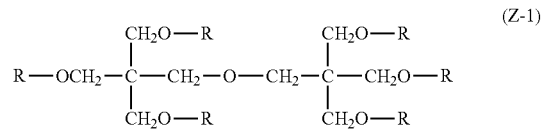

In General Formula (Z-1), all of six R's are a group represented by the following General Formula (L-2). Alternatively, one to five out of six R's are a group represented by the following General Formula (Z-2), and the remainder is a group represented by the following General Formula (Z-3).

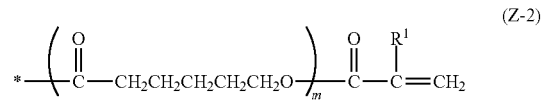

In General Formula (Z-2), $R^1$ represents a hydrogen atom or a methyl group, in represents a number 1 or 2, and "*" represents a direct bond.

(Z-3)

In General Formula (Z-3), $R^1$ represents a hydrogen atom or a methyl group, and "*" represents a direct bond.

The polyfunctional monomer having such a caprolactone structure is commercially available from Nippon Kayaku Co., Ltd., as a KANTARAD DPCA series, and examples thereof include DPCA-20 (a compound in which m=1 in Formulae (1) to (3), the number of the group represented by Formula (2)=2, and all of $R^1$'s are hydrogen atoms), DPCA-30 (a compound in which m=1 in the same Formulae, the number of the group represented by Formula (2)=3, and all of $R^1$'s are hydrogen atoms), DPCA-60 (a compound in which m=1 in the same Formulae, the number of the group represented by Formula (2)=6, and all of $R^1$'s are hydrogen atoms), and DPCA-120 (a compound in which m=2 in the same Formulae, the number of the group represented by Formula (2)=6, and all of $R^1$'s are hydrogen atoms).

In the present invention, the polyfunctional monomer having a caprolactone structure can be used alone or as a mixture of two or more kinds thereof.

Moreover, the specific monomer in the present invention is preferably at least one kind selected from a group of compounds represented by the following General Formula (Z-4) or (Z-5).

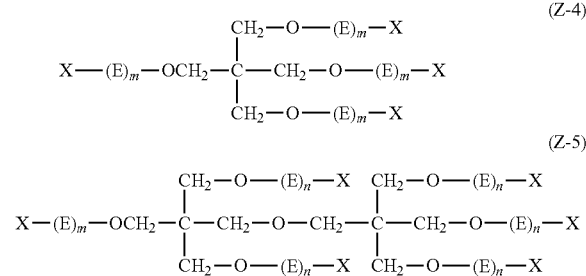

In General Formulae (Z-4) and (Z-5), E's each independently represent —$((CH_2)_yCH_2O)$— or —$((CH_2)_yCH(CH_3)O)$—, y's each independently represent an integer of 0 to 10, and X's each independently represent an acryloyl group, a methacryloyl group, a hydrogen atom, or a carboxyl group.

In General Formula (Z-4), the sum of the acryloyl group and the methacryloyl group is 3 or 4, m's each independently represent an integer of 0 to 10, and the sum of the respective m's is an integer of 0 to 40. Herein, in the case where the sum of the respective m's is 0, any one of X's is a carboxyl group.

In General Formula (ii), the sum of the acryloyl group and the methacryloyl group is 5 or 6, n's each independently represent an integer of 0 to 10, and the sum of the respective n's is an integer of 0 to 60. Herein, in the case where the sum of the respective n's is 0, one of X's is a carboxyl group.

In General Formula (Z-4), m is preferably an integer of 0 to 6, and more preferably an integer of 0 to 4. Further, the sum of the respective m's is preferably an integer of 2 to 40, more preferably an integer of 2 to 16, and particularly preferably an integer of 4 to 8.

In General Formula (Z-5), n is preferably an integer of 0 to 6, and more preferably an integer of 0 to 4.

Furthermore, the sum of the respective n's is preferably an integer of 3 to 60, more preferably an integer of 3 to 24, and particularly preferably an integer of 6 to 12.

In addition, —$((CH_2)_yCH_2O)$— or —$((CH_2)_yCH(CH_3)O)$— in General Formula (Z-4 or (Z-5) is preferably in the form in which the terminal at an oxygen atom side binds to X.

The compound represented by General Formula (Z-4) or (Z-5) may be used alone or in combination of two or more kinds thereof. In particular, a form in which all of six X's in General Formula (ii) are an acryloyl group is preferable.

Moreover, the total content of the compound represented by General Formula (Z-4) or (Z-5) in the polymerizable compound is preferably 20% by mass or more, and more preferably 50% by mass or more.

The compound represented by General Formula (Z-4) or (Z-5) can be synthesized by steps known in the related art, which includes a step of binding ethylene oxide or propylene oxide to pentaerythritol or dipentaerythritol by a ring-opening addition reaction to form a ring-opening skeleton, and a step of reacting, for example, (meth)acryloyl chloride to a terminal hydroxyl group of the ring-opening skeleton to introduce a (meth)acryloyl group. Since the respective steps are well-known, a person skilled in the art can easily synthesize the compound represented by General Formula (Z-4) or (Z-5).

Among the compounds represented by General Formula (Z-4) or (Z-5), a pentaerythritol derivative and/or a dipentaerythritol derivative is/are more preferable.

Specific examples of the compounds include compounds represented by the following Formulae (a) to (f) (hereinafter also referred to as "exemplary compounds (a) to (f)"). Among these, the exemplary compounds (a), (b), (e), and (f) are preferable.

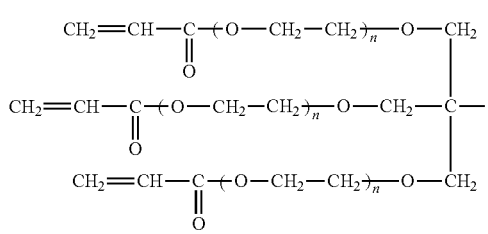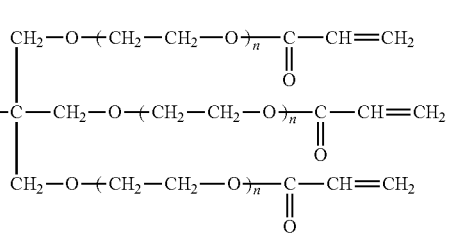

(a)

(the sum of the respective n's is 6)

-continued

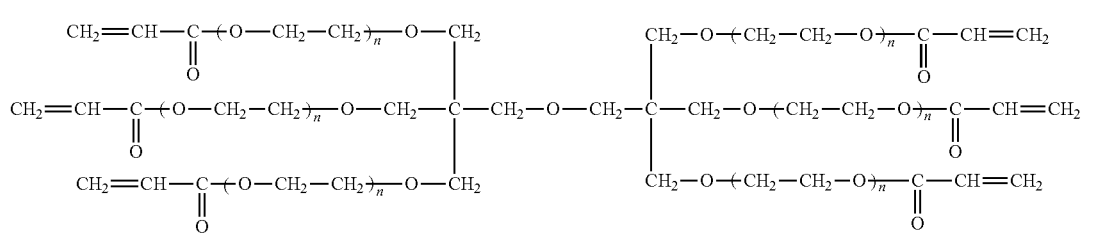

(b)

(the sum of the respective n's is 12)

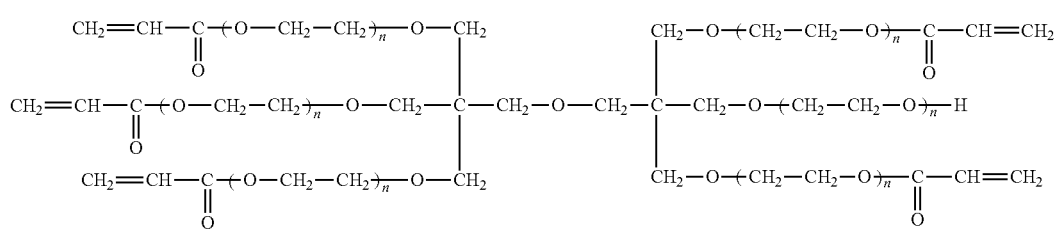

(c)

(the sum of the respective n's is 12)

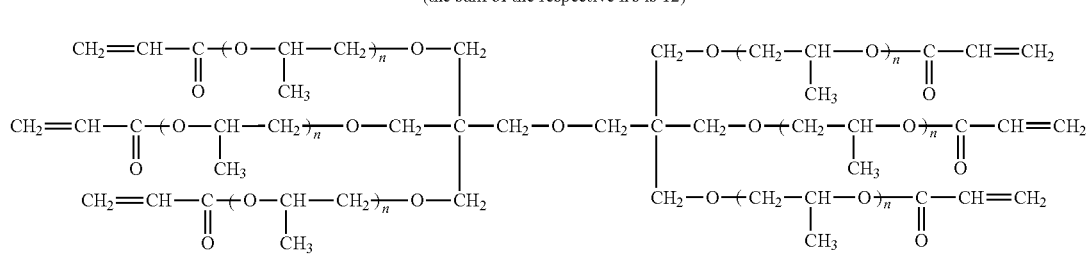

(d)

(the sum of the respective n's is 6)

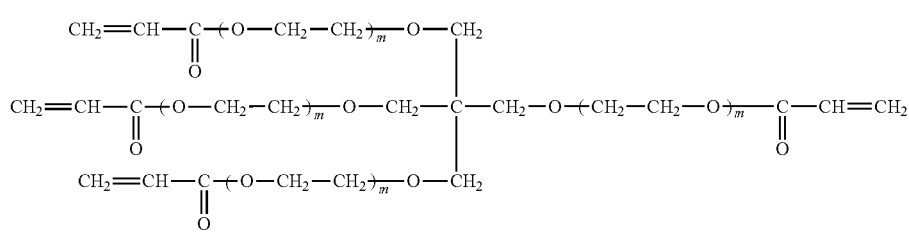

(e)

(the sum of the respective m's is 4)

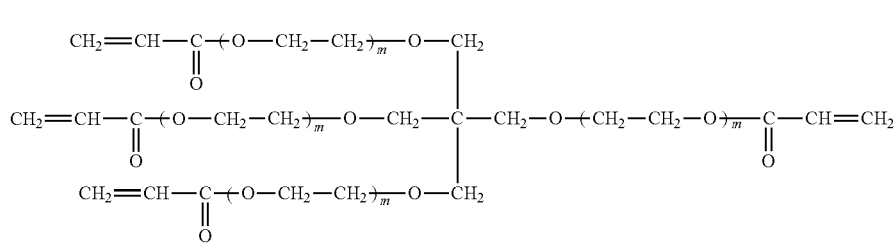

(f)

(the sum of the respective m's is 12)

Examples of commercially available products of the polymerizable compounds represented by General Formulae (Z-4) and (Z-5) include SR-494 which is a tetrafunctional acrylate having four ethyleneoxy chains, manufactured by Sartomer, and DPCA-60 which is a hexafunctional acrylate having six pentyleneoxy chains and TPA-330 which is a trifunctional acrylate having three isobutyleneoxy chains, manufactured by Nippon Kayaku Co., Ltd.

Moreover, as the polymerizable compounds, the urethane acrylates described in JP1973-41708B (JP-S48-41708B), JP1976-37193A (JP-S51-37193A), JP1990-32293B (JP-H02-32293B), and JP1990-16765B (JP-H02-16765B) or urethane compounds having an ethylene oxide-based skeleton described in JP1983-49860B (JP-S58-49860B), JP1981-17654B (JP-S56-17654B), JP1987-39417B (JP-S62-39417B), and JP1987-39418B (JP-S62-39418B) are also preferable. Furthermore, if addition-polymerizable compounds, which have an amino structure or a sulfide structure in a molecule and are described in JP1988-277653A (JP-S63-277653A), JP1988-260909A (JP-S63-260909A), and JP1989-105238A (JP-H01-105238A), are used as the polymerizable compounds, a curable composition which is extremely excellent in photosensitization speed can be obtained.

Examples of commercially available products of the polymerizable compounds include urethane oligomers UAS-10 and UAB-140 (manufactured by Sanyo-Kokusaku Pulp, Co., Ltd.), UA-7200 (manufactured by SHIN-NAKAMURA CHEMICAL CO., LTD.), DPHA-40H (manufactured by Nippon Kayaku Co., Ltd.), and UA-306H, UA-306T, UA-306I, AH-600. T-600, and AI-600 (manufactured by KYOEISHA CHEMICAL CO., LTD.).

As the cyclic ether (epoxy or oxethane), examples of a bisphenol A type epoxy resin, which have an epoxy group, include JER-827, JER-828, JER-834, JER-1001, JER-1002, JER-1003, JER-1055, JER-1007, JER-1009, and JER-1010 (all manufactured by Japan Epoxy Resins Co., Ltd.), and EPICLON 860, EPICLON 1050, EPICLON 1051, and EPICLON 1055 (all manufactured by DIC Corporation); examples of a bisphenol F type epoxy resin include JER-806, JER-807, JER-4004, JER-4005, JER-4007, and JER-4010 (all manufactured by Japan Epoxy Resins Co., Ltd.), EPICLON 830 and EPICLON 835 (both manufactured by DIC Corporation), and LCE-21 and RE-602S (all manufactured by Nippon Kayaku Co., Ltd.); examples of a phenol novolac type epoxy resin include JER-152, JER-154, JER-157 S70, and JER-157 S65 (all manufactured by Japan Epoxy Resins Co., Ltd.), and EPICLON N-770, and EPICLON N-775 (all manufactured by DIC Corporation); examples of a cresol novolac type epoxy resin include EPICLON N-660, EPICLON N-665, EPICLON N-670, EPICLON N-673, EPICLON N-680, EPICLON N-690, and EPICLON N-695 (all manufactured by DIC Corporation), and EOCN-1020 (all manufactured by Nippon Kayaku Co., Ltd.); and examples of an aliphatic epoxy resin include ADEKA RESIN EP-4080S, ADEKA RESIN EP-4085S, and ADEKA RESIN EP-4088S (all manufactured by ADEKA CORPORATION), CELLOXIDE 2021P, CELLOXIDE 2081, CELLOXIDE 2083, CELLOXIDE 2085, EHPE-3150 (a 1,2-epoxy-4-(2-oxiranyl)cyclohexane adduct of 2,2-bis(hydroxymethyl)-1-butanol), EPOLEAD PB 3600, and EPOLEAD PB 4700 (all manufactured by Daicel Chemical Industries, Ltd.), DENACOL EX-211L, EX-212L, EX-214L, EX-216L, EX-321L, and EX-850L (all manufactured by Nagase ChemteX Corporation), ADEKA RESIN EP-4000S, ADEKA RESIN EP-4003S, ADEKA RESIN EP-4010S, and ADEKA RESIN EP-4011S (all manufactured by ADEKA CORPORATION), NC-2000, NC-3000, NC-7300, XD-1000, EPPN-501, and EPPN-502 (all manufactured by ADEKA CORPORATION), and JER-1031S (manufactured by Japan Epoxy Resins Co., Ltd.). Such polymerizable compounds are suitable for a case of forming a pattern by a dry etching method.

Details of how to use these polymerizable compounds, such as the structure, whether the polymerizable compounds are used singly or used in combination thereof, and the amount of the polymerizable compounds added, can be arbitrarily set according to the designed final performance of the coloring composition. For example, from the viewpoint of sensitivity, a structure in which the content of an unsaturated group per molecule is large is preferable, and in many cases, it is preferable that the polymerizable compound has 2 or more functional groups. Moreover, from the viewpoint of enhancing the strength of a cured film formed of the coloring composition, it is preferable that the polymerizable compound has 3 or more functional groups. In addition, a method for adjusting both the sensitivity and the strength by using a combination of compounds which differ in the number of functional groups and have different polymerizable groups (for example, an acrylic ester, a methacrylic ester, a styrene-based compound, and a vinylether-based compound) is also effective. Further, it is preferable to use polymerizable compounds having 3 or more functional groups and differing in the length of an ethylene oxide chain since the developability of the coloring composition can be adjusted, and excellent pattern formability is obtained.

In addition, from the viewpoints of the compatibility with other components (for example, a photopolymerization initiator, a substance to be dispersed, and an alkali-soluble resin) contained in the coloring composition, and the dispersibility, how to select and use the polymerizable compound is an important factor. For example, if a low-purity compound is used or a combination of two or more kinds thereof is used, the compatibility can be improved in some cases. In addition, from the viewpoint of improving the adhesiveness of the composition to a hard surface of a support or the like, specific structures may be selected in some cases.

In the case where of the polymerizable compound is blended into the coloring composition of the present invention, the content thereof is preferably 0.1% by mass to 90% by mass, more preferably 1.0% by mass to 60% by mass, and particularly preferably 2.0% by mass to 40% by mass, with respect to the total solid contents of the coloring composition.

The composition of the present invention may include one kind or two or more kinds of polymerizable compound. In the case where the composition includes two or more kinds of polymerizable compound, the total amount thereof is preferably within the range.

<Pigment (C)>

It is preferable that the coloring composition of the present invention further contains a pigment (C).

As the pigment which is used in the present invention, various inorganic or organic pigments known in the related art can be used, and the organic pigments are preferably used. As the pigment, one having a high transmittance is preferable.

Examples of the inorganic pigment include black pigments such as carbon black and titanium black, metal compounds represented by a metal oxide, a metal complex salt, or the like, and specific examples thereof include metal oxides of iron, cobalt, aluminum, cadmium, lead, copper, titanium, magnesium, chromium, zinc, antimony, and the like, and complex oxides of the metals.

Examples of the organic pigment include:

C. I. Pigment Yellow 11, 24, 31, 53, 83, 93, 99, 108, 109, 110, 138, 139, 147, 150, 151, 154, 155, 167, 180, 185, 199;

C. I. Pigment Orange 36, 38, 43, 71;

C. I. Pigment Red 81, 105, 122, 149, 150, 155, 171, 175, 176, 177, 179, 209, 220, 224, 242, 254, 255, 264, 270;

C. I. Pigment Violet 19, 23, 32, 39;

C. I. Pigment Blue 1, 2, 15, 15:1, 15:3, 15:6, 16, 22, 60, 66;

C. I. Pigment Green 7, 36, 37, 58;

C. I. Pigment Brown 25, 28; and

C. I. Pigment Black 1.

Examples of the pigment which can be preferably used in the present invention include the following ones, but the present invention is not limited thereto:

C. I. Pigment Yellow 11, 24, 108, 109, 110, 138, 139, 150, 151, 154, 167, 180, 185, C. I. Pigment Orange 36, 71;

C. I. Pigment Red 122, 150, 171, 175, 177, 209, 224, 242, 254, 255, 264,

C. I. Pigment Violet 19, 23, 32,

C. I. Pigment Blue 15:1, 15:3, 15:6, 16, 22, 60, 66,

C. I. Pigment Green 7, 36, 37, 58, and

C. I. Pigment Black 1.

These organic pigments can be used alone or in various combinations for spectral adjustment or improvement of color purity.

In the case where the coloring composition of the present invention has a partial structure derived from a xanthene pigment, an azo dye or a squarylium pigment (preferably a partial structure derived from a xanthene pigment) as the aforementioned pigment multimer, it can be made into a red coloring composition by using a red coloring agent (preferably a red pigment) or a yellow coloring agent (preferably a yellow pigment) in combination therewith. The mass ratio of the aforementioned pigment multimer to the red coloring agent or yellow coloring agent is preferably 10:100 to 100:10.

Specific examples of the combination are shown below. For example, as a red pigment, an anthraquinone-based pigment, a perylene-based pigment, or a diketopyrrolopyrrole-based pigment can be used alone or as a mixture of at least one kind of these with a disazo-based yellow pigment, an isoindoline-based yellow pigment, a quinophthalone-based yellow pigment, or a perylene-based red pigment. Examples of the anthraquinone-based pigment include C. I. Pigment Red 177, examples of the perylene-based pigment include C. I. Pigment Red 155, and C. I. Pigment Red 224, and examples of the diketopyrrolopyrrole-based pigment include C. I. Pigment Red 254. In view of chromatic resolving properties, a mixture of the above pigment with C. I. Pigment Yellow 139 is preferable. The mass ratio between the red pigment and the yellow pigment is preferably 100:5 to 100:50. If the mass ratio is 100:4 or less, it is difficult to reduce the light transmittance at 400 nm to 500 nm, and if it is 100:51 or more, a dominant wavelength moves closer to a short wavelength, so a color separating power cannot be improved in some cases. In particular, the mass ratio is optimally in a range of 100:10 to 100:30. In addition, in the case of a combination of red pigments, the mass ratio can be adjusted according to the required spectrum.

In addition, as a green pigment, a halogenated phthalocyanine-based pigment can be used alone or as a mixture of this pigment with a disazo-based yellow pigment, a quinophthalone-based yellow pigment, an azomethine-based yellow pigment, or an isoindoline-based yellow pigment. As an example of such pigments, a mixture of C. I. Pigment Green 7, 36, or 37 with C. I. Pigment Yellow 83, C. I. Pigment Yellow 138, C. I. Pigment Yellow 139, C. I. Pigment Yellow 150, C. I. Pigment Yellow 180, or C. I. Pigment Yellow 185 is preferable. The mass ratio between the green pigment and the yellow pigment is preferably 100:5 to 100:150. The mass ratio is particularly preferably in a range of 100:30 to 100:120.

As a blue pigment, a phthalocyanine-based pigment can be used alone or as a mixture of this pigment with a dioxazine-based violet pigment. For example, a mixture of C. I. Pigment Blue 15:6 with C. I. Pigment Violet 23 is preferable. The mass ratio between the blue pigment and the violet pigment is preferably 100:0 to 100:100 and more preferably 100:10 or less.

Moreover, as a pigment for a black matrix, carbon, titanium black, iron oxide, or titanium oxide may be used alone or as a mixture, and a combination of carbon with titanium black is preferable. The mass ratio between carbon and titanium black is preferably in a range of 100:0 to 100:60.

For the coloring composition of the present invention, it is preferable to blend pigments other than black one, which is suitable for a blue pigment.

In the case where the coloring composition is used for a color filter, the primary particle size of the pigment is preferably 100 nm or less from the viewpoint of color unevenness or contrast. From the viewpoint of dispersion stability, the primary particle size is preferably 5 nm or more. The primary particle size of the pigment is more preferably 5 nm to 75 nm, still more preferably 5 nm to 55 nm, and particularly preferably 5 nm to 35 nm.

The primary particle size of the pigment can be measured by a known method such as electron microscopy.

Among these, the pigment is preferably a pigment selected from an anthraquinone pigment, a diketopyrrolopyrrole pigment, a phthalocyanine pigment, a quinophthalone pigment, an isoindoline pigment, an ozomethine pigment, and a dioxazine pigment. In particular, C. I. Pigment Red 177 (anthraquinone pigment), C. I. Pigment Red 254 (diketopyrrolopyrrole pigment), C. I. Pigment Green 7, 36, 58, C. I. Pigment Blue 15:6 (phthalocyanine pigment), C. I. Pigment Yellow 138 (quinophthalone pigment), C. I. Pigment Yellow 139, 185 (isoindoline pigments), C. I. Pigment Yellow 150 (azomethine pigment), and C. I. Pigment Violet 23 (dioxazine pigment) are particularly preferable.

The content of the pigment is preferably 10% by mass to 70% by mass, more preferably 20% by mass to 60% by mass, and still more preferably 25% by mass to 50% by mass, with respect to the total amount of components excluding a solvent, contained in the coloring composition.

The composition of the present invention may include one kind or two or more kinds of pigment. In the case where the composition includes two or more kinds of pigment, the total amount thereof is preferably within the range.

<Photopolymerization Initiator (D)>

From the viewpoint of further improving sensitivity, it is preferable that the coloring composition of the present invention contains a photopolymeriation initiator.

The photopolymerization initiator is not particularly limited as long as the photopolymerization initiator has a function of initiating polymerization of the polymerizable compound, and can be appropriately selected from known photopolymerization initiators. For example, photopolymerization initiators sensitive to light rays in a range from ultraviolet region to visible light are preferable. In addition, the photopolymerization initiator may be either an activator which interacts with a photo-excited sensitizer in any way and generates active radicals or an initiator which initiates cationic polymerization according to the type of monomer.

Furthermore, it is preferable that the photopolymerization initiator contains at least one kind of compound having at least a molar absorption coefficient of about 50 in a range of about 300 nm to 800 nm (more preferably 330 nm to 500 nm).

Examples of the photopolymerization initiator include halogenated hydrocarbon derivatives (for example, a derivative having a triazine skeleton, and a derivative having an oxadiazole skeleton), acyl phosphine compounds such as acyl phosphine oxide, oxime compounds such as hexaaryl biimidazole and oxime derivatives, organic peroxides, thio compounds, ketone compounds, aromatic onium salts, ketoxime ethers, aminoacetophenone compounds, and hydroxyacetophenone, and the oxime compounds are preferable.

Furthermore, from the viewpoint of exposure sensitivity, the compound is preferably a compound selected from a group consisting of a trihalomethyl triazine compound, a benzyl dimethyl ketal compound, an α-hydroxyketone compound, an α-aminoketone compound, an acyl phosphine compound, a phosphine oxide compound, a metallocene compound, an oxime compound, a triallyl imidazole dimer, an onium compound, a benzothiazole compound, a cyclobenzophenone compound, an acetophenone compound and a derivative thereof, a cyclopentadiene-benzene-iron complex and a salt thereof a halomethyl oxadiazole compound, and a 3-aryl-substituted coumarin compound.

The compound is more preferably a trihalomethyl triazine compound, an α-aminoketone compound, an acyl phosphine compound, a phosphine oxide compound, an oxime compound, a triallylimidazole dinner, a triarylimidazole compound, a benzoimidazole compound, an onium compound, a benzophenone compound, or an acetophenone compound, and particularly preferably at least one kind of compound selected from a group consisting of a trihalomethyl triazine compound, an α-aminoketone compound, an oxime compound, a triallylimidazole compound, a benzophenone compound, a triarylimidazole compound, and a benzoimidazole compound. Further, the triarylimidazole compound may be a mixture thereof with benzoimidazole.

Specifically, the trihalomethyltriazine compound is exemplified as follows. Incidentally, Ph is a phenyl group.

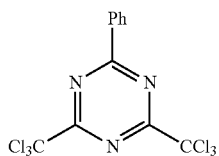

As the triarylimidazole compound and the benzoimidazole compound, the following compounds are exemplified.

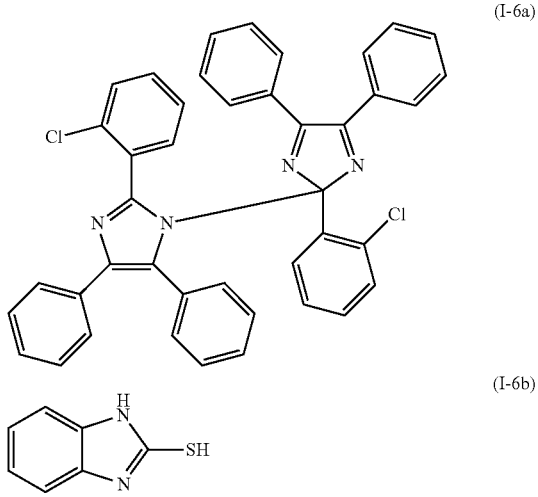

As the trihalomethyltriazine compound, a commercially available product can also be used, and for example, TAZ-107 (manufactured by Midori Kagaku Co., Ltd.) can also be used.

In particular, in the case where the coloring composition of the present invention is used for the manufacture of a color filter for a solid-state imaging element, a fine pattern needs to be formed in a sharp shape. Accordingly, it is important that the composition has curability and is developed without residues in an unexposed area. From this viewpoint, an oxime compound is particularly preferable as a polymerization initiator. In particular, in the case where a fine pattern is formed in the solid-state imaging element, stepper exposure is used for exposure for curing. However, the exposure machine used at this time is damaged by halogen in some cases, so it is necessary to reduce the amount of a polymerization initiator added. In consideration of this point, in order to form a fine pattern as in a solid-state imaging element, it is particularly preferable to use an oxime compound as the photopolymerization initiator (D).

Examples of the halogenated hydrocarbon compound having a triazine skeleton include the compounds described in Wakabayashi, et al., Bull. Chem. Soc. Japan, 42, 2924 (1969), the compounds described in UK 1388492B, the compounds described in JP1978-133428A (JP-S53-133428A), the compounds described in GE3337024B, the compound described in F. C. Schaefer, et al., J. Org. Chem.; 29, 1527 (1964), the compounds described in JP1987-58241A (JP-S62-58241A), the compounds described in JP1993-281728A (JP-H05-281728A), the compounds described in JP1993-34920A (JP-H05-34920A), and the compounds described in U.S. Pat. No. 4,212,976A, in particular, the compounds described in paragraph No. "0075" of JP2013-077009A.

In addition, as photopolymerization initiators other than those above, acridine derivatives are exemplified. Specific examples thereof include the compound described in paragraph No. "0076" of JP2013-077009A, the contents of which are incorporated herein.

Examples of the ketone compound include the compound described in paragraph No. "0077" of JP2013-077009A, the contents of which are incorporated herein, As the photopolymerization initiator, a hydroxyacetophenone compound, an aminoacetophenone compound, and an acyl phosphine compound can also be suitably used. More specifically, for example, the aminoacetophenone-based initiator described in JP1998-291969A (JP-H10-291969A), and the acyl phosphine oxide-based initiator described in JP4225898B can also be used, As the hydroxyacetophenone-based initiator, IRGACURE (registered trademark)-184, DAROCUR (registered trademark)-1173, IRGACURE (registered trademark)-500, IRGACURE (registered trademark)-2959, and IRGACURE (registered trademark)-127 (product names, all manufactured by BASF) can be used. As the aminoacetophenone-based initiator, IRGACURE (registered trademark)-907, IRGACURE (registered trademark)-369, and IRGACURE (registered trademark)-379 (product names, all manufactured by BASF) which are commercially available products can be used. In addition, as the aminoacetophenone-based initiator, the compound described in JP2009-191179A, of which an absorption wavelength matches a light source of a long wavelength of 365 nm, 405 nm, or the like, can be used. Moreover, as the acyl phosphine-based initiator, IRGACURE (registered trademark)-819 or DAROCUR (registered trademark)-TPO (product name, both manufactured by BASF) which are commercially available products can be used.

Examples of the photopolymerization initiator more preferably include oxime compounds. As specific examples of the oxime compounds, the compound described in JP2001-233842A, the compound described in JP2000-80068A, or the compound described in JP2006-342166A can be used.

Examples of the oxime compound such as an oxime derivative, which is suitably used as the photopolymerization initiator in the present invention, include 3-benzoyloxyiminobutan-2-one, 3-acetoxyiminobutan-2-one, 3-propionyloxyiminobutan-2-one, 2-acetoxyiminopentan-3-one, 2-acetoxymino-1-phenylpropan-1-one, 2-benzoyloxymino- 1-phenylpropan-1-one, 3-(4-toluenesulfonyloxy)iminobutan-2-one, and 2-ethoxycarbonyloxyimino-1-phenylpropan-1-one.

Examples of the oxime compound include the compounds described in J. C. S. Perkin II (1979), pp. 1653-1660, J. C. S. Perkin II (1979), pp. 156-162, Journal of Photopolymer Science and Technology (1995), pp. 202-232, and JP2000-66385A; and the compounds described respectively in JP2000-80068A, JP2004-534797A, and JP2006-342166A.

As the commercially available product, IRGACURE (registered trademark)-OXE01 (manufactured by BASF) and IRGACURE (registered trademark)-OXE02 (manufactured by BASF) are also suitably used.

Furthermore, as the oxime compound, TRONLY TR-PBG-304, TRONLY TR-PBG-309, and TRONLY TR-PBG-305 (manufactured by Changzhou Tronly New Electronic Materials CO., LTD.), and ADEKA, ARKLS NCI-831, and ADEKA ARKLS NCI-930 (manufactured by ADEKA Corporation) are also suitably used.

Furthermore, as oxime compounds other than the above, the compound described in JP2009-519904A in which oxime is linked to an N-position of carbazole, the compound described in U.S. Pat. No. 7,626,957B in which a hetero-substituent is introduced into a benzophenone moiety, the compounds described in JP2010-15025A and US2009/292039A in which a nitro group is introduced into a pigment moiety, the ketoxine compound described in WO2009/131189A, the compound described in U.S. Pat. No. 7,556,910B which contains a triazine skeleton and an oxime skeleton in the same molecule, the compound described in JP2009-221114A, which has maximum absorption at 405 nm and has excellent sensitivity to a light source of a g-ray, and the like may be used.

In addition, the cyclic oxime compounds described in JP2007-231000A and JP2007-322744A can also be suitably used. Among the cyclic oxime compounds, the cyclic oxime compounds ring-fused to a carbazole pigment, which are described in JP2010-32985A and JP2010-185072A, are preferable from the viewpoint of high sensitivity since these compounds have high light absorptivity.

Furthermore, the compound described in JP2009-242469A, which is an oxime compound having an unsaturated bond in a specific moiety, can also be suitably used since this compound makes it possible to improve sensitivity by reproducing active radicals from polymerization-inactive radicals.

Particularly preferred examples of the oxime compounds include the oxime compound having a specific substituent described in JP2007-269779A and the oxime compound having a thioaryl group described in JP2009-191061A.

Specifically, the oxime compound which is a photopolymerization initiator is preferably a compound represented by the following General Formula (OX-1). Incidentally, the compound may be an oxime compound in which an N—O bond of oxime forms an (E) isomer, an oxime compound in which the N—O bond forms a (Z) isomer, or a mixture in which the N—O bond forms a mixture of an (E) isomer and a (Z) isomer.

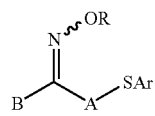

(OX-1)

In General Formula (OX-1), R and B each independently represent a monovalent substituent, A represents a divalent organic group, and Ar represents an aryl group.

In General Formula (OX-1), the monovalent substituent represented by R is preferably a monovalent non-metal atomic group.

Examples of the monovalent non-metal atomic group include an alkyl group, an aryl group, an acyl group, an alkoxycarbonyl group, an aryloxycarbonyl group, a heterocyclic group, an alkylthiocarbonyl group, and an arylthiocarbonyl group. Further, these groups may have one or more substituents. Moreover, the aforementioned substituents may be further substituted with other substituents.

Examples of the substituents include a halogen atom, an aryloxy group, an alkoxycarbonyl or aryloxycarbonyl group, an acyloxy group, an acyl group, an alkyl group, and an aryl group.

The alkyl group is preferably an alkyl group having 1 to 30 carbon atoms, and specific examples thereof include a methyl group, an ethyl group, a propyl group, a butyl group, a hexyl group, an octyl group, a decyl group, a dodecyl group, an octadecyl group, an isopropyl group, an isobutyl group, a sec-butyl group, a tert-butyl group, a 1-ethylpentyl group, a cyclonentyl group, a cyclohexyl group, a trifluoromethyl group, a 2-ethylhexyl group, a phenacyl group, a 1-naphthoylmethyl group, a 2-naphthoylmethyl group, a 4-methylsulfanylphenacyl group, 4-phenylsulfanylphenacyl group, a 4-dimethylaminophenacyl group, a 4-cyanophenacyl group, a 4-methylphenacyl group, a 2-methylphenacyl group, a 3-fluorophenacyl group, a 3-trifluoromethylphenacyl group, and a 3-nitrophenacyl group.

The aryl group is preferably an aryl group having 6 to 30 carbon atoms, and specific examples thereof include, a phenyl group, a biphenyl group, a 1-naphthyl group, a 2-naphthyl group, a 9-anthryl group, a 9-phenanthryl group, a 1-pyrenyl group, a 5-naphthacenyl group, a 1-indenyl group, a 2-azulenyl group, a 9-fluorenyl group, a terphenyl group, an quaterphenyl group, an o-tolyl group, an m-tolyl group, a p-tolyl group, a xylyl group, an o-cumenyl group, an m-cumenyl group, a p-cumenyl group, a mesityl group, a pentalenyl group, a binaphthalenyl group, a ternaphthalenyl group, a quaternaphthalenyl group, a heptalenyl group, a biphenylenyl group, an indacenyl group, a fluoranthenyl group, an acenaphthylenyl group, an aceanthrylenyl group, a phenalenyl group, a fluorenyl group, an anthryl group, a bianthracenyl group, a teranthracenyl group, a quateranthracenyl group, an anthraquinolyl group, a phenanthryl group, a triphenylenyl group, a pyrenyl group, a chrysenyl group, a naphthacenyl group, a pleiadenyl group, a picenyl group, a perylenyl group, a pentaphenyl group, a pentacenyl group, a tetraphenylenyl group, a hexanhenyl group, a hexacenyl group, a rubicenyl group, a coronenyl group, a trinaphthylenyl group, a heptaphenyl group, a heptacenyl group, a pyranthrenyl group, and an ovalenyl group.

The acyl group is preferably an acyl group having 2 to 20 carbon atoms, and specific examples thereof include an acetyl group, a propanoyl group, a butanoyl group, a trifluoroacetyl group, a pentanoyl group, a benzoyl group, a 1-naphthoyl group, a 2-naphthoyl group, a 4-methylsulfanythenzoyl group, a 4-phenylsulfanylbenzoyl group, a 4-dimethylaminobenzoyl group, a 4-diethylaminobenzoyl group, a 2-chlorobenzoyl group, a 2-methylbenzoyl group, a 2-methoxybenzoyl group, a 2-butoxybenzoyl group, a 3-chlorobenzoyl group, a 3-trifluoromethylbenzoyl group, a 3-cyanobenzoyl group, a 3-nitrobenzoyl group, a 4-fluorobenzoyl group, a 4-cyanobenzoyl group, and a 4-methoxybenzoyl group.

The alkoxycarbonyl group is preferably an alkoxycarbonyl group having 2 to 20 carbon atoms, and specific examples thereof include a methoxycarbonyl group, an ethoxycarbonyl group, a propoxycarbonyl group, a butoxycarbonyl group, a hexyloxycarbonyl group, an octyloxycarbonyl group, a decyloxycarbonyl group, an octadecyloxycarbonyl group, and a trifluoromethyloxycarbanyl group.

Specific examples of the aryloxycarbonyl group include a phenoxycarbonyl group, a 1-naphthyloxycarbonyl group, a 2-naphthyloxycarbonyl group, a 4-methylsulfanylphenyloxycarbonyl group, a 4-phenylsulfanylphenyloxycarbonyl group, a 4-dimethylaminophenyloxycarbonyl group, a 4-diethylaminophenyloxycarbonyl group, a 2-chlorophenyloxycarbonyl group, a 2-methylphenyloxycarbonyl group, a 2-methoxyphenyloxycarbonyl group, a 2-butoxyphenyloxycarbonyl group, a 3-chlorophenyloxycarbonyl group, a 3-trifluoromethylphenyloxycarbonyl group, a 3-cyanophenyloxycarbonyl group, a 3-nitrophenyloxycarbonyl group, a 4-fluorophenyloxycarbonyl group, a 4-cyanophenyloxycarbonyl group, and 4-methoxyphenyloxycarbonyl group.

As the heterocyclic group, an aromatic or aliphatic heterocycle having a nitrogen atom, an oxygen atom, a sulfur atom, or a phosphorus atom is preferable.

Specific examples of the heterocyclic group include a thienyl group, a benzo[b]thienyl group, a naphtho[2,3-b] thienyl group, a thianthrenyl group, a furyl group, a pyranyl group, an isobenzofuranyl group, a chromenyl group, a xanthenyl group, a phenoxathiinyl group, a 2H-pyrrolyl group, a pyrrolyl group, an imidazolyl group, a pyrazolyl group, a pyridyl group, a pyrazinyl group, a pyrimidinyl group, a pyridazinyl group, an indolizinyl group, an isoindolyl group, a 3H-indolyl group, an indolyl group, a 1H-indazolyl group, a purinyl group, a 4H-quinolizinyl group, an isoquinolyl group, a quinolyl group, a phthalazinyl group, a naplithyridinyl group, a quinoxalinyl group, a quinazolinyl group, a cinnolinyl group, a pteridinyl group, a 4aH-carbazolyl group, a carbazolyl group, a β-carbolinyl group, a phenanthridinyl group, an acridinyl group, a perimidinyl group, a phenanthrolinyl group, a phenazinyl group, a phenarsazinyl group, an isothiazolyl group, a phenothiazinyl group, an isoxazolyl group, a furazanyl group, a phenoxazinyl group, an isochromanyl group, a chromanyl group, a pyrrolidinyl group, a pyrrolinyl group, an imidazolidinyl group, an imidazolinyl group, a pyrazolidinyl group, a pyrazolinyl group, a piperidyl group, a piperazinyl group, an indolinyl group, an isoindolinyl group, a quinuclidinyl group, a morpholinyl group, and a thioxantolyl group.

Specific examples of the alkylthiocarbanyl group include a methylthiocarbonyl group, a propylthiocarbonyl group, a butylthiocarbonyl group, a hexylthiocarbonyl group, an octylthiocarbonyl group, a decylthiocarbonyl group, an octadecylthiocarbonyl group, and a trifluoromethylthiocarbonyl group.

Specific examples of the arylthiocarbonyl group include a 1-naphthylthiocarbonyl group, a 2-naphthylthiocarbonyl group, a 4-methylsulfanylphenylthiocarbonyl group, a 4-phenylsulfanylphenylthiocarbonyl group, a 4-dimethylaminophenylthiocarbonyl group, a 4-diethylaminophenylthiocarbonyl group, a 2-chlorophenylthiocarbonyl group, a 2-methylphenylthiocarbonyl group, a 2-methoxyphenylthiocarbonyl group, a 2-butoxyphenylthiocarbonyl group, a 3-chlorophenylthiocarbonyl group, a 3-trifluoromethylphenylthio carbonyl group, a 3-cyanophenylthiocarbonyl group, a 3-nitrophenylthiocarbonyl group, a 4-fluorophenylthiocarbony group, a 4-cyanophenylthiocarbonyl group, and a 4-methoxyphenylthiocarbonyl group.

In General Formula (OX-1), the monovalent substituent represented by B represents an aryl group, a heterocyclic group, an arylcarbonyl group, or a heterocyclic carbonyl group. These groups may have one or more substituents, and examples of the substituents include the aforementioned substituents. In addition, the aforementioned substituents may be further substituted with other substituents.

Among these, the structure shown below is particularly preferable.

In the following structures, Y, X, and n have the same definitions as Y X, and n, respectively, in General Formula (OX-2) which will be described later, and the preferred examples thereof are also the same.

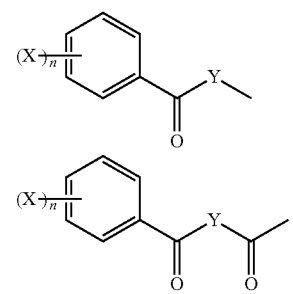

In Formula (OX-1), examples of the divalent organic group represented by A include an alkylene group having 1 to 12 carbon atoms, a cycloalkylene group, and an alkynylene group, and these groups may have one or more substituents. Examples of the substituents include the aforementioned substituents. Further, the aforementioned substituents may further substituted with other substituents.

Among these, as A in Formula (OX-1), from the viewpoints of improving sensitivity and inhibiting coloring caused by elapse of time during heating, an unsubstituted alkylene group, an alkylene group substituted with an alkyl group (for example, a methyl group, an ethyl group, a tert-butyl group, and a dodecyl group), an alkylene group substituted with an alkenyl group (for example, a vinyl group and an allyl group), and an alkylene group substituted with an aryl group (for example, a phenyl group, a p-tolyl group, a xylyl group, a cumenyl group, a naphthyl group, an anthryl group, a phenanthryl group, and a styryl group) are preferable.

In Formula (OX-1), the aryl group represented by Ar is preferably an aryl group having 6 to 30 carbon atoms, and may have a substituent. Examples of the substituent include the same ones as the substituents introduced into the substituted aryl groups, which are exemplified above as specific examples of the aryl group which may have a substituent.

Among these, from the viewpoints of improving sensitivity and inhibiting coloration caused by elapse of time during heating, a substituted or unsubstituted phenyl group is preferable.

In Formula (OX-1), a structure "SAr" formed of Ar and S adjacent thereto in Formula (OX-1) is preferably the following structure from the viewpoints of sensitivity. Incidentally, Me represents a methyl group, and Et represents an ethyl group.

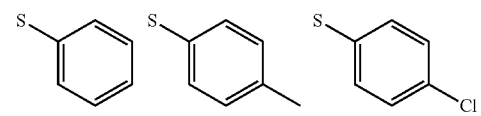

-continued

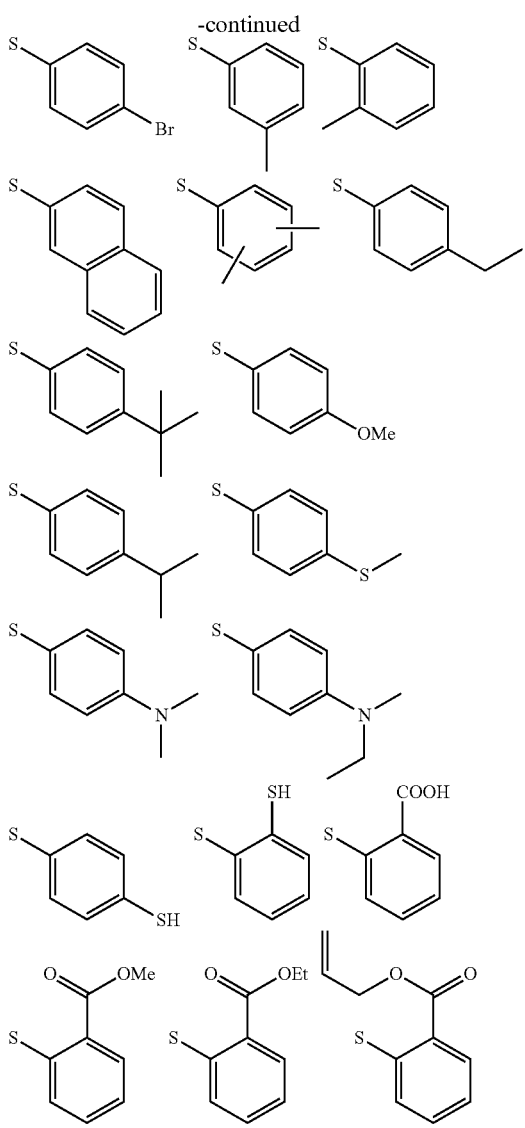

The oxime compound is preferably a compound represented by the following General Formula (OX-2).

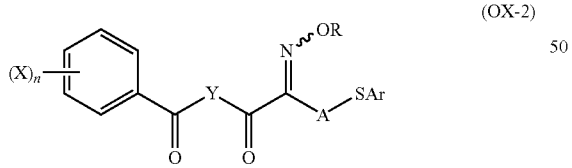

(OX-2)

In General Formula (OX-2), R and X each independently represent a monovalent substituent, A and Y each independently represent a divalent organic group, Ar represents an aryl group, and n represents an integer of 0 to 5. R, A, and Ar in General Formula (OX-2) have the same definitions as R, A, and Ar, respectively, in General Formula (OX-1), and the preferred examples thereof are also the same.

Examples of the monovalent substituent represented by X in General Formula (OX-2) include an alkyl group, an aryl group, an alkoxy group, an aryloxy group, an acyloxy group, an acyl group, an alkoxycarbonyl group, an amino group, a heterocyclic group, and a halogen atom. These groups may have one or more substituents, and examples of the substituents include the aforementioned substituents. Moreover, the aforementioned substituents may be further substituted with other substituents.

Among these, from the viewpoints of improving solvent solubility and absorption efficiency in a long-wavelength region, X in General Formula (OX-2) is preferably an alkyl group.

Furthermore, n in Formula (2) represents an integer of 0 to 5 and preferably represents an integer of 0 to 2.

Examples of the divalent organic group represented by Y in General Formula (OX-2) include the following structures, in the following groups, "*" represents a binding position to a carbon atom adjacent to Y in Formula (OX-2).

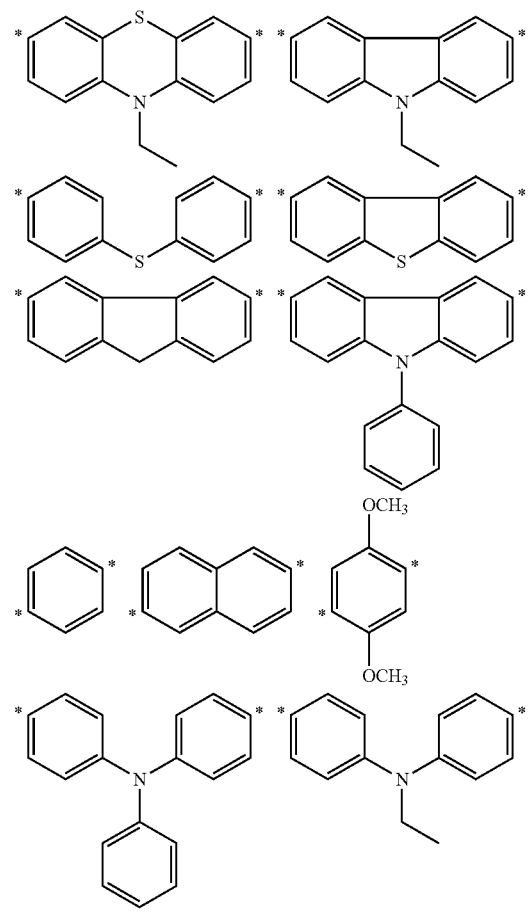

Among these, from the viewpoints of improving sensitivity, the following structures are preferable.

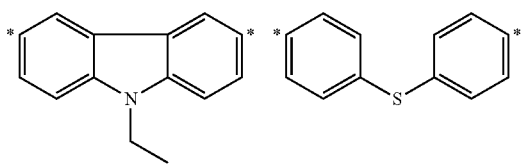

Moreover, the oxime compound is preferably a compound represented by the following General Formula (OX-3) or (OX-4).

(OX-3)

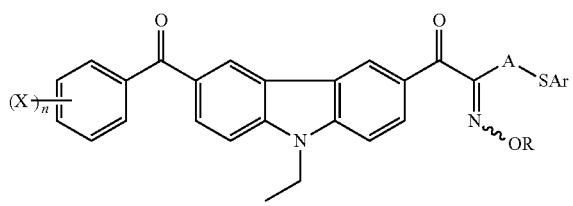

(OX-4)

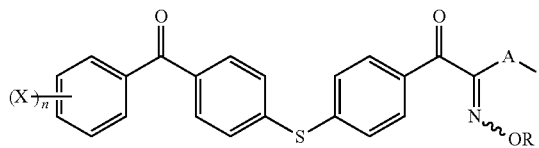

In General Formula (OX-3) or (OX-4), R and X each independently represent a monovalent substituent, A represents a divalent organic group, Ar represents an aryl group, and n represents an integer of 0 to 5.

R, X, A, Ar, and n in General Formula (OX-3) or (OX-4) have the same definitions as R, X, A, Ar, and n, respectively, in General Formula (OX-2), and the preferred examples thereof are also the same.

Specific examples (C-4) to (C-13) of the oxime compound which are preferably used are shown below, but the present invention is not limited thereto.

(C-4)

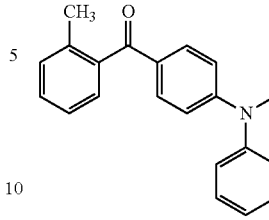

(C-5)

(C-6)

(C-7)

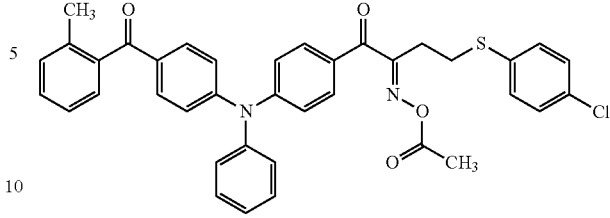

(C-8)

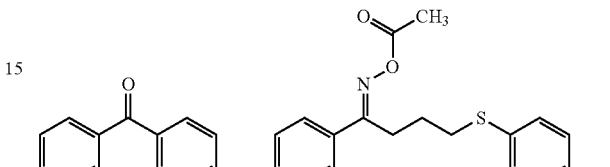

(C-9)

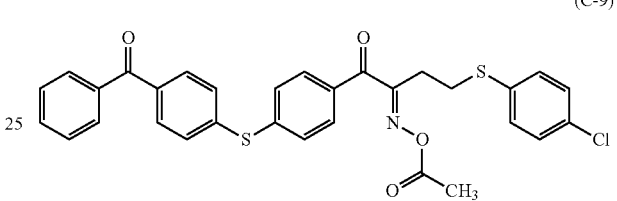

(C-10)

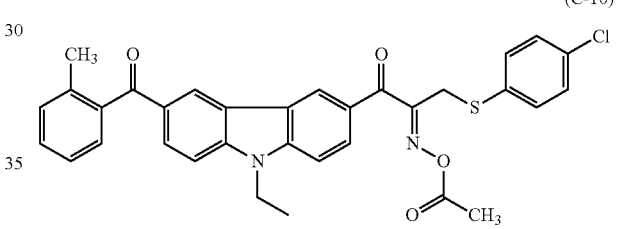

(C-11)

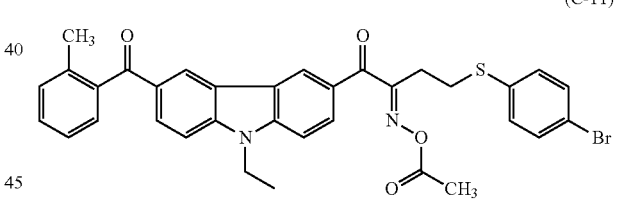

(C-12)

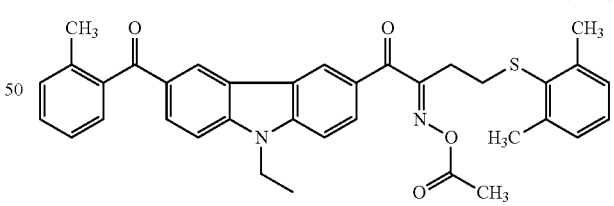

(C-13)

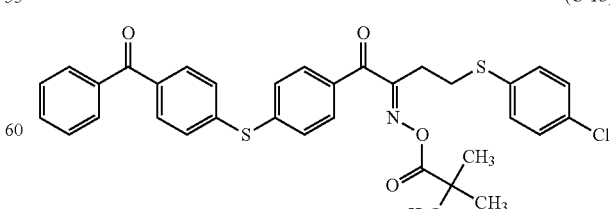

The oxime compound has a maximum absorption wavelength in a wavelength region of 350 nm to 500 nm and preferably has an absorption wavelength in a wavelength region of 360 nm to 480 nm, and an oxime compound showing a high absorbance at 365 nm and 455 nm is particularly preferable.

From the viewpoint of sensitivity, the molar absorption coefficient at 365 nm or 405 nm of the oxime compound is preferably 1,000 to 300,000, and more preferably 2,000 to 300,000, and particularly preferably 5,000 to 200,000.

The molar absorption coefficient of the compound can be measured using a known method, but specifically, it is preferable to measure the molar absorption coefficient by means of, for example, a UV-visible spectrophotometer (Carry-5 spectrophotometer manufactured by Varian) by using an ethyl acetate solvent at a concentration of 0.01 g/L.

In the case where the coloring composition of the present invention contains the photopolymerization initiator (D), the content of the photopolymerization initiator is preferably from 0.1% by mass to 50% by mass, more preferably from 0.5% by mass to 30% by mass, and still more preferably from 1% by mass to 20% by mass, with respect to the total solid contents of the coloring composition. Within this range, improved sensitivity and pattern formability are obtained.

The composition of the present invention may include one kind or two or more kinds of photopolymerization initiator. In the case where the composition includes two or more kinds of the photopolymerization initiator, the total amount thereof is preferably within the range.

<Pigment Dispersant>

In the case where the coloring composition of the present invention has a pigment, a pigment dispersant cart be used in combination with other components, as desired.

Examples of the pigment dispersant which can be used in the present invention include polymer dispersants [for example, a polyamide amine and a salt thereof, a polycarboxylic acid and a salt thereof, a high-molecular-weight unsaturated acid ester, a modified polyurethane, a modified polyester, a modified poly(meth)acrylate, a (meth)acrylic copolymer, and a naphthalene sulfonate formalin condensate], surfactants such as a polyoxyethylene alkyl phosphoric ester, a polyoxyethylene alkylamine, and an alkanolamine; and pigment derivatives.

The polymer dispersants can be further classified into straight-chain polymers, terminal-modified polymers, graft polymers, and block polymers, according to the structure.

Examples of the terminal-modified polymers which has a moiety anchored to the pigment surface include a polymer having a phosphoric acid group in the terminal as described in JP1991-112992A (JP-H03-112992A), JP2003-533455A, and the like, a polymer having a sulfonic acid group in the terminal as described in JP2002-273191A, a polymer having a partial skeleton or a heterocycle of an organic pigment as described in JP1997-77994A (JP-H09-77994A), and the like. Moreover, a polymer obtained by introducing two or more moieties (acid groups, basic groups, partial skeletons of an organic pigment, heterocycles, or the like) anchored to the pigment surface into a polymer terminal as described in JP2007-277514A is also preferable since this polymer is excellent in dispersion stability.

Examples of the graft polymers having a moiety anchored to the pigment surface include polyester-based dispersant and the like, and specific examples thereof include a product of a reaction between a poly(lower alkylenimine) and a polyester, which is described JP1979-37082A (JP-S54-37082A), JP1996-507960A (JP-H08-507960A), JP2009-258668A, and the like, a product of a reaction between a polyallylamine and a polyester, which is described in JP1997-169821A (JP-H09-169821A) and the like, a copolymer of a macromonomer and a nitrogen atom monomer, which is described in JP1998-339949A (JP-H10-339949A), JP2004-37986A, WO2010/110491A, and the like, a graft polymer having a partial skeleton or a heterocycle of an organic pigment, which is described in JP2003-238837A, JP2008-9426A, JP2008-81732A, and the like, and a copolymer of a macromonomer and an acid group-containing monomer, which is described in JP2010-106268A, and the like. From the viewpoint of dispersibility of a pigment dispersion, dispersion stability, and developability which a coloring composition using the pigment exhibits, an amphoteric dispersion resin having basic and acid groups, which is described in JP2009-203462A, is particularly preferable.

As the macromonomer used in production of a graft polymer having a moiety anchored to the pigment surface by radical polymerization, known macromonomers can be used. Examples thereof include macromonomers AA-6 (polymethyl methacrylate having a methacryloyl group as a terminal group), AS-6 (polystyrene having methacryloyl group as a terminal group), AN-6S (a copolymer of styrene and acrylonitrile which has a methacryloyl group as a terminal group), and AB-6 (polybutyl acrylate having a methacryloyl group as a terminal group) manufactured by TOAGOSEL CO., LTD.; Placcel FM 5 (a product obtained by adding 5 molar equivalents of ϵ-caprolactone to 2-hydroxyethyl methacrylate) and FA10L (a product obtained by adding 10 molar equivalents of ϵ-caprolactone to 2-hydroxyethyl acrylate) manufactured by DAICEL Corporation; a polyester-based macromonomer described in JP1990-272009A (JP-H02-272009A), and the like. Among these, from the viewpoint of dispersibility of the pigment, dispersion stability, and the developability which the coloring composition using the pigment dispersion exhibits, the polyester-based macromonomer excellent in flexibility and solvent compatibility is particularly preferable. Further, a polyester-based macromonomer represented by the polyester-based macromonomer described in JP1990-272009A (JP-H02-272009A) is particularly preferable.

As the block polymer having a moiety anchored to the pigment surface, block polymers described in JP2003-49110A, JP2009-52010A, and the like are preferable.

The pigment dispersants which can be used in the present invention can be obtained in the form of commercially available products, and specific examples thereof include "DA-7301" manufactured by Kusumoto Chemicals, Ltd., "Disperbyk-101 (polyamidamine phosphate), 107 (carboxylic ester), 110, 111 (copolymer including an acid group), 130 (polyamide), 161, 162, 163, 164, 165, 166, and 170 (polymeric copolymer)", and "BYK-P104 and P105 (high-molecular-weight unsaturated polycarboxylic acid)", manufactured by BYK-Chemie, "EFKA 4047, 4050~4010~4165 (polyurethane-based dispersant), EFKA 4330 to 4340 (block copolymer), 4400 to 4402 (modified polyacrylate), 5010 (polyesteramide), 5765 (high-molecular-weight polycarboxylate), 6220 (aliphatic polyester), 6745 (phthalocyanine derivative), and 6750 (azo pigment derivative)" manufactured by EFKA, "Ajisper PB821, PB822, PB880, and PB881" manufactured by Ajinomoto Fine-Techno Co., Inc., "Flowlen TG-710 (urethane oligomer)" and "Polyflow No. 50E, No. 300 (acrylic copolymer), manufactured by KYOEISHA CHEMICAL CO., LTD., "Disparlon KS-860, 873SN, 874, #2150 (aliphatic polyvalent carboxylic acid), #7004 (polyether ester), DA-703-50, DA-705, and DA-725", manufactured by Kusumoto Chemicals, Ltd., "Demol RN, N (naphthalene sulfonate formaldehyde condensate), MS, C, SN-B (aromatic sulfonate formaldehyde condensate)", "Homogenol L-18 (polymeric polycarboxylic acid), "Emulgen 920, 930, 935, and 985 (polyoxyethylene nonyl phenyl ether)", and "Acetamine 86 (stearylamine acetate)", manufactured by Kao Corporation, "Solsperse 5000 (phthalocyanine derivative), 22000 (azo pigment derivative), 13240 (polyesterarnine), 3000, 17000, and 27000 (polymers having a functional portion in the terminal portion), and 24000, 28000, 32000, and 38500 (graft polymers)", manufactured by Lubrizol Japan Ltd., "Nikkol T106 (polyoxyethylene sorbitan monooleate) and MYS-IEX (polyoxyethylene monostearate)" manufactured by NIKKO CHEMICALS Co., Ltd., "Hinoact T-8000E" and the like manufactured by Kawaken Fine Chemicals Co., Ltd., "organosiloxane polymer KP341" manufactured by Shin-Etsu Chemical Co., Ltd., cationic surfactants such as "W001" manufactured by Yusho Co., Ltd., nonionic surfactants such as polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate, and sorbitan aliphatic ester, and anionic surfactants such as "W004, W005, and W017", "EFKA-46, EFKA-47, EFKA-47EA, EFKA polymer 100, EFKA polymer 400, EFKA polymer 401, and EFKA polymer 450" manufactured by MORISHITA SANGYO Corporation, polymer dispersants such as "Disperse aid 6, Disperse aid 8, Disperse aid 15, and Disperse aid 9100" manufactured by SAN NOPCO Ltd., "Adeka Pluronic L31, F38, L42, L44, L61, L64, F68, L72, P95, F77, P84, F87, P94, L101, P103, F108, L121, and P-123" manufactured by ADEKA Corporation, and "Ionet (product name) S-20" manufactured by Sanyo Chemical Industries, Ltd.

These pigment dispersants may be used alone or in combination of two or more kinds thereof. In the present invention, it is particularly preferable to use a combination of a pigment derivative and a polymer dispersant. Further, the pigment dispersant may be used in combination with an alkali-soluble resin, together with a terminal-modified polymer having a moiety anchored to the pigment surface, a graft polymer, or a block polymer. Examples of the alkali-soluble resin include a (meth)acrylic acid copolymer, an itaconic acid copolymer, a crotonic acid copolymer, a maleic acid copolymer, a partially esterified maleic acid copolymer, and an acidic cellulose derivative having a carboxylic acid in a side chain, and a (meth)acrylic acid copolymer is particularly preferable. In addition, the N-position-substituted maleimide monomers copolymer described in JP1998-300922A (JP-H10-300922A), the ether dimer copolymers described in JP2004-300204A, and the alkali-soluble resins containing a polymerizable group described in JP1995-319161A (JP-H07-319161A) are also preferable. Specifically, alkali-soluble resins: a benzyl methacrylate/methacrylic acid/2-hydroxyethyl methacrylate copolymer is exemplified.

In the case where the coloring composition contains a pigment dispersant, the total content of the pigment dispersant in the coloring composition is preferably 1 part by mass to 80 parts by mass, more preferably 5 parts by mass to 70 parts by mass, and still more preferably 10 parts by mass to 60 parts by mass, with respect to 100 parts by mass of the pigment. The content of the specific dispersed resin in the dispersant components contained in the coloring composition is preferably 50% by mass or more, more preferably 60% by mass or more, and still more preferably 70% by mass or more.

The composition of the present invention may include one kind or two or more kinds of pigment dispersant. In the case where the composition includes two or more kinds of the pigment dispersant, the total amount thereof is preferably within the range.

Specifically, in the case where a polymer dispersant is used, the amount of the polymer dispersant used is preferably 5 parts by mass to 100 parts by mass, and more preferably 10 parts by mass to 80 parts by mass, with respect to 100 parts by mass of the pigment.

Moreover, in the case where a pigment derivative is used in combination with other components, the amount of the pigment derivative used is preferably 1 part by mass to 30 parts by mass, more preferably 3 parts by mass to 20 parts by mass, and particularly preferably 5 parts by mass to 15 parts by mass, with respect to 100 parts by mass of the pigment.

In the coloring composition, from the viewpoint of curing sensitivity and color density, the total content of the coloring agent components and the pigment dispersant is preferably 50% by mass to 90% by mass, more preferably 55% by mass to 85% by mass, and still more preferably 60% by mass to 80% by mass, with respect to the total solid contents constituting the coloring composition.

<Alkali Soluble Resin (F)>

It is preferable that the coloring composition of the present invention further contains an alkali-soluble resin.

The molecular weight of the alkali-soluble resin is not particularly defined, but Mw is preferably 5,000 to 100,000. Further, Mn is preferably 1,000 to 20,000.

The alkali-soluble resin can be appropriately selected from alkali-soluble resins which are linear organic high molecular-weight polymers and have at least one group enhancing alkali-solubility in a molecule (preferably, a molecule having an acrylic copolymer or a styrene-based copolymer as a main chain). From the viewpoint of heat resistance, a polyhydroxystyrene-based resin, a polysiloxane-based resin, an acrylic resin, an acrylamide-based resin, and an acryl/acrylamide copolymer resin are preferable. Further, from the viewpoint of controlling developability, an acryl-based resin, an acrylamide-based resin, and an acryl/acrylamide copolymer resin are preferable.

Examples of the group promoting alkali-solubility (hereinafter also referred to as an "acid group") include a carboxyl group, a phosphoric acid group, a sulfonic acid group, a phenolic hydroxyl group, and the like. The group promoting alkali-solubility is preferably a group which is soluble in an organic solvent and can be developed by an aqueous weak alkaline solution, and particularly preferred examples thereof include a (meth)acrylic acid. These acid groups may be used alone or in combination of two or more kinds thereof.

Examples of the monomer which can give the acid group after polymerization include monomers having a hydroxyl group, such as 2-hydroxyethyl(meth)acrylate, monomers having an epoxy group, such as glycidyl(meth)acrylate, and monomers having an isocyanate group, such as 2-isocyanatoethyl(meth)acrylate. The monomers for introducing these acid groups may be used alone or in combination of two or more kinds thereof. In order to introduce the acid group into the alkali-soluble resin, for example, the monomer having the acid group and/or the monomer which can give the acid group after polymerization (hereinafter referred to as a "monomer for introducing an acid group" in some cases) may be polymerized as a monomer component.

Incidentally, in the case where a monomer which can give the acid group after polymerization is used as a monomer component to introduce the acid group, a treatment for giving the acid group, which will be described later, needs to be performed after polymerization.

For production of the alkali-soluble resin, for example, a method using known radical polymerization can be applied. Various polymerization conditions for producing the alkali-soluble resin by radical polymerization, such as a temperature, a pressure, the type and amount of a radical initiator, and the type of a solvent, can be easily set by those skilled in the art, and the conditions can also be determined experimentally.

As the linear organic high-molecular weight polymer used as the alkali-soluble resin, polymers having a carboxylic acid in a side chain are preferable, and examples thereof include methacrylic acid copolymer, an acrylic acid copolymer, an itaconic acid copolymer, a crotonic acid copolymer, a maleic acid copolymer, a partially esterified maleic acid copolymer, an alkali-soluble phenol resin or the like such as a novolac resin, an acidic cellulose derivative having a carboxylic acid in a side chain, and a polymer obtained by adding an acid anhydride to a polymer having a hydroxyl group. In particular, a copolymer of a (meth)acrylic acid and another monomer copolymerizable with the (meth)acrylic acid is suitable as the alkali-soluble resin. Examples of another monomer copolymerizable with a (meth)acrylic acid include alkyl(meth)acrylate, aryl(meth)acrylate, and a vinyl compound. Examples of the alkyl(meth)acrylate and aryl (meth)acrylate include methyl(meth)acrylate, ethyl(meth) acrylate, propyl(meth)acrylate, butyl(meth)acrylate, isobutyl(meth)acrylate, pentyl(meth)acrylate, hexyl(meth) acrylate, octyl(meth)acrylate, phenyl(meth)acrylate, benzyl (meth)acrylate, tolyl(meth)acrylate, naphthyl(meth)acrylate, and cyclohexyl(meth)acrylate. Examples of the vinyl compound include styrene, α-methylstyrene, vinyltoluene, glycidyl methacrylate, acrylonitrile, vinyl acetate, N-vinylpyrrolidone, tetrahydrofurfuryl methacrylate, a polystyrene macromonomer, and a polymethyl methacrylate macromonomer. Examples of the N-position-substituted maleimide monomer disclosed in JP1998-300922A (JR-H10-300922A) include N-phenylmaleimide and N-cyclohexylmaleimide. Incidentally, other monomers copolymerizable with a (meth)acrylic acid may be used alone or in combination, of two or more kinds thereof.

It is also preferable that the coloring composition contains, as the alkali-soluble resin, a polymer (a) obtained by polymerizing monomer components including a compound represented by the following General Formula (ED) and/or a compound represented by the following General Formula (ED2) (hereinafter also referred to as an "ether dimer" in some cases) as an essential component.

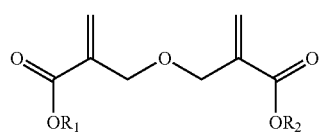

General Formula (ED)

In General Formula (ED), $R^1$ and $R^2$ each independently represent a hydrogen atom or a hydrocarbon group having 1 to 25 carbon atoms, which may have a substituent.

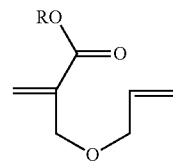

General Formula (ED2)

In General Formula (ED2), R represents a hydrogen atom or an organic group having 1 to 30 carbon atoms. With respect to specific examples of General Formula (ED2), a reference can be made to the description of JP2010-168539A.

Thus, the coloring composition of the present invention can form a cured coating film which is extremely excellent in heat resistance as well as transparency. In General Formula (ED) which represents the ether dimer, the hydrocarbon group having 1 to 25 carbon atom, represented by $R^1$ and $R^2$, which may have a substituent, is not particularly limited, and examples thereof include linear or branched alkyl groups such as methyl, ethyl, n-propyl, isopropyl, n-butyl, isobutyl, tert-butyl, tert-amyl, stearyl, lauryl, and 2-ethylhexyl; aryl groups such as phenyl; alicyclic groups such as cyclohexyl, tert-butylcyclohexyl, dicyclopentadienyl, tricyclodecanyl, isobornyl, adamantyl, and 2-methyl-2-adamantyl; alkyl groups substituted with alkoxy such as 1-methoxyethyl and 1-ethoxyethyl; and alkyl groups substituted with an aryl group such as benzyl. Among these, from the viewpoints of heat resistance, substituents of primary or secondary carbon, which are not easily eliminated by an acid or heat, such as methyl, ethyl, cyclohexyl, and benzyl, are preferable.

Specific examples of the ether dimer include dimethyl-2, 2'-[oxybis(methylene)]bis-2-propenoate, diethyl-2,2'-[oxybis(methylene)]bis-2-propenoate, di(n-propyl)-2,2'-[oxybis(methylene)]bis-2-propenoate, di(isopropyl)-2,2'-[oxybis(methylene)]bis-2-propenoate, di(n-butyl)-2,2'-[oxybis(methylene)]bis-2-propenoate, di(isobutyl)-2,2'-[oxybis(methylene)]bis-2-propenoate, di(tert-butyl)-2,2'-[oxybis(methylene)]bis-2-propenoate, di(tert-amyl)-2,2'-[oxybis(methylene)]bis-2-propenoate, di(stearyl)-2,2'-[oxybis(methylene)]bis-2-propenoate, di(lauryl)-2,2'-[oxybis(methylene)]bis-2-propenoate, di(2-ethylhexyl)-2,2'-[oxybis(methylene)]bis-2-propenoate, di(1-methoxyethyl)-2,2'-[oxybis(methylene)]bis-2-propenoate, di(1-ethoxyethyl)-2, 2'-[oxybis(methylene)]bis-2-propenoate, dibenzyl-2,2'-[oxybis(methylene)]bis-2-propenoate, diphenyl-2,2'-[oxybis(methylene)]bis-2-propenoate, dicyclohexyl-2,2'-[oxybis(methylene)]bis-2-propenoate, di(tert-butylcyclohexyl)-2, 2'-[oxybis(methylene)]bis-2-propenoate, di(dicyclopentadienyl)-2,2'-[oxybis(methylene)]bis-2-propenoate, di(tricyclodecanyl)-2,2'-[oxybis(methylene)]bis-2-propenoate, di(isobornyl)-2,2'-[oxybis(methylene)]bis-2-propenoate, diadamantyl-2,2'-[oxybis(methylene)]bis-2-propenoate, and di(2-methyl-2-adamantyl)-2,2'-[oxybis methylene)]bis-2-propenoate. Among these, dimethyl-2,2'-[oxybis(methylene)]bis-2-propenoate, diethyl-2,2'-[oxybis(methylene)]bis-2-propenoate, dicyclohexyl-2,2'-[oxybis(methylene)]bis-2-propenoate, and dibenzyl-2,2'-[oxybis(methylene)]bis-2-propenoate are particularly preferable. These ether dimers may be used alone or in combination of two or more kinds thereof. The structure derived from the compound represented by General Formula (ED) may be copolymerized with other monomers.

Moreover, in order to improve the crosslinking efficiency of the coloring composition in the present invention, an alkali-soluble resin having a polymerizable group may be used. As the alkali-soluble resin having polymerizable group, an alkali-soluble resins and the like containing an allyl group, a (meth)acryl group, an allyloxyalkyl group, and the like on a side chain thereof are useful. Examples of the polymer containing the above polymerizable group include Dianal NR series (manufactured by Mitsubishi Rayon Co., Ltd.), Photomer 6173 (a polyurethane acrylic oligomer containing COOH, manufactured by Diamond Shamrock Co., Ltd.), Biscoat R-264 and KS Resist 106 (all manufactured by OSAKA ORGANIC CHEMICAL INDUSTRY LTD.), Cyclomer P series and Placcel CF200 series (all manufactured by DAICEL Corporation), and Ebecryl 3800 (manufactured by DAICEL-UCB Co., Ltd.). As the alkali-soluble resin containing a polymerizable group, a polymerizable double bond-containing acryl-based resin modified with urethane, which is a resin obtained by reacting an isocyanate group and an group in advance to leave one unreacted isocyanate group and performing a reaction between a compound having a (meth)acryloyl group and an acryl-based resin having a carboxyl group, an unsaturated bond-containing acryl-based resin which is obtained by a reaction between an acryl-based resin having a carboxyl group and a compound having both an epoxy group and a polymerizable double bond in a molecule, a polymerizable double bond-containing acryl-based resin which is obtained by a reaction between an acid pendant type epoxy acrylate resin, an acryl-based resin having an OH group, and a dibasic acid anhydride having a polymerizable double bond, a resin obtained by a reaction between an acryl-based resin having an OH group and a compound having isocyanate and a polymerizable group, a resin which is obtained by treating a resin, which has an ester group having an elimination group such as a halogen atom or a sulfonate group in an α-position or a β-position described in JP2002-229207A and JP2003-335814A on a side chain, with a base, and the like are preferable.

Furthermore, the alkali-soluble resin may include a structural unit derived from an ethylenically unsaturated monomer represented by the following Formula (X).

General Formula (X)

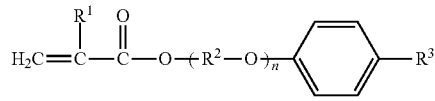

(In Formula (X), $R^1$ represents a hydrogen atom or a methyl group, $R^2$ represents an alkylene group having 2 to 10 carbon atoms, $R^3$ represents a hydrogen atom or an alkyl group having 1 to 20 carbon atoms, which may contain a benzene ring, and n represents an integer of 1 to 15.)

In Formula (X), the number of carbon atoms of the alkylene group of $R^2$ is preferably 2 to 3. Further, the number of carbon atoms of the alkyl group of $R^3$ is 1 to 20, and more preferably 1 to 10, and the alkyl group of $R^3$ may contain a benzene ring. Examples of the alkyl group containing a benzene ring, represented by $R^3$, include a benzyl group and a 2-phenyl(iso)propyl group.

As the alkali-soluble resin, a benzyl(meth)acrylate/(meth) acrylic acid copolymer or a multicomponent copolymer including benzyl(meth)acrylate/(meth)acrylic acid/other monomers is particularly suitable. Examples thereof also include a benzyl(meth)acrylate/(meth)acrylic acid/2-hydroxyethyl(meth)acrylate copolymer obtained by copolymerizing 2-hydroxyethyl methacrylate, a 2-hydroxypropyl (meth)acrylate/a polystyrene macromonomer/benzyl methacrylate/methacrylic acid copolymer described in JP1995-140654A (JP-H07-140654A), a 2-hydroxy-3-phenoxypropyl acrylate/a polymethyl methacrylate macromonomer/benzyl methacrylate/methacrylic acid copolymer, a 2-hydroxyethyl methacrylate/a polystyrene macromonomer/methyl methacrylate/methacrylic acid copolymer, and a 2-hydroxyethyl methacrylate/a polystyrene macromonomer/benzyl methacrylate/methacrylic acid copolymer, and particularly preferably a benzyl methacrylate/methacrylic acid copolymer.

With respect to the alkali-soluble resin, a reference can be made to the descriptions in paragraphs "0558" to "0571" of JP2012-208494A ("0685" to "0700" of the corresponding US2012/0235099A), the contents of which are incorporated herein.

Furthermore, it is preferable to use the copolymers (B) described in paragraph Nos. "0029" to "0063" of JP2012-32767A and the alkali-soluble resins used in Examples of the document; the binder resins described in paragraph Nos. "0088" to "0098" of JP2012-208474A and the hinder resins used in Examples of the document; the binder resins described in paragraph Nos. "0022" to "0032" of JP2012-13753A and the binder resins in Examples of the document; the binder resins described in paragraph Nos. "0132" to "0143" of JP2013-024934A and the binder resins used in Examples of the document; the binder resins described in paragraph Nos. "0092" to "0098" of JP2011-242752A and used in Examples; or the binder resins described in paragraph Nos. "0030" to 0072" of JP2012-032770A, the contents of which are incorporated herein. More specifically, the following resins are preferable.

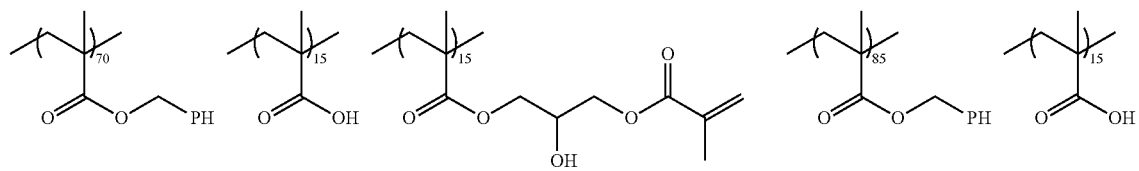

-continued
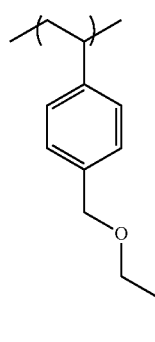 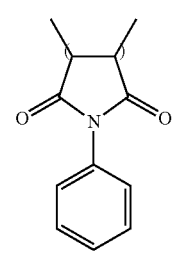 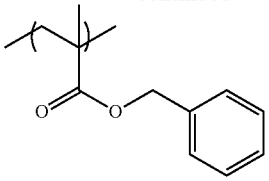
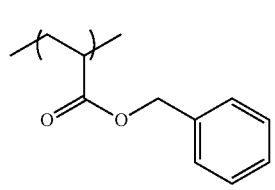 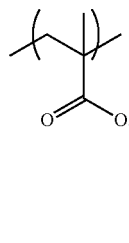 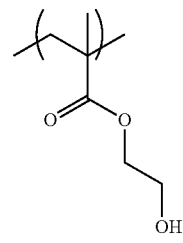 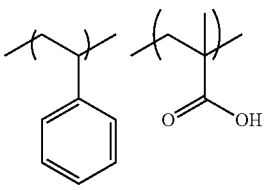
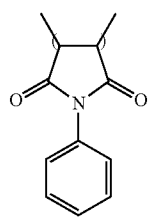  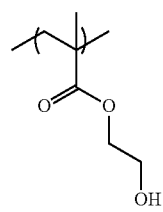
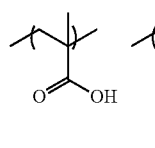 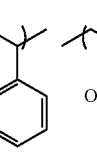 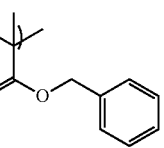 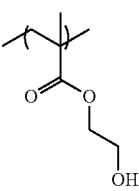 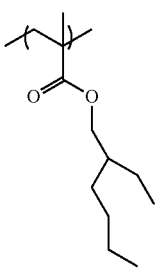 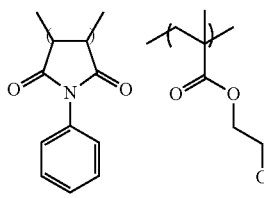 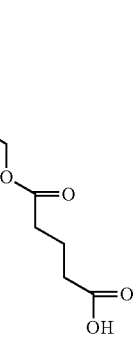
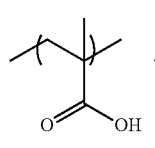 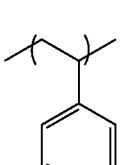 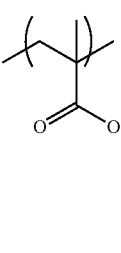 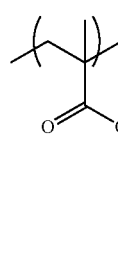 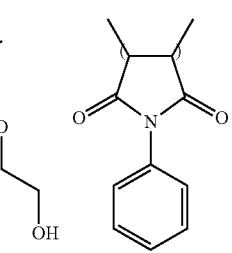

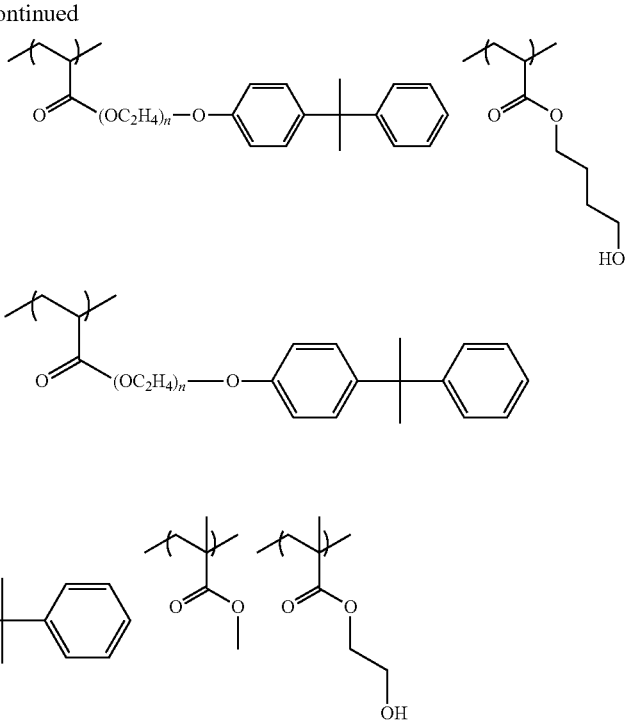

The acid value of the alkali-soluble resin is preferably 30 mgKOH/g to 200 mgKOH/g, more preferably 50 mgKOH/g to 150 mgKOH/g, and particularly preferably 70 mgKOH/g to 120 mgKOH/g.

Furthermore, the weight-average molecular weight (Mw) of the alkali-soluble resin is preferably 2,000 to 50,000, more preferably 5,000 to 30,000, and particularly preferably 7,000 to 20,000.

In the case where the coloring composition contains an alkali-soluble resin, the content of the alkali-soluble resin is preferably 1% by mass to 15% by mass, more preferably 2% by mass to 12% by mass, and particularly preferably 3% by mass to 10% by mass, with respect to the total solid contents of the coloring composition.

The composition of the present invention may include one kind or two or more kinds of alkali-soluble resin. In the case where the composition includes two or more kinds of the alkali-soluble resin, the total amount thereof is preferably within the range.

<Other Components>

The coloring composition of the present invention may further contain other components such as an organic solvent, a crosslinking agent, a polymerization inhibitor, a surfactant, an organic carboxylic acid, and an organic carboxylic anhydride in addition to the respective components described above, within a range which does not diminish the effects of the present invention.

<<Organic Solvent>>

The coloring composition of the present invention may contain an organic solvent.

Basically, the organic solvent is not particularly limited as long as the solvent satisfies the solubility of the respective components or the coatability of the coloring composition. In particular, it is preferable to select the organic solvent in consideration of the solubility, coatability, and safety of an ultraviolet absorber, the alkali-soluble resin, the dispersant, or the like. In addition, when the coloring composition in the present invention is prepared, the coloring composition preferably includes at least two kinds of organic solvents.

Suitable examples of the organic solvent include esters such as ethyl acetate, n-butyl acetate, isobutyl acetate, amyl formate, isoamyl acetate, isobutyl acetate, butyl propionate, isopropyl butyrate, ethyl butyrate, butyl butyrate, methyl lactate, ethyl lactate, alkyl oxyacetate (for example, methyl oxyacetate, ethyl oxyacetate, and butyl oxyacetate (for example, methyl methoxyacetate, ethyl methoxyacetate, butyl methoxyacetate, methyl ethoxyacetate, and ethyl ethoxyacetate)), alkyl 3-oxypropionate esters (for example, methyl 3-oxypropionate and ethyl 3-oxypropionate (for example, methyl 3-methoxypropionate, ethyl 3-methoxypropionate, methyl 3-ethoxypropionate, and ethyl 3-ethoxypropionate)), alkyl 2-oxypropionate esters (for example, methyl 2-oxypropionate, ethyl 2-oxypropionate, or propyl 2-oxypropionate (for example, methyl 2-methoxypropionate, ethyl 2-methoxypropionate, propyl 2-methoxypropionate, methyl 2-ethoxypropionate, or ethyl 2-ethoxypropionate)), methyl 2-oxy-2-methyl propionate and ethyl 2-oxy-2-methyl propionate (for example, methyl 2-methoxy-2-methyl propionate and ethyl 2-ethoxy-2-methyl propionate), methyl pyruvate, ethyl pyruvate, propyl pyruvate, methyl acetoacetate, ethyl acetoacetate, methyl 2-oxobutanoate, and ethyl 2-oxobutanoate; ethers such as diethylene glycol dimethyl ether, tetrahydrofuran, ethylene glycol monomethyl ether, ethylene glycol monoethyl ether, methyl cellosolve acetate, ethyl cellosolve acetate, diethylene glycol monomethyl ether, diethylene glycol monoethyl ether, diethylene glycol monobutyl ether, propylene glycol monomethyl ether, propylene glycol monomethy ether acetate, propylene glycol monoethyl ether acetate, and propylene glycol monopropyl ether acetate; ketones such as methyl ethyl ketone, cyclohexanone, cyclopentanone, 2-heptanone, and 3-butanone; and aromatic hydrocarbons such as toluene and xylene.

From the viewpoint of the solubility of an ultraviolet absorber and the alkali-soluble resin, and improvement of the shape of the coated surface, it is also preferable to mix two or more kinds of these organic solvents. In this case, a mixed solution consisting of two or more kinds selected from the aforementioned methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethylcarbitol acetate, butylcarbitol acetate, propylene glycol methyl ether, and propylene glycol methyl ether acetate is particularly preferable.

From the viewpoint of coatability, the content of the organic solvent in the coloring composition is set such that the concentration of the total solid contents of the composition becomes preferably 5% by mass to 80% by mass, more preferably 5% by mass to 60% by mass, and particularly preferably 10% by mass to 50% by mass.

The composition of the present invention may include one kind or two or more kinds of organic solvent. In the case where the composition includes two or more kinds of the organic solvent, the total amount thereof is preferably within the range.

<<Crosslinking Agent>>

It is also possible to improve the hardness of the cured film obtained by curing the coloring composition by using a crosslinking agent complementarily in the coloring composition of the present invention.

The crosslinking agent is not particularly limited as long as it makes it possible to cure a film by a crosslinking reaction, and examples thereof include (a) an epoxy resin, (b) a melamine compound, a guanamine compound, a glycoluril compound, or a urea compound substituted with at least one substituent selected from a methylol group, on alkoxymethyl group, and an acyloxymethyl group, and (c) a phenol compound, a naphthol compound, or a hydroxyanthracene compound, which is substituted with at least one substituent selected from a methylol group, an alkoxymethyl group, and an acyloxymethyl group. Among these, a polyfunctional epoxy resin is preferable.

With regard to the details of specific examples and the like of the crosslinking agent, a reference can be made to the description of paragraphs "0134" to "0147" of JP2004-295116A.

In the case where the coloring composition of the present invention contains a crosslinking agent, the blending amount of the crosslinking agent is not particularly limited, but is preferably 2% by mass to 30% by mass, and more preferably 3% by mass to 20% by mass, with respect to the total solid contents of the composition.

The composition of the present invention may include one kind or two or more kinds of crosslinking agent. In the case where the composition includes two or more kinds of the crosslinking agent, the total amount thereof is preferably within the range.

<<Polymerization Inhibitor>>

It is preferable to add a small amount of a polymerization inhibitor to the coloring composition of the present invention in order to suppress the occurrence of unnecessary thermal polymerization of the polymerizable compound during production or storage of the coloring composition.

Examples of the polymerization inhibitor which can be used in the present invention include hydroquinone, p-methoxyphenol, di-tert-butyl-p-cresol, pyrogallol, tert-butylcatechol, benzoquinone, 4,4'-thiobis(3-methyl-6-tert-butylphenol), 2,2'-methylenebis(4-methyl-6-tert-butylphenol), and a cerium (III) salt of N-nitrosophenyl hydroxylamine.

In the case where the coloring composition of the present invention contains a polymerization inhibitor, the amount of the polymerization inhibitor added is preferably about 0.01% by mass to about 5% by mass, with respect to the total mass of the composition.

The composition of the present invention may include one kind or two or more kinds of polymerization inhibitor. In the case where the composition includes two or more kinds of the polymerization inhibitor, the total amount thereof is preferably within the range.

<<Surfactant>>

From the viewpoint of further improving coatability, various surfactants may be added to the coloring composition of the present invention. As the surfactants, it is possible to use various surfactants such as a fluorine-based surfactant, a nonionic surfactant, a cationic surfactant, an anionic surfactant, and a silicone-based surfactant.

In particular, if the coloring composition of the present invention contains a fluorine-based surfactant, liquid characteristics (particularly, fluidity) are further improved when the composition is prepared as a coating liquid, whereby evenness of the coating thickness or liquid saving properties can be further improved.

That is, in the case where a coating liquid obtained by applying the coloring composition containing a fluorine-based surfactant is used to form a film, the surface tension between a surface to be coated and the coating liquid is reduced to improve wettability with respect to the surface to be coated, and enhance coatability with respect to the surface to be coated. Therefore, even in the case where a thin film of about several μm is formed of a small amount of liquid, the coloring composition containing a fluorine-based surfactant is effective in that a film with a uniform thickness which exhibits a small extent of thickness unevenness can be more suitably formed.

The fluorine content in the fluorine-based surfactant is preferably 3% by mass to 40% by mass, more preferably 5% by mass to 30% by mass, and particularly preferably 7% by mass to 25% by mass. The fluorine-based surfactant in which the fluorine content is within this range is effective in terms of the uniformity of the thickness of the coating film or liquid saving properties, and the solubility of the surfactant in the coloring composition is also good.

Examples of the fluorine-based surfactant include Megaface F171, Megaface F172, Megaface F173, Megaface F176, Megaface F177, Megaface F141, Megaface F142, Megaface F143, Megaface F144, MegafaceR30, Megaface F437, Megaface F475, Megaface F479, Megaface F482, Megaface F554, Megaface F780, and Megaface F781 (all manufactured by DIC Corporation), Fluorad FC430, FC431, and FC171 (all manufactured by Sumitomo 3M), and Surflon S-382, Surflon SC-101, Surflon SC-103, Surflon SC-104, Surflon SC-105, Surflon SC1068, Surflon SC-381, Surflon SC-383, Surflon SC-393, and Surflon KH-40 (all manufactured by ASAHI GLASS Co., Ltd.).

Specific examples of the nonionic surfactant include glycerol, trimethylolpropane, trimethylolethane, and ethoxylate and propoxylate thereof (for example, glycerol propoxylate and glycerin ethoxylate), polyoxyethylene lauryl ether, polyoxyethylene stearyl ether, polyoxyethylene oleyl ether, polyoxyethylene octyl phenyl ether, polyoxyethylene nonyl phenyl ether, polyethylene glycol dilaurate, polyethylene glycol distearate, sorbitan fatty acid esters (Pluronic L10, L31, L61, L62, 10R5, 17R2, and 25R2, and Tetronic 304, 701, 704, 901, 904, and 150R1 manufactured by BASF), and Solseperse 20000 (manufactured by Lubrizol Japan Ltd.).

Specific examples of the cationic surfactant include phthalocyanine derivatives (product name: EFKA-745 manufactured by MORISHITA SANGYO Corporation), organosiloxane polymer KP341 (manufactured by Shin-Etsu Chemical Co., Ltd.), (meth)acrylic acid-based (co)polymer Polyflow No. 75, No. 90, and No. 95 (manufactured by KYOEISHA CHEMICAL CO., LTD.), and W001 (manufactured by Yusho Co., Ltd.).

Specific examples of the anionic surfactant include W004, W005, and W017 (manufactured by Yusho Co., Ltd.).

Examples of the silicone-based surfactant include "Toray Silicone DC3PA", "Toray Silicone SH7PA", "Toray Silicone DC11PA", "Toray Silicone SH21PA", "Toray Silicone SH28PA", "Toray Silicone SH29PA", "Toray Silicone SH30PA", and "Toray Silicone SH8400", manufactured by Dow Corning Toray, "TSF-4440", "TSF-4300", "TSF-4445", "TSF-4460", and "TSF-4452", manufactured by Momentive Performance Materials Inc., "KP341", "KF6001", and "KF6002", manufactured by Shin-Etsu Silicones, and "BYK307", "BYK323", and "BYK330", manufactured by BYK-Chemie.

In the case where the coloring composition of the present invention contains a surfactant, the amount of the surfactant added is preferably 0.001% by mass to 2.0% by mass and more preferably 0.005% by mass to 1.0% by mass, with respect to the total mass of the coloring composition.

The composition of the present invention may include one kind or two or more kinds of surfactant. In the case where the composition includes two or more kinds of the surfactant, the total amount thereof is preferably within the range.

<<Organic Carboxylic Acid and Organic Carboxylic Anhydride>>

The coloring composition of the present invention may contain an organic carboxylic acid having a molecular weight of 1,000 or less, and/or an organic carboxylic anhydride.

Specific examples of the organic carboxylic acid compound include an aliphatic carboxylic acid and an aromatic carboxylic acid. Examples of the aliphatic carboxylic acid include monocarboxylic acids such as formic acid, acetic acid, propionic acid, butyric acid, valeric acid, pivalic acid, caproic acid, glycolic acid, acrylic acid, and methacrylic acid, dicarboxylic acids such as oxalic acid, malonic acid, succinic acid, glutaric acid, adipic acid, pimelic acid, cyclohexanedicarboxylic acid, cyclohexenedicarboxylic acid, itaconic acid, citraconic acid, maleic acid, and fumaric acid, tricarboxylic acids such as tricarboxylic acid, and aconitic acid, and the like. Examples of the aromatic carboxylic acid include carboxylic acids in which a carboxyl group is directly bonded to a phenyl group such as a benzoic acid and a phthalic acid, and carboxylic acids in which a phenyl group is bonded to a carboxyl group via a carbon bond. Among these, carboxylic acids having a molecular weight of 600 or less, particularly those having a molecular weight of 50 to 500, and specifically, maleic acid, malonic acid, succinic acid, and itaconic acid are preferable.

Examples of the organic carboxylic anhydride include aliphatic carboxylic anhydride and aromatic carboxylic anhydride. Specific examples thereof include aliphatic carboxylic anhydrides such as acetic anhydride, trichloroacetic anhydride, trifluoroacetic anhydride, tetrahydrophthalic anhydride, succinic anhydride, maleic anhydride, citraconic anhydride, itaconic anhydride, glutaric anhydride, 1,2-cyclohexenedicarboxylic anhydride, n-octadecylsuccinic anhydride, and 5-norbornene-2,3-dicarboxylic anhydride. Examples of the aromatic carboxylic anhydride include phthalic anhydride, trimellitic anhydride, pyromellitic anhydride, and naphthalic anhydride. Among these, those having a molecular weight of 600 or less, particularly having a molecular weight of 50 to 500, specifically, for example, maleic anhydride, succinic anhydride, citraconic anhydride, and itaconic anhydride are preferable.

If the coloring composition of the present invention contains an organic carboxylic acid or an organic carboxylic anhydride, the amount of these organic carboxylic acids and/or the organic carboxylic anhydrizdes added is generally in a range of 0.01% by weight to 10% by weight, preferably 0.03% by weight to 5% by weight, and more preferably 0.05% by weight to 3% by weight in the total solid contents.

The composition of the present invention may include one kind or two or more kinds of each of an organic carboxylic acid and/or an organic carboxylic anhydride. In the case where the composition includes two or more kinds of the organic carboxylic acid and/or the organic carboxylic anhydride, the total amount thereof is preferably within the range.

By adding these organic carboxylic acids and/or the organic carboxylic anhydrides having a molecular weight of 1,000 or less, it is possible to further reduce the amount of the residual undissolved substance of the coloring composition while maintaining high pattern adhesiveness.

If desired, various additives such as a filler, an adhesion promoting agent, an antioxidant, an ultraviolet absorber, and an anti-aggregation agent may be blended into the coloring composition. Examples of these additives include those described in paragraphs "0155" and "0156" of JP2004-295116A, the contents of which are incorporated herein.

The coloring composition of the present invention can contain the sensitizer or the light stabilizer described in paragraph "0078" of JP2004-295116A, and the thermal polymerization inhibitor described in paragraph "0081" of TP2004-295116A.

The composition of the present invention may include one kind or two or more kinds of each of the components. In the case where the composition includes two or more kinds of each of the components, the total amount thereof is preferably within the range.

<Method for Preparing Coloring Composition>

The coloring composition of the present invention is prepared by mixing the aforementioned components.

Furthermore, when the coloring composition is prepared, the respective components constituting the coloring composition may be mixed together at the same time or mixed together sequentially after being dissolved and dispersed in a solvent. Further, the order of adding the components and the operation conditions during the mixing are not particularly restricted. For example, all the components may be dissolved and dispersed in a solvent at the same time to prepare the composition. Alternatively, if desired, the respective components may be appropriately prepared as two or more solutions or dispersions and mixed at the time of use (at the time of coating) to prepare the composition.

The coloring composition prepared above can be filtered and separated using a filter or the like, and then used.

It is preferable that the coloring composition of the present invention is filtered using a filter for the purpose of removing impurities or reducing deficit. Filters that have been used in the related art for filtration use and the like may be used without particular limitation. Examples thereof include filters formed of a fluorine resin such as polytetrafluoroethylene (PTFE), a polyamide-based resin such as Nylon-6 and Nylon-6,6, and a polyolefin resin (including a high density and a ultrahigh molecular weight) such as polyethylene and polypropylene (PP). Among these materials, polypropylene (including high density polypropylene is preferable.

The pore diameter of the filter is preferably 0.01 µm or more, and more preferably 0.05 µm or more. Further, the pore diameter of the filter is preferably 7.0 µm or less, preferably 3.0 µm or less, still more preferably 2.5 µm or less, even still more preferably 2.0 µm or less, and particularly preferably 0.5 µm or less. Be setting the pore diameter to this range, it is possible to reliably remove fine impurities which interfere with preparation of uniform and smooth coloring composition in a subsequent step.

When a filter is used, other filters may be used in combination therewith. At that time, filtering at a first filter may be performed only once or two or more times.

In addition, first filters having different pore diameters within the aforementioned range may be combined. As the pore diameter herein, a reference may be made to nominal values of a filter maker. A commercially available filter may be selected from various filters provided by, for example, Pall Corporation, Advantec Toyo Kaisha, Ltd., Nihon Entegris K.K. (former Nippon Microlith Co., Ltd.), Kitz Micro Filter Corporation, or the like.

As a second filter, a filter formed of a material which is the same as the material for the aforementioned first filter and the like can be used.

For example, the filtering at the first filter may be performed with only the liquid dispersion, and the other components may be mixed and then the second filtering may be performed.

The coloring composition of the present invention is preferably used for forming a colored layer of a color filter. More specifically, since the coloring composition of the present invention can form a cured film having excellent heat resistance and color characteristics, it is suitably used for forming a colored pattern (colored layer) of a color filter. Further, the coloring composition of the present invention can be suitably used for forming a colored pattern of a color filter or the like used in a solid-state imaging element (for example, a CCD and a CMOS) or an image display device such as a liquid crystal display (LCD). Further, the composition can also be suitably used in an application of the manufacture of a print ink, an ink jet ink, a coating material, or the like. Among these, the composition can be suitably used in an application of the manufacture of a color filter for a solid-state imaging element such as a CCD and a CMOS.

<Cured Film, Pattern Forming Method, Color Filter, and Method for Manufacturing Color Filter>

Next, the cured film, the pattern forming method, and the color filter in the present invention will be described in detail by an explanation of production methods thereof.

The cured film of the present invention is formed by curing the coloring composition of the present invention. Such a cured film is preferably used in a color filter.

In the pattern forming method of the present invention, the coloring composition of the present invention is applied onto a support to form a coloring composition layer, and an undesired area is removed to form a colored pattern.

The pattern forming method of the present invention can be suitably applied for forming a colored pattern (pixel) included in a color filter.

With the composition of the present invention, a color filter may be produced by forming a pattern using a so-called photolithography method and a pattern may be formed by a dry etching method.

That is, a first method for manufacturing a color filter of the present invention includes a step of applying the coloring composition of the present invention onto a support to form a coloring composition layer, a step of patternwise exposing the coloring composition layer, and a step of removing an unexposed area by development to form a colored pattern.

Furthermore, as a second method for manufacturing a color filter of the present invention, a method for manufacturing a color filter, including a step of applying the coloring composition of the present invention onto a support to form a coloring composition layer, followed by curing, to form a colored layer, a step of forming a photoresist layer on the colored layer, a step of patterning the photoresist layer by exposure and development to obtain a resist pattern, and a step of dry-etching the colored layer using the resist pattern as an etching mask is exemplified.

In the present invention, it is preferable to manufacture the color filter using a photolithography method.

Hereinafter, details of these will be described.

The respective steps in the pattern forming method of the present invention will be described in detail below with reference to the method for manufacturing a color filter for a solid-state imaging element, but the present invention is not limited to this method. Hereinafter, the color filter for a solid-state imaging element may be simply referred to as a "color filter" in some cases.

<<Coloring Composition Layer Forming Step>>

In the coloring composition layer forming step, the coloring composition of the present invention is applied onto a support to form a coloring composition layer forming step.

As the support which can be used in the present step, for example, it is possible to use a substrate for a solid-state imaging element, which is formed by providing an imaging element (light-receiving element) such as a charge coupled device (CCD) or a complementary metal-oxide semiconductor (CMOS) onto a substrate (for example, a silicon substrate).

The colored pattern in the present invention may be formed on the surface (front surface) on which an imaging element is formed or on the surface (back surface) where an imaging element is not formed, of a substrate for a solid-state imaging element.

A light shielding film may be disposed between the colored pattern in a solid-state imaging element or onto the back surface of the substrate for a solid-state imaging element.

In addition, if desired, an undercoat layer may be disposed onto the support in order to improve adhesiveness between the support and the upper layer, prevent diffusion of substances, or planarize the substrate surface. A solvent, an alkali-soluble resin, a polymerizable compound, a polymerization inhibitor, a surfactant, a photopolymerization initiator, or the like can be blended into the undercoat layer, and it is preferable that these respective components are properly selected from the components blended into the aforementioned composition of the present invention.

As the method for applying the coloring composition of the present invention onto the support, various coating methods such as slit coating, ink jet coating, spin coating, cast coating, roll coating, and a screen printing method can be applied.

Drying (pre-baking) of the coloring composition layer applied onto the support can be carried out using a hot plate, an oven, or the like at a temperature of 50° C. to 140° C. for 10 seconds to 300 seconds.

<Pattern Forming Step by Photolithography Method>
<<Exposing Step>>

In the exposing step, the coloring composition layer formed in the coloring composition layer forming step is patternwise exposed through a mask having a predetermined mask pattern by using, for example, an exposure device such as a stepper. Thus, a cured film is obtained.

As radiation (light) usable in exposure, particularly, ultraviolet rays such as a g-ray and an i-ray are preferably used (particularly, an i-ray is preferably used). The irradiation dose (exposure dose) is preferably 30 mJ/cm$^2$ to 1,500 mJ/cm$^2$, more preferably 50 mJ/cm$^2$ to 1,000 mJ/cm$^2$, and particularly preferably 80 mJ/cm$^2$ to 500 mJ/cm$^2$.

The film thickness of the cured film (colored film) is preferably 1.0 μm or less, more preferably 0.1 μm to 0.9 μm, and still more preferably 0.2 μm to 0.8 μm.

It is preferable to set the film thickness to be 1.0 μm or less since a high degree of resolution and adhesiveness are obtained.

Moreover, in this step, a cured film having a small film thickness of 0.7 μm or less can be suitably formed. Further, if the obtained cured film is subjected to a development process in a pattern forming step which will be described later, it is possible to obtain a thin film having a colored pattern which exhibits excellent developability and reduced surface roughness and has an excellent pattern shape.

<<Developing Step>>

Next, by carrying out an alkaline developing treatment, the coloring composition layer in an area not irradiated with light in the exposing step is eluted into an aqueous alkaline solution, and as a result, only a photocured area remains.

As a developing liquid, an organic alkaline developing liquid not damaging an imaging element, a circuit, or the like in an underlayer is preferable. The development temperature is usually from 20° C. to 30° C., and the development time is 20 seconds to 90 seconds in the related art. In order to further remove residues, development is recently carried out for 120 seconds to 180 seconds in some cases. Further, in order to improve residue removal properties, a step of sufficiently shaking the developing liquid every 60 seconds and newly supplying a developing liquid is repeated plural times in some cases.

Examples of an alkaline agent used for the developing liquid include organic alkaline compounds such as aqueous ammonia, ethylamine, diethylamine, dimethyl ethanolamine, tetramethyl ammonium hydroxide, tetraethyl ammonium hydroxide, tetrapropyl ammonium hydroxide, tetrabutyl ammonium hydroxide, benzyltrimethyl ammonium hydroxide, choline, pyrrole, piperidine, and 1,8-diazabicyclo-[5,4,0]-7-undecene. An aqueous alkaline solution obtained by diluting these alkaline agents with pure water so as to yield a concentration of the alkaline agent of 0.001% by mass to 10% by mass, and preferably 0.01% by mass to 1% by mass is preferably used as the developing liquid.

Incidentally, inorganic alkali may be used for the developing liquid, and as the inorganic alkali, for example, sodium hydroxide, potassium hydroxide, sodium carbonate, sodium hydrogen carbonate, sodium silicate, sodium metasilicate, and the like are preferable.

Furthermore, in the case where a developing liquid formed of such an aqueous alkaline solution is used, the pattern is generally cleaned (rinsed) with pure water after development.

Next, it is preferable to carry out a heating treatment (post-baking) after drying. If a multi-colored pattern is formed, the above steps can be sequentially repeated for each color to produce a cured coat. Thus, a color filter is obtained.

The post-baking is a heating treatment performed after development so as to complete curing, and in the post-baking, a thermal curing treatment is carried out usually at 100° C. to 240° C., and preferably at 200° C. to 240° C.

The post-baking treatment can be carried out on the coating film obtained, after development in a continuous or batch manner, by using heating means such as a hot plate, a convection oven (a hot-air circulation type drier), and a high-frequency heater under the conditions described above.

<Case of Forming Pattern by Dry Etching Method>

With the colored layer, the dry etching can be carried out with an etching gas, using a patterned photoresist layer as a mask. Specifically, a positive-type or negative-type radiation-sensitive composition is applied onto the colored layer and dried to form a photoresist layer. In the formation of the photoresist layer, it is preferable to further carry out a pre-baking treatment. In particular, as a process for forming a photoresist, a configuration in which a post-exposure heating treatment (PEB) or a post-development heating treatment (post-baking treatment) is carried out is preferable.

As the photoresist, for example, a positive-type radiation-sensitive composition is used. As the positive-type radiation-sensitive composition, a positive-type resist composition suitable for a positive-type photoresist, which responds to radiation, for example, an ultraviolet ray (a g-ray, an h-ray, or an i-ray), a far ultraviolet ray including an excimer laser and the like, an electron beam, an ion beam, or an X-ray, can be used. Among the radiations, a g-ray, an h-ray, or an i-ray is preferable, among which the i-ray is more preferable.

Specifically, as the positive-type radiation-sensitive composition, a composition containing a quinonediazide compound and an alkali-soluble resin is preferable. The positive-type radiation-sensitive composition containing a quinonediazide compound and an alkali-soluble resin utilizes that a quinonediazide group is decomposed to generate a carboxyl group by light irradiation at a wavelength of 500 nm or less, and as a result, the quinonediazide compound is shifted from an alkali-insoluble state to an alkali-soluble state. Since this positive-type photoresist is remarkably excellent in the resolving power, it is used for the manufacture of an integrated circuit, for example, IC and LSI. Examples of the quinonediazide compound include a naphthoquinonediazide compound. Examples of commercially available products thereof include "FHi622BC" (manufactured by FUJIFILM Electronics Materials Co., Ltd.).

The thickness of the photoresist layer is preferably 0.1 μm to 3 μm, more preferably 0.2 μm to 2.5 μm, and still more preferably 0.3 μm to 2 μm. Incidentally, coating of the photoresist layer can be suitably carried out using the coating method described with respect to the above-described colored layer.

Next, a resist pattern (patterned photoresist layer) in which a resist through-hole group is disposed is formed by exposing and developing the photoresist layer. The formation of the resist pattern can be carried out by appropriately optimizing heretofore known techniques of photolithography without particular limitation. By providing the resist through-hole group in the photoresist layer by exposure and development, the resist pattern which is used as an etching mask in the subsequent etching is provided on the colored layer.

Exposure of the photoresist layer can be carried out by exposing a positive-type or negative-type radiation-sensitive composition to a g-ray, an h-ray; or an i-ray; and preferably to an i-ray through a predetermined mask pattern. After the exposure, a development treatment is carried out using a developing liquid to remove the photoresist corresponding to the region where a colored pattern is to be formed.

As the developing liquid, any developing liquid which does not affect a colored layer containing a coloring agent and dissolves the exposed area of a positive resist or the uncured area of a negative resist may be used, and for example, a combination of various organic solvents or an aqueous alkaline solution is used. As the aqueous alkaline solution, an aqueous alkaline solution prepared by dissolving an alkaline compound to yield a concentration of 0.001% by mass to 10% by mass, and preferably 0.01% by mass to 5% by mass is suitable. Examples of the alkaline compound include sodium hydroxide, potassium hydroxide, sodium carbonate, sodium silicate, sodium metasilicate, aqueous ammonia, ethylamine, diethylamine, dimethylethanolamine, tetramethylatrimonium hydroxide, tetraethylammonium hydroxide, choline, pyrrole, piperidine, and 1,8-diazabicyclo-[5,4.0]-7-undecene. Incidentally, in the case where an aqueous alkaline solution is used as the developing liquid, a cleaning treatment with water is generally carried out after development.

Next, the colored layer is patterned by dry etching so as to form a through-hole group in the colored layer using the resist pattern as an etching mask. Thus, a colored pattern is formed. The through-hole group is provided checkerwise in the colored layer. Thus, a first colored pattern having the through-hole group provided in the colored layer has a plurality of first quadrangular colored pixels checkerwise.

Specifically, the dry etching is carried out by dry etching the colored layer using the resist pattern as an etching mask. Representative examples of the dry etching include the methods described in JP1984-126506A (JP-S59-126506A) JP1984-46628A (JP-S59-46628A), JP1983-9108A (JP-S58-9108A), JP1983-2809A (JP-S58-2809A), JP1982-148706A (JP-S57-148706A), JP1986-41102A (JP-S61-41102A), or the like.

It is preferable that the dry etching is carried out in a configuration as described below from the viewpoint of forming a pattern cross-section closer to that of a rectangle or of further reducing damage to a support.

A configuration is preferable, which includes a first-stage etching of etching up to an area (depth) where the support is not revealed by using a mixed gas of a fluorine-based gas and an oxygen gas ($O_2$), a second-stage etching of preferably etching up to the vicinity of an area (depth) where the support is revealed by using a mixed gas of a nitrogen gas ($N_2$) and an oxygen gas ($O_2$) after the first-stage etching, and an over-etching carried out after the support has been revealed. A specific manner of the dry etching as well as the first-stage etching, the second-stage etching, and the oven-etching will be described below.

The dry etching is carried out by determining the etching conditions in advance in the following manner.

(1) An etching rate (nm/min) in the first-stage etching and an etching rate (nm/min) in the second-stage etching are calculated, respectively. (2) A time for etching a predetermined thickness in the first-stage etching and a time for etching a predetermined thickness in the second-stage etching are calculated, respectively. (3) The first-stage etching is carried out according to the etching time calculated in (2) above. (4) The second-stage etching is carried out according to the etching time calculated in (2) above. Alternatively, an etching time is determined by endpoint detection, and the second-stage etching may be carried out according to the etching time determined. (5) The over-etching time is calculated in response to the total time of (3) and (4) above, and the over-etching is carried out.

The mixed gas used in the first-stage etching step preferably contains a fluorine-based gas and an oxygen gas ($O_2$) from the viewpoint of processing an organic material of the film to be etched into a rectangle shape. The first-stage etching step may avoid damage to the support by adopting the configuration of etching up to an area where the support is not revealed. After the etching is carried out up to an area where the support is not revealed by the mixed gas of a fluorine-based gas and an oxygen gas in the first-stage etching step, etching treatment in the second-stage etching step and etching treatment in the over-etching step are preferably carried out by using the mixed gas of a nitrogen gas and an oxygen gas from the viewpoint of avoiding damage to the support.

It is important that a ratio between the etching amount in the first-stage etching step and the etching amount in the second-stage etching step is determined so as not to deteriorate the rectangularity by the etching treatment in the first-stage etching step. Further, the ratio of the etching amount in the second-stage etching step in the total etching amount (the sum of the etching amount in the first-stage etching step and the etching amount in the second-stage etching step) is preferably in a range of more than 0% and 50% or less, and more preferably 10% to 20%. The etching amount means an amount determined by a difference between the remaining film thickness of the film etched and the film thickness of the film before the etching.

Furthermore, the etching preferably includes an over-etching treatment. The over-etching treatment is preferably carried out by determining an over-etching rate. The over-etching rate is preferably calculated from an etching treatment time which is carried out at first. Although the over-etching rate may be arbitrarily determined, it is preferably 30% or less, more preferably 5% to 25%, and particularly preferably 10% to 15%, of the etching processing time in the etching steps, from the viewpoint of etching resistance of the photoresist and preservation of the rectangularity of the etched pattern.

Next, the resist pattern (that is, the etching mask) remaining after the etching is removed. The removal of the resist pattern preferably includes a step of supplying a peeling solution or a solvent on the resist pattern to make the resist pattern be in a removable state, and a step of removing the resist pattern using cleaning water.

The step of supplying a peeling solution or a solvent on the resist pattern to make the resist pattern be in a removable state includes, for example, a step of paddle development by supplying a peeling solution or a solvent at least on the resist pattern and retaining for a predetermined time. The time for retaining the peeling solution or a solvent is not particularly limited, and is preferably several tens of seconds to several minutes.

Moreover, the step of removing the resist pattern using cleaning water includes, for example, a step of removing the resist pattern by spraying cleaning water from a spray-type or shower-type spray nozzles onto the resist pattern. As the cleaning water, pure water is preferably used. The spray nozzles include spray nozzles having a spray area which covers the entire support and mobile spray nozzles having a mobile area which covers the entire support. In the case where the spray nozzles are mobile spray nozzles, the resist pattern can be more effectively removed by moving the mobile spray nozzles two or more times from the center of support to the edge of the support to spray cleaning water in the step of removing the resist pattern.

The peeling solution generally contains an organic solvent and may further contain an inorganic solvent. Examples of the organic solvent include 1) a hydrocarbon-based compound, 2) a halogenated hydrocarbon-based compound, 3) an alcohol-based compound, 4) an ether- or acetal-based compound, 5) a ketone- or aldehyde-based compound, 6) an ester-based compound, 7) a polyhydric alcohol-based compound, 8) a carboxylic acid or its acid anhydride-based compound, 9) a phenol-based compound, 10) a nitrogen-containing compound, 11) a sulfur-containing compound, and 12) a fluorine-containing compound. The peeling solution preferably contains a nitrogen-containing compound, and more preferably contains an acyclic nitrogen-containing compound and a cyclic nitrogen-containing compound.

The acyclic nitrogen-containing compound is preferably an acyclic nitrogen-containing compound having a hydroxyl group. Specific examples thereof include monoisopropanolamine, diisopropanolamine, triisopropanolamine, N-ethylethanolamine, N,N-dibutylethanolamine, N-butylethanolamine, monoethanolamine, diethanolamine, and triethanolamine, among which monoethanolamine, diethanolamine, and triethanolamine are preferable, and monoethanolamine ($H_2NCH_2CH_2OH$) is more preferable. Further, examples of the cyclic nitrogen-containing compound include isoquinoline, imidazole, N-ethylmorpholine, ∈-capeolactam, quinoline, 1,3-dimethyl-2-imidazolidinone, α-picoline, β-picoline, γ-picoline, 2-pipecoline, 3-pipecoline, 4-pipecoline, piperazine, piperidine, pyrazine, pyridine, pyrrolidine, N-methyl-2-pyrrolidone, N-phenyl morpholine, 2,4-lutidine, and 2,6-lutidine, among which N-methyl-2-pyrrolidone and N-ethyl morpholine are preferable, and N-methyl-2-pyrrolidone (NMP) is more preferable.

The peeling solution preferably includes both the acyclic nitrogen-containing compound and the cyclic nitrogen-containing compound, more preferably contains at least one selected from monoethanolamine, diethanolamine, and triethanolamine as the acyclic nitrogen-containing compound, and at least one selected from N-methyl-2-pyrrolidone and N-ethyl morpholine as the cyclic nitrogen-containing compound, and still more preferably contains monoethanolamine and N-methyl-2-pyrrolidone.

In the removal with the peeling solution, it is sufficient that the resist pattern 52 formed on the first colored pattern 12 is removed, and in a case where a deposit of an etching product is attached to the side wall of the first colored pattern 12, it is not always necessary to completely remove the deposit. The deposit means an etching product attached and deposited to the side wall of colored layer.

For the peeling solution, it is preferable that the content of the acyclic nitrogen-containing compound is 9 parts by mass to 11 parts by mass based on 100 parts by mass of the peeling solution, and the content of the cyclic nitrogen-containing compound is 65 parts by mass to 70 parts by mass based on 100 parts by mass of the peeling solution. Further, the peeling solution is preferably one prepared by diluting a mixture of the acyclic nitrogen-containing compound and the cyclic nitrogen-containing compound with pure water.

Furthermore, the manufacturing method of the present invention may have a step known as a method for manufacturing a color filter for a solid-state imaging element, if desired, as a step other than the above steps. For example, the method may include a curing step of curing the formed colored pattern by heating and/or exposure, if desired, after the coloring composition layer forming step, the exposing step, and the pattern forming step are carried out.

Moreover, in the case of using the coloring composition according to the present invention, contaminations or the like occur in some cases, for example, when a nozzle of an ejection portion or a piping portion of a coating device is clogged, or the coloring composition or a pigment adheres to or is precipitated or dried inside the coating machine. Accordingly, in order to efficiently clean off the contaminations according to the present composition as described above, it is preferable to use the solvent relating to the coloring composition of the present invention as a cleaning liquid. In addition, the cleaning liquids described in JP1995-128867A (JP-H07-128867A), JP1995-146562A (JP-H07-146562A), JP1996-278637A (JP-H08-278637A), JP2000-273370A, JP2006-85140A, JP2006-291191A, JP2007-2101A, JP2007-2102A, JP2007-281523A, and the like can also be suitably used to remove the coloring composition according to the present invention by cleaning.

Among those, alkylene glycol monoalkyl ether carboxylate and alkylene glycol monoalkyl ether are preferable.

These solvents may be used alone or as a mixture of two or more kinds thereof. In the case where two or more kinds thereof are mixed, it is preferable to mix a solvent having a hydroxyl group with a solvent not having a hydroxyl group. The mass ratio between the solvent having a hydroxyl group and the solvent not having a hydroxyl group is 1/99 to 99/1, preferably 10/90 to 90/10, and still more preferably 20/80 to 80/20. A mixed solvent in which propylene glycol monomethyl ether acetate (PGMEA) is mixed with propylene glycol monomethyl ether (PGME) at a ratio of 60/40 is particularly preferable. Further, in order to improve the permeability of the cleaning liquid with respect to the contaminant, it is preferable to add the aforementioned surfactants relating to the present composition to the cleaning liquid.

Since the color filter of the present invention uses the coloring composition of the present invention, exposure having an excellent exposure margin can be carried out, and the thrilled colored pattern (colored pixel) has an excellent pattern shape. Further, since the surface roughness of the pattern and the amount of residues in a developed area are inhibited, excellent color characteristics are exhibited.

The color filter of the present invention can be suitably used for a solid-state imaging element such as a CCD and a CMOS, and is particularly preferable for a CCD, a CMOS, and the like with a high resolution, having more than 1,000,000 pixels. The color filter for a solid-state imaging element of the present invention can be used as, for example, a color filter disposed between a light-receiving portion of each pixel constituting a CCD or a CMOS and a microlens for condensing light.

Furthermore, the film thickness of the colored pattern (colored pixel) in the color filter of the present invention is preferably 2.0 μm or less, more preferably 1.0 μm or less, and still more preferably 0.7 μm or less.

Moreover, the size (pattern width) of the colored pattern (colored pixel) is preferably 2.5 μm or less, more preferably 2.0 μm or less, and particularly preferably 1.7 μm or less.

<Solid-State Imaging Element>

The solid-state imaging element of the present invention includes the color filter of the present invention. The constitution of the solid-state imaging element of the present invention is not particularly limited as long as the solid-state imaging element is constituted to include the color filter in the present invention and functions as a solid-state imaging element. However, for example, the solid-state imaging element can be constituted as below.

The solid-state imaging element has a configuration in which transfer electrodes consisting of a plurality of photodiodes and transfer electrodes formed of polysilicon or the like constituting a light-receiving area of a solid-state imaging element (a CCD image sensor, a CMOS image sensor, or the like) are arranged onto a support; a light shielding film which is opened only to the light-receiving portion of the photodiode and is formed of tungsten or the like is disposed onto the photodiodes and the transfer electrodes; a device protecting film which is formed for covering the entire surface of the light shielding film and the light receiving portion of the photodiodes and is formed of silicon nitride or the like is disposed onto the light shielding film; and the color filter for a solid-state imaging element of the present invention is disposed onto the device protecting film.

In addition, the solid-state imaging element may have a constitution in which light-condensing means (for example, a microlens or the like, which shall apply hereinafter) is disposed to a portion positioned on the device protecting layer and under the color filter (side close to the support), a constitution in which light-condensing means is disposed on the color filter, and the like.

<Image Display Device>

The color filter of the present invention can be used not only for a solid-state imaging element, but also for an image display device such as a liquid crystal display device and an organic EL display device. In particular, the color filter is suitable for the applications of a liquid crystal display device. The liquid crystal display device including the color filter of the present invention can display a high-quality image showing a good tone of a display image and having excellent display characteristics.

The definition of display devices or details of the respective display devices are described in, for example, "Electronic Display Device (Akio Sasaki, Kogyo Chosakai Publishing Co., Ltd., published in 1990)", "Display Device (Sumiaki Ibuki, Sangyo Tosho Co., Ltd., published in 1989), and the like. In addition, the liquid crystal display device is described in, for example, "Liquid Crystal Display Technology for Next Generation (edited by Tatsuo Uchida, Kogyo Chosakai Publishing Co., Ltd., published in 1994)". The liquid crystal display device to which the present invention can be applied is not particularly limited, and for example, the present invention can be applied to liquid crystal display devices employing various systems described in the "Liquid Crystal Display Technology for Next Generation".

The color filter of the present invention may be used for a liquid crystal display device using a color TFT system. The liquid crystal display device using a color TFT system is described in, for example, "Color TFT Liquid Crystal Display (KYORITSU SHUPPAN Co., Ltd., published in 1996)". Further, the present invention can be applied to a liquid crystal display device having an enlarged view angle, which uses an in-plane switching driving system such as IPS and a pixel division system such as MVA, or to STN, TN, VA, OCS, FFS, R—OCB, and the like.

In addition, the color filter in the present invention can be provided to a Color-filter On Array (COA) system which is a bright and high-definition system. In the liquid crystal display device of the COA system, the characteristics required for a color filter layer need to include characteristics required for an interlayer insulating film, that is, a low dielectric constant and resistance to a peeling solution in some cases, in addition to the generally required characteristics as described above. In the color filter of the present invention, a pigment multimer having an excellent hue is used. Accordingly, the color purity, light-transmitting properties, and the like are excellent, and the tone of the colored pattern (pixel) is excellent. Consequently, a liquid crystal display device of a COA system which has a high resolution and is excellent in long-term durability can be provided. Further, in order to satisfy the characteristics required for a low dielectric constant, a resin coat may be provided on the color filter layer.

These image display systems are described in, for example, p. 43 of "EL, PDP, and LCD Display Technologies and Recent Trend in Market (TORAY RESEARCH CENTER, Research Department, published in 2001)", and the like.

The liquid crystal display device including the color filter in the present invention is constituted with various members such as an electrode substrate, a polarizing film, a phase difference film, a backlight, a spacer, and a view angle compensation film, in addition to the color filter of the present invention. The color filter of the present invention can be applied to a liquid crystal display device constituted with these known members. These members are described in, for example, "'94 Market of Peripheral Materials And Chemicals of Liquid Crystal Display (Kentaro Shima, CMC Publishing Co., Ltd., published in 1994)" and "2003 Current Situation of Market Relating to Liquid Crystal and Prospects (Vol. 2) (Ryokichi Omote, Fuji Chimera Research Institute, Inc., published in 2003)".

The backlight is described in SID Meeting Digest 1380 (2005) (A. Konno, et al.), December Issue of Monthly "Display", 2005, pp. 18-24 (Yasuhiro Shima) and pp. 25-30 (Takaaki Yagi) of the documents, and the like.

If the color filter in the present invention is used in a liquid crystal display device, high contrast can be realized when the color filter is combined with a three-wavelength tube of a cold cathode tube known in the related art. Further, if a light source of LED in red, green, and blue (RGB-LED) is used as a backlight, a liquid crystal display device having high luminance, high color purity, and good color reproducibility can be provided.

EXAMPLES

Hereinafter, the present invention will be described in more detail with reference to Examples, but the present invention is not limited to Examples below as long as the gist of the present invention is not impaired. Further, "%" and "part(s)" are based on mass unless otherwise specified.

Synthesis Example 1

Synthesis of Pigment Monomer (X-1)

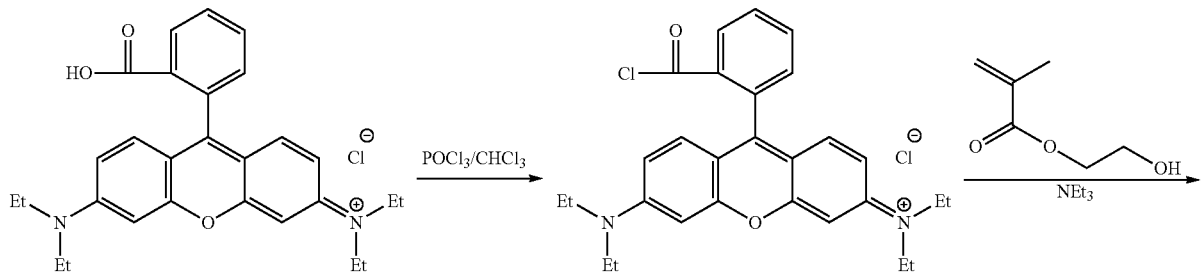

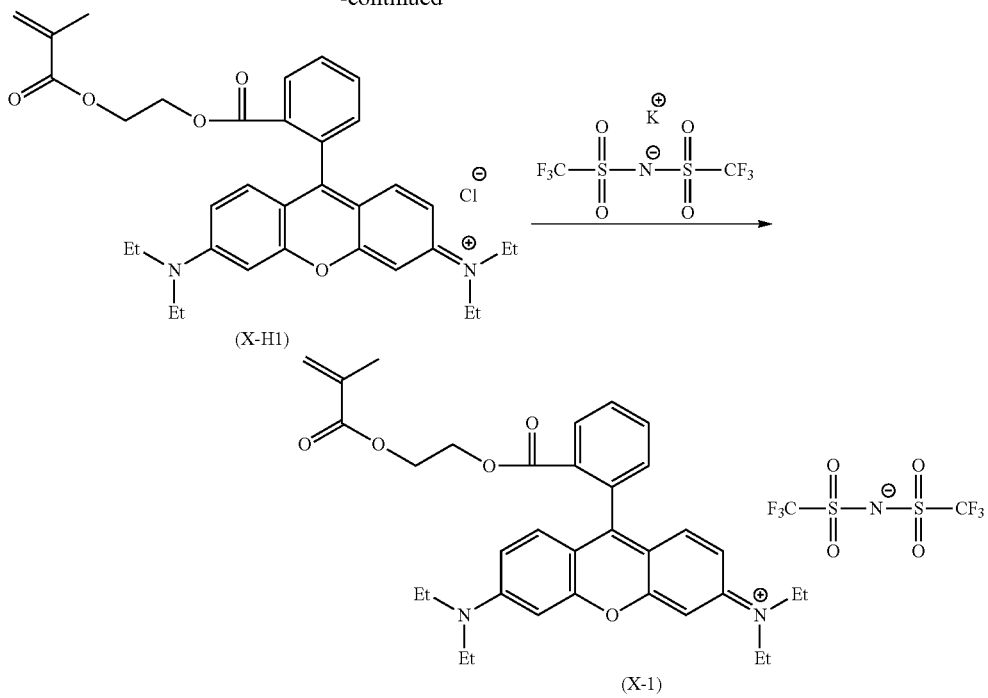

20.0 g (41.8 mmol) of Rhodamine B was dissolved in 125 g of chloroform, and then 9.6 g (62.6 mmol) of phosphorus oxychloride was added dropwise thereto while cooling in an ice bath. Thereafter, the mixture was heated at an external temperature of 65° C. for 3 hours. After cooling to 20° C., 9.8 g (75.2 mmol) of 2-hydroxyethyl methacrylate was added to the mixture while cooling in an ice bath, and 30.8 g (304 mmol) of triethylamine was added thereto. After stirring for 3 hours at an internal temperature set to 20° C., 1.00 g of chloroform was added thereto, the mixture was subjected to liquid separation with water, and then the chloroform layer was concentrated. The concentrate was purified by silica gel column with chloroform:methanol=9:1 as an eluent to obtain 19.5 g of (X—H1). The obtained compound was added to 100 mL of methanol, 13.3 g (41.8 mmol) of potassium=bis(trifluoromethanesulfonyl)imide was added thereto, and the mixture was stirred at 25° C. for 2 hours. The mixture was subjected to liquid separation with 200 mL of ethyl acetate and 100 mL of water, and the ethyl acetate layer was concentrated to obtain 17.2 g of (X-1). Maximum absorption wavelength (λmax)=552 nm (methanol solution). (m/z) (posi)=555 (posi), (m/z) (nega)=280.

Synthesis Example 2

Synthesis of Pigment Monomer (X-2)

The same procedure was carried out except that potassium=bis(trifluoromethanesulfonyl)imide of Synthesis Example 1 was changed to potassium=bis(trifluoromethanesulfonyl)imide (17.4 g) to obtain 19.5 g of a pigment monomer (X-2).

Synthesis Example 3

Synthesis of Pigment Monomer (X-3)

The same procedure was carried out except that potassium=bis(trifluoromethanesulfonyl)imide of Synthesis Example 1 was changed to a cyclohexafluoropopane-1,3-bis(sulfonyl)imide potassium salt (13.8 g) to obtain 18.5 g of a pigment monomer (X-3).

Synthesis Example 4

Synthesis of Pigment Monomer (X-4)

The same procedure was carried out except that potassium=bis(trifluoromethanesulfonyl)imide of Synthesis Example 1 was changed to potassium=tris(trifluoromethanesulfonyl)methide (25.9 g) to obtain 19.4 g of a pigment monomer (X-4).

Synthesis Example 5

Synthesis of Pigment Monomer (X-5)

The same procedure was carried out except that potassium=bis(trifluoromethanesulfonyl)imide of Synthesis Example 1 was changed to tetramethylammonium tris(pentafluoroethyl)trifluorophosphate (21.7 g) to obtain 18.5 g of a pigment monomer (X-5).

Synthesis Example 6

Synthesis of Pigment Monomer (X-6)

The same procedure was carried out except that potassium=bis(trifluoromethanesulfonyl)imide of Synthesis Example 1 was changed to lithium=tetracyanoborate (5.10 g) to obtain 14.2 g of a pigment monomer (X-6).

Synthesis Example 7

Synthesis of Pigment Monomer (X-7)

The same procedure was carried out except that potassium=bis(trifluoromethanesulfonyl)imide of Synthesis Example 1 was changed to sodium tetrakis[3,5-bis(trifluoromethyl)phenyl]borate hydrate (37.0 g) to obtain 45.2 g of a pigment monomer (X-7).

Synthesis Example 8

Synthesis of Pigment Monomer (X-8)

The same procedure was carried out except that potassium=bis(trifluoromethanesulfonyl)imide of Synthesis Example 1 was changed to sodium tetrakis[4-fluorophenyl] borate hydrate (17.3 g) to obtain 32.2 g of a pigment monomer (X-8).

Synthesis Example 9

Synthesis of Pigment Monomer (X-9)

The same procedure was carried out except that 2-hydroxyethyl methacrylate of Synthesis Example 1 was changed to 2-hydroxyethyl acrylate (8.73 g) to obtain 17.4 g of a pigment monomer (X-9).

Synthesis Example 10

Synthesis of Pigment Monomer (X-10)

The same procedure was carried out except that 2-hydroxyethyl methacrylate of Synthesis Example 1 was changed to N-(2-hydroxyethyl)acrylamide (8.65 g) to obtain 17.1 g of a pigment monomer (X-10).

Synthesis Example 11

Synthesis of Pigment Monomer (X-11)

The same procedure was carried out except that 2-hydroxyethyl methacrylate of Synthesis Example 1 was changed to N-(2-hydroxyethyl)methacrylamide (8.92 g) to obtain 17.2 g of a pigment monomer (X-11).

Synthesis Example 12

Synthesis of Pigment Monomer (X-12)

The same procedure was carried out except that 2-hydroxyethyl methacrylate of Synthesis Example 1 was changed to 2-hydroxyethyl 4-vinylbenzoate (14.4 g) to obtain 18.4 g of a pigment monomer (X-12).

Synthesis Example 13

Synthesis of Pigment Monomer (X-13)

The same procedure was carried out except that 2-hydroxyethyl methacrylate of Synthesis Example 1 was changed to 5-hydroxypentyl methacrylate (12.9 g) to obtain 17.9 g of a pigment monomer (X-13).

Synthesis Example 14

Synthesis of Pigment Monomer (X-14)

The same procedure was carried out except that Rhodamine B of Synthesis Example 1 was changed to the following compound (a) (18.9 g) to obtain 19.5 g of a pigment monomer (X-14).

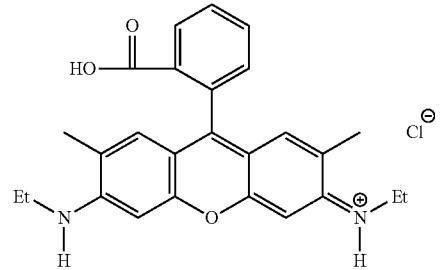

(a)

Synthesis Example 15

Synthesis of Pigment Monomer (X-15)

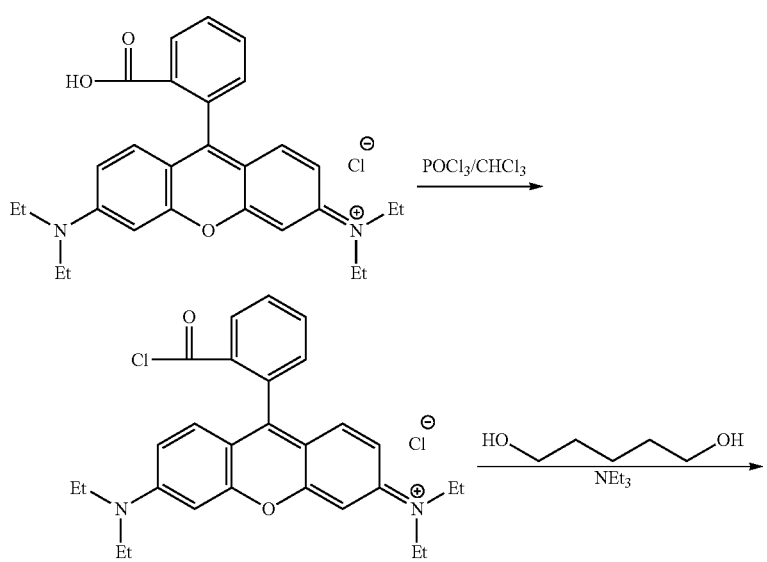

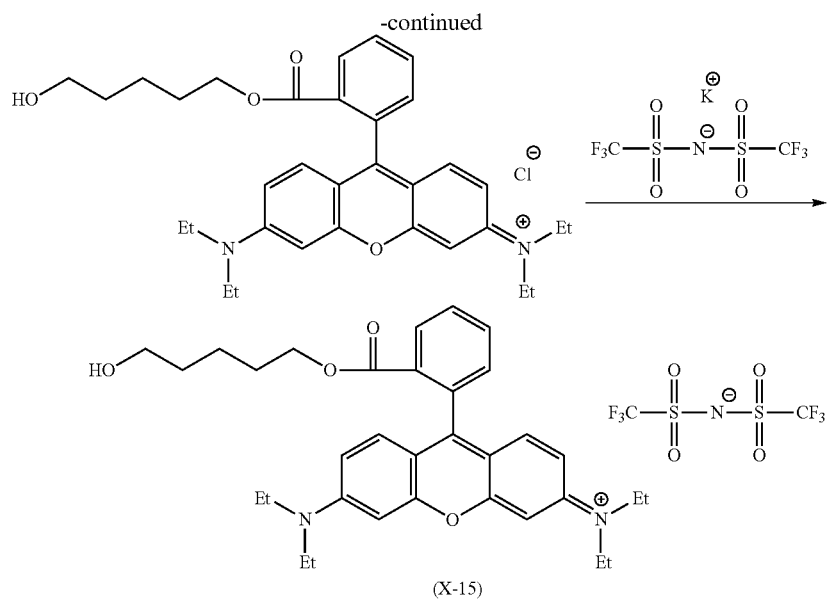

(X-15)

20.0 g (41.8 mmol) of Rhodamine B was dissolved in 125 g of chloroform, and then 9.6 g (62.6 mmol) of phosphorus oxychloride was added dropwise thereto while cooling in an ice bath. Thereafter, the mixture was heated at an external temperature of 65° C. for 3 hours. After cooling to 20° C., the mixture was transferred to a dropping funnel and added dropwise to a solution of 200 g of 1,5-pentanediol and 30.8 g (304 mmol) of triethylamine under ice-cooling. After stirring for 3 hours at an internal temperature set to 20° C., 100 g of chloroform was added thereto, the mixture was subjected to liquid separation with water, and then the chloroform layer was concentrated. The obtained concentrate was purified by silica gel column with chloroform:methanol=9:1 as an eluent. The obtained compound was added to 100 mL of methanol, 13.3 g (41.8 mmol) of potassium=bis(trifluoromethanesulfonyl)imide was added thereto, and the mixture was stirred at 25° C. for 2 hours. The mixture was subjected to liquid separation with 200 mL of ethyl acetate and 100 mL of water, and the ethyl acetate layer was concentrated to obtain 17.2 g of (X-1). λmax=552 nm (methanol solution). m/z (posi)=529, m/z (nega)=280.

Synthesis Example 16

Synthesis of Pigment Monomer (X-16)

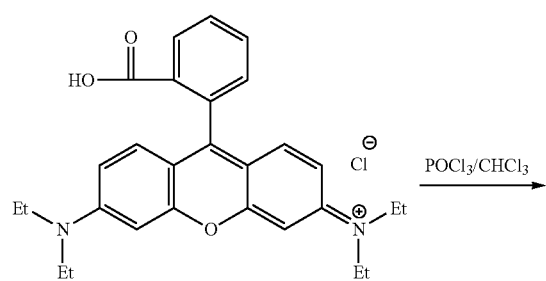

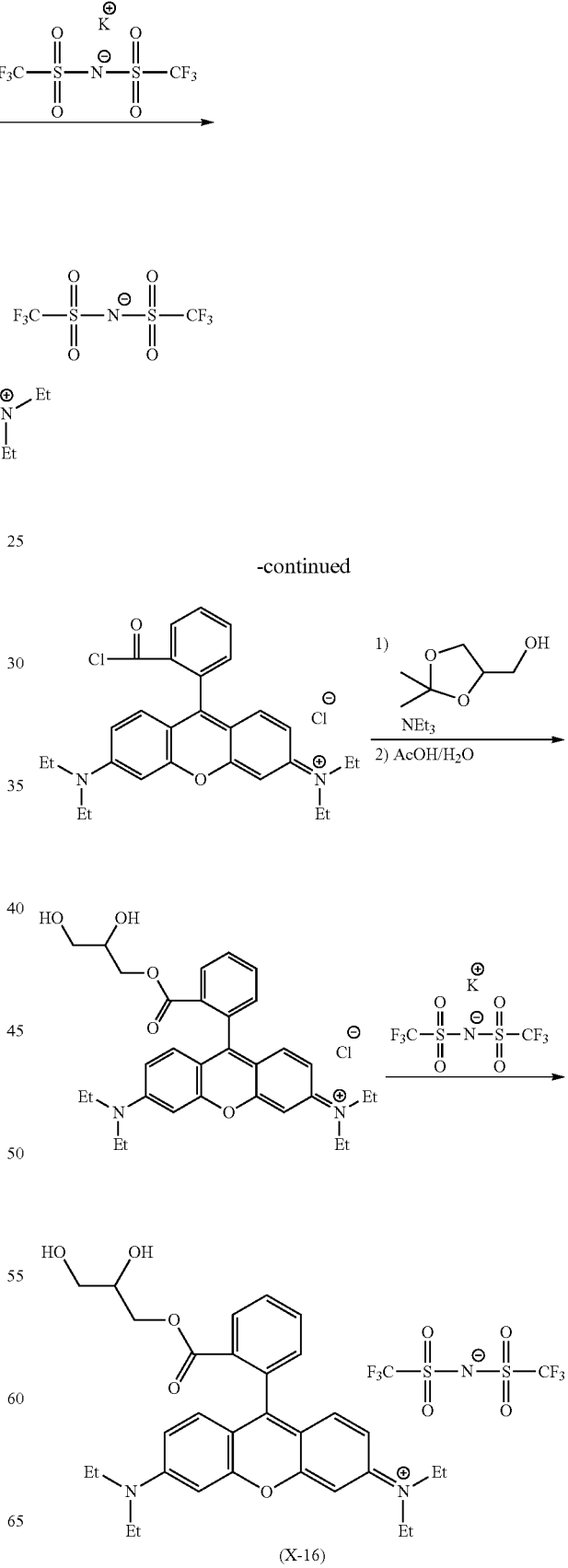

(X-16)

20.0 g (41.8 mmol) of Rhodamine B was dissolved in 125 g of chloroform, and then 9.6 g (62.6 mmol) of phosphorus oxychloride was added dropwise thereto while cooling in an ice bath. Thereafter, the mixture was heated at an external temperature of 65° C. for 3 hours. After cooling to 20° C., 9.9 g (75.2 mmol) of 2,2-dimethyl-1,3-dioxolane-4-methanol was added thereto while cooling in an ice bath, and 30.8 g (304 mmol) of triethylamine was added to the mixture. After stirring for 3 hours at an internal temperature set to 20° C., 100 g of chloroform was added thereto, the mixture was subjected to liquid separation with water, and then the chloroform layer was concentrated. 100 mL of acetate and 10 mL of water were added to the solution, and the mixture was heated at 50° C. for 24 hours. The reaction solution was concentrated, and the obtained concentrate was purified by silica gel column with chloroform:methanol=9:1 as an eluent. The obtained compound was added to 100 mL of methanol, 13.3 g (41.8 mmol) of potassium=bis(trifluoromethanesulfonyl)imide was added thereto, and the mixture was stirred at 25° C. for 2 hours. The mixture was subjected to liquid separation with 200 mL of ethyl acetate and 100 mL of water, and the ethyl acetate layer was concentrated to obtain 14.6 g of (X-16). λmax=552 nm (methanol solution). m/z (posi)=517 posi, m/z (nega)=280.

Synthesis Example 17

Synthesis of Pigment Monomer X-17

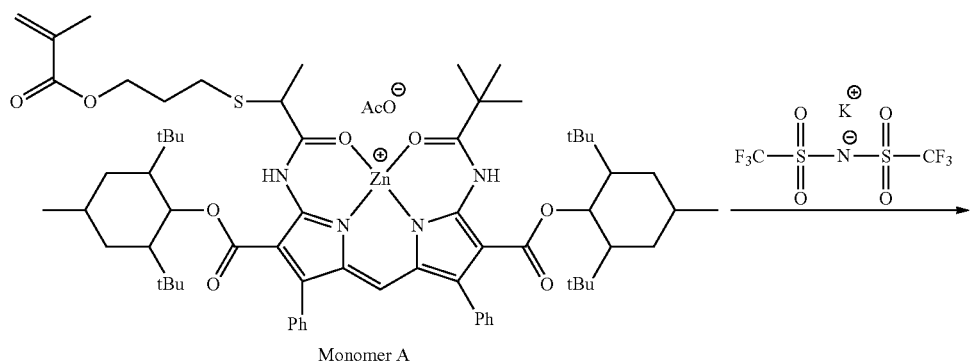

Monomer A

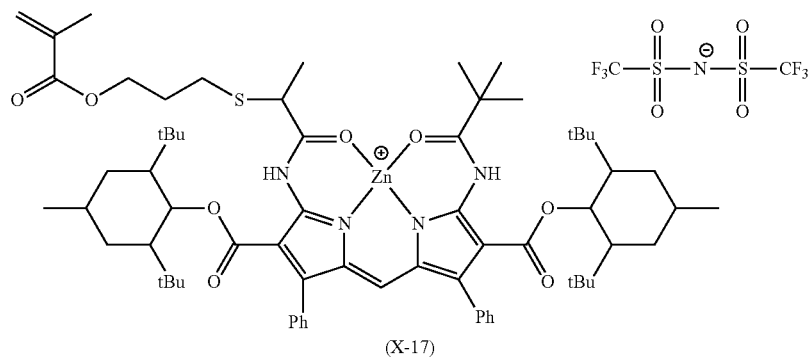

(X-17)

10.0 g (8.0 mmol) of a monomer A was dissolved in 100 mL of chloroform. Next, 3.63 g (12.0 mmol) of potassium=bis(trifluoromethanesulfonyl)imide and 50 mL of ion exchange water were added thereto, and the mixture was stirred at 40° C. for 3 hours. The aqueous layer was removed and the chloroform layer was concentrated to obtain 9.4 g of (X-17). Maximum absorption wavelength (λmax)=553 nm (methanol solution). (m/z) (posi)=1191 (posi), (m/z) (nega)=280.

Synthesis Example 18

Synthesis of Pigment Monomer X-18

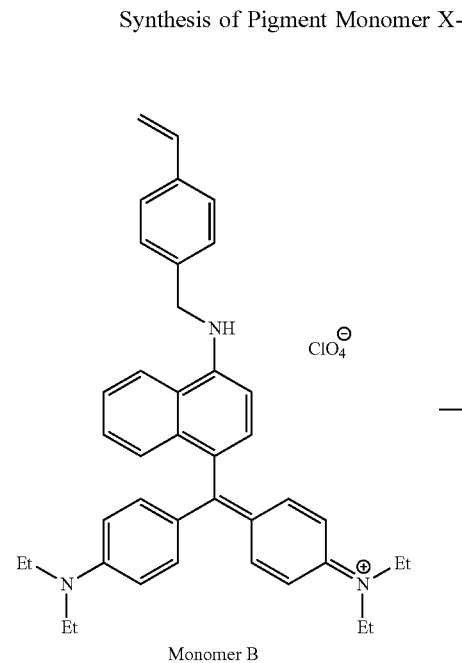

Monomer B

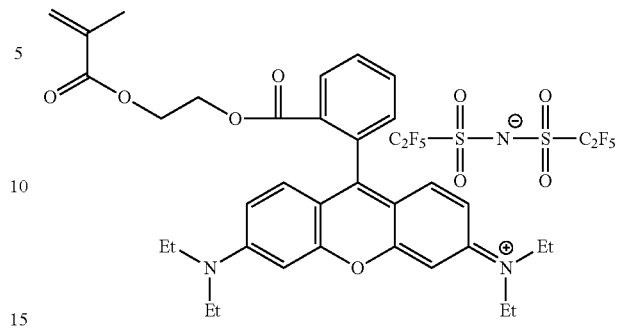

(X-2)

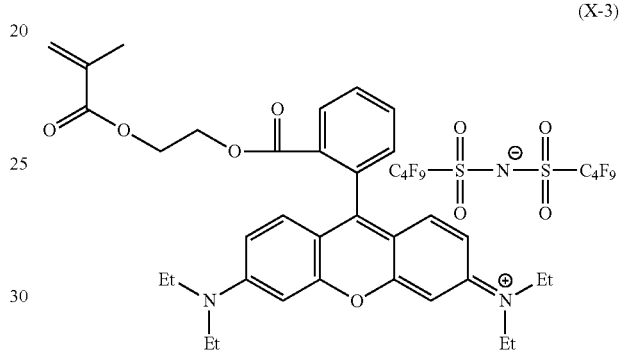

(X-3)

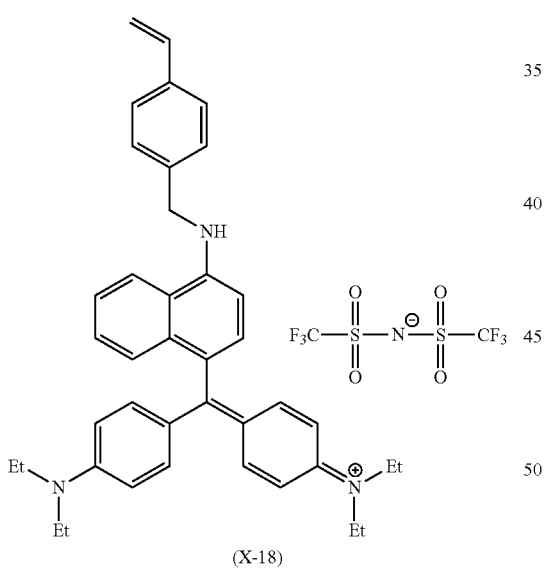

(X-18)

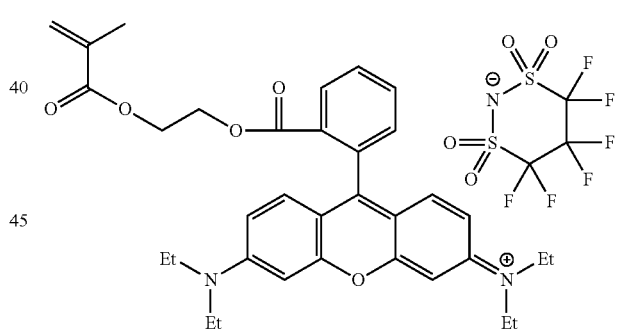

(X-4)

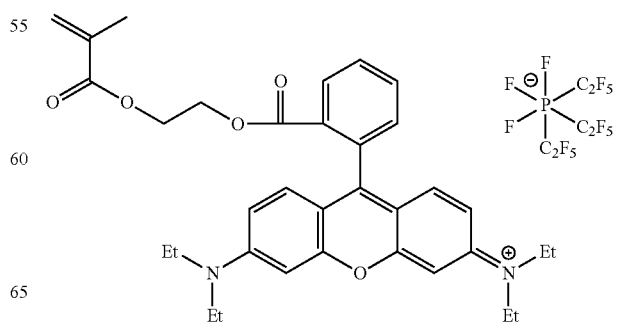

(X-5)

10.0 g (8.0 mmol) of a monomer B was dissolved in 100 mL of chloroform. Next, 3.63 g (12.0 mmol) of potassium=bis(trifluoromethanesulfonyl)imide and 50 mL of ion exchange water were added thereto, and the mixture was stirred at 40° C. for 3 hours. The aqueous layer was removed and the chloroform layer was concentrated to obtain 9.4 g of (X-18). Maximum absorption wavelength ($\lambda$max)=595 nm (methanol solution). (m/z) (posi)=566 (posi), (m/z) (nega)=280.

(X-6)
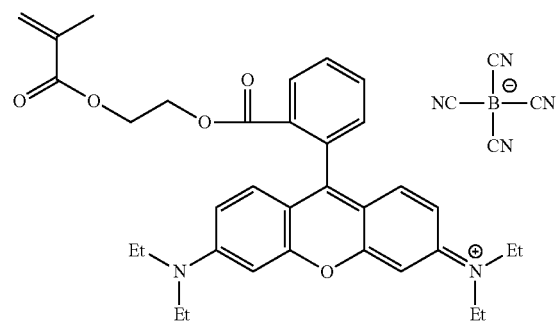
(X-7)
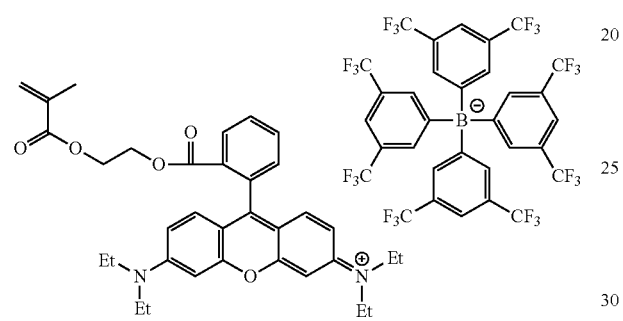
(X-8)
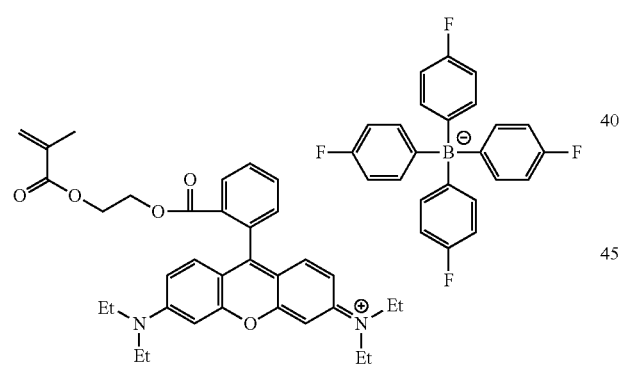
(X-9)
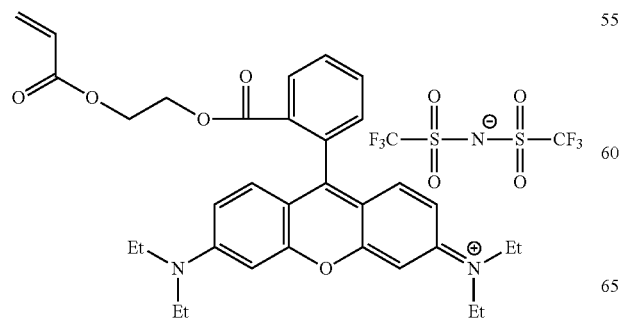
(X-10)
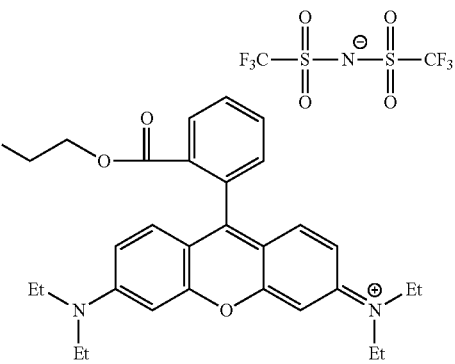
(X-11)
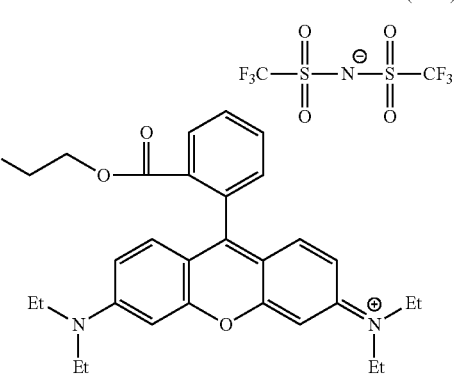
(X-12)
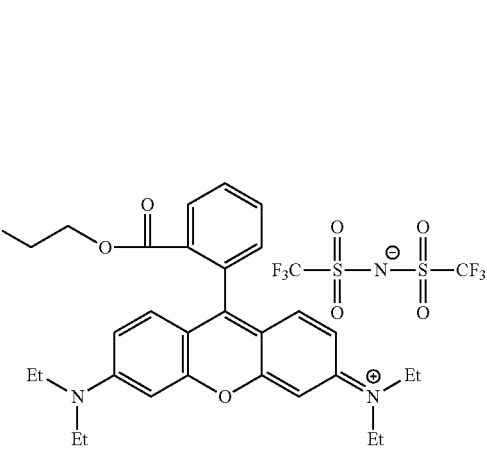

-continued

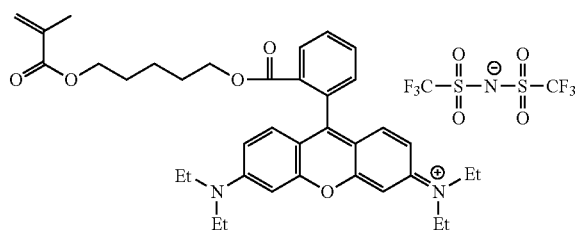

(X-13)

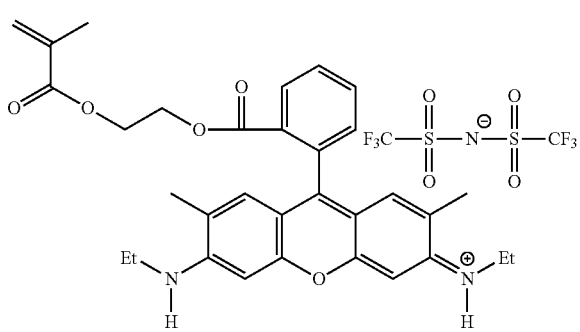

(X-14)

The physical properties of (X-1) to (X-18) are shown below.

TABLE 3

| Pigment monomer | λmax (nm) | m/z (posi) | m/z (nega) |
|---|---|---|---|
| (X-1) | 552 | 555 | 280 |
| (X-2) | 552 | 555 | 380 |
| (X-3) | 552 | 555 | 580 |
| (X-4) | 551 | 555 | 292 |
| (X-5) | 552 | 555 | 445 |
| (X-6) | 552 | 555 | 115 |
| (X-7) | 552 | 555 | 863 |
| (X-8) | 551 | 555 | 391 |
| (X-9) | 553 | 541 | 280 |
| (X-10) | 552 | 540 | 280 |
| (X-11) | 552 | 554 | 280 |
| (X-12) | 552 | 617 | 280 |
| (X-13) | 552 | 597 | 280 |
| (X-14) | 527 | 527 | 280 |
| (X-15) | 553 | 529 | 280 |
| (X-16) | 552 | 517 | 280 |
| (X-17) | 553 | 1191 | 280 |
| (X-18) | 596 | 566 | 280 |

In the table above, m/z (posi) represents a molecular weight measured in a positive mode of MALDI TOFMASS, and m/z (nega) represents a molecular weight measured in a negative mode of MALDI TOFMASS.

Synthesis Example 17

Synthesis of Pigment Multimer (S-1)

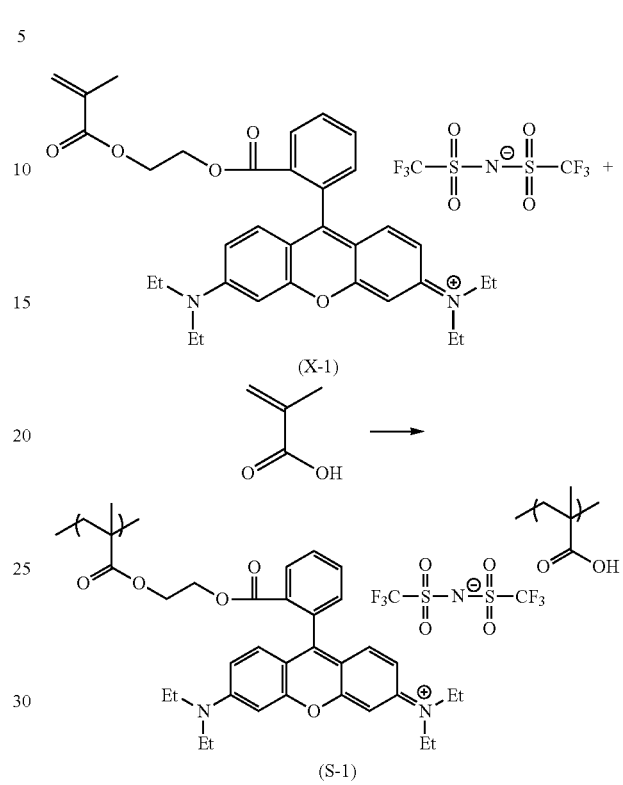

The monomer (X-1) (16.4 g), methacrylic acid (0.80 g), dodecylmercaptan (0.51 g), and propylene glycol 1-monomethylether 2-acetate (hereinafter also referred to as "PGMEA") (46.6 g) were mixed, and a half amount thereof was put into a three-neck flask. The mixture was heated at 80° C. under a nitrogen atmosphere. Dimethyl 2,2'-azobis (isobutyrate) [product name: V601, manufactured by Wako Pure Chemical Industries, Ltd.] (0.58 g) was added to the residual solution and dissolved therein, and the solution was put dropwise into a three-neck flask for 2 hours. Thereafter, the solution was stirred for 3 hours, then warmed to 90° C., heated and stirred for 2 hours, and then left to be cooled. After cooling to room temperature, the mixture was added dropwise to a mixed solvent of methanol/ion exchange water=100 mL/10 mL to perform reprecipitation. After filtration, the solution was dried by air-blowing at 40° C. for 2 days to obtain 15.6 g of a pigment multimer (S-1).

<Synthesis of Pigment Multimers (S-2) to (S-23), (S-28), (S-29), and (S-H1)>

The same procedure was carried out except that the monomer (X-1) and methacrylic acid in Synthesis Example 1 were changed to the monomers and the introduction amounts described in Table 4 below, pigment multimers (S-2) to (S-23), (S-28), (S-29), and (S-H1) were synthesized.

TABLE 4

| | Repeating unit 1 | | Repeating unit 2 | | Repeating unit 3 | |
|---|---|---|---|---|---|---|
| Pigment multimer | Raw monomer | Total introduction amount (g) | Raw monomer | Total introduction amount (g) | Raw monomer | Total introduction amount (g) |
| (S-1) | (X-1) | 16.4 | Methacrylic acid | 0.80 | | |

TABLE 4-continued

| Pigment multimer | Repeating unit 1 | | Repeating unit 2 | | Repeating unit 3 | |
|---|---|---|---|---|---|---|
| | Raw monomer | Total introduction amount (g) | Raw monomer | Total introduction amount (g) | Raw monomer | Total introduction amount (g) |
| (S-2) | (X-2) | 16.4 | Methacrylic acid | 0.80 | | |
| (S-3) | (X-3) | 16.4 | Methacrylic acid | 0.80 | | |
| (S-4) | (X-4) | 16.4 | Methacrylic acid | 0.80 | | |
| (S-5) | (X-5) | 16.4 | Methacrylic acid | 0.80 | | |
| (S-6) | (X-6) | 16.4 | Methacrylic acid | 0.80 | | |
| (S-7) | (X-7) | 16.4 | Methacrylic acid | 0.80 | | |
| (S-8) | (X-8) | 16.4 | Methacrylic acid | 0.80 | | |
| (S-9) | (X-9) | 16.4 | Methacrylic acid | 0.80 | | |
| (S-10) | (X-10) | 16.4 | Methacrylic acid | 0.80 | | |
| (S-11) | (X-11) | 16.4 | Methacrylic acid | 0.80 | | |
| (S-12) | (X-12) | 16.4 | Methacrylic acid | 0.80 | | |
| (S-13) | (X-13) | 16.4 | Methacrylic acid | 0.80 | | |
| (S-14) | (X-14) | 16.4 | Methacrylic acid | 0.80 | | |
| (S-15) | (X-1) | 13 | Methacrylic acid | 0.80 | HEMA | 3.5 |
| (S-16) | (X-1) | 13 | Methacrylic acid | 0.80 | BzMA | 3.5 |
| (S-17) | (X-1) | 16.4 | Acrylic acid | 0.65 | | |
| (S-18) | (X-1) | 16.4 | A | 2.30 | | |
| (S-19) | (X-1) | 16.4 | B | 3.00 | | |
| (S-20) | (X-1) | 16.4 | C | 3.00 | | |
| (S-21) | (X-1) | 16.4 | D | 3.00 | | |
| (S-22) | (X-1) | 16.4 | Methacrylic acid | 1.80 | | |
| (S-23) | (X-1) | 16.4 | Methacrylic acid | 3.20 | | |
| (S-28) | (X-17) | 16.4 | Methacrylic acid | 0.80 | | |
| (S-29) | (X-18) | 16.4 | Methacrylic acid | 0.80 | | |
| (S-H1) | (X-H1) | 16.4 | Methacrylic acid | 0.80 | | |

In the table, the monomers A to D as raw materials represent monomers represented by the following structural formulae. HEMA represents 2-hydroxyethyl methacrylate and BzMA represents benzyl methacrylate.

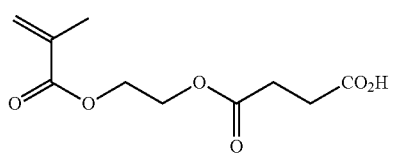

A

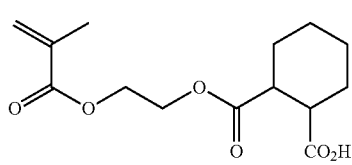

B

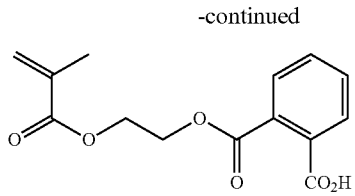

C

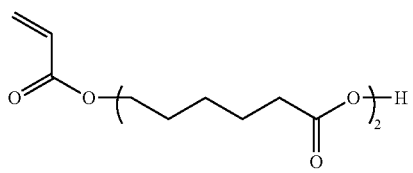

D

Synthesis Example 41

Synthesis of Pigment Multimer (S-24)

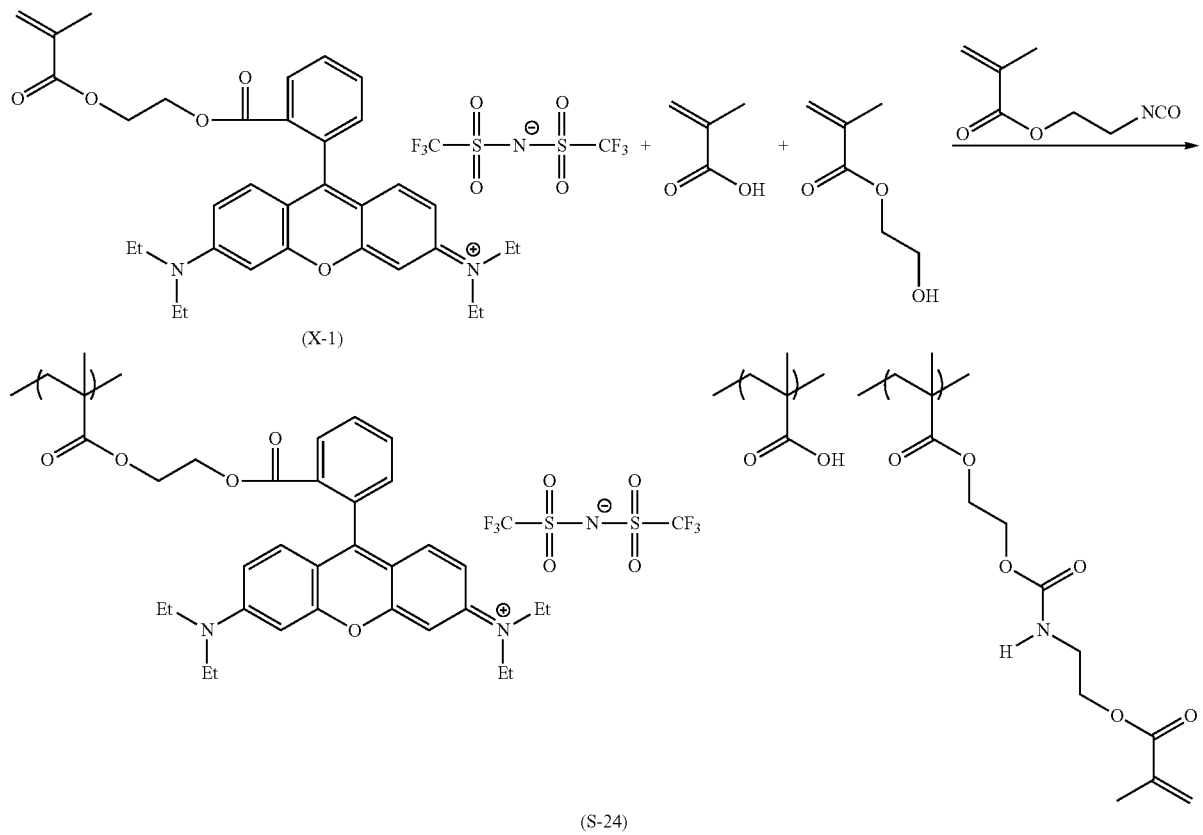

The monomer (X-1) (13.0 g), methacrylic acid (0.80 g), 2-hydroxyethyl methacrylate (3.5 g), dodecylmercaptan (0.51 g), and PGMEA (46.6 g) were mixed, and a half amount thereof was put into a three-neck flask. The mixture was heated at 80° C. under a nitrogen atmosphere. Dimethyl 2,2'-azobis(isobutyrate) [product name: V601, manufactured by Wako Pure Chemical Industries, Ltd.] (0.58 g) was added to the residual solution and dissolved therein, and the solution was put dropwise into a three-neck flask for 2 hours. Thereafter, the solution was stirred for 3 hours, then warmed to 90° C., heated and stirred for 2 hours, and then cooled to 80° C. Next, (2-isocyanatoethyl)methacrylate (4.17 g) and NEOSTANN U-100 (0.050 g) were added thereto, and the mixture was stirred for 2 hours and then left to be cooled. After cooling to room temperature, the mixture was added dropwise to a mixed solvent of methanol/ion exchange water=100 mL/10 mL to perform reprecipitation. After filtration, the solution was dried by air-blowing at 40° C. for 2 days to obtain 17.6 g of a pigment multimer (S-24).

Synthesis Example 42

Synthesis of Pigment Multimer (S-25)

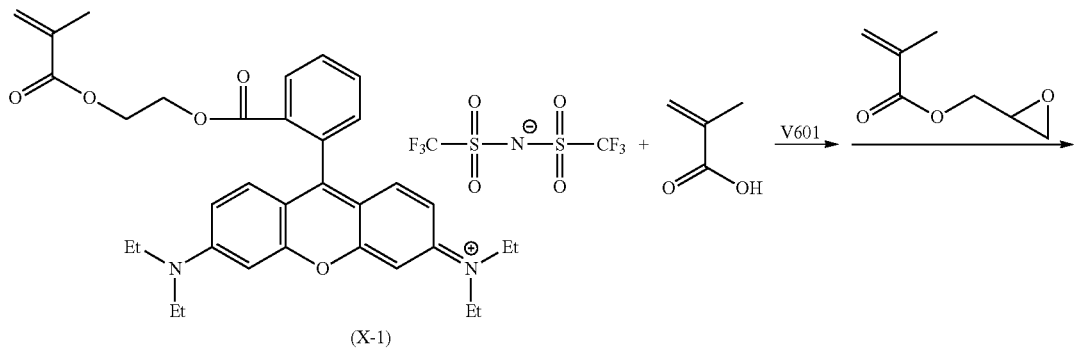

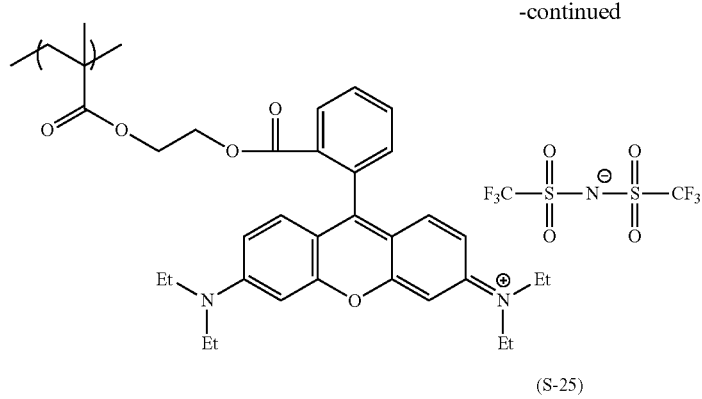

(S-25)

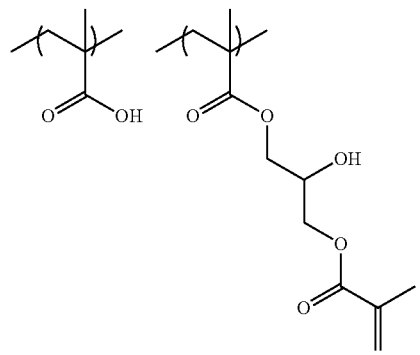

The monomer (X-1) (16.4 g), methacrylic acid (1.60 g), dodecylmercaptan (0.51 g), and propylene glycol 1-monomethylether 2-acetate (hereinafter also referred to as "PGMEA") (46.6 g) were mixed, and a half amount thereof was put into a three-neck flask. The mixture was heated at 80° C. under a nitrogen atmosphere. Dimethyl 2,2'-azobis (isobutyrate) [product name: V601, manufactured by Wako Pure Chemical Industries, Ltd.] (0.58 g) was added to the residual solution and dissolved therein, and the solution was put dropwise into a three-neck flask for 2 hours. Thereafter, the solution was stirred for 3 hours, then warmed to 90° C., heated and stirred for 2 hours. Next, glycidyl methacrylate (1.60 g) and tetrabutylammonium bromide (0.10 g) were added thereto, and the mixture was heated at 90° C. for 10 hours. After cooling to room temperature, the mixture was added dropwise to a mixed solvent of methanol/ion exchange water=100 mL/10 mL to perform reprecipitation. After filtration, the solution was dried by air-blowing at 40° C. for 2 days to obtain 15.6 g of a pigment multimer (S-25).

Synthesis Example 43

Synthesis of Pigment Multimer (S-26)

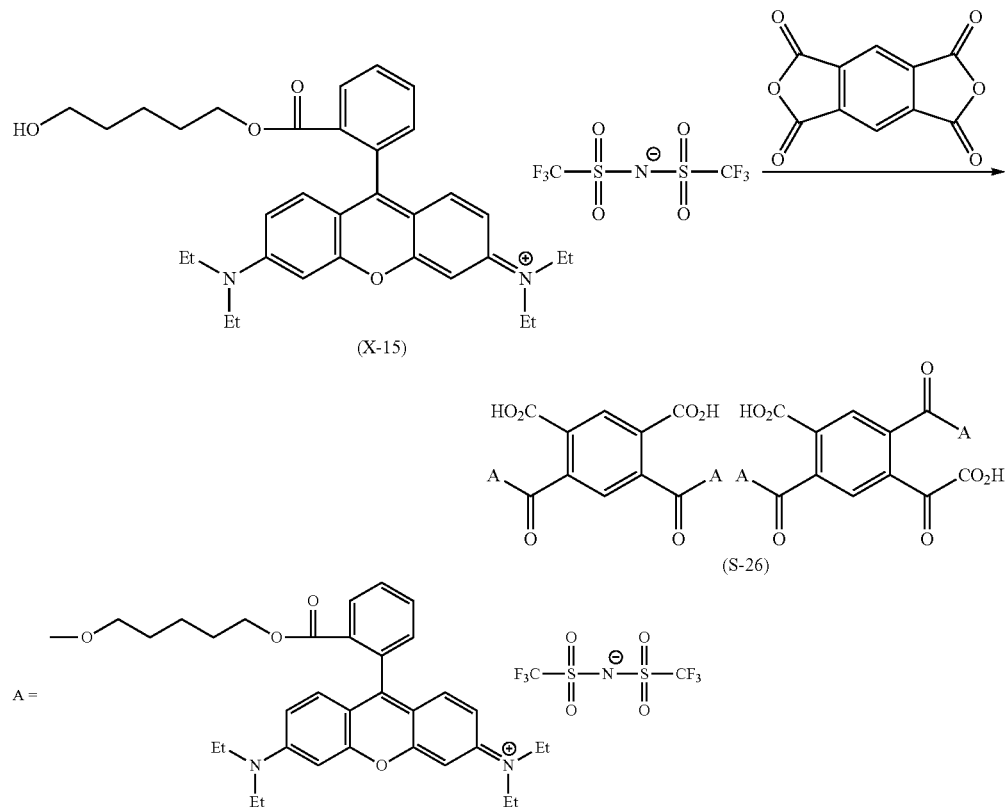

20.0 g (24.7 mmol) of a compound (X-15) and 2.69 g (12.4 mmol) of pyromellitic anhydride were added to 50 g of PGMEA, and the mixture was heated and refluxed for 10 hours in a nitrogen atmosphere. After cooling to room temperature, the mixture was added to 1,000 mL of hexane, and the obtained solid was filtered and dried by air-blowing at 40° C. for 2 days to obtain 17.5 g of a pigment multimer (S-26).

Synthesis Example 44

Synthesis of Pigment Multimer (S-27)

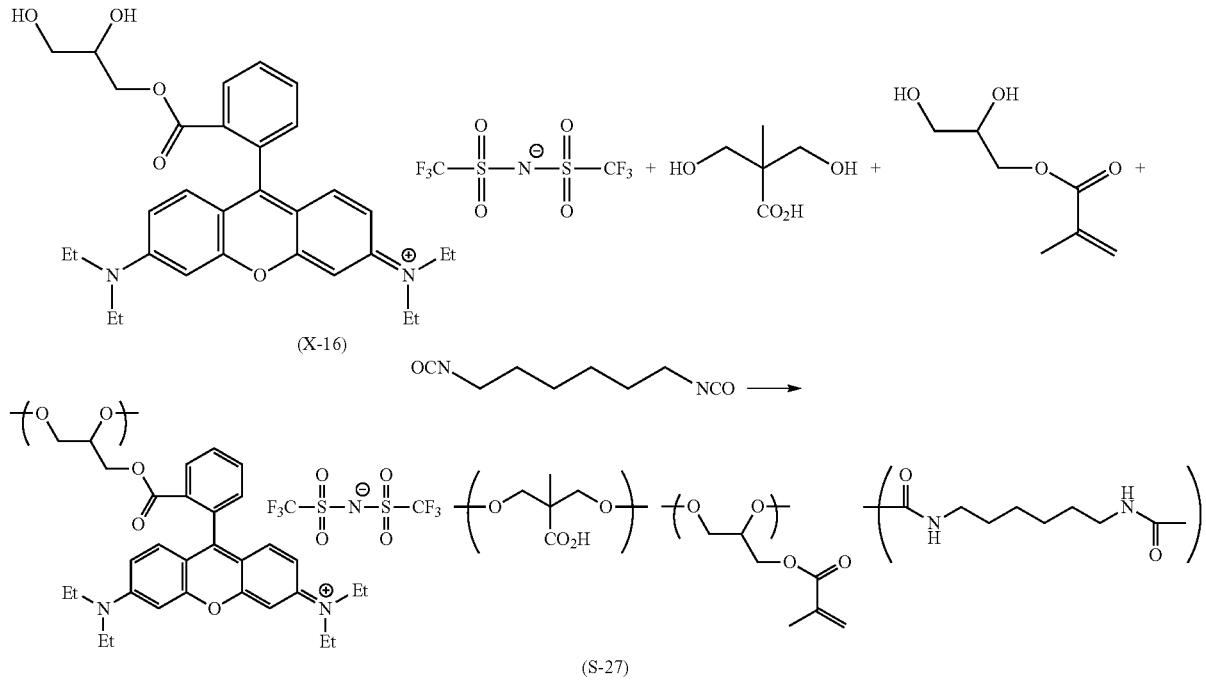

10.8 g (13.5 mmol) of a compound (X-16), 2.2 g (16.5 mmol) of 1,1-bis(hydroxymethyl)propionic acid, 6.3 g (39.1 mmol) of 2,3-dihydroxypropyl methacrylate, 11.6 g (69.1 mmol) of 1,6-diisocyanatohexane, and NEOSTANN U-1000 (0.1 g) were added to 100 g of methyl ethyl ketone, and the mixture was heated at 80° C. for 10 hours in a nitrogen atmosphere. After cooling to room temperature, the mixture was added to 1,000 mL of hexane, and the obtained gummy material was transferred to a Petri dish and dried by air-blowing at 40° C. for 2 days to obtain 18.4 g of a pigment multimer (S-27).

<Physical Properties of (S-1) to (S-29), and (S-H1)>
<<Measurement of Acid Values>>

The acid value was measured in accordance with a potentiometric titration method. Specifically, a compound was dissolved in a 9:1 mixed solvent of propylene glycol monomethyl ether and water, and the solution was titrated with a 0.1 mol/L aqueous potassium hydroxide solution, and an acid value (mgKOH/g) was calculated from a titer up to an inflection point on a titration curve.

<<Reduced Viscosity>>

19.0 g of PGMEA was added to 1.0 g of a pigment multimer, and dissolved therein. This solution was put into an Ubbelohde tube with a viscometer constant of 0.003 mm$^2$/s $\{$cst/s$\}$ to measure the reduced viscosity at 30° C.

The unit of the reduced viscosity is g (pigment multimer)/g (a total mass of the pigment multimer+PGMEA).

<<Maximum Absorption Wavelength (λmax)>>

The maximum absorption wavelength was measured with a spectrophotometer Cary 5 (manufactured by Varian).

TABLE 5

| Pigment multimer | Acid value (mgKOH/g) | Reduced viscosity | λmax (nm) |
|---|---|---|---|
| (S-1) | 30.2 | 6.2 | 552 |
| (S-2) | 30.5 | 6.5 | 552 |
| (S-3) | 29.9 | 6.4 | 552 |

TABLE 5-continued

| Pigment multimer | Acid value (mgKOH/g) | Reduced viscosity | λmax (nm) |
|---|---|---|---|
| (S-4) | 30.5 | 6.2 | 551 |
| (S-5) | 30.3 | 6.5 | 552 |
| (S-6) | 31.1 | 6.1 | 552 |
| (S-7) | 30.5 | 5.9 | 552 |
| (S-8) | 29.8 | 6.2 | 551 |
| (S-9) | 30.1 | 6.5 | 553 |
| (S-10) | 30.1 | 6.3 | 552 |
| (S-11) | 29.6 | 6.5 | 552 |
| (S-12) | 29.8 | 6.2 | 552 |
| (S-13) | 29.7 | 6.1 | 552 |
| (S-14) | 30.2 | 6.3 | 527 |
| (S-15) | 30.0 | 6.5 | 553 |
| (S-16) | 30.2 | 6.3 | 552 |
| (S-17) | 29.7 | 6.3 | 552 |
| (S-18) | 30.0 | 6.2 | 551 |
| (S-19) | 30.5 | 6.5 | 552 |
| (S-20) | 31.2 | 6.3 | 552 |
| (S-21) | 28.9 | 6.1 | 551 |
| (S-22) | 64.4 | 6.3 | 550 |
| (S-23) | 106.4 | 6.2 | 553 |
| (S-24) | 30.6 | 6.4 | 552 |
| (S-25) | 30.4 | 6.3 | 551 |
| (S-26) | 30.2 | 4.3 | 552 |
| (S-27) | 30.5 | 6.2 | 552 |
| (S-28) | 30.8 | 6.5 | 553 |
| (S-29) | 30.4 | 6.7 | 596 |
| (S-H1) | 30.2 | 6.6 | 551 |

1. Preparation of Resist Solution

A resist solution for an undercoat layer was prepared by mixing and dissolving components having the following composition.

<Composition of Resist Solution for Undercoat Layer>

| | |
|---|---|
| Solvent: propylene glycol monomethyl ether acetate (PGMEA) | 19.20 parts |
| Solvent: ethyl lactate | 36.67 parts |
| Alkali-soluble resin: 40% PGMEA solution of a benzyl methacrylate/methacrylic acid/2-hydroxyethyl methacrylate copolymer (molar ratio = 60/22/18, weight-average molecular weight of 15,000, number-average molecular weight of 9,000) | 30.51 parts |
| Dipentaerythritol hexaacrylate | 12.20 parts |
| Polymerization inhibitor: p-methoxyphenol | 0.0061 parts |
| Fluorine-based surfactant: F-475, manufactured by DIC Corporation | 0.83 parts |
| Photopolymerization initiator: trihalomethyl triazine-based photopolymerization initiator (TAZ-107, manufactured by Midori Kagaku Co., Ltd.) | 0.586 parts |

2. Manufacture of Undercoat Layer-Attached Silicon Wafer Substrate

A 6-inch silicon wafer was heated in an oven at 200° C. for 30 minutes. Next, the resist solution was applied onto this silicon wafer such that the dry film thickness became 1.5 μm. Further, the resultant was further heated and dried in an oven at 220° C. for 1 hour to form an undercoat layer to obtain an undercoat layer-attached silicon wafer substrate.

3. Preparation of Coloring Composition 3-1. Preparation of Blue (Blue 15:6) Pigment Dispersion A blue pigment dispersion 1 was prepared in the following manner.

A mixed solution including 13.0 parts of C. I. Pigment Blue 15:6 (blue pigment, average particle size of 55 nm), 5.0 parts of Disperbyk111 as a pigment dispersant, and 82.0 parts of PGMEA was mixed and dispersed for 3 hours by a beads mill (zirconia beads having a diameter of 0.3 mm) to prepare a pigment dispersion. Thereafter, the pigment dispersion was further subjected to a dispersion treatment under a pressure of 2,000 kg/cm$^3$ and at a flow rate of 500 g/min, by using a high-pressure dispersing machine equipped with a depressurizing mechanism, NANO-3000-10 (manufactured by Nihon B. E. E Co., Ltd.). This dispersion treatment was repeated 10 times to obtain a blue pigment dispersion 1 (a dispersion of C. I. Pigment Blue 15:6, pigment concentration of 13%) used in the coloring compositions of Examples or Comparative Examples.

For the obtained blue pigment dispersion, the particle size of the pigment was measured using a dynamic light scattering method (Microtrac Nanotrac UPA-EX150 (manufactured by Nikkiso Co., Ltd.)), and as a result, was found to be 24 nm.

In the same manner as in Preparation of Blue Pigment Dispersion 1 above except that a combination of the pigment shown in the table below and Disperbyk111 was used instead of the combination of C. I. Pigment Blue 15:6 used as the blue pigment and Disperbyk111 as the pigment dispersant in the blue pigment dispersion 1 in "3-1. Preparation of Blue Pigment Dispersion", a red pigment (PR254) dispersion and a yellow pigment (PY139) dispersion were prepared.

Furthermore, details of the pigments (PR254, PY139) shown in the table are as follows.

~Red Pigment~

C. I. Pigment Red 254 (PR254) (Particle size of 26 nm)

~Yellow Pigment~

C. I. Pigment Yellow 139 (PY139) (particle size of 29 nm)

3-2. Preparation of Coloring Composition (1) Coloring Compositions of Examples 1 to 39 and Comparative Examples 1 and 2

The following respective components were mixed, dispersed, and dissolved to prepare solutions of coloring compositions, and then the solutions were filtered through a 0.45-μm nylon filter to obtain the respective coloring compositions of Examples 1 to 39 and Comparative Examples 1 and 2.

| | |
|---|---|
| Cyclohexanone | 1.133 parts |
| Alkali-soluble resin (J1 or J2 shown below: the compound shown in the following table) | 0.030 parts |
| Solsperse 20000 (1% cyclohexane solution, manufactured by Lubrizol Japan Ltd.) | 0.125 parts |
| Photopolymerization initiator (I-1) to (I-8) below: the compound described below | 0.012 parts |
| Pigment multimer (the compound described in the following table) (provided that in Comparative Examples 1 and 2, a predetermined pigment monomer was used.) | 0.040 parts in terms of a solid content |
| Pigment dispersion including the pigment described in the following table (pigment concentration of 13.0%) | 0.615 parts |
| Dipentaerythritol hexaacrylate | 0.070 parts |
| Glycerol propoxylate (1% cyclohexane solution) | 0.048 parts |

In the following description, (I-1) is IRGACURE (registered trademark)-OXE01, (I-2) is IRGACURE (registered trademark)-OXE02 (manufactured by BASF), (I-3) is IRGACURE (registered trademark)-379, and (I-4) is DAROCUR (registered trademark)-TPO (all manufactured by BASF).

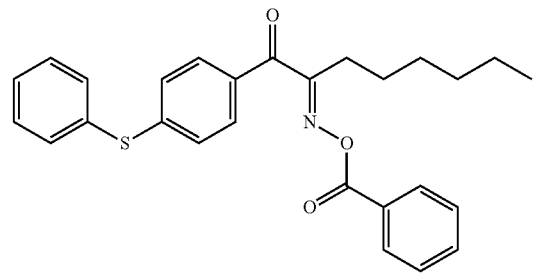

(I-1)

-continued (I-2)
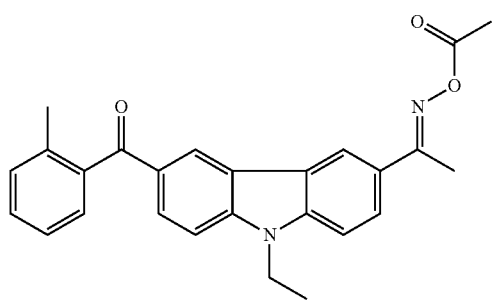

(I-3)
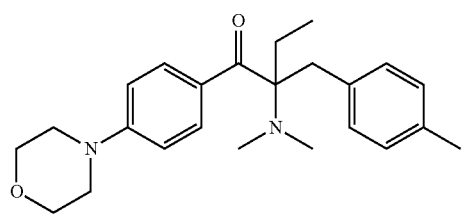

(I-4)
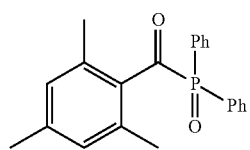

(I-5)
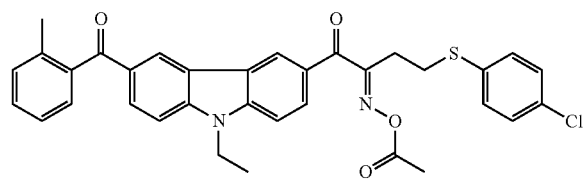

(I-6): (I-6a)/(I-6b) = 20/10 (mass ratio)

(I-6a)
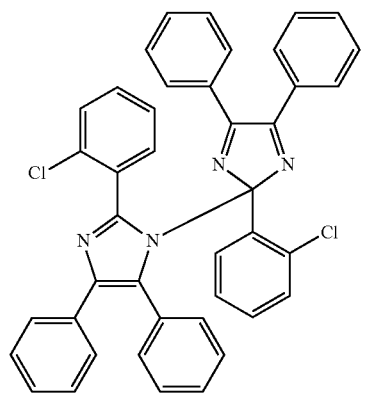

(I-6b)
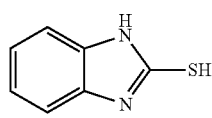

-continued (I-7)
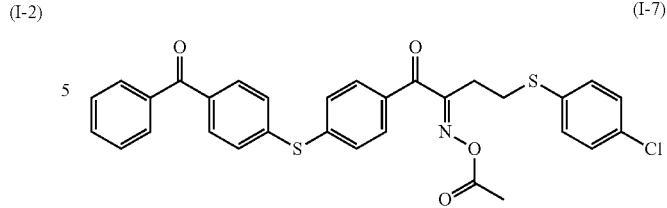

(I-8)
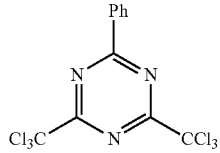

Alkali-Soluble Resin (J1)
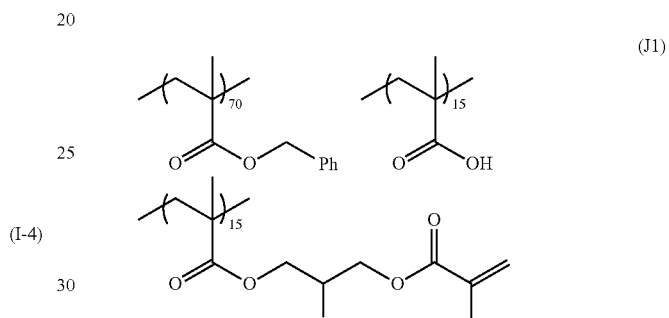

Mw 15,000

J2
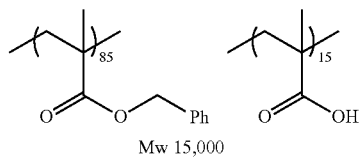

Mw 15,000

4. Manufacture of Color Filter Using Coloring Composition

<Pattern Formation>

Each of the coloring compositions of Examples and Comparative Examples, which had been prepared as above, was applied onto the undercoat layer of the undercoat layer-attached silicon wafer substrate obtained in the above section 2, thereby forming a coloring composition layer (coating film). Then, a heating treatment (pre-baking) was carried out for 120 seconds by using a hot plate at 100° C. such that the dry film thickness of the coating film became 0.6 μm.

Next, by using an i-ray stepper exposure device FPA-3000i5+ (manufactured by CANON Inc.), the wafer was exposed at a wavelength of 365 nm through an island pattern mask having a 1.0 μm×1.0 μm pattern, by varying the exposure dose in a range from 50 mJ/cm² to 1,200 mJ/cm².

Subsequently, the silicon wafer substrate, which had been irradiated with light and had a coating film formed thereon, was loaded onto a horizontal spin table of a spin shower developing machine (Model DW-30, manufactured by Chemitronics Co., Ltd.), and subjected to paddle development at 23° C. for 60 seconds by using CD-2000 (manufactured by FUJIFILM Electronic Materials CO., LTD.), thereby forming a colored pattern on the silicon wafer substrate.

The silicon wafer on which the colored pattern had been formed was fixed onto the horizontal spin table by a vacuum chuck method, and the silicon wafer substrate was rotated at a rotation frequency of 50 r.p.m. by using a rotation device. In this state, from the position above the rotation center, pure water was supplied onto the wafer from a spray nozzle in the form of a shower so as to perform rinsing treatment, and then the wafer was spray-dried.

In the manner described above, a monochromic color filter having the colored pattern formed of the coloring compositions of Examples or Comparative Examples were manufactured.

Thereafter, the size of the colored pattern was measured by using a length measuring SEM "S-9260A" (manufactured by Hitachi High-Technologies Corporation). An exposure dose at which the pattern size became 1.0 μm was determined as an optimal exposure dose.

5. Evaluation of Performance 5-1. Pattern Deficit 100 colored patterns were observed, and the number of patterns with deficit was counted. The larger the number is, the more pattern deficit is, leading to deterioration. The results are shown in the following table.

5-2. Pattern Linearity 100 patterns were observed with a length measuring SEM to evaluate the pattern linearity A: It has a rectangular shape and the side of the pattern is linear.

B: It has a rectangular shape and the side of the pattern is slightly distorted linear, but it was at a level such that there was no problem in practical use.

C: It is rounded and the side of the pattern is not smooth, but it was at a level such that there was a problem in practical use.

5-3. Heat Resistance

The glass substrate on which the coloring composition obtained above had been applied was loaded onto a hot plate at 200° C. such that the glass substrate came into contact with the substrate surface, and was heated for 1 hour. Then, the color difference (ΔE*ab value) before and after the heating was measured using a colorimeter MCPD-1000 (manufactured by Otsuka Electronics Co., Ltd.), and used as an index for evaluating the heat fastness, and the index was evaluated in accordance with the following evaluation criteria. A smaller ΔE*ab value indicates higher heat resistance. Incidentally, the ΔE*ab value is a value determined from the following color-difference formula according to CIE 1976 (L*, a*, b*) color space (New Edition of Color Science Handbook (1985) p. 266, edited by The Color Science Association of Japan).

$$\Delta E^*ab = \{(\Delta L^*)^2 + (\Delta a^*)^2 + (\Delta b^*)^2\}^{1/2}$$

5-4. Evaluation of Color Migration

The absorbance of the colored pattern in each of the color filters was measured by MCPD-3000 (manufactured by Otsuka Electronics Co., Ltd.) (Absorbance A).

A CT-2000L solution (a transparent undercoating agent, manufactured by FUJIFILM Electronics Materials Co., Ltd.) was applied onto the surface, on which the colored pattern of a color filter had been formed, such that the dried film thickness became 1 μm, and dried to form a transparent film, and the film was subjected to a heating treatment at 280° C. for 5 minutes.

After the completion of heating, the absorbance of the transparent film adjacent to the colored pattern was measured by MCPD-3000 (manufactured by Otsuka Electronics Co., Ltd.) (Absorbance B).

The ratio [%] of the absorbance B value of the obtained transparent film to the absorbance A value of the colored pattern which had been measured before heating was calculated [(Equation A) below]. The ratio was used as an index for evaluating the color migration to adjacent pixels.

Color migration (%) = Absorbance B/Absorbance A × 100 (Equation A)

TABLE 6

| Example | Pigment multimer | Pigment | Photopolymerization initiator | Alkali-soluble resin | Pattern deficit | Pattern linearity | Heat resistance | Color migration |
|---|---|---|---|---|---|---|---|---|
| 1 | (S-1) | PB15:6 | (I-1) | J1 | 0 | A | 1.2 | 0 |
| 2 | (S-2) | PB15:6 | (I-1) | J1 | 0 | A | 1.3 | 0 |
| 3 | (S-3) | PB15:6 | (I-1) | J1 | 0 | A | 1.2 | 0 |
| 4 | (S-4) | PB15:6 | (I-1) | J1 | 0 | A | 1.2 | 0 |
| 5 | (S-5) | PB15:6 | (I-1) | J1 | 0 | A | 1.2 | 0 |
| 6 | (S-6) | PB15:6 | (I-1) | J1 | 5 | A | 2.1 | 6 |
| 7 | (S-7) | PB15:6 | (I-1) | J1 | 6 | A | 2.2 | 7 |
| 8 | (S-8) | PB15:6 | (I-1) | J1 | 5 | A | 2.1 | 5 |
| 9 | (S-9) | PB15:6 | (I-1) | J1 | 0 | A | 1.3 | 0 |
| 10 | (S-10) | PB15:6 | (I-1) | J1 | 0 | A | 1.2 | 0 |
| 11 | (S-11) | PB15:6 | (I-1) | J1 | 0 | A | 1.1 | 0 |
| 12 | (S-12) | PB15:6 | (I-1) | J1 | 0 | A | 1.3 | 0 |
| 13 | (S-13) | PB15:6 | (I-1) | J1 | 0 | A | 1.1 | 0 |
| 14 | (S-14) | PB15:6 | (I-1) | J1 | 0 | A | 1.2 | 0 |
| 15 | (S-15) | PB15:6 | (I-1) | J1 | 0 | A | 1.3 | 0 |
| 16 | (S-16) | PB15:6 | (I-1) | J1 | 0 | A | 1.2 | 0 |
| 17 | (S-17) | PB15:6 | (I-1) | J1 | 0 | A | 1.3 | 0 |
| 18 | (S-18) | PB15:6 | (I-1) | J1 | 0 | A | 1.2 | 0 |
| 19 | (S-19) | PB15:6 | (I-1) | J1 | 0 | A | 1.1 | 0 |
| 20 | (S-20) | PB15:6 | (I-1) | J1 | 0 | A | 1.2 | 0 |
| 21 | (S-21) | PB15:6 | (I-1) | J1 | 0 | A | 1.3 | 0 |
| 22 | (S-22) | PB15:6 | (I-1) | J1 | 5 | A | 2.2 | 8 |
| 23 | (S-23) | PB15:6 | (I-1) | J1 | 7 | A | 2.3 | 7 |
| 24 | (S-24) | PB15:6 | (I-1) | J1 | 0 | A | 0.3 | 0 |
| 25 | (S-25) | PB15:6 | (I-1) | J1 | 0 | A | 0.4 | 0 |
| 26 | (S-26) | PB15:6 | (I-1) | J1 | 5 | B | 2.3 | 12 |
| 27 | (S-27) | PB15:6 | (I-1) | J1 | 7 | A | 2.2 | 6 |
| 28 | (S-1) | PR254 | (I-1) | J1 | 5 | A | 2.1 | 7 |
| 29 | (S-1) | PY139 | (I-1) | J1 | 2 | A | 2.3 | 4 |

TABLE 6-continued

| Example | Pigment multimer | Pigment | Photopolymerization initiator | Alkali-soluble resin | Pattern deficit | Pattern linearity | Heat resistance | Color migration |
|---|---|---|---|---|---|---|---|---|
| 30 | (S-1) | PB15:6 | (I-2) | J1 | 0 | A | 1.3 | 0 |
| 31 | (S-1) | PB15:6 | (I-3) | J1 | 11 | B | 4.5 | 11 |
| 32 | (S-1) | PB15:6 | (I-4) | J1 | 13 | B | 4.9 | 12 |
| 33 | (S-1) | PB15:6 | (I-5) | J1 | 0 | A | 1.3 | 0 |
| 34 | (S-1) | PB15:6 | (I-6) | J1 | 5 | A | 2.1 | 5 |
| 35 | (S-1) | PB15:6 | (I-7) | J1 | 0 | A | 1.3 | 0 |
| 36 | (S-1) | PB15:6 | (I-8) | J1 | 12 | B | 4.3 | 11 |
| 37 | (S-1) | PB15:6 | (I-1) | J2 | 15 | B | 4.2 | 10 |
| 38 | (S-28) | PB15:6 | (I-1) | J1 | 3 | A | 2.3 | 3 |
| 39 | (S-29) | PB15:6 | (I-1) | J1 | 4 | A | 2.4 | 4 |
| Comparative Example 1 | (S-H1) | PB15:6 | (I-1) | J1 | 13 | C | 7.1 | 2 |
| Comparative Example 2 | (X-1) | PB15:6 | (I-1) | J1 | 16 | C | 3.2 | 32 |

As apparent from the above table, it could be seen that in the case where a color filter was manufactured with a photoresist using the composition of the present invention, the pattern deficit was small, the pattern linearity was excellent, the heat resistance was high, and the color migration was small. In particular, it could be seen that by using a pigment multimer having a polymerizable group, the heat resistance is further improved.

In contrast, it could be seen that in the case where a pigment multimer having no non-nucleophilic counter anion or a monomer-type pigment is used, any one or more of the above effects cannot be accomplished.

6. Pattern Formation to Which Dry Etching Method is Applied

Preparation of Coloring Composition

The following components were mixed and dissolved to obtain the respective coloring compositions of Examples 37 to 72 and Comparative Examples 3 and 4.

| | |
|---|---|
| Cyclohexanone | 1.133 parts |
| Pigment multimer (the compound described in the following table) | 0.040 parts in terms of a solid content |
| Blue pigment dispersion above (pigment concentration of 13.0%) | 0.615 parts |
| Polymerizable compound (EHPE-3150 (1,2-epoxy-4-(2-oxiranyl)cyclohexane adduct of 2,2-bis(hydroxymethyl)-1-butanol, manufactured by Daicel Chemical Industries, Ltd.)) | 0.070 parts |
| Glycerol propoxylate (1% cyclohexane solution) | 0.048 parts |

7. Evaluation of Performance 7-1. Resistance to Alkaline Developing Liquid (Resistance to Developing Liquid)

The coloring composition was applied onto a glass substrate, using a spin coater such that the film thickness became 0.6 μm, and subjected to a heating treatment (pre-baking) using a hot plate at 100° C. for 120 seconds. Subsequently, a heating treatment (post-baking) was carried out by using a hot plate at 220° C. for 300 seconds to prepare a cured film.

The transmittance of the color filter thus obtained was measured at a wavelength region of 300 nm to 800 nm by a spectrophotometer (reference: glass substrate), which is a UV-VIS-NIR spectrophotometer, UV3600 (manufactured by SHIMADZU Corporation). In addition, differential interference images were observed through reflective observation (50× magnifications) by using an optical microscope, BX60, manufactured by OLYMPUS Corporation.

Next, the color filter was immersed in an alkaline developing liquid, FHD-5 (manufactured by FUJIFILM Electronic Materials CO., LTD.) for 5 minutes, dried, and then subjected to spectrometry again. Thus, the change in the transmittance at a wavelength of 550 nm before and after solvent immersion (a value represented by an equation |T0−T1|, in the case where the transmittance before solvent immersion is defined as T0 and the transmittance after solvent immersion is defined as T1) was evaluated.

7-2. Resistance to Peeling Solution

Then, a positive-type photoresist "FHi622BC" (manufactured by FUJIFILM Electronic Materials CO., LTD.) was applied onto the colored film manufactured in the section 7-1, and subjected to pre-baking to form a photoresist layer having a film thickness of 0.8 μm. Then, the photoresist layer was subjected to pattern exposure using an i-ray stepper (manufactured by CANON Inc.) in an exposure dose of 350 mJ/cm$^2$ and then to a heating treatment for 1 minute at temperature at which the temperature of the photoresist layer or ambient temperature reached 90° C. Thereafter, a peeling treatment was carried out using a photoresist peeling solution "MS230C" (manufactured by FUJIFILM Electronic Materials CO., LTD.) for 120 seconds to remove the resist pattern, and then cleaning with pure water and spin drying were carried out. Thereafter, dehydration and baking treatments at 100° C. for 2 minutes were carried out.

The obtained colored film was subjected to spectrometry and the change in the transmittance at 550 nm after peeling (a value represented by an equation |T0−T2|, in the case where the transmittance before solvent immersion is defined as T0 and the transmittance after solvent immersion is defined as T2) was evaluated.

TABLE 7

| Example | Pigment multimer | Pigment | Resistance to developing liquid | Resistance to peeling solution |
|---|---|---|---|---|
| 40 | (S-1) | PB15:6 | 0 | 0 |
| 41 | (S-2) | PB15:6 | 0 | 0 |

TABLE 7-continued

| Example | Pigment multimer | Pigment | Resistance to developing liquid | Resistance to peeling solution |
|---|---|---|---|---|
| 42 | (S-3) | PB15:6 | 0 | 0 |
| 43 | (S-4) | PB15:6 | 0 | 0 |
| 44 | (S-5) | PB15:6 | 0 | 0 |
| 45 | (S-6) | PB15:6 | 5 | 6 |
| 46 | (S-7) | PB15:6 | 4 | 5 |
| 47 | (S-8) | PB15:6 | 5 | 6 |
| 48 | (S-9) | PB15:6 | 0 | 0 |
| 49 | (S-10) | PB15:6 | 0 | 0 |
| 50 | (S-11) | PB15:6 | 0 | 0 |
| 51 | (S-12) | PB15:6 | 0 | 0 |
| 52 | (S-13) | PB15:6 | 0 | 0 |
| 53 | (S-14) | PB15:6 | 0 | 0 |
| 54 | (S-15) | PB15:6 | 0 | 0 |
| 55 | (S-16) | PB15:6 | 0 | 0 |
| 56 | (S-17) | PB15:6 | 0 | 0 |
| 57 | (S-18) | PB15:6 | 0 | 0 |
| 58 | (S-19) | PB15:6 | 0 | 0 |
| 59 | (S-20) | PB15:6 | 0 | 0 |
| 60 | (S-21) | PB15:6 | 0 | 0 |
| 61 | (S-22) | PB15:6 | 7 | 5 |
| 62 | (S-23) | PB15:6 | 5 | 8 |
| 63 | (S-24) | PB15:6 | 0 | 0 |
| 64 | (S-25) | PB15:6 | 0 | 0 |
| 65 | (S-26) | PB15:6 | 11 | 12 |
| 66 | (S-27) | PB15:6 | 6 | 5 |
| 67 | (S-1) | PR254 | 4 | 5 |
| 68 | (S-1) | PY139 | 3 | 4 |
| 69 | (S-1) | PB15:6 | 5 | 6 |
| 70 | (S-1) | PB15:6 | 11 | 13 |
| 71 | (S-1) | PB15:6 | 12 | 12 |
| 72 | (S-1) | PB15:6 | 0 | 0 |
| 73 | (S-1) | PB15:6 | 3 | 4 |
| 74 | (S-1) | PB15:6 | 0 | 0 |
| 75 | (S-1) | PB15:6 | 13 | 11 |
| 76 | (S-1) | PB15:6 | 14 | 10 |
| 77 | (S-28) | PB15:6 | 3 | 2 |
| 78 | (S-29) | PB15:6 | 3 | 4 |
| Comparative Example 3 | (S-H1) | PB15:6 | 33 | 35 |
| Comparative Example 4 | (X-1) | PB15:6 | 26 | 28 |

It could be seen that the resistance to a developing liquid and the resistance to a peeling solution were excellent in the case where color filters were manufactured using etching resists with the coloring compositions of Examples 40 to 78. Whereas those properties deteriorated with the compositions of Comparative Examples 3 and 4.

What is claimed is:

1. A colorant multimer (A) having a non-nucleophilic counter anion,
wherein the non-nucleophilic counter anion is an imide anion represented by the following formula (AN-1):

$$X^1-Y^1-N^--Y^2-X^2 \quad (AN\text{-}1)$$

wherein $X^1$ and $X^2$ each independently represents a halogen atom, an alkyl group, or an aryl group; $X^1$ and $X^2$ may be bonded to each other to form a ring; at least one of $X^1$ and $X^2$ is a fluorine atom-containing alkyl group having 1 to 10 carbon atoms; and $Y^1$ and $Y^2$ each independently represents —SO$_2$— or —CO—,
and further wherein the colorant multimer (A) having a non-nucleophilic counter anion has a partial structure derived from a colorant selected from the group consisting of a dipyrromethene colorant and a xanthene colorant, and
wherein the colorant multimer achieves a combination of high heat resistance and reduced color migration.

2. The colorant multimer according to claim 1, wherein the colorant multimer having a non-nucleophilic counter anion has a partial structure derived from a xanthene colorant.

3. The colorant multimer according to claim 1, wherein the colorant multimer has the following repeating unit:

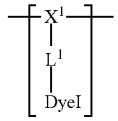

Formula (A)

wherein in Formula (A), $X^1$ represents a group capable of forming a main chain, $L^1$ represents a single bond or a divalent linking group; and DyeI represents a colorant structure having a cationic moiety;

Formula (C)

wherein in Formula (C), $L^3$ represents a single bond or a divalent linking group; DyeIII represents a colorant pigment-structure having a cationic moiety; and m represents 0 or 1;

$$(L^4-(-)-DyeIV)_n \quad \text{Formula (D)}$$

wherein in Formula (D), $L^4$ represents an n-valent linking group; n represents an integer of 2 to 20; and DyeIV represents a colorant structure having a cationic moiety.

4. The colorant multimer according to claim 1, wherein the colorant multimer has a polymerizable group.

5. The colorant multimer according to claim 1, which has a polymerizable group in an amount of 0.1 mmol to 2.0 mmol, with respect to 1 g of the colorant multimer (A).

6. The colorant multimer according to claim 1, wherein the colorant multimer has a group containing an ethylenically unsaturated bond.

7. The colorant multimer according to claim 1, wherein the colorant multimer has a repeating unit having an acid group.

8. A coloring composition comprising:
the colorant multimer (A) according to claim 1;
a curable compound (B);
and a colorant (C).

9. The coloring composition according to claim 8, further comprising a photopolymerization initiator (D).

10. The coloring composition according to claim 9, wherein the photopolymerization initiator (D) is an oxime compound.

11. The coloring composition according to claim 8, which is used for forming a colored layer of a color filter.

12. A cured film formed by curing the coloring composition according to claim 8.

13. A color filter having the cured film according to claim 12.

14. A solid-state imaging element comprising the color filter according to claim 13.

15. An image display device comprising the color filter according to claim 13.

16. A method for manufacturing a color filter, comprising:
applying the coloring composition according to claim 8 onto a support to form a coloring composition layer;

patternwise-exposing the coloring composition layer; and removing an unexposed area by development to form a colored pattern.

17. A method for manufacturing a color filter, comprising:

applying the coloring composition according to claim 8 onto a support to form a coloring composition layer, and curing the coloring composition layer to form a colored layer;

forming a photoresist layer on the colored layer;

patterning the photoresist layer by exposure and development to obtain a resist pattern; and dry-etching the colored layer using a resist pattern as an etching mask.

18. The colorant multimer according to claim 1, wherein the colorant multimer has a partial structure derived from a xanthene compound represented by the following General Formula (J):

General Formula (J)

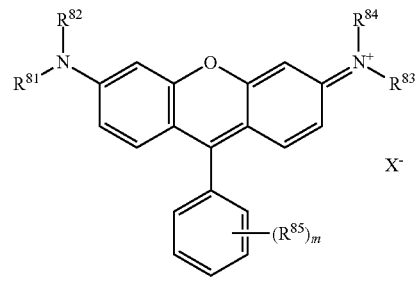

wherein in General Formula (J), $R^{81}$, $R^{82}$, $R^{83}$, and $R^{84}$ each independently represents a hydrogen atom or a monovalent substituent; each $R^{85}$ independently represents a monovalent substituent; m represents an integer of 0 to 5; and $X^-$ represents a non-nucleophilic counter anion.

* * * * *